(12) United States Patent
Prien et al.

(10) Patent No.: US 8,653,076 B2
(45) Date of Patent: Feb. 18, 2014

(54) OXO-SUBSTITUTED IMIDAZO[1,2B]PYRIDAZINES, THEIR PREPARATION AND USE AS PHARMACEUTICALS

(75) Inventors: Olaf Prien, Berlin (DE); Knut Eis, Berlin (DE); Benjamin Bader, Berlin (DE); Judith Guenther, Berlin (DE); Arne Von Bonin, Glienicke-Nordbahn (DE)

(73) Assignee: Bayer Intellectual Property GmbH, Moneheim (DE)

( * ) Notice: Subject to any disclaimer, the term of this patent is extended or adjusted under 35 U.S.C. 154(b) by 0 days.

(21) Appl. No.: 11/765,638

(22) Filed: Jun. 20, 2007

(65) Prior Publication Data

US 2009/0093475 A1    Apr. 9, 2009

Related U.S. Application Data

(60) Provisional application No. 60/815,252, filed on Jun. 21, 2006.

(30) Foreign Application Priority Data

Jun. 21, 2006   (DE) ............ 10 2006 02 944

(51) Int. Cl.
   C07D 487/04    (2006.01)
   A61K 31/5025   (2006.01)
   A61P 29/00     (2006.01)
   A61P 3/10      (2006.01)
   A61P 11/06     (2006.01)

(52) U.S. Cl.
   USPC .......................................... 514/248; 544/236

(58) Field of Classification Search
   USPC .......................................... 544/236; 514/248
   See application file for complete search history.

(56) References Cited

U.S. PATENT DOCUMENTS

| | | | |
|---|---|---|---|
| 6,844,341 B2 * | 1/2005 | Thomas | 514/248 |
| 7,632,937 B2 * | 12/2009 | Mirkov et al. | 536/23.6 |
| 7,759,349 B2 * | 7/2010 | Winzenberg et al. | 514/252.05 |
| 2004/0097506 A1 | 5/2004 | Thomas | |

FOREIGN PATENT DOCUMENTS

| | | | |
|---|---|---|---|
| EP | 1813613 A1 | | 8/2007 |
| WO | WO 02/066481 A | | 8/2002 |
| WO | WO 2007013673 | * | 7/2005 |
| WO | WO 2006/049339 A | | 5/2006 |
| WO | WO 2006049339 | * | 5/2006 |
| WO | WO 2007/013673 A | | 2/2007 |

OTHER PUBLICATIONS

Banan, et al., J. Pharmacol. & Experimen. Therap., 2005, vol. 313, #3, 962-982.*
Wepsic, et al., Immunopharm. & Immunotox., vol. 11, # Mar. 1, 1989, pp. 81-99.*
Sasase, Drugs of the Future, 2006, 31(6): 503.*
Menne, et al., Nephrol. Dial. Transplant. (2009) 1 of 3.*
K.F. Byth, et al.: "Imidazo [1,2-b]pyridazines: a potent and selective class of CDK inhibitors"; Bioorganic and Medicinal Chemistry Letters; 2004; pp. 2249-2252; Bd. 14.

* cited by examiner

*Primary Examiner* — Susanna Moore
*Assistant Examiner* — Cecilia M Jaisle

(57) ABSTRACT

The invention relates to novel inhibitors of kinases of the general formula (I):

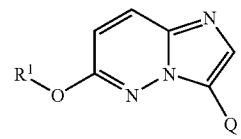

in which Q and $R^1$ are defined in the claims, method for preparing such inhibitors, intermediates for preparing such inhibitors and uses of such inhibitors.

17 Claims, No Drawings

OXO-SUBSTITUTED IMIDAZO[1,2B]PYRIDAZINES, THEIR PREPARATION AND USE AS PHARMACEUTICALS

This application claims the benefit of the filing date of U.S. Provisional Application Ser. No. 60/815,252, filed Jun. 21, 2006, which is incorporated by reference herein.

The present invention relates to novel oxo-substituted imidazo[1,2b]pyridazines, their preparation and use as medicament for the treatment of various disorders.

The compounds described in this invention are suitable for inhibiting kinases, preferably kinases of the protein kinase (PK) family and, in this connection, especially for inhibiting kinases of the PKC subfamily, very especially for inhibiting the PKC theta kinase (PKC θ kinase). The present compounds are suitable as kinase inhibitors for the treatment of a large number of disorders which are attributable to a dysfunction of a kinase; this includes immunological and general inflammatory processes and oncological processes, but also disorders such as, for example, diabetes of type II and asthma, and transplantations; preferably inflammatory processes and immune responses which exhibit the clinical appearance of acute dermatitis, of contact dermatitis but also of psoriasis.

Activation of T cells depends on a series of interactions between antigen-presenting cells (APC) and T cells. Of central importance in this connection is presentation of antigen via MHC (major histon compatibility complex) molecules on APC to the T-cell receptor (TCR) on T cells. In addition, further molecules such as the so-called costimulatory molecules (e.g. CD28) are required for complete activation of T cells. The various activation signals in total eventually lead to regulation of the transcription of genes which code for example for cell messengers (=cytokines). A cytokine of central importance in the cell response is interleukin 2 (IL-2) which in turn stimulates other T cells to proliferate and advances the adaptive immune response further.

The T-cell system is regulated in healthy individuals by a large number of mechanisms. This leads to an immune response to foreign antigen and a suppression of an immune response to self antigen. In addition, an immune response is downregulated again after effector functions have succeeded. If control of these mechanisms is inadequate, dysregulated T-cell responses may contribute to the development of a number of disorders such as autoimmune diseases, inflammatory diseases, and transplant rejections. T-cell responses also play a central part in the pathological event in inflammatory skin disorders such as psoriasis, atopic dermatitis, contact allergy.

Investigations in recent years atest that the protein kinase C (PKC) family has an important part in T-cell activation and T-cell response (Newton 1997. *Regulation of protein kinase C. Curr. Opin. Cell Biol.* 9:161-167; Altman et al. 1990. *Molecular events mediating T cell activation. Adv. Immunol.* 48:227-360). Inhibition of PKC leads to an inhibition of T-cell activation and T-cell response. It has also been possible to show that a PKC deficiency in T cells allows only inadequate TCR-triggered proliferation of T cells.

The PKC family is divided into a plurality of isoforms. A particular central role in the regulation of T-cell activation is played by the $Ca^{2+}$-dependent isoform PKC-θ. This is selectively expressed in T cells and to a small extent in cells of skeletal muscles (Meller et al. 1998. *New perspectives on PKCθ, a member of the novel subfamily of protein kinase C. Stem Cells* 16:178-192; Altman et al. 2000. *Protein kinase C θ: a new essential superstar on the T-cell stage. Immunol. Today* 21:567-573; Arendt et al. 2002. *Protein kinase C-theta: signaling from the center of the T cell synapse. Current Opinion in Immunology.* 14: 323-330). Whereas 7 different PKC isoforms (α, δ, ε, ζ, η, θ and ι) are expressed in primary human T cells, only PKC-θ (but not the other isoforms) shows the ability to regulate the central transcription factors AP-1 and NF-kappaB. Stimulation of the TCR and CD28 is followed by localization of PKC-θ (but not other PKC isoforms) in so-called 'lipid rafts' in the center of the immunological synapse, it being directly involved in the transmission of the activation signal from the TCR to further target molecules of the T cell (via phosphorylations of these molecules) as far as transcription factors (Baier-Bitterlich et al. 1996. *Protein kinase C-theta isoenzyme selective stimulation of the transcription factor complex AP-1 in T lymphocytes. Mol. Cell. Biol.* 16:1842-1850; Lin et al. 2000. *Protein kinase C θ-participates in NF-kB activation induced by CD3-CD28 costimulation through selective activation of IkappaB kinase B. Mol. Cell. Biol.* 20:2933-2940; Coudronniere et al. 2000. *NF-kB activation induced by T cell receptor/CD28 costimulation is mediated by protein kinase C-θ. Proc. Natl. Acad. Sci. USA* 97:3394-3399).

Because of this close linkage to the TCR signaling pathway, PKC-θ represents an interesting molecule in the search for novel therapeutic approaches to regulating the adaptive immune response.

It has been possible to provide a functional demonstration of the central role of this of PKC-θ in the T-cell response in particular by generating so-called knockout mice (Sun et al. 2000. *PKCθ is required for TCR-induced NF-kappaB activation in mature but not immature T lymphocytes. Nature* 404: 402-407; Pfeifhofer et al. 2003. *Protein Kinase C theta affects calcium mobilization and NFAT cell activation in primary mouse T cells. J. Exp. Med.* 197:1525-1535; Marsland et al. 2004. *Protein Kinase C theta is critical for the development of in vivo T helper (TH)2 cell but not Th1 cell responses. J. Exp. Med.* 200:181-189; Lin et al. 2000. *Protein kinase C θ-participates in NF-kB activation induced by CD3-CD28 costimulation through selective activation of IkappaB kinase B. Mol. Cell. Biol.* 20:2933-2940).

These mice are characterized by a particular phenotype:
1) reduced ability to mount an optimal T-cell response. T cells show a strongly nonreactive phenotype, even including immunosuppression.
2) on stimulation of the T cells via the TCR, the subsequent activation of transcription factors is greatly reduced. IL-2 as key cytokine in the T-cell response is produced to only a reduced extent. In addition, the ability of the T cells to proliferate is significantly inhibited.
3) defects relate only to mature T cells, because immature T cells in the thymus exhibit a normal phenotype.
4) these animals are characterized by a greatly reduced in vivo T-cell response of the T helper (TH) type 2 (TH2 response=characterized for example by a typical TH2 cytokine IL-4) shown in TH2 models to infection with nematodes, asthma models and models of skin inflammation.
5) these mice otherwise showed a normal phenotype and are not generally immunosuppressed. In addition, the ability to reproduce is not impaired.

On the basis of these special properties of knockout mice, it is to be expected that a specific inhibition of PKC-θ by selective inhibitors will inhibit only one arm of the adaptive immune response (T cells), whereas a second arm of the adaptive immune system, the B cells, will be unaffected. This would represent an advantage by comparison with classical immunosuppressants (e.g. cyclosporin A) in the therapy of inflammatory disorders with T-cell involvement (TH2-dependent disorders [atopic dermatitis, asthma, etc] and because of the central role of PKC-θ in the TCR signaling pathway also TH1 disorders [psoriasis, rheumatoid arthritis, transplant rejection, inflammatory bowel disorders etc.]) in the pathogenesis.

A single publication (*Bioorg. Med. Chem. Lett.* 2004, 14, 2249-2252.) of Astra Zeneca discloses pyrimidine derivatives having an attached imidazo-[1,2b]pyridazine residue as kinase inhibitors. These compounds differ from the compounds of the invention through their structure, especially on the imidazo[1,2b]pyridazine ring. Only methoxy and trifluoroethoxy radicals are mentioned. In addition, all the compounds mentioned by Astra Zeneca in WO 2002/066481 (A1) also comprise a pyrimidine ring which—owing to the synthesis—is directly linked to the imidazo[1,2b]pyridazine basic structure.

Although WO 2006/015737 describes by formula IX compounds which are similar in the basic structure to those disclosed herein, they are not comparable in the choice and number of the substituents.

WO 2005/041971 likewise describes imidazo[1,2b]pyridazines similar to the compounds disclosed herein. However, no example of this class of substances is specifically disclosed, nor is a synthetic route permitting adequate preparation of compounds of this class of substances described.

There continues to be a great need for effective pharmaceuticals for the treatment of immunological and also cell-proliferative disorders.

It has now been found that oxo-substituted imidazo[1,2b]pyridazines of the general formula I represent excellent PKC-θ inhibitors. They are compounds of the general formula (I),

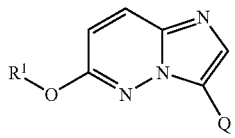

in which
Q is an aryl or heteroaryl radical which may be linked at any position to the imidazo[1,2b]pyridazine residue and which may optionally be substituted independently of one another by
  1-3 hydroxy groups, halogen atoms, nitro groups or cyano groups
  1-3 $C_1$-$C_6$-alkyl or $C_3$-$C_8$-cycloalkyl groups which may optionally be substituted by 1-3 hydroxy and/or 1-3 halogen or cyano groups and/or 1-3 ($C_1$-$C_5$)-alkoxy groups and/or 1-3 $COOR^6$ groups and/or 1-3 $NHR^6$ groups and/or 1-3 $NHCOR^6$ groups and/or 1-3 $N(R^2)_2$ groups or be interrupted by 1-3 keto groups,
  1-3 $C_1$-$C_6$-fluoroalkyl groups which may optionally be substituted by 1-3 hydroxy and/or 1-3 optionally fluorinated ($C_1$-$C_5$)-alkoxy groups and/or 1-3 $COOR^2$ groups,
  1-3 pyrrolidine groups,
  1-3 $(CH_2)_u$—$SO_2$—$R^2$ groups in which u is the numbers 1, 2 or 3,
  1-3 $R^2$ groups,
  1-3 O—CO—$R^6$ groups,
  1-3 CO—O—$R^6$ groups,
  1-3 CO—N($R^6$)$_2$ groups,
  1-3 NH—CO—$R^6$ groups,
  1-3 $CONR^7R^8$ groups,
  1-3 $(CH_2)_n$—$NR^7R^8$ groups,
  1-3 NH—$CONHR^6$ groups,
  1-3 $OR^6$ groups,
  1-3 $SO_2$—$R^2$ groups,
  1-3 $SO_2$—$OR^2$ groups,
  1-3 $SO_2$—$N(R^2)_2$ groups,
  1-3 $NHSO_2R^2$ groups,
  and/or
  1-3 $SR^2$ groups,
in which $R^2$ is in each case independently of one another
  a hydrogen atom, a phenyl radical, an optionally partly or completely fluorinated $C_1$-$C_5$-alkyl radical or
  a $C_1$-$C_5$-alkyl radical which is in turn optionally substituted 1-5 times by hydroxy radicals, cyano groups, phenyl groups, $C_3$-$C_7$-cycloalkyl radicals, $SO_2(C_1$-$C_3$-alkyl) radicals, $NH(C_1$-$C_3$-alkyl) radicals, $N[(C_1$-$C_3$-alkyl)]_2$ radicals, and/or $C_1$-$C_5$-alkoxy radicals,
  or a $C_3$-$C_7$-cycloalkyl radical,
in which $R^6$ is in each case independently of one another either
  a radical $R^2$,
  an aryl or heteroaryl radical which may in turn optionally be substituted independently of one another 1-3 times by hydroxy radicals, halogen atoms, cyano groups and/or $C_1$-$C_5$-alkoxy radicals,
  a radical —$(CH_2)_u$-Qs in which u is the numbers 1, 2 or 3, and in which QS is an aryl or heteroaryl radical which may in turn optionally be substituted independently of one another 1-3 times by hydroxy radicals, halogen atoms, cyano groups and/or $C_1$-$C_5$-alkoxy radicals,
  where the vicinal hydroxy groups present in the aryl or heteroaryl group may also be condensed with aldehydes or ketones or halogenated aldehydes or halogenated ketones,
  and in which
$R^1$ is a $C_1$-$C_6$-alkyl radical which may be substituted 1-3 times by —$R^2$, —$NR^3R^4$, —$NR^7R^8$ or —$OR^2$ in which $R^2$ has the abovementioned meaning and $R^3$, $R^4$, $R^7$ and $R^8$ has the meaning specified hereinafter,
  is a $C_1$-$C_6$-alkenyl radical which may be substituted 1-3 times by —$R^2$, —$NR^3R^4$, —$NR^7R^8$ or —$OR^2$ in which $R^2$ has the abovementioned meaning and $R^3$, $R^4$, $R^7$ and $R^8$ has the meaning specified hereinafter,
  is a $C_1$-$C_6$-alkynyl radical which may be substituted 1-3 times by —$R^2$, —$NR^3R^4$, —$NR^7R^8$ or —$OR^2$ in which $R^2$ has the abovementioned meaning and $R^3$, $R^4$, $R^7$ and $R^8$ has the meaning specified hereinafter,
  a —$(CH_2)_n$—$NR^3R^4$ radical where n is a number 2-6 and in which $R^3$ and $R^4$ are independently of one another a hydrogen atom, a —$COR^6$ radical, a —$SO_2R^2$ radical, or a $C_1$-$C_5$-alkyl radical which is in turn optionally substituted 1-3 times by a halogen atom, a hydroxy group, a cyano group, a nitro group, a group —$R^2$, a group —$NHR^2$, a group —$N(R^2)_2$, a group —$CO_2R^6$, a group —$OCOR^6$, a group —$SO_2R^2$ or a group —$OR^2$,
  a —$(CH_2)_t$—Z—$(CH_2)_m$—$NR^3R^4$ radical,
  where Z is a group —O—, —S—, —$NR^2$—, —$CHR^5$— or —$C(R^5)_2$—,
  m is a number 0, 1 or 2, t is a number 0, 1, 2 or 3, and in which $R^3$ and $R^4$ has the abovementioned meaning,
  and in which $R^5$ is a $C_1$-$C_3$-alkyl, $C_2$-$C_3$-alkenyl, $C_2$-$C_3$-alkynyl, a phenyl or a $C_3$-$C_6$-cycloalkyl radical,
  a —$(CH_2)_n$—$NR^7R^8$ radical where n is a number 1-6 and in which $R^7$ and $R^8$ together form a 3-7-membered ring, where the 3-7-membered ring may comprise a further heteroatom, and where the 3-7-membered ring is optionally substituted 1-3 times by a halogen atom, a hydroxy group, a cyano group, a nitro group, a group —$R^6$, a group —$NHR^2$, a group —$N(R^2)_2$, a group —$CO_2R^6$, a group —OCOR⁶, a group —SO₂R² or a group —OR²,
or is interrupted by 0-3 keto groups,
a —(CH₂)ₙ—(CH)R⁷R⁸ radical where n, R⁷ and R⁸ have the abovementioned meaning,
a —(CH₂)ₜ—Z—(CH₂)ₘ—NR⁷R⁸ radical,
where t, m, Z, R⁷ and R⁸ have the abovementioned meaning,
a —(CH₂)ₜ—Z—(CH₂)ₘ—(CH)R⁷R⁸ radical,
where t, m, Z, R⁷ and R⁸ have the abovementioned meaning,
a —(CH₂)ᵣ—Y¹ radical where r is a number 0-3, and Y¹ is a piperidine or pyrrolidine ring, where the piperidine or pyrrolidine ring is optionally substituted 1-3 times independently of one another by a halogen atom, a hydroxy group, a cyano group, a nitro group, a group —R⁶, a group —NHR², a group —N(R²)₂, a group —CO₂R⁶, a group —OCOR⁶, a group —SO₂R² or a group —OR²,
a —(CH₂)ₜ—Z—(CH₂)ₘ—Y¹ radical
in which t, m, z, Y¹ have the abovementioned meaning,
a —(CH₂)ᵣ—Y² radical where r is a number 0-3, and Y² is a morpholine ring, where the morpholine ring is optionally substituted 1-3 times by a halogen atom, a hydroxy group, a cyano group, a nitro group, a group —R⁶, a group —NHR², a group —N(R²)₂, a group —CO₂R⁶, a group —OCOR⁶, a group —SO₂R² or a group —OR²,
a —(CH₂)ₜ—Z—(CH₂)ₘ—Y² radical
where t, m, Z, Y² have the abovementioned meaning,
a —(CH₂)ᵣ—Y³ radical where r is a number 0-3, and Y³ is a piperazine ring which optionally has a C₁-C₃-alkyl or a C₁-C₃-acyl group on the nitrogen atom, where the piperazine ring is optionally substituted 1-3 times by a halogen atom, a hydroxy group, a cyano group, a nitro group, a group —R⁶, a group —NHR², a group —N(R²)₂, a group —CO₂R⁶, a group —OCOR⁶, a group —SO₂R² or a group —OR²,
a —(CH₂)ₜ—Z—(CH₂)ₘ—Y³ radical
where t, m, Z, Y³ have the abovementioned meaning,
a —(CH₂)ᵣ—Y⁴ radical where r is a number 0-3, and Y⁴ is a C₃-C₈-cycloalkyl ring which is optionally substituted 1-3 times by a halogen atom, a hydroxy group, a cyano group, a nitro group, a group —R⁶, a group —NHR², a group —N(R²)₂, a group —CO₂R⁶, a group —OCOR⁶, a group —SO₂R² or a group —OR²,
a —(CH₂)ₜ—Z—(CH₂)ₘ—Y⁴ radical
where t, m, Z, Y⁴ have the abovementioned meaning,
a —(CH₂)ᵣ—Y⁵ radical where r is a number 0-3, and Y⁵ is an aryl or heteroaryl ring which is optionally substituted 1-3 times by a halogen atom, a hydroxy group, a cyano group, a nitro group, a group R⁶, a group —NHR², a group —N(R²)₂, a group —CO₂R⁶, a group —OCOR⁶, a group —SO₂R², a group —SO₂N(R²)₂, a group —NHSO₂R², a group —NHCOR⁶, a group —NH-CONHR⁶ or a group —OR²,
a —(CH₂)ₜ—Z—(CH₂)ₘ—Y⁵ radical
where t, m, Z, Y⁵ have the abovementioned meaning,
a —(CH₂)ᵣ—Y⁶ radical where r is a number 0-3, and Y⁶ is a radical

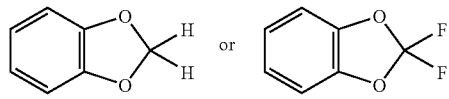 [SMILES: c1ccc2c(c1)OCO2 ; FC1(F)Oc2ccccc2O1]

which may be linked at any position to the (CH₂)ᵣ group,
a —(CH₂)ₜ—Z—(CH₂)ₘ—Y⁶ radical
where t, m, Z, Y⁶ have the abovementioned meaning
in the form of the various stereoisomers of the compounds of the general formula I
and the salts of the stereoisomers of the general formula I with physiologically tolerated counterions.

Alkyl means in each case a straight-chain or branched alkyl radical such as, for example, methyl, ethyl, propyl, isopropyl, butyl, isobutyl, sec-butyl, tert-butyl, pentyl, isopentyl, neopentyl and hexyl.

Fluoroalkyl means in each case a straight-chain or branched alkyl radical in which at least one hydrogen atom is replaced by a fluorine atom, such as, for example, fluoromethyl, difluoromethyl, trifluoroethyl, trifluoroethyl, pentafluoroethyl, perfluoropropyl and perfluoroisopropyl.

Alkoxy means in each case a straight-chain or branched alkoxy radical such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy or decyloxy.

The alkenyl substituents are in each case straight-chain or branched, with the following radicals being meant for example: vinyl, propen-1-yl, propen-2-yl, but-1-en-1-yl, but-1-en-2-yl, but-2-en-1-yl, but-2-en-2-yl, 2-methylprop-2-en-1-yl, 2-methylprop-1-en-1-yl, but-1-en-3-yl, but-3-en-1-yl, allyl.

Alkynyl means in each case a straight-chain or branched alkynyl radical which comprises 2-6, preferably 2-4, C atoms. The following radicals may be mentioned as examples: acetylenyl, propyn-1-yl, propyn-3-yl (propargyl), but-1-yn-1-yl, but-1-yn-4-yl, but-2-yn-1-yl, but-1-yn-3-yl, 3-methylbut-1-yn-3-yl.

C₃-C₆-Cycloalkyl is an alkyl ring which comprises 3-6 carbon atoms and which may optionally comprise one or more double bonds in the ring.

A heteroatom is a multivalent atom different from carbon, preferably a nitrogen, oxygen or sulfur atom.

The expression "independently of one another" means that multiple substituents may be different from one another. For example, the compound 3-(3-chloro-4-fluorophenyl)-6-[3-(4-methylpiperazin-1-yl)propoxy]imidazo[1,2-b]pyridazine comprises a phenyl ring substituted by two halogen atoms. The halogen atoms are, however, different from one another (fluorine and chlorine).

In the general formula I, Q can be an aryl or heteroaryl radical which may be linked at any position to the imidazo[1,2b]pyridazine residue. It is clear to the skilled worker in this connection that all synthetically accessible aryl or heteroaryl compounds which are stable under physiological conditions are meant.

Preferred radicals Q are the phenyl, thiophenyl, biphenyl, furanyl, benzofuranyl, indolyl, pyridinyl, benzothiophenyl and the naphthalenyl group It is clear to the skilled worker that the aryl or heteroaryl groups present in Q may be substituted in many ways. Preferred substituents in Q are cyclopropylmethoxy-, fluorine, chlorine, hydroxyl-, cyano-, trifluoromethyl-, trifluoromethoxy-, methyl-, methoxy-, pyrrolidinyl-, —CO—OCH₃, —CO—CH₃, —CO₂H, —CO—NH₂, —CH₂—CN, —CH₂—OH, —CH₂—S—CH₃, —S—CH₃, —SO₂—CH₂CH₃ or —NHCOCH₃. In addition, Q may be phenyl, naphthyl, tetralinyl, anthranyl, indanyl, indenyl, pyridinyl, pyrazinyl, pyrimidinyl, pyridazinyl, triazinyl, azaindolizinyl, furanyl, thiophenyl, oxazolyl, thiazolyl, furazanyl, isoxazolyl, isothiazolyl, oxadiazolyl, triazolyl, tetrazolyl, thiadiazolyl, phthalidyl, thiophthalidyl, indolyl, isoindolyl, indazolyl, benzothiazolyl, indolonyl, isoindolonyl, benzofuranyl, benzimidazolyl, benzoxazinonyl, phthalazinonyl, quinolinyl, isoquinolinyl, quinolonyl, isoquinolonyl, quinazolinyl, quinoxalinyl, cinnolinyl, phthalazinyl, 1,7- or 1,8-naphthyridinyl, coumarinyl, isocoumarinyl, indolizinyl, isobenzofuranyl, azaindolyl, azaisoindolyl, furanopyridyl, furanopyrimidinyl, furanopyrazinyl, furanopyidazinyl, dihydrobenzofuranyl, dihydrofuranopyridyl, dihydrofuranopyrimidinyl, dihydrofuranopyrazinyl, dihydrofuranopyridazinyl, dihydrobenzofuranyl, chromenyl, isochromenyl, chromenonyl, isochromenonyl group, piperidyl, 4-aminopyridyl, 1H-pyridin-4-ylidenaminyl, chromanyl, isochromanyl, thiochromanyl, decahydroquinolinyl, tetrahydroquinolinyl, dihydroquinolinyl, 5,6,7,8-tetrahydro-1H-quinolin-4-onyl, decahydroisoquinolinyl, tetrahydroisoqunolinyl dihydroisoquinolinyl, 3,4-dihydro-2H-benz[1,4]oxazinyl, 1,2-dihydro[1,3]-benzoxazin-4-onyl, 3,4-dihydrobenz[1,4]oxazin-4-onyl, 3,4-dihydro-2H-benzo[1,4]thiazinyl, 4H-benzo[1,4]thiazinyl, 1,2,3,4-tetrahydroquinoxalinyl, 1H-cinnolin-4-onyl, 3H-quinazolin-4-onyl, 1H-quinazolin-4-onyl, 3,4-dihydro-1H-quinoxalin-2-onyl, 1,2,3,4-tetrahydro[1,5]naphthyridinyl, dihydro-1H-[1,5]naphthyridyl, 1H-[1,5]naphthyrid-4-onyl, 5,6,7,8-tetrahydro-1H-naphthyridin-4-onyl, 1,2-dihydropyrido[3,2-d]-[1,3]oxazin-4-onyl, octahydro-1H-indolyl, 2,3-dihydro-1H-indolyl, octahydro-2H-isoindolyl, 1,3-dihydro-2H-isoindolyl, 1,2-dihydroindazolyl, 1H-pyrrolo[2,3-b]pyridyl, or 2,3-dihydro-1H-pyrrolo[2,3-b]pyridyl, 2,2-dihydro-1H-pyrrolo[2,3-b]pyridin-3-onyl.

The aryl or heteroaryl groups optionally present in the radical $R^6$ may be for example the abovementioned aryl or heteroaryl systems. The aryl or heteroaryl groups optionally present in the radical $R^6$ are preferably phenyl, thiophenyl, biphenyl, furanyl, benzofuranyl, indolyl, pyridinyl, benzothiophenyl and the napthalenyl group.

A preferred class of compounds of the general formula I is formed by those in which $R^1$ is
3-dimethylaminopropyl-
3-diethylaminopropyl-
3-piperidin-1-ylpropyl-
2-dimethylaminoethyl-
2-diethylaminoethyl-
1-methylpiperidin-3-ylmethyl-
1-methylpyrrolidin-2-ylethyl-
4-diethylamino-1-methylbutyl-
or
3-(4-methyl)piperazin-1-ylpropyl.

A further preferred class of compounds of the general formula I is formed by those compounds in which $R^1$ is a —$(CH_2)_n$—$NR^3R^4$ radical where n is 3 or 4, and in which $R^3$ and $R^4$ are independently of one another a $C_1$-$C_3$ alkyl radical.

A further preferred class of compounds of the general formula I is formed by those compounds in which $R^1$ is a —$(CH_2)_n$—$NR^7R^8$ radical where n is 3 or 4, and in which $R^7$ and $R^8$ together form a 5-7-membered ring.

It is clear to the skilled worker that the compounds of the general formula I may exist in various stereoisomeric forms. It is therefore clear that the compounds of the general formula I include all such stereoisomeric compounds, especially all enantiomers and diastereomers, both in pure form and as racemates.

The term stereoisomers further includes also all possible regioisomers and tautomers (e.g. keto-enol tautomers) in which the stereoisomers of the invention may be present, which are thus likewise an aspect of the invention.

The compounds of the invention may also be in the form of salts with pharmacologically acceptable cations or anions, for example in the form of the sodium salt, potassium salt, magnesium salt, ammonium salt, N-methylglucamine salt, N,N-dimethylglucamine salt, of the hydrochloride, sulfate, nitrate, phosphate, pivalate, maleate, fumarate, tartrate, benzoate, mesylate, citrate or succinate.

Pharmacologically acceptable derivatives or prodrugs of the compounds of the general formula I are also encompassed by the invention. Derivatives or prodrugs refer for example to esters, ethers or amides of the compounds of the general formula I or other compounds which metabolize in the body to compounds of the general formula I. Suitable compounds are listed for example in Hans Bundgaard (ed.), Design of Prodrugs, Elsevier, Amsterdam 1985.

Uses of the Compounds of the Invention

Compounds of the invention are suitable as kinase inhibitors, especially of tyrosine and serine/threonine kinases. The compounds of the invention of the general formula I are inter alia inhibitors of the protein kinase C family, such as, for example, PKC theta, delta, iota, alpha and zeta.

An inhibitor of a kinase can therefore be employed on the one hand for investigating the mechanisms of functioning of the kinase, in particular research into a disorder derived from a dysfunction of the kinase. However, a disorder derived from the dysfunction of the kinase can also be treated or prevented with the kinase inhibitor.

The invention therefore relates further to the use of a compound of the invention of the general formula I for producing a pharmaceutical composition, in particular for inhibiting a cellular kinase, preferably kinases of the protein kinase (PK) family and in this connection especially for inhibiting kinases of the PKC subfamily, very particularly for inhibiting the PKC theta kinase, and for the treatment or for the prophylaxis of a disorder which is associated with overexpression or mutation of a cellular kinase, especially of such a cellular kinase. Disorders of this type are in particular inflammatory disorders, oncological disorders and autoimmune diseases. The compounds of the invention are likewise suitable for preparing compounds for immunosuppression. The compounds of the invention are very particularly suitable for producing pharmaceuticals for the treatment of diabetes of type II, asthma, dermatitis, psoriasis, rheumatoid arthritis, contact dermatitis, atopic dermatitis, contact allergy, multiple sclerosis, inflammatory bowel disorders or transplant rejections. The present compounds can additionally, however, also be employed for modulating an immune response, for example after transplantation has taken place to prevent rejection of an organ.

A pharmaceutical composition of the invention can be produced by mixing a physiologically effective dose of a compound of the invention with at least one pharmaceutical excipient, and manufacturing the desired dosage form.

A suitable physiologically effective dose is for example an amount of from 1 to 1000 mg, in particular from 50 to 500 mg, per dose unit per day for a person weighing 75 kg, it being possible to give the dose as a single dose to be administered once or divided into 2 or more daily doses.

The pharmaceutical manufacturing of a pharmaceutical composition of the invention can take place in a manner known in the art. Examples of suitable counterions for ionic compounds are $Na^+$, $K^+$, $Li^+$ or cyclohexylammonium, and $Cl^-$, $Br^-$, acetate, trifluoroacetate, propionate, lactate, oxalate, malonate, maleate, citrate, benzoate, salicylate etc. Suitable solid or liquid pharmaceutical presentations are for example granules, powders, coated tablets, tablets, (micro)capsules, suppositories, syrups, solutions, ointments, suspensions, emulsions, drops or solutions for injection (i.v., i.p., i.m., s.c.) or atomization (aerosols), transdermal systems, and products with protracted release of active ingredient, in the production of which conventional aids such as carriers, disintegrants, binders, coated agents, swelling agents, glidants or lubricants, and preservatives, stabilizers, wetting agents or emulsifiers; salts to alter the osmotic pressure or buffers, flavorings, sweeteners and solubilizers, are used. It is also possible to use as carrier systems surface-active excipients such as salts of bile acids or animal or vegetable phospholipids, but also mixtures thereof, and liposomes or constituents thereof. Excipients which may be mentioned are magnesium carbonate, magnesium stearate, gum arabic, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycols and solvents such as, for example sterile water and monohydric or polyhydric alcohols, for example glycerol. Preferred dosage forms are for topical application (ointments, transdermal systems, patches, dressings), for oral administration (tablets, coated tablets, solutions, powders) or for parenteral use (suspension, injection).

A pharmaceutical composition of the invention can be produced by mixing at least one inhibitor used according to the invention in defined dose with a pharmaceutically suitable and physiologically tolerated carrier and where appropriate further suitable active ingredients, additives or excipients with defined dose of inhibitor, and manufacturing the desired dosage form. These pharmaceutical products are likewise an aspect of the present invention.

Finally, the invention also relates to a method for the treatment or prophylaxis of a disorder which is associated with overexpression of a cellular kinase, where a pharmaceutical composition comprising a physiologically effective dose of a compound of the general formula I is administered to a person suffering from or under threat of suffering from the disorder.

Preparation Method (Synthesis Scheme):

The inventions can be prepared by the synthesis scheme depicted below.

The invention therefore further relates also to a method for preparing a compound of the invention with the following stages of the method:

In the synthesis diagram, $R^1$ and Q have the meanings specified in claim 1. Hal and X are the halogen atoms chlorine, bromine and iodine.

A further aspect of the present invention places a compound of the general formula IIb

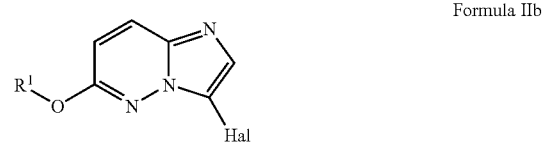

Formula IIb in which $R^1$ has the meaning defined in claim 1, and in which Hal is a chlorine, bromine or iodine atom.

Preferred compounds of the formula IIb are 3-bromo-6-(3-morpholin-4-ylpropoxy)imidazo[1,2-b]pyridazine, 3-bromo-6-(3-piperidin-1-ylpropoxy)imidazo[1,2-b]pyridazine, 3-bromo-6-[2-(1-methylpyrrolidin-2-yl)ethoxy]imidazo[1,2-b]pyridazine, 3-bromo-6-(1-methylpiperidin-3-ylmethoxy)imidazo[1,2-b]pyridazine, 3-bromo-6-(1-ethylpyrrolidin-3-yloxy)imidazo[1,2-b]pyridazine, [3-(3-bromoimidazo[1,2-b]pyridazin-6-yloxy)propyl]diethylamine, 3-bromo-6-[3-(4-methylpiperazin-1-yl)propoxy]imidazo[1,2b]pyridazine, [4-(3-bromoimidazo[1,2-b]pyridazin-6-yloxy)butyl]dimethylamine, [4-(3-bromoimidazo[1,2-b]pyridazin-6-yloxy)pentyl]diethylamine, 3-bromo-6-(1-methylpiperidin-3-yloxy)imidazo[1,2-b]pyridazine and 3-bromo-6-phenoxyimidazo[1,2b]pyridazine.

A further aspect of the invention is formed by the reaction of the compounds of the general formula IIb with an aryl or heteroaryl derivative in an optionally metal-catalyzed cross-coupling reaction to give a compound of the general formula I.

Methods of this type are described for example in King, Yasuda: Topics Organomet Chem (2004) δ: 205-245.

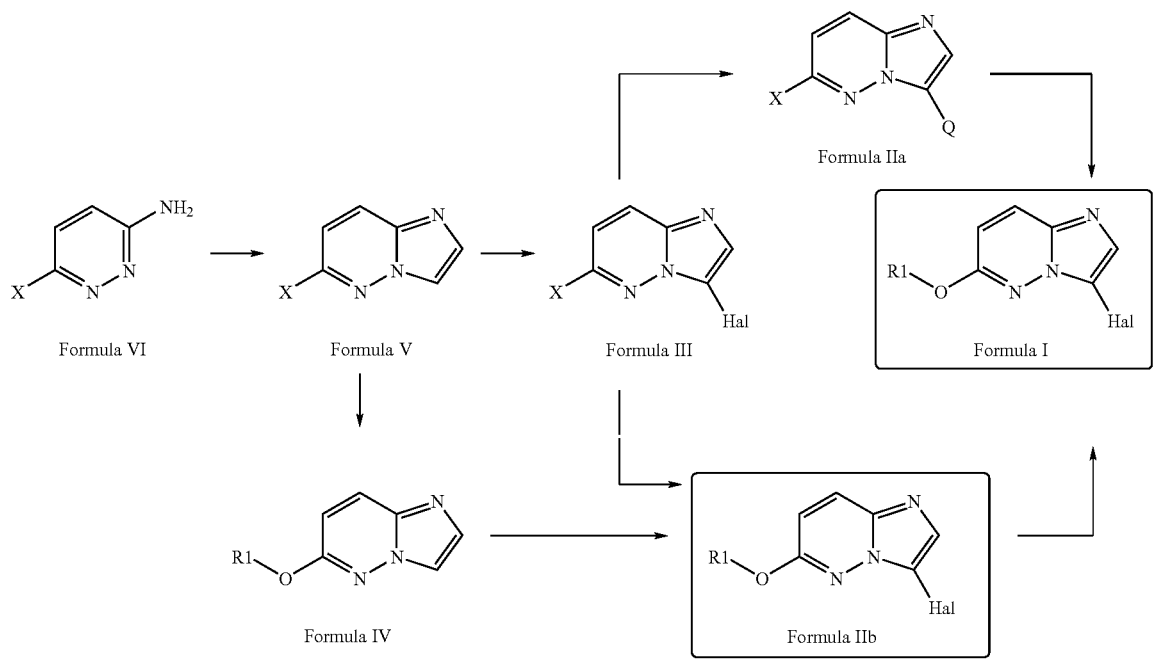

EXAMPLES

Preparation of the compounds of the invention is illustrated in the following examples without the examples being intended to be limiting.

The naming of the compounds drawn using ISIS/draw 2.4 in accordance with a IUPAC nomenclature took place using the AutoNom 2000 software from MDL.

Preparation of the Starting Materials

6-Chloroimidazo[1,2-b]pyridazine

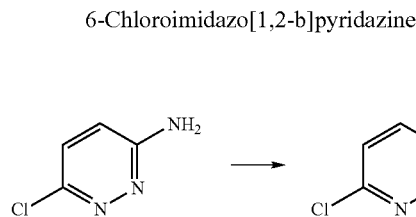

5.0 g (38.6 mmol) of 3-amino-6-chloropyridazine were heated together with 4.7 ml (40 mmol) of chloracetaldehyde (55% strength in water) in 15 ml of n-butanol at 120° C. for a period of 5 days. After the reaction was complete, the reaction mixture was added to saturated sodium bicarbonate solution and extracted three times with ethyl acetate. The combined organic phases were then washed with sat. sodium chloride solution and dried over sodium sulfate, and the solvent was removed in vacuo. In the final purification by chromatography on silica gel, 4.17 g (70%) of the desired product were isolated in the form of an amorphous white solid.

$^1$H-NMR (CDCl$_3$, stored over molecular sieves): δ=7.06 (d, 1H); 7.79 (d, 1H); 7.92, (d, 1H); 7.96 (d, 1H) ppm.

3-Bromo-6-chloroimidazo[1,2-b]pyridazine

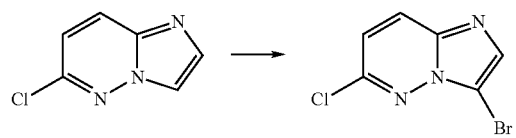 [SMILES: Clc1ccc2nccn2n1 ; Clc1ccc2ncc(Br)n2n1]

478 mg (3.11 mmol) of 6-chloroimidazo[1,2-b]pyridazine were introduced into 10 ml of chloroform under argon and, while cooling in ice, 664 mg (3.73 mmol) of N-bromo-succuinimide were added. After the addition was complete, the reaction mixture was stirred at room temperature overnight. The reaction mixture was then mixed with water and ethyl acetate and, after addition of saturated sodium bicarbonate solution, the phases were separated. The aqueous phase was extracted three more times with ethyl acetate. The combined organic phases were then washed with sat. sodium chloride solution and dried over sodium sulfate. In the final removal of the solvent in vacuo, the desired product was isolated in quantitative yield in the form of an amorphous white solid which was employed without further chromatographic purification in subsequent reactions.

$^1$H-NMR (CDCl$_3$, stored over molecular sieves): δ=7.12 (d, 1H); 7.79 (s, 1H); 7.90, (d, 1H) ppm.

Preparation of the Intermediates of the Invention

Intermediate A

3-Bromo-6-(3-morpholin-4-ylpropoxy)imidazo[1,2-b]pyridazine

Variant 1

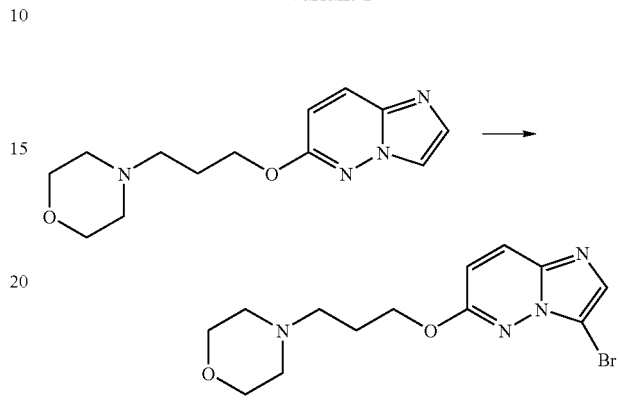

1.36 g (5.18 mmol) of 6-chloroimidazo[1,2-b]pyridazine were dissolved in 40 ml of chloroform under argon and, after addition of 1.11 g (6.22 mmol, 1.2 eq.) of N-bromo-succinimide, the reaction mixture was stirred at RT overnight.

For working up the reaction mixture is mixed with water and, after addition of saturated sodium bicarbonate solution, the phases were separated. The aqueous phase was extracted three more times with ethyl acetate. The combined organic phases were then washed in each case once with saturated sodium dithionite solution and saturated sodium chloride solution and dried over sodium sulfate. In the final purification by chromatography on silica gel, 1.08 g (61%) of the desired product were isolated.

$^1$H-NMR (CDCl$_3$, stored over molecular sieves): δ=1.98-2.14 (m, 2H); 2.45-2.64 (m, 6H); 3.75 (m, 4H); 4.48 (m, 2H); 6.71 (d, 1H); 7.60 (s, 1H); 7.77 (d, 1H) ppm.

MS (Cl+): m/z=341/343 [M+H]$^+$ 100%

Intermediate B

3-Bromo-6-(3-piperidin-1-ylpropoxy)imidazo[1,2-b]pyridazine

Variant 2

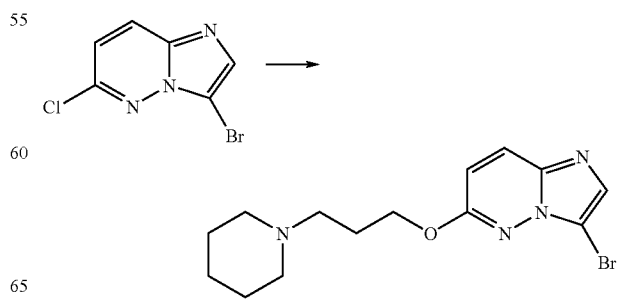

3.7 g (25.8 mmol) of 1-piperidinepropanol are added dropwise to a suspension of 620 mg (25.8 mmol) of sodium hydride in 30 ml of tetrahydrofuran while cooling in an ice bath. After the addition is complete, the reaction mixture is stirred for 15 minutes and then 3.0 g (12.9 mmol) of 3-bromo-6-chloroimidazo[1,2-b]pyridazine are put into the reaction mixture, which is stirred at RT overnight.

The reaction mixture was then with a little saturated ammonium chloride solution and, after addition of water, the phases were separated. The aqueous phase was extracted twice more with ethyl acetate. The combined organic phases were then washed with sat. sodium chloride solution and dried over sodium sulfate. In the final purification by chromatography on silica gel, 1.75 g (40%) of the desired product were isolated.

$^1$H-NMR (CDCl$_3$, stored over molecular sieves): δ=1.98-2.14 (m, 2H); 2.45-2.64 (m, 6H); 3.75 (m, 4H); 4.48 (m, 2H); 6.71 (d, 1H); 7.60 (s, 1H); 7.77 (d, 1H) ppm.

MS (CI+): m/z=341/343 [M+H]$^+$ 100%

The following were prepared in an analogous manner:

TABLE 1

| Intermediate | Structure and name of the main isomer | $^1$H-NMR | Mol. weight/ MS (ESI) [M +]$^+$ |
|---|---|---|---|
| C | 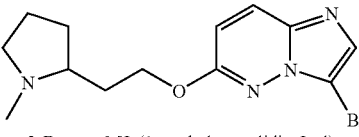<br>3-Bromo-6-[2-(1-methyl-pyrrolidin-2-yl)-ethoxy]-imidazo[1,2-b]pyridazine | (CDCl$_3$, stored over molecular sieves):<br>δ = 1.55-1.90(m, 4H);<br>2.07(m, 1H);<br>2.14-2.33 (m, 3H)<br>2.38 (s, 3H); 3.12 (m, 1H); 4.46 (m, 2H);<br>6.68 (d, 1H); 7.58 (s, 1H);<br>7.74 (d, 1H) ppm. | MW: 325.21<br>MS (ES+) [M + 1]$^+$:<br>325/327 (100%) |
| D | 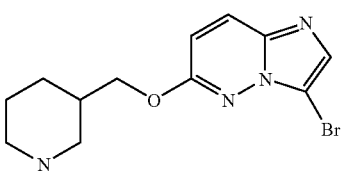<br>3-Bromo-6-(1-methyl-piperidin-3-ylmethoxy)-imidazo[1,2-b]pyridazine | (CDCl$_3$, stored over molecular sieves):<br>δ = 1.12 (m, 1H);<br>1.62-1.95 (m, 4H);<br>2.01 (m, 1H); 2.32 (s, 3H); 2.82 (br s, 1H);<br>2.98 (br s, 1H);<br>4.18 (m, 2H);<br>6.66 (d, 1H);<br>7.59 (s, 1H);<br>7.77 (d, 1H) ppm. | MW: 325.21<br>MS (ES+) [M + 1]$^+$:<br>325/327 (100%) |
| E | 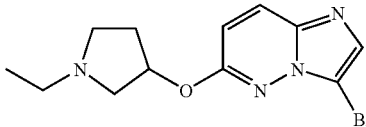<br>3-Bromo-6-(1-ethyl-pyrrolidin-3-yloxy)-imidazo[1,2-b]pyridazine | (CDCl$_3$, stored over molecular sieves):<br>δ = 1.18 (t, 3H);<br>2.09 (m, 1H);<br>2.48-2.67 (m, 4H)<br>2.96 (m, 3H);<br>5.48 (m, 1H);<br>6.72 (d, 1H); 7.60 (s, 1H);<br>7.76 (d, 1H) ppm. | MW: 311.18<br>MS (ES+) [M + 1]$^+$:<br>311/313 (100%) |
| F | 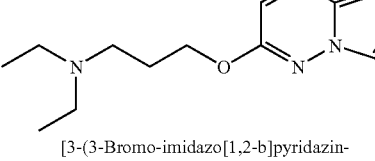<br>[3-(3-Bromo-imidazo[1,2-b]pyridazin-6-yloxy)-propyl]-diethyl-amine | (CDCl$_3$, stored over molecular sieves):<br>δ = 1.05 (t, 6H);<br>2.03 (m, 2H);<br>2.52-2.70 (m, 6H);<br>4.46 (m, 1H);<br>6.70 (d, 1H);<br>7.59 (s, 1H);<br>7.75 (d, 1H) ppm. | MW: 327.23<br>MS (ES+) [M + 1]$^+$:<br>327/329 (100%) |
| G | 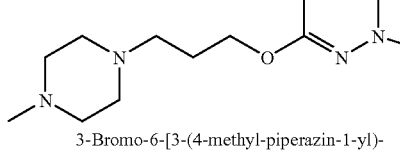<br>3-Bromo-6-[3-(4-methyl-piperazin-1-yl)-propoxy]-imidazo[1,2-b]pyridazine | (CDCl$_3$, stored over molecular sieves):<br>δ =<br>2.05 (m, 2H);<br>2.33 (s, 3H);<br>2.45-2.65(m, 10H);<br>6.69 (d, 1H);<br>7.58 (s, 1H); 7.75 (d, 1H) ppm. | MW: 354.25<br>MS (ES+) [M + 1]$^+$:<br>354/356 (62%);<br>141 (100%) |
| H | 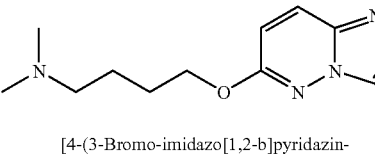<br>[4-(3-Bromo-imidazo[1,2-b]pyridazin-6-yloxy)-butyl]-dimethyl-amine | (CDCl$_3$, stored over molecular sieves):<br>δ = 1.88(m,2H);<br>2.27 (s, 6H);<br>2.39 (m, 2H);<br>4.42 (t, 2H);<br>6.69 (d, 1H);<br>7.58 (s, 1H);<br>7.75 (d, 1H) ppm. | MW: 313.20<br>MS (ES+) [M + 1]$^+$:<br>313/315 (53%);<br>100 (100%) |

TABLE 1-continued

| Intermediate | Structure and name of the main isomer | ¹H-NMR | Mol. weight/ MS (ESI) [M +]⁺ |
|---|---|---|---|
| I | 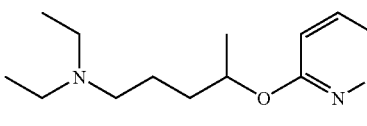 [4-(3-Bromo-imidazo[1,2-b]pyridazin-6-yloxy)-pentyl]-dimethyl-amine | (CDCl₃, stored over molecular sieves): δ = 1.05 (m, 6H); 1.42 (d, 3H); 1.56-1.76 (m, 4H); 2.41-2.62 (m, 6H); 5.22 (m, 1H); 6.67 (d, 1H); 7.58 (s, 1H); 7.74 (d, 1H) ppm. | MW: 355.28 MS (ES+) [M + 1]⁺: 355/357 (67%); 160 (100%) |
| J | 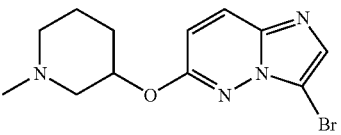 [SMILES: CN1CCCC(Oc2ccc3ncc(Br)n3n2)C1] 3-Bromo-6-(1-methyl-piperidin-3-yloxy)-imidazo[1,2-b]pyridazine | (CDCl₃, stored over molecular sieves): δ = 1.64-1.82 (m, 2H); 1.86-2.04 (m,2H); 2.34 (s, 3H); 2.45 (m, 2H); 2.61 (m, 1H); 2.82 (m, 1H); 5.27 (m, 1H); 6.77 (d, 1H); 7.57 (s, 1H); 7.76 (d, 1H) ppm. | MW: 311.18 MS (ES+) [M + 1]⁺: 311/313 (100%) |
| K | 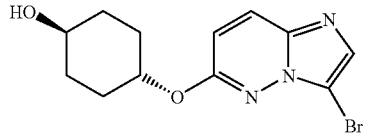 | (DMSO-D₆): δ = 1.25-1.40 (m, 2H); 1.45-1.65 (m, 2H); 1.77-1.93 (m, 2H); 2.04-2.20 (m, 2H); 3.48 (d, 1H); 4.83-4.99 (m, 1H); 6.86 (d, 1H); 7.69 (s, 1H); 7.98 (d, 1H) | MW: 312.17 MS (ES+) [M + 1]⁺: 312/314 |
| L | 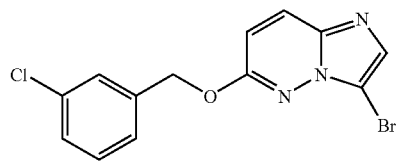 [SMILES: Clc1cccc(COc2ccc3ncc(Br)n3n2)c1] | (DMSO-D₆): δ = 5.39 (s, 1H); 6.99 (d, 1H); 7.35-7.44 (m, 2H); 7.48-7.50 (m, 1H); 7.63 (s, 1H); 7.72 (s, 1H); 8.05 (d, 1H) ppm. | MW: 338.6 MS (ES+) [M + 1]⁺: 340 |
| M | 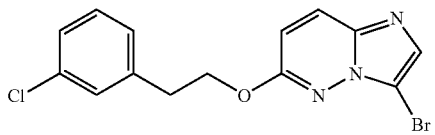 [SMILES: Clc1cccc(CCOc2ccc3ncc(Br)n3n2)c1] | (DMSO-D₆): δ = 3.10 (t, 2H); 4.53 (t, 2H); 6.89 (d, 1H); 7.25-7.32 (m, 3H); 7.52 (s, 1H); 7.70 (s, 1H); 8.00 (s, 1H) ppm. | MW: 352.62 MS (ES+) [M + 1]⁺: 354 |
| N | 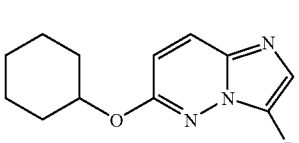 | (DMSO-D₆): δ = 1.17-1.44 (m, 3H); 1.46-1.61 (m, 3H); 1.65-1.79 (m, 2H); 1.94-2.11 (m, 2H); 4.96 (septet, 1H); 6.87 (d, 1H); 7.68 (s, 1H); 7.98 (d, 1H) ppm. | MW: 296.17 MS (ES+) [M + 1]⁺: 296/2984 |

Intermediate P

3-Bromo-6-(3-chlorophenoxy)imidazo[1,2-b]pyridazine

Variant 3

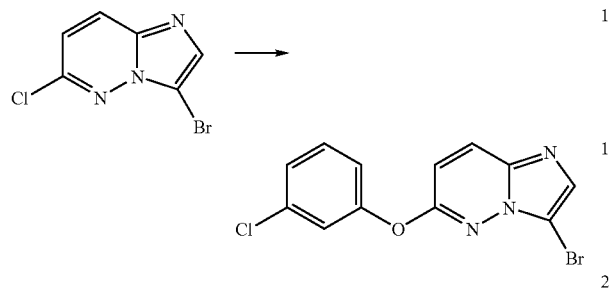

5 g (21.5 mmol) of 3-bromo-6-chloroimidazo[1,2-b]pyridazine, 3 g (23.7 mmol) of 3-chlorophenyl, 246 mg (0.27 mmol) of tris(dibenzylidineacetone)dipalladium, 500 mg of rac-BINAP and 4.1 g of sodium tert-butoxide are stirred in a mixture of 100 ml of dimethylformamide and 200 ml of tetrahydrofuran at 100° C. under a protective gas atmosphere for 12 h.

The reaction mixture is then mixed with saturated sodium chloride solution. The aqueous phase is extracted with ethyl acetate. The organic phase is washed twice with dilute aqueous NaCl solution and once with saturated aqueous NaCl solution and dried over sodium sulfate. In the final purification by chromatography on silica gel, 2.78 g (40%) of the desired product were isolated.

$^1$H-NMR (DMSO-D$_6$): δ=7.22 (d, 1H); 7.31-7.42 (m, 2H); 7.51 (d, 1H); 7.55 (t, 1H); 7.83 (s, 1H); 8.25 (d, 1H) ppm.

MS (ESI): m/z=324/326 [M+H]$^+$

Intermediate Q

6-Chloro-3-(3-chlorophenyl)imidazo[1,2-b]pyridazine

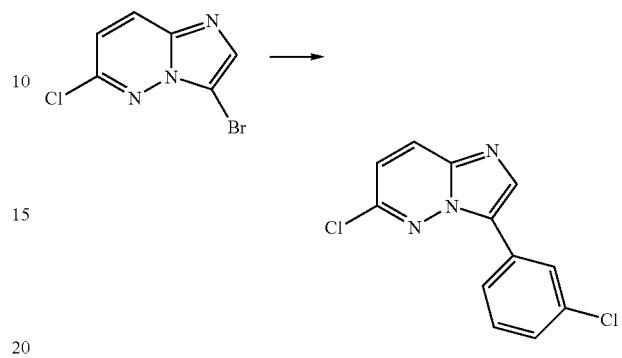

A mixture of 4.18 g (18 mmol) of 3-bromo-6-chloroimidazo[1,2-b]pyridazine, 2.95 g (18.9 mmol) of 3-chlorophenylbronic acid, 0.83 g (0.72 mmol) of tetrakis(triphenylphosphine)palladium (0) and 32.3 ml of 2 M aqueous sodium carbonate solution are heated to boiling under in 188 ml of 1,4-dioxane for 12 h.

The reaction mixture obtained in this way is mixed with sat. aqueous ammonium chloride solution and extracted with ethyl acetate. The organic phase is washed with sat. aqueous sodium chloride solution and dried over sodium sulfate, and the solvent is evaporated off. In the final purification by chromatography on silica gel, 3.46 g (73%) of the desired product were isolated.

$^1$H-NMR (DMSO-D$_6$): δ=7.43 (d, 1H); 7.44 (dd, 1H); 7.53 (t, 1H); 8.05 (dt, 1H); 8.16 (t, 1H); 8.29 (d, 1H); 8.38 (s, 1H) ppm.

MS (ESI$^+$): m/z=264 [M+H]$^+$

The following were prepared in an analogous manner:

TABLE 2

| Intermediate | Structure of the main isomer | $^1$H-NMR | Mol. weight/ MS (ESI) [M + 1]$^+$ |
|---|---|---|---|
| R | ![structure] | (DMSO-D$_6$): δ = 7.35-7.40 (m, 1H); 7.44 (d, 1H); 7.65 (t, 1H); 8.11 (dt, 1H); 8.14 (s, 1H); 8.30 (d, 1H); 8.42 (s, 1H) ppm. | MW: 313.67 MS (ES+) [M + 1]$^+$: 314 |
| S | ![structure] | (DMSO-D$_6$): δ = 7.39 (d, 1H); 7.72 (dd, 1H); 7.78 (dd, 1H); 8.27 (d, 1H); 8.30 (dd, 1H); 8.32 (s, 1H) ppm. | MW: 235.7 MS (ES+) [M + 1]$^+$: 236 |

Intermediate T

6-(3-Morpholin-4-ylpropoxy)imidazo[1,2-b]pyridazine

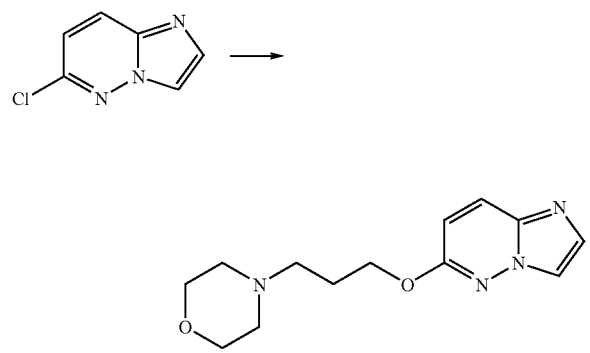

3.8 g (26.05 mmol) of 1-morpholinopropanol are added dropwise to a suspension of 1.04 g (26.05 mmol) of sodium hydride in 18 ml of tetrahydrofuran while cooling in an ice bath. After the addition is complete, the reaction mixture is stirred for 15 minutes and then 2.0 g (13.02 mmol) of 6-chloroimidazo[1,2-b]pyridazine are put into the reaction mixture, which is stirred at RT overnight.

The reaction mixture was then mixed with water and ethyl acetate and, after addition of saturated sodium bicarbonate solution, the phases were separated. The aqueous phase was extracted three times more with ethyl acetate. The combined organic phases were then washed with sat. sodium chloride solution and dried over sodium sulfate. In the final purification by chromatography on silica gel, 1.36 g (40%) of the desired product were obtained.

$^1$H-NMR (CDCl$_3$, stored over molecular sieves): δ=2.04 (m, 2H); 2.51 (m, 6H); 3.74 (m, 4H); 4.37 (m, 2H); 6.67 (d, 1H); 7.60, (d, 1H); 7.72 (d, 1H); 7.78 (d, 1H) ppm.

The following is prepared in an analogous manner:

Preparation of the Final Products of the Invention

Variant A

Example 1

3-(3-Chlorophenyl)-6-(3-morpholin-4-ylpropoxy)imidazo[1,2-b]pyridazine

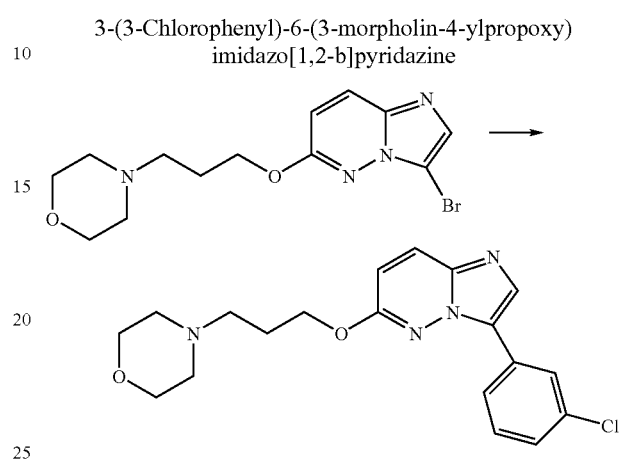

1.08 g (3.17 mmol) of 3-bromo-6-(3-morpholin-4-ylpropoxy)imidazo[1,2-b]pyridazine were introduced into 20 ml of dimethoxyethane under argon. 544 mg (3.48 mmol, 1.1 eq.) of m-chlorophenylboronic acid, 364 mg (0.63 mmol, 0.2 eq.) of bis(dibenzylideneacetone)palladium(0) and 193 mg (0.63 mmol, 0.2 eq.) of tri-o-tolyl-phosphine, and 4.8 ml of saturated sodium bicarbonate solution, were successively added, and the reaction mixture was heated under reflux for 4 hours.

The mixture was mixed with saturated sodium bicarbonate solution and diluted with water. The aqueous phase was extracted three times more with ethyl acetate. The combined organic phases were then washed once with saturated sodium chloride solution and dried over sodium sulfate. In the final purification by chromatography of the crude product on silica gel, 200 mg (17%) of the desired product were isolated.

$^1$H-NMR (CDCl$_3$, stored over molecular sieves): δ=2.03 (m, 2H); 2.46 (m, 4H); 2.052 (m, 2H); 3.70 (m, 4H); 4.43 (m, 2H); 6.70 (d, 1H); 7.28 (m, 1H); 7.37 (m, 1H); 7.82 (m, 2H); 7.89 (s, 1H); 8.19 (m, 1H) ppm.

TABLE 3

| Intermediate | Structure and name of the main isomer | $^1$H-NMR | Mol. weight/ MS (ESI) [M + 1]$^+$ |
|---|---|---|---|
| U | 6-(1-Methyl-piperidin-3-ylmethoxy)-imidazo[1,2-b]pyridazine | (CDCl$_3$, stored over molecular sieves): δ = 1.12(m, 1H); 1.6-1.92 (m, 4H); 1.99 (m, 1H); 2.22 (m, 1H); 2.31 (s, 3H); 2.81 (d, 1H); 2.97 (d, 1H); 4.18 (m, 2H); 6.67 (d, 1H); 7.58 (s, 1H); 7.71 (s, 1H); 7.78 (d, 1H) ppm. | |

As alternative to the management of the reaction described above, the final compounds of the invention can also be prepared by parallel synthesis, for example in an automatic synthesizer.

Example 2

6-[3-(4-Methylpiperazin-1-yl)propoxy]-3-thiophen-2-ylimidazo[1,2-b]pyridazine

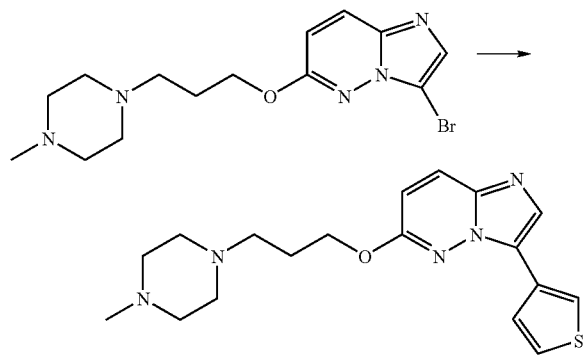

Firstly a solution of 38.4 mg (0.3 mmol) of thiophen-3-ylboronic acid in 0.73 ml of THF were added to a solution of 48.8 mg (0.15 mmol) in 1 ml of a mixture of THF and DMF (1:1) under an argon atmosphere. Subsequently, a mixture of 8.9 mg (0.02 mmol) of 1,3-bis(2,6-dipropylphenyl)imidazolium chloride and 9.6 mg (0.01 mmol) of tris(dibenzylideneacetone)palladium dissolved in 0.91 ml of THF was added. Addition of 147 mg (0.45 mmol) of cesium carbonate dissolved in 0.25 ml of water was followed by shaking the reaction mixture at 80° C. for 12 h. Addition of 1 ml of water and 3 ml of ethyl acetate is followed by extraction of the reaction mixture. The organic phase is separated off and the solvent is distilled off.

The crude product obtained in this way was purified by preparative HPLC. 40 mg (75%) of a solid were obtained.

HPLC-MS (analytical) of the purified product:

(Detection: UV=254 nM; column: Purospher STAR RP18e, 125×4 mm, 5µ (Merck KgGa, Darmstadt); eluent: A: $H_2O$/0.1% TFA, B: $CH_3CN$/0.1% TFA, gradient: 5 to 95% B in 10 min; flow rate: 1 ml/min):

Retention time of the product=4.17 min; MS of the product: m/z=358 ([M+H]$^+$)

The following are prepared in the manner described:

| EXAMPLE No. | STRUCTURE | Retention time [min] | MW calc. | MW found |
|---|---|---|---|---|
| 3 | 3-(2,4-Dichloro-phenyl)-6-[3-(4-methyl-piperazin-1-yl)-propoxy]-imidazo[1,2-b]pyridazine | 4.89 | 419.0 | 420.0 |
| 4 | 6-[3-(4-Methyl-piperazin-1-yl)-propoxy]-3-m-tolyl-imidazo[1,2-b]pyridazine | 4.67 | 365.0 | 366.0 |
| 5 | 3-(3-Chloro-phenyl)-6-[3-(4-methyl- | 4.77 | 385.0 | 386.0 |

| EXAMPLE No. | STRUCTURE | Retention time [min] | MW calc. | MW found |
|---|---|---|---|---|
| | piperazin-1-yl)-propoxy]-imidazo[1,2-b]pyridazine | | | |
| 6 | 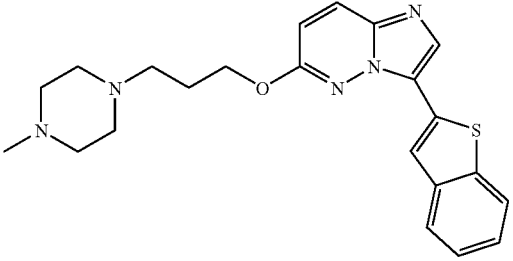 [SMILES: CN1CCN(CCCOc2ccc3ncc(-c4cc5ccccc5s4)n3n2)CC1]<br>3-Benzo[b]thiophen-2-yl-6-[3-(4-methyl-piperazin-1-yl)-propoxy]-imidazo[1,2-b]pyridazine | 5.15 | 407.0 | 408.0 |
| 7 | 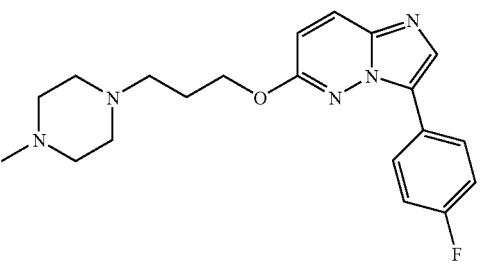 [SMILES: CN1CCN(CCCOc2ccc3ncc(-c4ccc(F)cc4)n3n2)CC1]<br>3-(4-Fluoro-phenyl)-6-[3-(4-methyl-piperazin-1-yl)-propoxy]-imidazo[1,2-b]pyridazine | 4.39 | 369.0 | 370.0 |
| 8 | 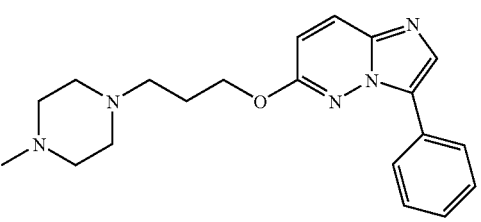 [SMILES: CN1CCN(CCCOc2ccc3ncc(-c4ccccc4)n3n2)CC1]<br>6-[3-(4-Methyl-piperazin-1-yl)-propoxy]-3-phenyl-imidazo[1,2-b]pyridazine | 4.32 | 351.0 | 352.0 |
| 9 | 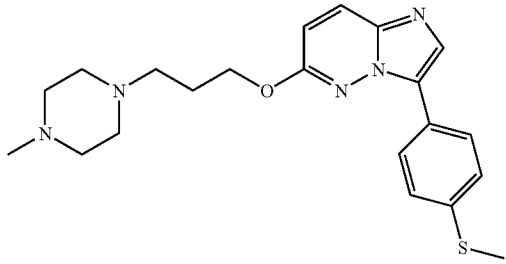<br>6-[3-(4-Methyl-piperazin-1-yl)-propoxy]-3-(4-methylsulfanyl-phenyl)-imidazo[1,2-b]pyridazine | 4.85 | 397.0 | 398.0 |
| 10 | 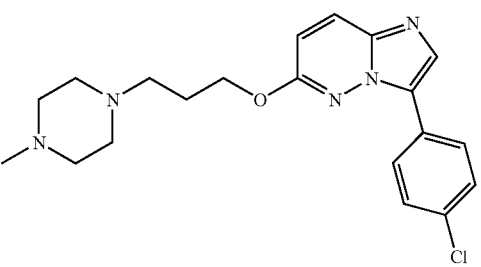 | 4.82 | 385.0 | 386.0 |

| EXAMPLE No. | STRUCTURE | Retention time [min] | MW calc. | MW found |
|---|---|---|---|---|
| | 3-(4-Chloro-phenyl)-6-[3-(4-methyl-piperazin-1-yl)-propoxy]-imidazo[1,2-b]pyridazine | | | |
| 11 | 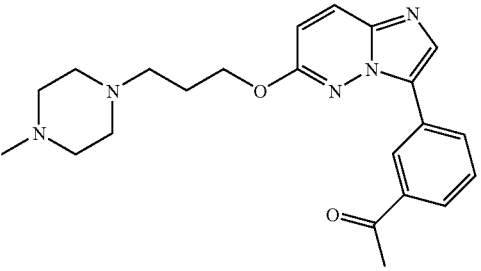 [SMILES: CC(=O)c1cccc(-c2cnc3ccc(OCCCN4CCN(C)CC4)nn23)c1]<br>1-(3-{6-[3-(4-Methyl-piperazin-1-yl)-propoxy]-imidazo[1,2-b]pyridazin-3-yl}-phenyl)-ethanone | 4.24 | 393.0 | 394.0 |
| 12 | 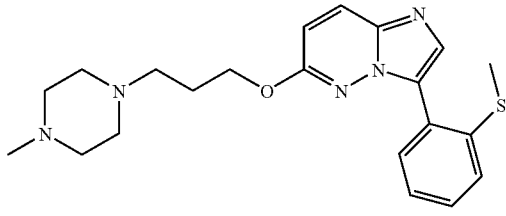 [SMILES: CSc1ccccc1-c1cnc2ccc(OCCCN3CCN(C)CC3)nn12]<br>6-[3-(4-Methyl-piperazin-1-yl) propoxy]-3-(2-methylsulfanyl-phenyl)-imidazo[1,2-b]pyridazine | 4.57 | 397.0 | 398.0 |
| 13 | 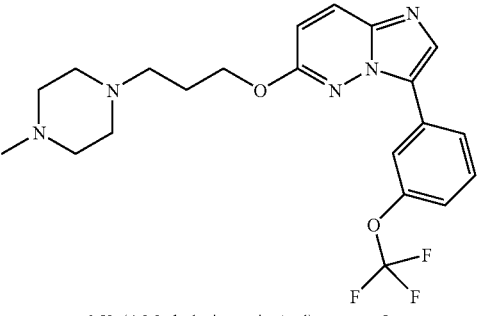<br>6-[3-(4-Methyl-piperazin-1-yl)-propoxy]-3-(3-trifluoromethoxy-phenyl)-imidazo[1,2-b]pyridazine | 5.17 | 435.0 | 436.0 |
| 14 | 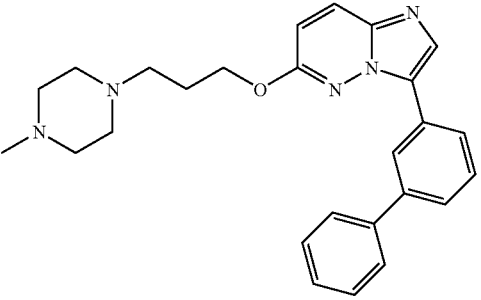 [SMILES: CN1CCN(CCCOc2ccc3ncc(-c4cccc(-c5ccccc5)c4)n3n2)CC1]<br>3-Biphenyl-3-yl-6-[3-(4-methyl-piperazin-1-yl)-propoxy]-imidazo[1,2-b]pyridazine | 5.42 | 427.0 | 428.0 |

| EXAMPLE No. | STRUCTURE | Retention time [min] | MW calc. | MW found |
|---|---|---|---|---|
| 15 | (3-{6-[3-(4-Methyl-piperazin-1-yl)-propoxy]-imidazo[1,2-b]pyridazin-3-yl}-phenyl)-methanol | 3.84 | 381.0 | 382.0 |
| 16 | 6-[3-(4-Methyl-piperazin-1-yl)-propoxy]-3-(3-methylsulfanyl-phenyl)-imidazo[1,2-b]pyridazine | 4.84 | 397.0 | 398.0 |
| 17 | 3-(2-Chloro-phenyl)-6-[3-(4-methyl-piperazin-1-yl)-propoxy]-imidazo[1,2-b]pyridazine | 4.5 | 385.0 | 386.0 |
| 18 | 6-[3-(4-Methyl-piperazin-1-yl)-propoxy]-3-(4-trifluoromethoxy-phenyl)-imidazo[1,2-b]pyridazine | 5.24 | 435.0 | 436.0 |

| EXAMPLE No. | STRUCTURE | Retention time [min] | MW calc. | MW found |
|---|---|---|---|---|
| 19 | 3-(3-Chloro-4-methyl-phenyl)-6-[3-(4-methyl-piperazin-1-yl)-propoxy]-imidazo[1,2-b]pyridazine | 4.97 | 399.0 | 400.0 |
| 20 | 3-(5-Methyl-furan-2-yl)-6-[3-(4-methyl-piperazin-1-yl)-propoxy]-imidazo[1,2-b]pyridazine | 3.54 | 355.0 | 356.0 |
| 21 | 3-(3-Fluoro-4-methoxy-phenyl)-6-[3-(4-methyl-piperazin-1-yl)-propoxy]-imidazo[1,2-b]pyridazine | 4.55 | 399.0 | 400.0 |
| 22 | 6-[3-(4-Methyl-piperazin-1-yl)-propoxy]-3-o-tolyl-imidazo[1,2-b]pyridazine | 4.44 | 365.0 | 366.0 |
| 23 | 3-(3-Chloro-4-fluoro-phenyl)-6-[3-(4-methyl-piperazin-1-yl)-propoxy]-imidazo[1,2-b]pyridazine | 4.84 | 403.0 | 404.0 |

| EXAMPLE No. | STRUCTURE | Retention time [min] | MW calc. | MW found |
|---|---|---|---|---|
| 24 | 3-(5-Chloro-thiophen-2-yl)-6-[3-(4-methyl-piperazin-1-yl)-propoxy]-imidazo[1,2-b]pyridazine | 4.78 | 391.0 | 392.0 |
| 25 | 3-{6-[3-(4-Methyl-piperazin-1-yl)-propoxy]-imidazo[1,2-b]pyridazin-3-yl}-benzonitrile | 4.35 | 376.0 | 377.0 |
| 26 | 6-[3-(4-Methyl-piperazin-1-yl)-propoxy]-3-(4-methyl-thiophen-2-yl)-imidazo[1,2-b]pyridazine | 4.59 | 371.0 | 372.0 |
| 27 | (4-{6-[3-(4-Methyl-piperazin-1-yl)-propoxy]-imidazo[1,2-b]pyridazin-3-yl}-phenyl)-acetonitrile | 4.22 | 390.0 | 391.0 |
| 28 | 3-{6-[3-(4-Methyl-piperazin-1-yl)-propoxy]-imidazo[1,2-b]pyridazin-3-yl}-benzoic acid methyl ester | 4.55 | 409.0 | 410.0 |

| EXAMPLE No. | STRUCTURE | Retention time [min] | MW calc. | MW found |
|---|---|---|---|---|
| 29 | 3-(1H-Indol-4-yl)-6-[3-(4-methyl-piperazin-1-yl)-propoxy]-imidazo[1,2-b]pyridazine | 4.28 | 390.0 | 391.0 |
| 30 | 3-Benzofuran-2-yl-6-[3-(4-methyl-piperazin-1-yl)-propoxy]-imidazo[1,2-b]pyridazine | 5.15 | 391.0 | 392.0 |
| 31 | 6-[3-(4-Methyl-piperazin-1-yl)-propoxy]-3-p-tolyl-imidazo[1,2-b]pyridazine | 4.59 | 365.0 | 366.0 |
| 32 | 3-(3-Fluoro-phenyl)-6-[3-(4-methyl-piperazin-1-yl)-propoxy]-imidazo[1,2-b]pyridazine | 4.47 | 369.0 | 370.0 |
| 33 | 3-Benzo[b]thiophen-3-yl-6-[3-(4-methyl-piperazin-1-yl)-propoxy]-imidazo[1,2-b]pyridazine | 4.94 | 407.0 | 408.0 |

-continued

| EXAMPLE No. | STRUCTURE | Retention time [min] | MW calc. | MW found |
|---|---|---|---|---|
| 34 | 3-(4-Chloro-phenyl)-6-[3-(4-methyl-piperazin-1-yl)-propoxy]-imidazo[1,2-b]pyridazine | 4.82 | 385.0 | 386.0 |
| 35 | 3-(6-Fluoro-5-methyl-pyridin-3-yl)-6-[3-(4-methyl-piperazin-1-yl)-propoxy]-imidazo[1,2-b]pyridazine | 4.22 | 384.0 | 385.0 |
| 36 | 3-(2-Chloro-6-methyl-pyridin-3-yl)-6-[3-(4-methyl-piperazin-1-yl)-propoxy]-imidazo[1,2-b]pyridazine | 3.94 | 400.0 | 401.0 |
| 37 | 6-[3-(4-Methyl-piperazin-1-yl)-propoxy]-3-(2-trifluoromethoxy-phenyl)-imidazo[1,2-b]pyridazine | 4.94 | 435.0 | 436.0 |

| EXAMPLE No. | STRUCTURE | Retention time [min] | MW calc. | MW found |
|---|---|---|---|---|
| 38 | 3-(4-Ethanesulfonyl-phenyl)-6-[3-(4-methyl-piperazin-1-yl)-propoxy]-imidazo[1,2-b]pyridazine | 4.5 | 443.0 | 444.0 |
| 39 | 6-[3-(4-Methyl-piperazin-1-yl)-propoxy]-3-(3-pyrrolidin-1-yl-phenyl)-imidazo[1,2-b]pyridazine | 4.75 | 420.0 | 421.0 |
| 40 | 3-(4-Cyclopropylmethoxy-phenyl)-6-[3-(4-methyl-piperazin-1-yl)-propoxy]-imidazo[1,2-b]pyridazine | 5.17 | 421.0 | 422.0 |
| 41 | Diethyl-[4-(3-thiophen-3-yl-imidazo[1,2-b]pyridazin-6-yloxy)-pentyl]-amine | 5.15 | 358.0 | 359.0 |

| EXAMPLE No. | STRUCTURE | Retention time [min] | MW calc. | MW found |
|---|---|---|---|---|
| 42 | 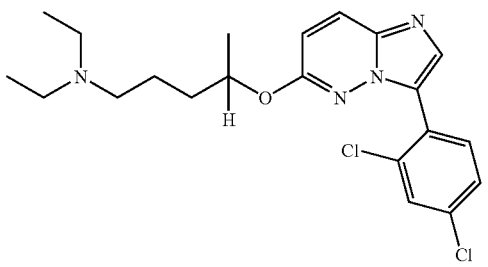 [SMILES: CCN(CC)CCCC(C)Oc1ccc2ncc(-c3ccc(Cl)cc3Cl)n2n1]<br>{4-[3-(2,4-Dichloro-phenyl)-imidazo[1,2-b]pyridazin-6-yloxy]-pentyl}-diethyl-amine | 5.78 | 420.0 | 421.0 |
| 43 | <br>Diethyl-[4-(3-m-tolyl-imidazo[1,2-b]pyridazin-6-yloxy)-pentyl]-amine | 5.53 | 366.0 | 367.0 |
| 44 | 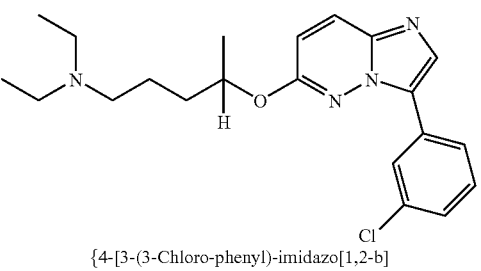<br>{4-[3-(3-Chloro-phenyl)-imidazo[1,2-b]pyridazin-6-yloxy]-pentyl}-diethyl-amine | 5.7 | 386.0 | 387.0 |
| 45 | 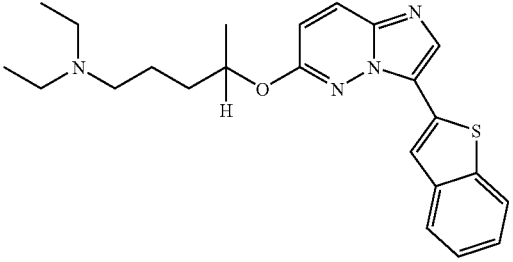 [SMILES: CCN(CC)CCCC(C)Oc1ccc2ncc(-c3cc4ccccc4s3)n2n1]<br>[4-(3-Benzo[b]thiophen-2-yl-imidazo[1,2-b]pyridazin-6-yloxy)-pentyl]-diethyl-amine | 6.12 | 408.0 | 409.0 |
| 46 | 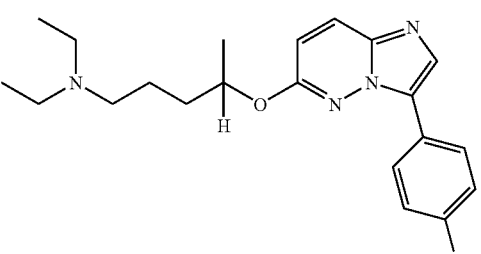<br>Diethyl-{4-[3-(4-fluoro-phenyl)-imidazo[1,2-b]pyridazin-6-yloxy]-pentyl}-amine | 5.3 | 370.0 | 371.0 |

| EXAMPLE No. | STRUCTURE | Retention time [min] | MW calc. | MW found |
|---|---|---|---|---|
| 47 | Diethyl-{4-[3-(4-methylsulfanyl-phenyl)-imidazo[1,2-b]pyridazin-6-yloxy]-pentyl}-amine | 5.72 | 398.0 | 399.0 |
| 48 | {4-[3-(4-Chloro-phenyl)-imidazo[1,2-b]pyridazin-6-yloxy]-pentyl}-diethyl-amine | 5.72 | 386.0 | 387.0 |
| 49 | 1-{3-[6-(4-Diethylamino-1-methyl-butoxy)-imidazo[1,2-b]pyridazin-3-yl]-phenyl}-ethanone | 5.07 | 394.0 | 395.0 |
| 50 | Diethyl-{4-[3-(2-methylsulfanyl-phenyl)-imidazo[1,2-b]pyridazin-6-yloxy]-pentyl}-amine | 5.42 | 398.0 | 399.0 |

-continued

| EXAMPLE No. | STRUCTURE | Retention time [min] | MW calc. | MW found |
|---|---|---|---|---|
| 51 | Diethyl-{4-[3-(3-trifluoromethoxy-phenyl)-imidazo[1,2-b]pyridazin-6-yloxy]-pentyl}-amine | 6.07 | 436.0 | 437.0 |
| 52 | [4-(3-Biphenyl-3-yl-imidazo[1,2-b]pyridazin-6-yloxy)-pentyl]-diethyl-amine | 6.27 | 428.0 | 429.0 |
| 53 | {3-[6-(4-Diethylamino-1-methyl-butoxy)-imidazo[1,2-b]pyridazin-3-yl]-phenyl}-methanol | 4.59 | 382.0 | 383.0 |
| 54 | Diethyl-{4-[3-(3-methylsulfanyl-phenyl)-imidazo[1,2-b]pyridazin-6-yloxy]-pentyl}-amine | 5.69 | 398.0 | 399.0 |

| EXAMPLE No. | STRUCTURE | Retention time [min] | MW calc. | MW found |
|---|---|---|---|---|
| 55 | 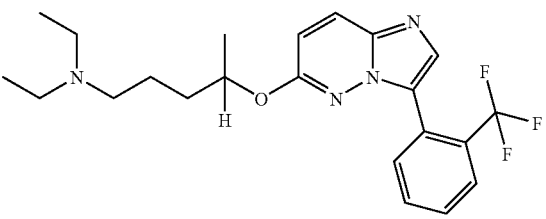 [SMILES: CCN(CC)CCCC(C)Oc1ccc2ncc(-c3ccccc3C(F)(F)F)n2n1]<br>Diethyl-{4-[3-(2-trifluoromethyl-phenyl)-imidazo[1,2-b]pyridazin-6-yloxy[-pentyl}-amine | 5.6 | 420.0 | 421.0 |
| 56 | 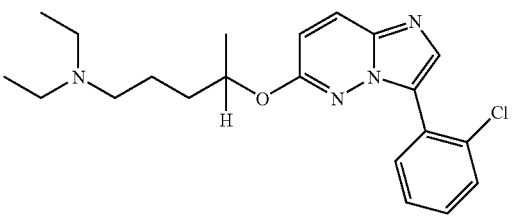 [SMILES: CCN(CC)CCCC(C)Oc1ccc2ncc(-c3ccccc3Cl)n2n1]<br>{4-[3-(2-Chloro-phenyl)-imidazo[1,2-b]pyridazin-6-yloxy]-pentyl}-diethyl-amine | 5.39 | 386.0 | 387.0 |
| 57 | 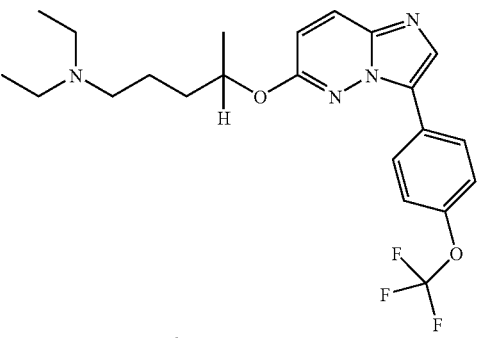 [SMILES: CCN(CC)CCCC(C)Oc1ccc2ncc(-c3ccc(OC(F)(F)F)cc3)n2n1]<br>Diethyl-{4-[3-(4-trifluoromethoxy-phenyl)-imidazo[1,2-b]pyridazin-6-yloxy]-pentyl}-amine | 6.03 | 436.0 | 437.0 |
| 58 | 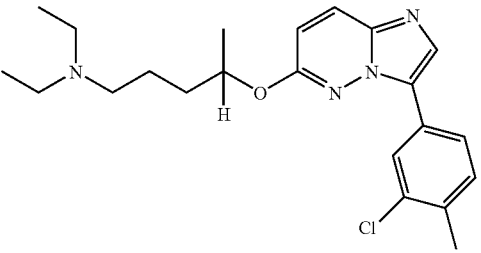 [SMILES: CCN(CC)CCCC(C)Oc1ccc2ncc(-c3ccc(C)c(Cl)c3)n2n1]<br>{4-[3-(3-Chloro-4-methyl-phenyl)-imidazo[1,2-b]pyridazin-6-yloxy]-pentyl}-diethyl-amine | 5.95 | 400.0 | 401.0 |
| 59 | 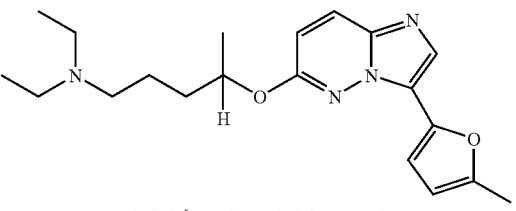<br>Diethyl-{4-[3-(5-methyl-furan-2-yl)-imidazo[1,2-b]pyridazin-6-yloxy]-pentyl}-amine | 4.85 | 356.0 | 357.0 |

| EXAMPLE No. | STRUCTURE | Retention time [min] | MW calc. | MW found |
|---|---|---|---|---|
| 60 | Diethyl-{4-[3-(3-fluoro-4-methoxy-phenyl)-imidazo[1,2-b]pyridazin-6-yloxy]-pentyl}-amine | 5.42 | 400.0 | 401.0 |
| 61 | Diethyl-[4-(3-o-tolyl-imidazo[1,2-b]pyridazin-6-yloxy)-pentyl]-amine | 5.27 | 366.0 | 367.0 |
| 62 | {4-[3-(3-Chloro-4-fluoro-phenyl)-imidazo[1,2-b]pyridazin-6-yloxy]-pentyl}-diethyl-amine | 5.84 | 404.0 | 405.0 |
| 63 | {4-[3-(5-Chloro-thiophen-2-yl)-imidazo[1,2-b]pyridazin-6-yloxy]-pentyl}-diethyl-amine | 5.78 | 392.0 | 393.0 |
| 64 | 3-[6-(4-Diethylamino-1-methyl-butoxy)-imidazo[1,2-b]pyridazin-3-yl]-benzonitrile | 5.27 | 377.0 | 378.0 |

-continued

| EXAMPLE No. | STRUCTURE | Retention time [min] | MW calc. | MW found |
|---|---|---|---|---|
| 65 | Diethyl-{4-[3-(4-methyl-thiophen-2-yl)-imidazo[1,2-b]pyridazin-6-yloxy]-pentyl}-amine | 5.44 | 372.0 | 373.0 |
| 66 | {4-[6-(4-Diethylamino-1-methyl-butoxy)-imidazo[1,2-b]pyridazin-3-yl]-phenyl}-acetonitrile | 5.15 | 391.0 | 392.0 |
| 67 | 3-[6-(4-Diethylamino-1-methyl-butoxy)-imidazo[1,2-b]pyridazin-3-yl]-benzoic acid methyl ester | 5.4 | 410.0 | 411.0 |
| 68 | Diethyl-{4-[3-(1H-indol-4-yl)-imidazo[1,2-b]pyridazin-6-yloxy]-pentyl}-amine | 5.12 | 391.0 | 392.0 |
| 69 | [4-(3-Benzofuran-2-yl-imidazo[1,2-b]pyridazin-6-yloxy)-pentyl]-diethyl-amine | 6.07 | 392.0 | 393.0 |

-continued

| EXAMPLE No. | STRUCTURE | Retention time [min] | MW calc. | MW found |
|---|---|---|---|---|
| 70 | 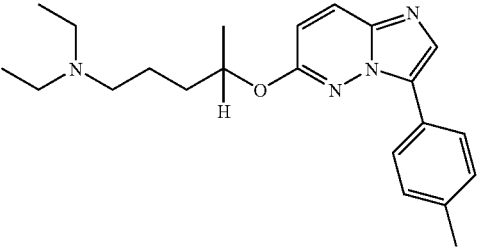 [SMILES: CCN(CC)CCCC(C)Oc1ccc2ncc(-c3ccc(C)cc3)n2n1]<br>Diethyl-[4-(3-p-tolyl-imidazo[1,2-b]pyridazin-6-yloxy)-pentyl]-amine | 5.53 | 366.0 | 367.0 |
| 71 | 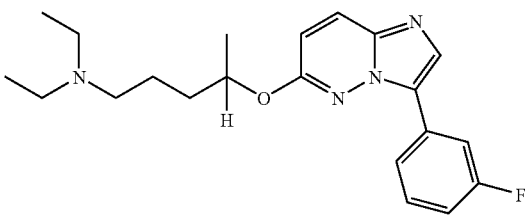 [SMILES: CCN(CC)CCCC(C)Oc1ccc2ncc(-c3cccc(F)c3)n2n1]<br>Diethyl-{4-[3-(3-fluoro-phenyl)-imidazo[1,2-b]pyridazin-6-yloxy]-pentyl}-amine | 5.42 | 370.0 | 371.0 |
| 72 | 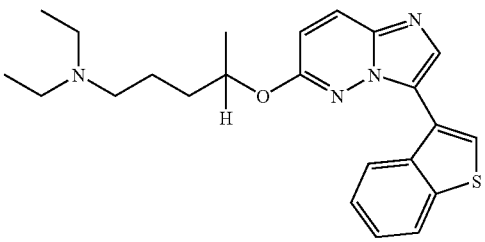 [SMILES: CCN(CC)CCCC(C)Oc1ccc2ncc(-c3csc4ccccc34)n2n1]<br>[4-(3-Benzo[b]thiophen-3-yl-imidazo[1,2-b]pyridazin-6-yloxy)-pentyl]-diethyl-amine | 5.75 | 408.0 | 409.0 |
| 73 | 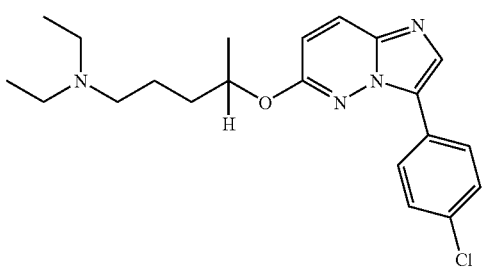<br>{4-[3-(4-Chloro-phenyl)-imidazo[1,2-b]pyridazin-6-yloxy]-pentyl}-diethyl-amine | 5.64 | 386.0 | 387.0 |
| 74 | 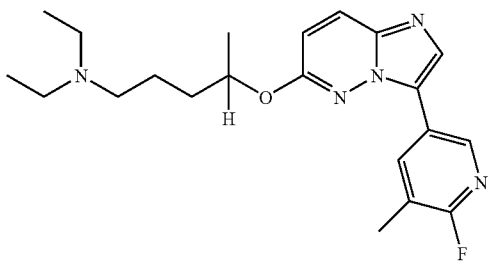 [SMILES: CCN(CC)CCCC(C)Oc1ccc2ncc(-c3cnc(F)c(C)c3)n2n1]<br>Diethyl-{4-[3-(6-fluoro-5-methyl-pyridin-3-yl)-imidazo[1,2-b]pyridazin-6-yloxy]-pentyl}-amine | 5.17 | 385.0 | 386.0 |

| EXAMPLE No. | STRUCTURE | Retention time [min] | MW calc. | MW found |
|---|---|---|---|---|
| 75 | 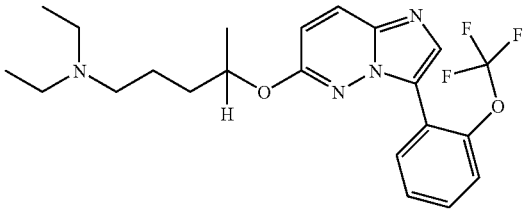 [SMILES: CCN(CC)CCCC(C)Oc1ccc2ncc(-c3ccccc3OC(F)(F)F)n2n1]<br>Diethyl-{4-[3-(2-trifluoromethoxy-phenyl)-imidazo[1,2-b]pyridazin-6-yloxy]-pentyl}-amine | 5.78 | 436.0 | 437.0 |
| 76 | 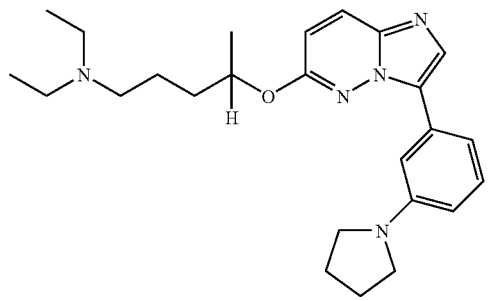 [SMILES: CCN(CC)CCCC(C)Oc1ccc2ncc(-c3cccc(N4CCCC4)c3)n2n1]<br>Diethyl-{4-[3-(3-pyrrolidin-1-yl-phenyl)-imidazo[1,2-b]pyridazin-6-yloxy]-pentyl]-amine | 5.75 | 421.0 | 422.0 |
| 77 | 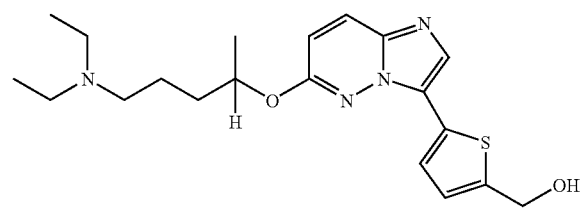 [SMILES: CCN(CC)CCCC(C)Oc1ccc2ncc(-c3ccc(CO)s3)n2n1]<br>{5-[6-(4-Diethylamino-1-methyl-butoxy)-imidazo[1,2-b]pyridazin-3-yl]-thiophen-2-yl}-methanol | 8.97 | 388.0 | 389.0 |
| 78 | 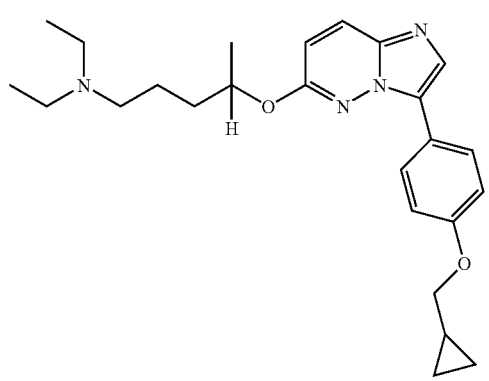 [SMILES: CCN(CC)CCCC(C)Oc1ccc2ncc(-c3ccc(OCC4CC4)cc3)n2n1]<br>{4-[3-(4-Cyclopropylmethoxy-phenyl)-imidazo[1,2-b]pyridazin-6-yloxy]-pentyl}-diethyl-amine | 6.0 | 422.0 | 423.0 |

-continued

| EXAMPLE No. | STRUCTURE | Retention time [min] | MW calc. | MW found |
|---|---|---|---|---|
| 79 | 6-[2-(1-Methyl-pyrrolidin-2-yl)-ethoxy]-3-thiophen-3-yl-imidazo[1,2-b]pyridazine | 4.5 | 328.1 | 329.1 |
| 80 | 3-(2,4-Dichloro-phenyl)-6-[2-(1-methyl-pyrrolidin-2-yl)-ethoxy]-imidazo-[1,2-b]pyridazine | 5.3 | 390.1 | 391.1 |
| 81 | 6-[2-(1-Methyl-pyrrolidin-2-yl)-ethoxy]-3-m-tolyl-imidazo[1,2-b]pyridazine | 5.03 | 336.2 | 337.2 |
| 82 | 3-(3-Chloro-phenyl)-6-[2-(1-methyl-pyrrolidin-2-yl)-ethoxy]-imidazo[1,2-b]pyridazine | 5.17 | 356.1 | 357.1 |
| 83 | 3-Benzo[b]thiophen-2-yl-6-[2-(1-methyl-pyrrolidin-2-yl)-ethoxy]-imidazo[1,2-b]pyridazine | 5.65 | 378.2 | 379.2 |

-continued

| EXAMPLE No. | STRUCTURE | Retention time [min] | MW calc. | MW found |
|---|---|---|---|---|
| 84 | 3-(4-Fluoro-phenyl)-6-[2-(1-methyl-pyrrolidin-2-yl)-ethoxy]-imidaza[1,2-b]pyridazine | 4.77 | 340.2 | 341.2 |
| 85 | 6-[2-(1-Methyl-pyrrolidin-2-yl)-ethoxy]-3-phenyl-imidazo[1,2-b]pyridazine | 4.67 | 322.2 | 323.2 |
| 86 | 6-[2-(1-Methyl-pyrrolidin-2-yl)-ethoxy]-3-(4-methylsulfanyl-phenyl)-imidazo[1,2-b]pyridazine | 5.24 | 368.2 | 369.2 |
| 87 | 3-(4-Chloro-phenyl)-6-[2-(1-methyl-pyrrolidin-2-yl)-ethoxy]-imidazo[1,2-b]pyridazine | 5.22 | 356.1 | 357.1 |
| 88 | 1-(3-{6-[2-(1-Methyl-pyrrolidin-2-yl)-ethoxy]-imidazo[1,2-b]pyridazin-3-yl}-phenyl)-ethanone | 4.59 | 364.2 | 365.2 |

| EXAMPLE No. | STRUCTURE | Retention time [min] | MW calc. | MW found |
|---|---|---|---|---|
| 89 | 6-[2-(1-Methyl-pyrrolidin-2-yl)-ethoxy]-3-(2-methylsulfanyl-phenyl)-imidazo[1,2-b]pyridazine | 4.9 | 368.2 | 369.2 |
| 90 | 6-[2-(1-Methyl-pyrrolidin-2-yl)-ethoxy]-3-(3-trifluoromethoxy-phenyl)-imidazo[1,2-b]pyridazine | 5.62 | 406.2 | 407.2 |
| 91 | 3-Biphenyl-3-yl-6-[2-(1-methyl-pyrrolidin-2-yl)-ethoxy]-imidazo[1,2-b]pyridazine | 5.85 | 398.2 | 399.2 |
| 92 | (3-{6-[2-(1-Methyl-pyrrolidin-2-yl)-ethoxy]-imidazo[1,2-b]pyridazin-3-yl}-phenyl)-methanol | 4.09 | 352.2 | 353.2 |

| EXAMPLE No. | STRUCTURE | Retention time [min] | MW calc. | MW found |
|---|---|---|---|---|
| 93 | 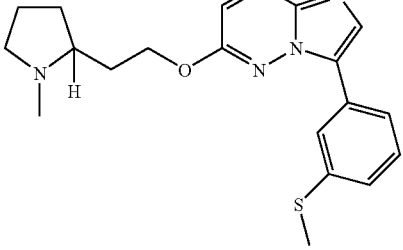<br>6-[2-(1-Methyl-pyrrolidin-2-yl)-ethoxy]-3-(3-methylsulfanyl-phenyl)-imidazo[1,2-b]pyridazine | 5.2 | 368.2 | 369.2 |
| 94 | 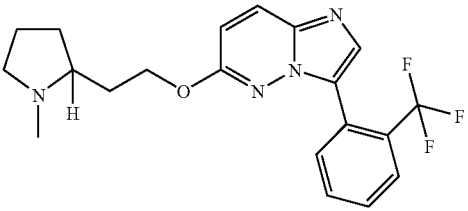 [SMILES: CN1CCCC1CCOc1ccc2ncc(-c3ccccc3C(F)(F)F)n2n1]<br>6-[2-(1-Methyl-pyrrolidin-2-yl)-ethoxy]-3-(2-trifluoromethyl-phenyl)-imidazo[1,2-b]pyridazine | 5.1 | 390.2 | 391.2 |
| 95 | 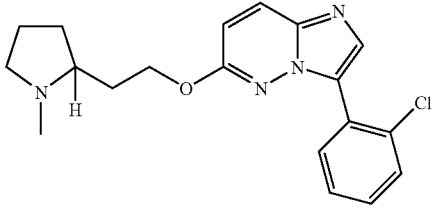 [SMILES: CN1CCCC1CCOc1ccc2ncc(-c3ccccc3Cl)n2n1]<br>3-(2-Chloro-phenyl)-6-[2-(1-methyl-pyrrolidin-2-yl)-ethoxy]-imidazo[1,2-b]pyridazine | 4.84 | 356.1 | 357.1 |
| 96 | 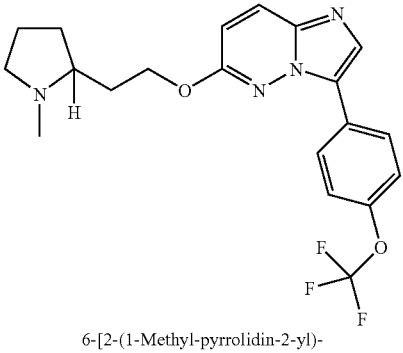<br>6-[2-(1-Methyl-pyrrolidin-2-yl)-ethoxy]-3-(4-trifluoromethoxy-phenyl)-imidazo[1,2-b]pyridazine | 5.6 | 406.2 | 407.2 |
| 97 | 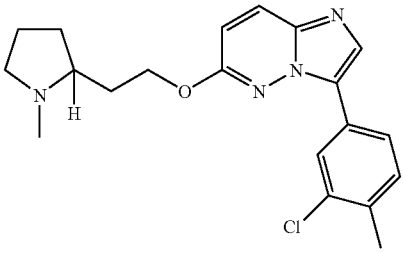 [SMILES: Cc1ccc(-c2cnc3ccc(OCCC4CCCN4C)nn23)cc1Cl]<br>3-(3-Chloro-4-methyl-phenyl)-6-[2-(1-methyl-pyrrolidin-2-yl)-ethoxy]-imidazo[1,2-b]pyridazine | 5.47 | 370.2 | 371.2 |

-continued

| EXAMPLE No. | STRUCTURE | Retention time [min] | MW calc. | MW found |
|---|---|---|---|---|
| 98 | 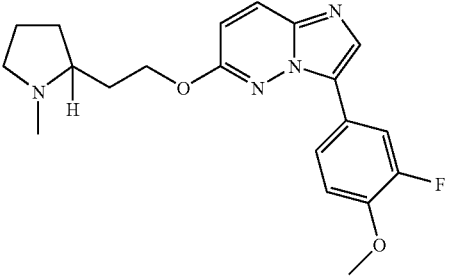 [SMILES: COc1ccc(-c2cnc3ccc(OCCC4CCCN4C)nn23)cc1F]<br>3-(3-Fluoro-4-methoxy-phenyl)-6-[2-(1-methyl-pyrrolidin-2-yl)-ethoxy]-imidazo[1,2-b]pyridazine | 4.9 | 370.2 | 371.2 |
| 99 | 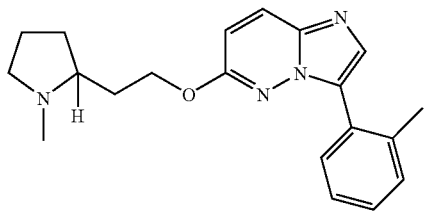 [SMILES: Cc1ccccc1-c1cnc2ccc(OCCC3CCCN3C)nn12]<br>6-[2-(1-Methyl-pyrrolidin-2-yl)-ethoxy]-3-o-tolyl-imidazo[1,2-b]pyridazine | 4.72 | 336.2 | 337.2 |
| 100 | 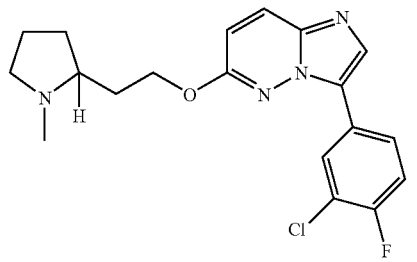<br>3-(3-Chloro-4-fluoro-phenyl)-6-[2-(1-methyl-pyrrolidin-2-yl)-ethoxy]-imidazo[1,2-b]pyridazine | 5.32 | 374.1 | 375.1 |
| 101 | 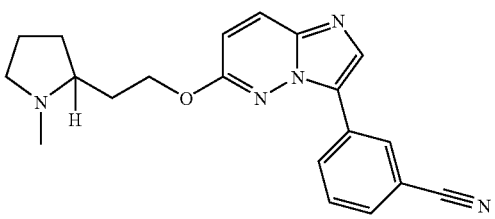 [SMILES: CN1CCCC1CCOc1ccc2ncc(-c3cccc(C#N)c3)n2n1]<br>3-{6-[2-(1-Methyl-pyrrolidin-2-yl)-ethoxy]-imidazo[1,2-b]pyridazin-3-yl}-benzonitrile | 4.7 | 347.2 | 348.2 |
| 102 | 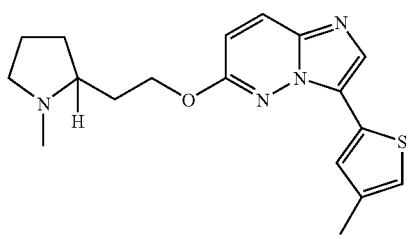 [SMILES: Cc1csc(-c2cnc3ccc(OCCC4CCCN4C)nn23)c1]<br>6-[2-(1-Methyl-pyrrolidin-2-yl)-ethoxy]-3-(4-methyl-thiophen-2-yl)-imidazo[1,2-b]pyridazine | 4.9 | 342.2 | 343.2 |

| EXAMPLE No. | STRUCTURE | Retention time [min] | MW calc. | MW found |
|---|---|---|---|---|
| 103 | 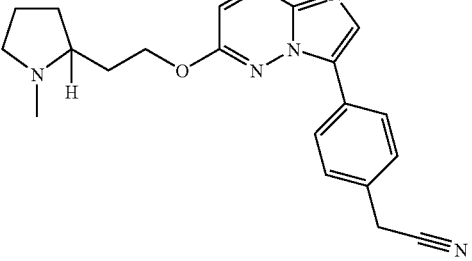<br>(4-{6-[2-(1-Methyl-pyrrolidin-2-yl)-ethoxy]-imidazo[1,2-b]pyridazin-3-yl}-phenyl)-acetonitrile | 4.62 | 361.2 | 362.2 |
| 104 | 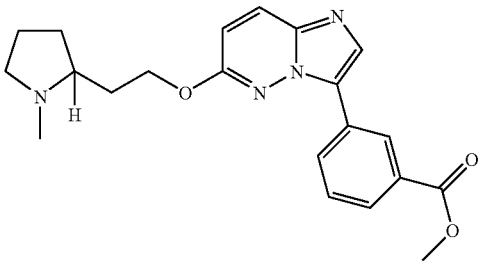 [SMILES: COC(=O)c1cccc(-c2cnc3ccc(OCCC4CCCN4C)nn23)c1]<br>3-{6-[2-(1-Methyl-pyrrolidin-2-yl)-ethoxy]-imidazo[1,2-b]pyridazin-3-yl}-benzoic acid methyl ester | 4.92 | 380.2 | 381.2 |
| 105 | 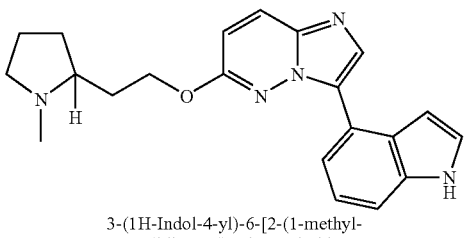<br>3-(1H-Indol-4-yl)-6-[2-(1-methyl-pyrrolidin-2-yl)-ethoxy]-imidazo[1,2-b]pyridazine | 4.55 | 361.2 | 362.2 |
| 106 | 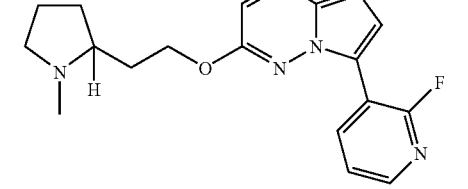<br>3-(2-Fluoro-pyridin-3-yl)-6-[2-(1-methyl-pyrrolidin-2-yl)-ethoxy]-imidazo[1,2-b]pyridazine | 4.02 | 341.2 | 342.2 |
| 107 | 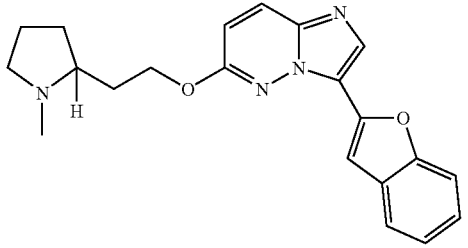 [SMILES: CN1CCCC1CCOc1ccc2ncc(-c3cc4ccccc4o3)n2n1]<br>3-Benzofuran-2-yl-6-[2-(1-methyl-pyrrolidin-2-yl)-ethoxy]-imidazo[1,2-b]pyridazine | 5.67 | 362.2 | 363.2 |

-continued

| EXAMPLE No. | STRUCTURE | Retention time [min] | MW calc. | MW found |
|---|---|---|---|---|
| 108 | 6-[2-(1-Methyl-pyrrolidin-2-yl)-ethoxy]-3-p-tolyl-imidazo[1,2-b]pyridazine | 5.05 | 336.2 | 337.2 |
| 109 | 3-(3-Fluoro-phenyl)-6-[2-(1-methyl-pyrrolidin-2-yl)-ethoxy]-imidazo[1,2-b]pyridazine | 4.87 | 340.2 | 341.2 |
| 110 | 3-Benzo[b]thiophen-3-yl-6-[2-(1-methyl-pyrrolidin-2-yl)-ethoxy]-imidazo[1,2-b]pyridazine | 5.2 | 378.2 | 379.2 |
| 111 | 3-(4-Chloro-phenyl)-6-[2-(1-methyl-pyrrolidin-2-yl)-ethoxy]-imidazo[1,2-b]pyridazine | 5.24 | 356.1 | 357.1 |
| 112 | 3-(6-Fluoro-5-methyl-pyridin-3-yl)-6-[2-(1-methyl-pyrrolidin-2-yl)-ethoxy]-imidazo[1,2-b]pyridazine | 4.62 | 355.2 | 356.2 |

| EXAMPLE No. | STRUCTURE | Retention time [min] | MW calc. | MW found |
|---|---|---|---|---|
| 113 | 3-(2-Chloro-6-methyl-pyridin-3-yl)-6-[2-(1-methyl-pyrrolidin-2-yl)-ethoxy]-imidazo[1,2-b]pyridazine | 4.32 | 371.2 | 372.2 |
| 114 | 6-[2-(1-Methyl-pyrrolidin-2-yl)-ethoxy]-3-(2-trifluoromethoxy-phenyl)-imidazo[1,2-b]pyridazine | 5.24 | 406.2 | 407.2 |
| 115 | 3-(4-Ethanesulfonyl-phenyl)-6-[2-(1-methyl-pyrrolidin-2-yl)-ethoxy]-imidazo[1,2-b]pyridazine | 4.62 | 414.2 | 415.2 |
| 116 | 6-[2-(1-Methyl-pyrrolidin-2-yl)-ethoxy]-3-(3-pyrrolidin-1-yl-phenyl)-imidazo[1,2-b]pyridazine | 5.2 | 391.2 | 392.2 |

-continued

| EXAMPLE No. | STRUCTURE | Retention time [min] | MW calc. | MW found |
|---|---|---|---|---|
| 117 | 3-(4-Cyclopropyl methoxy-phenyl)-6-[2-(1-methyl-pyrrolidin-2-yl)-ethoxy]-imidazo[1,2-b]pyridazine | 5.5 | 392.2 | 393.2 |
| 118 | 6-(1-Methyl-piperidin-3-ylmethoxy)-3-thiophen-3-yl-imidazo[1,2-b]pyridazine | 4.64 | 328.1 | 329.1 |
| 119 | 3-(2,4-Dichloro-phenyl)-6-(1-methyl-piperidin-3-ylmethoxy)-imidazo[1,2-b]pyridazine | 5.47 | 390.1 | 391.1 |
| 120 | 3-(3-Chloro-phenyl)-6-(1-methyl-piperidin-3-ylmethoxy)-imidazo[1,2-b]pyridazine | 5.24 | 356.1 | 357.1 |

| EXAMPLE No. | STRUCTURE | Retention time [min] | MW calc. | MW found |
|---|---|---|---|---|
| 121 | 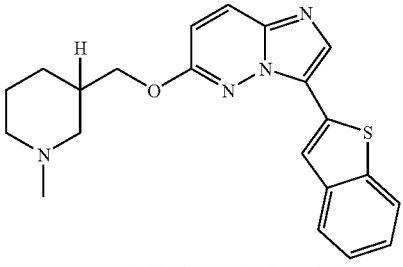 [SMILES: CN1CCCC(COc2ccc3ncc(-c4cc5ccccc5s4)n3n2)C1]<br>3-Benzo[b]thiophen-2-yl-6-(1-methyl-piperidin-3-ylmethoxy)-imidazo[1,2-b]pyridazine | 5.62 | 378.2 | 379.2 |
| 122 | 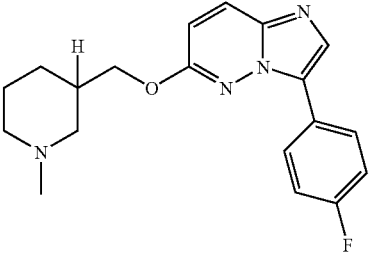 [SMILES: CN1CCCC(COc2ccc3ncc(-c4ccc(F)cc4)n3n2)C1]<br>3-(4-Fluoro-phenyl)-6-(1-methyl-piperidin-3-ylmethoxy)-imidazo[1,2-b]pyridazine | 4.92 | 340.2 | 341.2 |
| 123 | 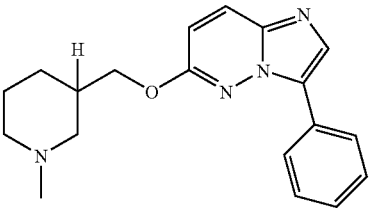 [SMILES: CN1CCCC(COc2ccc3ncc(-c4ccccc4)n3n2)C1]<br>6-(1-Methyl-piperidin-3-ylmethoxy)-3-phenyl-imidazo[1,2-b]pyridazine | 4.74 | 322.2 | 323.2 |
| 124 | 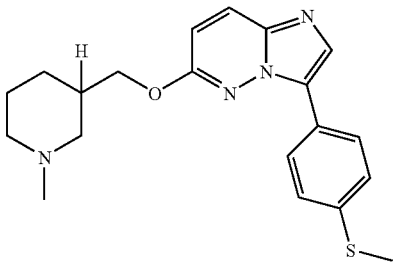 [SMILES: CSc1ccc(-c2cnc3ccc(OCC4CCCN(C)C4)nn23)cc1]<br>6-(1-Methyl-piperidin-3-ylmethoxy)-3-(4-methylsulfanyl-phenyl)-imidazo[1,2-b]pyridazine | 5.28 | 368.2 | 369.2 |
| 125 | 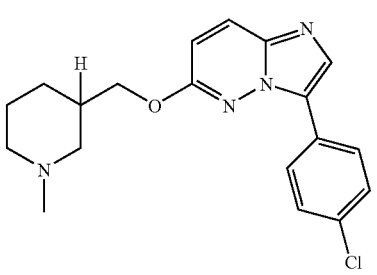 [SMILES: CN1CCCC(COc2ccc3ncc(-c4ccc(Cl)cc4)n3n2)C1]<br>3-(4-Chloro-phenyl)-6-(1-methyl-piperidin-3-ylmethoxy)-imidazo[1,2-b]pyridazine | 5.2 | 356.1 | 357.1 |

-continued

| EXAMPLE No. | STRUCTURE | Retention time [min] | MW calc. | MW found |
|---|---|---|---|---|
| 126 | 1-{3-[6-(1-Methyl-piperidin-3-ylmethoxy)-imidazo[1,2-b]pyridazin-3-yl]-phenyl}-ethanone | 4.69 | 364.2 | 365.2 |
| 127 | 6-(1-Methyl-piperidin-3-ylmethoxy)-3-(2-methylsulfanyl-phenyl)-imidazo[1,2-b]pyridazine | 4.99 | 368.2 | 369.2 |
| 128 | 6-(1-Methyl-piperidin-3-ylmethoxy)-3-(3-trifluoromethoxy-phenyl)-imidazo[1,2-b]pyridazine | 5.7 | 406.2 | 407.2 |
| 129 | 3-Biphenyl-3-yl-6-(1-methyl-piperidin-3-ylmethoxy)-imidazo[1,2-b]pyridazine | 5.8 | 398.2 | 399.2 |

| EXAMPLE No. | STRUCTURE | Retention time [min] | MW calc. | MW found |
|---|---|---|---|---|
| 130 | <br>{3-[6-(1-Methyl-piperidin-3-ylmethoxy)-imidazo[1,2-b]pyridazin-3-yl]-phenyl}-methanol | 4.25 | 352.2 | 353.2 |
| 131 | 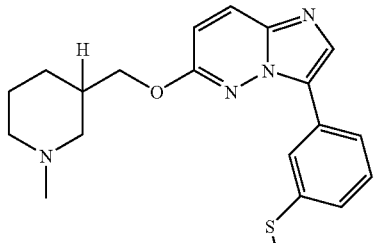<br>6-(1-Methyl-piperidin-3-ylmethoxy)-3-(3-methylsulfanyl-phenyl)-imidazo[1,2-b]pyridazine | 5.28 | 368.2 | 369.2 |
| 132 | <br>6-(1-Methyl-piperidin-3-ylmethoxy)-3-(2-trifluoromethyl-phenyl)-imidazo[1,2-b]pyridazine | 5.17 | 390.2 | 391.2 |
| 133 | 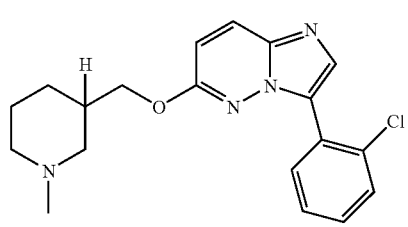 [SMILES: CN1CCCC(COc2ccc3ncc(-c4ccccc4Cl)n3n2)C1]<br>3-(2-Chloro-phenyl)-6-(1-methyl-piperidin-3-ylmethoxy)-imidazo[1,2-b]pyridazine | 4.84 | 356.1 | 357.1 |
| 134 | <br>6-(1-Methyl-piperidin-3-ylmethoxy)-3-(4-trifluoromethoxy-phenyl)-imidazo[1,2-b]pyridazine | 5.74 | 406.2 | 407.2 |

| EXAMPLE No. | STRUCTURE | Retention time [min] | MW calc. | MW found |
|---|---|---|---|---|
| 135 | 3-(3-Chloro-4-methyl-phenyl)-6-(1-methyl-piperidin-3-ylmethoxy)-imidazo[1,2-b]pyridazine | 5.55 | 370.2 | 371.2 |
| 136 | 3-(5-Methyl-furan-2-yl)-6-(1-methyl-piperidin-3-ylmethoxy)-imidazo[1,2-b]pyridazine | 4.15 | 326.2 | 327.2 |
| 137 | 3-(3-Fluoro-4-methoxy-phenyl)-6-(1-methyl-piperidin-3-ylmethoxy)-imidazo[1,2-b]pyridazine | 4.9 | 370.2 | 371.2 |
| 138 | 6-(1-Methyl-piperidin-3-ylmethoxy)-3-o-tolyl-imidazo[1,2-b]pyridazine | 4.89 | 336.2 | 337.2 |
| 139 | 3-(3-Chloro-4-fluoro-phenyl)-6-(1-methyl-piperidin-3-ylmethoxy)-imidazo[1,2-b]pyridazine | 5.4 | 374.1 | 375.1 |

-continued

| EXAMPLE No. | STRUCTURE | Retention time [min] | MW calc. | MW found |
|---|---|---|---|---|
| 140 | 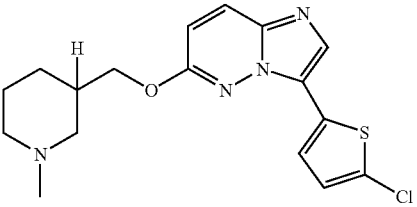 [SMILES: CN1CCCC(COc2ccc3ncc(-c4ccc(Cl)s4)n3n2)C1]<br>3-(5-Chloro-thiophen-2-yl)-6-(1-methyl-piperidin-3-ylmethoxy)-imidazo[1,2-b]pyridazine | 5.27 | 362.1 | 363.1 |
| 141 | 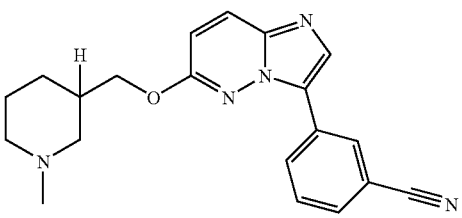 [SMILES: CN1CCCC(COc2ccc3ncc(-c4cccc(C#N)c4)n3n2)C1]<br>3-[6-(1-Methyl-piperidin-3-ylmethoxy)-imidazo[1,2-b]pyridazin-3-yl]-benzonitrile | 4.7 | 347.2 | 348.2 |
| 142 | 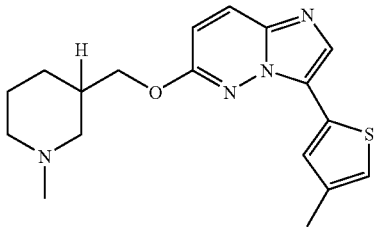 [SMILES: Cc1csc(-c2cnc3ccc(OCC4CCCN(C)C4)nn23)c1]<br>6-(1-Methyl-piperidin-3-ylmethoxy)-3-(4-methyl-thiophen-2-yl)-imidazo[1,2-b]pyridazine | 5.03 | 342.2 | 343.2 |
| 143 | 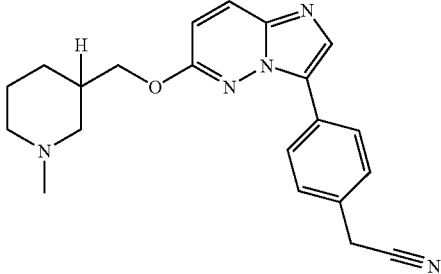 [SMILES: CN1CCCC(COc2ccc3ncc(-c4ccc(CC#N)cc4)n3n2)C1]<br>{4-[6-(1-Methyl-piperidin-3-ylmethoxy)-imidazo[1,2-b]pyridazin-3-yl]-phenyl}-acetonitrile | 4.69 | 361.2 | 362.2 |
| 144 | 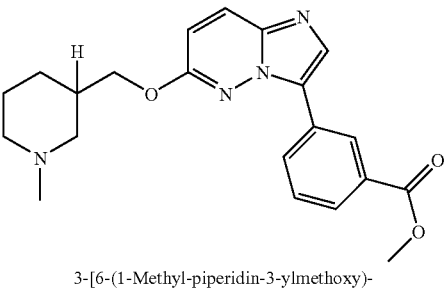<br>3-[6-(1-Methyl-piperidin-3-ylmethoxy)-imidazo[1,2-b]pyridazin-3-yl]-benzoic acid methyl ester | 4.97 | 380.2 | 381.2 |

-continued

| EXAMPLE No. | STRUCTURE | Retention time [min] | MW calc. | MW found |
|---|---|---|---|---|
| 145 | 3-(1H-Indol-4-yl)-6-(1-methyl-piperidin-3-ylmethoxy)-imidazo[1,2-b]pyridazine | 4.55 | 361.2 | 362.2 |
| 146 | 3-(2-Fluoro-pyridin-3-yl)-6-(1-methyl-piperidin-3-ylmethoxy)-imidazo[1,2-b]pyridazine | 4.17 | 341.2 | 342.2 |
| 147 | 3-Benzofuran-2-yl-6-(1-methyl-piperidin-3-ylmethoxy)-imidazo[1,2-b]pyridazine | 5.7 | 362.2 | 363.2 |
| 148 | 6-(1-Methyl-piperidin-3-ylmethoxy)-3-p-tolyl-imidazo[1,2-b]pyridazine | 5.09 | 336.2 | 337.2 |
| 149 | 3-(3-Fluoro-phenyl)-6-(1-methyl-piperidin-3-ylmethoxy)-imidazo[1,2-b]pyridazine | 4.85 | 340.2 | 341.2 |

| EXAMPLE No. | STRUCTURE | Retention time [min] | MW calc. | MW found |
|---|---|---|---|---|
| 150 | 3-Benzo[b]thiophen-3-yl-6-(1-methyl-piperidin-3-ylmethoxy)-imidazo[1,2-b]pyridazine | 5.37 | 378.2 | 379.2 |
| 151 | 3-(4-Chloro-phenyl)-6-(1-methyl-piperidin-3-ylmethoxy)-imidazo[1,2-b]pyridazine | 5.3 | 356.1 | 357.1 |
| 152 | 3-(6-Fluoro-5-methyl-pyridin-3-yl)-6-(1-methyl-piperidin-3-ylmethoxy)-imidazo[1,2-b]pyridazine | 4.8 | 355.2 | 356.2 |
| 153 | 6-(1-Methyl-piperidin-3-ylmethoxy)-3-(2-trifluoromethoxy-phenyl)-imidazo[1,2-b]pyridazine | 5.37 | 406.2 | 407.2 |

-continued

| EXAMPLE No. | STRUCTURE | Retention time [min] | MW calc. | MW found |
|---|---|---|---|---|
| 154 | 3-(4-Ethanesulfonyl-phenyl)-6-(1-methyl-piperidin-3-ylmethoxy)-imidazo[1,2-b]pyridazine | 4.67 | 414.2 | 415.2 |
| 155 | 6-(1-Methyl-piperidin-3-ylmethoxy)-3-(3-pyrrolidin-1-yl-phenyl)-imidazo[1,2-b]pyridazine | 5.27 | 391.2 | 392.2 |
| 156 | 3-(4-Cyclopropylmethoxy-phenyl)-6-(1-methyl-piperidin-3-ylmethoxy)-imidazo[1,2-b]pyridazine | 5.49 | 392.2 | 393.2 |
| 157 | Diethyl-[3-(3-thiophen-3-yl-imidazo[1,2-b]pyridazin-6-yloxy)-propyl]-amine | 4.64 | 330.0 | 331.0 |

| EXAMPLE No. | STRUCTURE | Retention time [min] | MW calc. | MW found |
|---|---|---|---|---|
| 158 | Diethyl-[3-(3-naphthalen-1-yl-imidazo[1,2-b]pyridazin-6-yloxy)-propyl]-amine | 5.24 | 374.0 | 375.0 |
| 159 | Diethyl-{3-[3-(4-methoxy-phenyl)-imidazo[1,2-b]pyridazin-6-yloxy]-propyl}-amine | 4.9 | 354.0 | 355.0 |
| 160 | Diethyl-[3-(3-m-tolyl-imidazo[1,2-b]pyridazin-6-yloxy)-propyl]-amine | 5.12 | 338.0 | 339.0 |
| 161 | {3-[3-(3-Chloro-phenyl)-imidazo[1,2-b]pyridazin-6-yloxy]-propyl}-diethyl-amine | 5.19 | 358.0 | 359.0 |
| 162 | [3-(3-Benzo[b]thiophen-2-yl-imidazo[1,2-b]pyridazin-6-yloxy)-propyl]-diethyl-amine | | 380.0 | 381.0 |

-continued

| EXAMPLE No. | STRUCTURE | Retention time [min] | MW calc. | MW found |
|---|---|---|---|---|
| 163 | 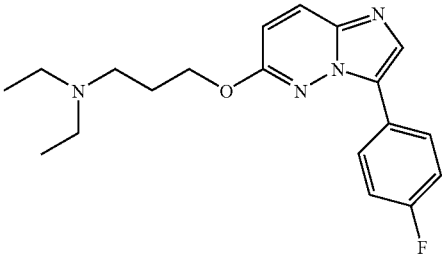 [SMILES: CCN(CC)CCCOc1ccc2ncc(-c3ccc(F)cc3)n2n1]<br>Diethyl-{3-[3-(4-fluoro-phenyl)-imidazo[1,2-b]pyridazin-6-yloxy]-propyl}-amine | 4.94 | 342.0 | 343.0 |
| 164 | 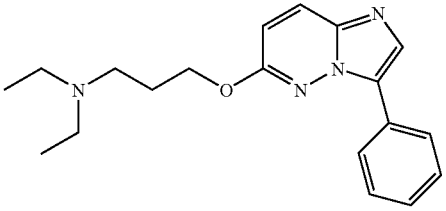 [SMILES: CCN(CC)CCCOc1ccc2ncc(-c3ccccc3)n2n1]<br>Diethyl-[3-(3-phenyl-imidazo[1,2-b]pyridazin-6-yloxy)-propyl]-amine | 4.74 | 324.0 | 325.0 |
| 165 | 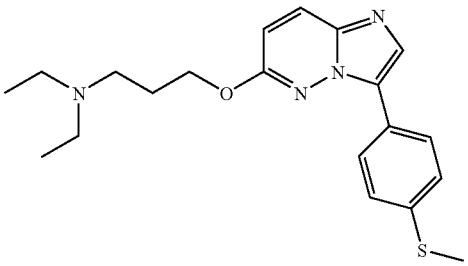 [SMILES: CCN(CC)CCCOc1ccc2ncc(-c3ccc(SC)cc3)n2n1]<br>Diethyl-{3-[3-(4-methylsulfanyl-phenyl)-imidazo[1,2-b]pyridazin-6-yloxy]-propyl}-amine | 5.24 | 370.0 | 371.0 |
| 166 | 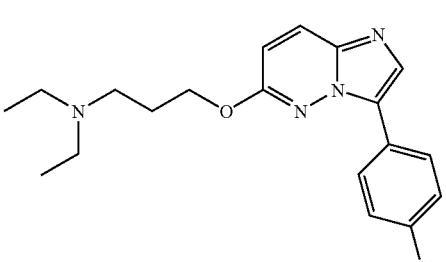<br>{3-[3-(4-Chloro-phenyl)-imidazo[1,2-b]pyridazin-6-yloxy]-propyl}-diethyl-amine | 5.32 | 358.0 | 359.0 |
| 167 | 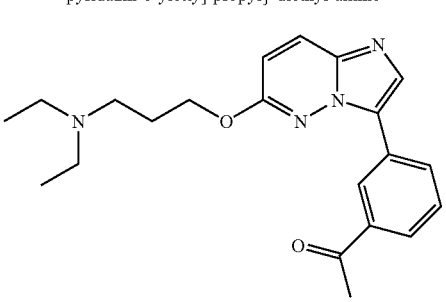<br>1-{3-[6-(3-Diethylamino-propoxy)-imidazo[1,2-b]pyridazin-3-yl]-phenyl}-ethanone | 4.74 | 366.0 | 367.0 |

-continued

| EXAMPLE No. | STRUCTURE | Retention time [min] | MW calc. | MW found |
|---|---|---|---|---|
| 168 | Diethyl-{3-[3-(2-methylsulfanyl-phenyl)-imidazo[1,2-b]pyridazin-6-yloxy]-propyl}-amine | 5.0 | 370.0 | 371.0 |
| 169 | Diethyl-{3-[3-(3-trifluoromethoxy-phenyl)-imidazo[1,2-b]pyridazin-6-yloxy]-propyl}-amine | 5.62 | 408.0 | 409.0 |
| 170 | Diethyl-{3-[3-(3-trifluoromethyl-phenyl)-imidazo[1,2-b]pyridazin-6-yloxy]-propyl}-amine | 5.59 | 392.0 | 393.0 |
| 171 | [3-(3-Biphenyl-3-yl-imidazo[1,2-b]pyridazin-6-yloxy)-propyl]-diethyl-amine | 5.95 | 400.0 | 401.0 |

| EXAMPLE No. | STRUCTURE | Retention time [min] | MW calc. | MW found |
|---|---|---|---|---|
| 172 | 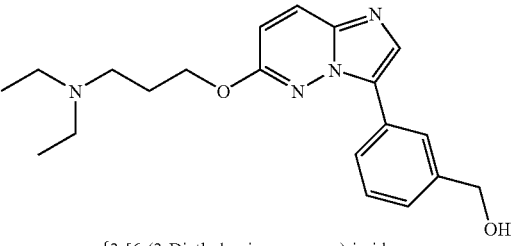<br>{3-[6-(3-Diethylamino-propoxy)-imidazo[1,2-b]pyridazin-3-yl]-phenyl}-methanol | 4.25 | 354.0 | 355.0 |
| 173 | 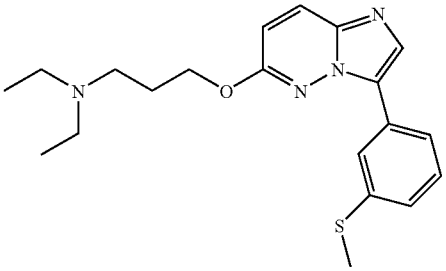 [SMILES: CCN(CC)CCCOc1ccc2ncc(-c3cccc(SC)c3)n2n1]<br>Diethyl-{3-[3-(3-methylsulfanyl-phenyl)-imidazo[1,2-b]pyridazin-6-yloxy]-propyl}-amine | 5.22 | 370.0 | 371.0 |
| 174 | 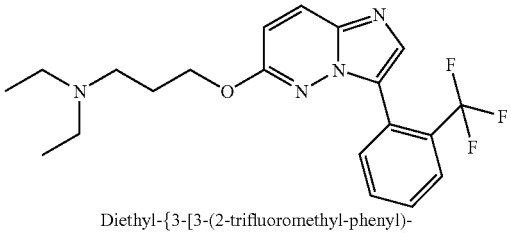<br>Diethyl-{3-[3-(2-trifluoromethyl-phenyl)-imidazo[1,2-b]pyridazin-6-yloxy]-propyl}-amine | 5.22 | 392.0 | 393.0 |
| 175 | 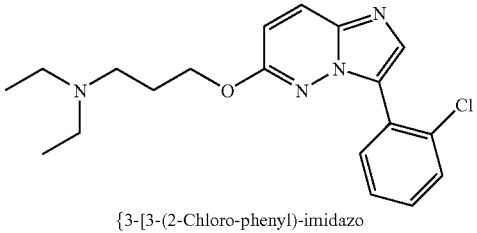<br>{3-[3-(2-Chloro-phenyl)-imidazo[1,2-b]pyridazin-6-yloxy]-propyl}-diethyl-amine | 4.97 | 358.0 | 359.0 |
| 176 | 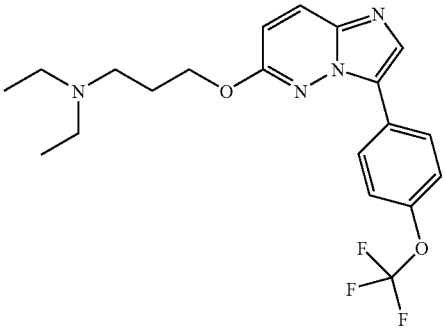 [SMILES: CCN(CC)CCCOc1ccc2ncc(-c3ccc(OC(F)(F)F)cc3)n2n1]<br>Diethyl-{3-[3-(4-trifluoromethoxy-phenyl)-imidazo[1,2-b]pyridazin-6-yloxy]-propyl}-amine | 5.77 | 408.0 | 409.0 |

| EXAMPLE No. | STRUCTURE | Retention time [min] | MW calc. | MW found |
|---|---|---|---|---|
| 177 | Diethyl-{3-[3-(4-trifluoromethyl-phenyl)-imidazo[1,2-b]pyridazin-6-yloxy]-propyl}-amine | 5.64 | 392.0 | 393.0 |
| 178 | {3-[3-(3-Chloro-4-methyl-phenyl)-imidazo[1,2-b]pyridazin-6-yloxy]-propyl}-diethyl-amine | 5.59 | 372.0 | 373.0 |
| 179 | Diethyl-{3-[3-(5-methyl-furan-2-yl)-imidazo[1,2-b]pyridazin-6-yloxy]-propyl}-amine | 4.2 | 328.0 | 329.0 |
| 180 | Diethyl-{3-[3-(3-fluoro-4-methoxy-phenyl)-imidazo[1,2-b]pyridazin-6-yloxy]-propyl}-amine | 5.02 | 372.0 | 373.0 |

| EXAMPLE No. | STRUCTURE | Retention time [min] | MW calc. | MW found |
|---|---|---|---|---|
| 181 | Diethyl-[3-(3-o-tolyl-imidazo[1,2-b]pyridazin-6-yloxy)-propyl]-amine | 4.84 | 338.0 | 339.0 |
| 182 | {3-[3-(3-Chloro-4-fluoro-phenyl)-imidazo[1,2-b]pyridazin-6-yloxy]-propyl}-diethyl-amine | 5.44 | 376.0 | 377.0 |
| 183 | Diethyl-{3-[3-(3-methoxy-phenyl)-imidazo[1,2-b]pyridazin-6-yloxy]-propyl}-amine | 4.95 | 354.0 | 355.0 |
| 184 | {3-[3-(5-Chloro-thiophen-2-yl)-imidazo[1,2-b]pyridazin-6-yloxy]-propyl}-diethyl-amine | 5.34 | 364.0 | 365.0 |
| 185 | 3-[6-(3-Diethylamino-propoxy)-imidazo[1,2-b]pyridazin-3-yl]-benzonitrile | 4.75 | 349.0 | 350.0 |

-continued

| EXAMPLE No. | STRUCTURE | Retention time [min] | MW calc. | MW found |
|---|---|---|---|---|
| 186 | 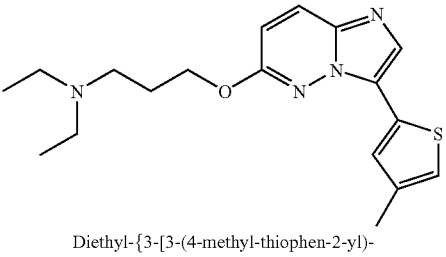<br>Diethyl-{3-[3-(4-methyl-thiophen-2-yl)-imidazo[1,2-b]pyridazin-6-yloxy]-propyl}-amine | 5.1 | 344.0 | 345.0 |
| 187 | 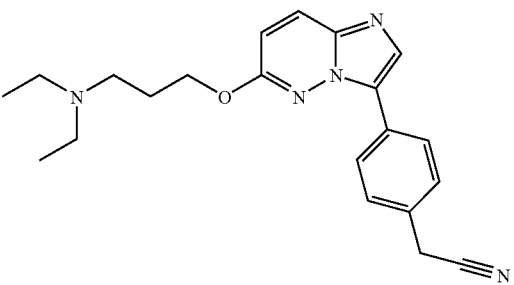 [SMILES: CCN(CC)CCCOc1ccc2ncc(-c3ccc(CC#N)cc3)n2n1]<br>{4-[6-(3-Diethylamino-propoxy)-imidazo[1,2-b]pyridazin-3-yl]-phenyl}-acetonitrile | 4.72 | 363.0 | 364.0 |
| 188 | 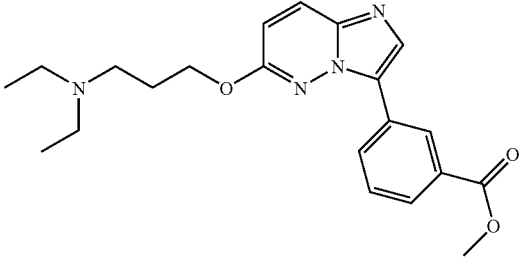 [SMILES: CCN(CC)CCCOc1ccc2ncc(-c3cccc(C(=O)OC)c3)n2n1]<br>3-[6-(3-Diethylamino-propoxy)-imidazo[1,2-b]pyridazin-3-yl]-benzoic acid methyl ester | 5.0 | 382.0 | 383.0 |
| 189 | 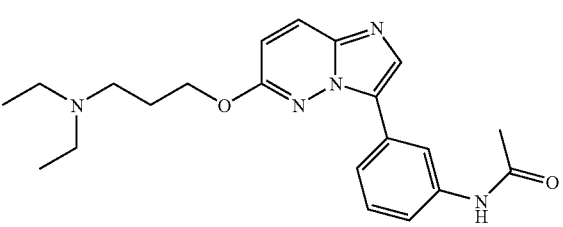 [SMILES: CCN(CC)CCCOc1ccc2ncc(-c3cccc(NC(C)=O)c3)n2n1]<br>N-{3-[6-(3-Diethylamino-propoxy)-imidazo[1,2-b]pyridazin-3-yl]-phenyl}-acetamide | 4.27 | 381.0 | 382.0 |
| 190 | 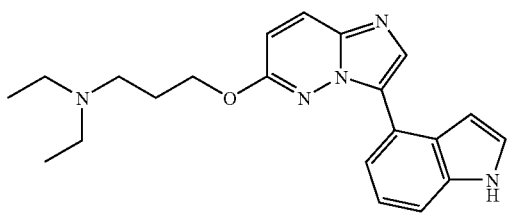 [SMILES: CCN(CC)CCCOc1ccc2ncc(-c3cccc4[nH]ccc34)n2n1]<br>Diethyl-{3-[3-(1H-indol-4-yl)-imidazo[1,2-b]pyridazin-6-yloxy]-propyl}-amine | 4.69 | 363.0 | 364.0 |

| EXAMPLE No. | STRUCTURE | Retention time [min] | MW calc. | MW found |
|---|---|---|---|---|
| 191 | [3-(3-Benzofuran-2-yl-imidazo[1,2-b]pyridazin-6-yloxy)-propyl]-diethyl-amine | 5.74 | 364.0 | 365.0 |
| 192 | Diethyl-[3-(3-p-tolyl-imidazo[1,2-b]pyridazin-6-yloxy)-propyl]-amine | 5.05 | 338.0 | 339.0 |
| 193 | Diethyl-{3-[3-(3-fluoro-phenyl)-imidazo[1,2-b]pyridazin-6-yloxy]-propyl}-amine | 4.97 | 342.0 | 343.0 |
| 194 | [3-(3-Benzo[b]thiophen-3-yl-imidazo[1,2-b]pyridazin-6-yloxy)-propyl]-diethyl-amine | 5.44 | 380.0 | 381.0 |
| 195 | {3-[3-(4-Chloro-phenyl)-imidazo[1,2-b]pyridazin-6-yloxy]-propyl}-diethyl-amine | 5.32 | 358.0 | 359.0 |

-continued

| EXAMPLE No. | STRUCTURE | Retention time [min] | MW calc. | MW found |
|---|---|---|---|---|
| 196 | Diethyl-{3-[3-(6-fluoro-5-methyl-pyridin-3-yl)-imidazo[1,2-b]pyridazin-6-yloxy]-propyl}-amine | 4.65 | 357.0 | 358.0 |
| 197 | Diethyl-{3-[3-(2-trifluoromethoxy-phenyl)-imidazo[1,2-b]pyridazin-6-yloxy]-propyl}-amine | 5.44 | 408.0 | 409.0 |
| 198 | {3-[3-(4-Ethanesulfonyl-phenyl)-imidazo[1,2-b]pyridazin-6-yloxy]-propyl}-diethyl-amine | 4.75 | 416.0 | 417.0 |
| 199 | Diethyl-{3-[3-(3-pyrrolidin-1-yl-phenyl)-imidazo[1,2-b]pyridazin-6-yloxy]-propyl}-amine | 5.22 | 393.0 | 394.0 |

-continued

| EXAMPLE No. | STRUCTURE | Retention time [min] | MW calc. | MW found |
|---|---|---|---|---|
| 200 | {3-[3-(4-Cyclopropylmethoxy-phenyl)-imidazo[1,2-b]pyridazin-6-yloxy]-propyl}-diethyl-amine | 5.69 | 394.0 | 395.0 |
| 201 | 6-(1-Methyl-piperidin-3-yloxy)-3-thiophen-3-yl-imidazo[1,2-b]pyridazine | 4.42 | 314.0 | 315.0 |
| 202 | 6-(1-Methyl-piperidin-3-yloxy)-3-naphthalen-1-yl-imidazo[1,2-b]pyridazine | 5.05 | 358.0 | 359.0 |
| 203 | 3-(4-Methoxy-phenyl)-6-(1-methyl-piperidin-3-yloxy)-imidazo[1,2-b]pyridazine | 4.72 | 338.0 | 339.0 |

-continued

| EXAMPLE No. | STRUCTURE | Retention time [min] | MW calc. | MW found |
|---|---|---|---|---|
| 204 | 3-(2,4-Dichloro-phenyl)-6-(1-methyl-piperidin-3-yloxy)-imidazo[1,2-b]pyridazine | 5.34 | 376.0 | 377.0 |
| 205 | 6-(1-Methyl-piperidin-3-yloxy)-3-m-tolyl-imidazo[1,2-b]pyridazine | 4.92 | 322.0 | 323.0 |
| 206 | 3-(3-Chloro-phenyl)-6-(1-methyl-piperidin-3-yloxy)-imidazo[1,2-b]pyridazine | 5.0 | 342.0 | 343.0 |
| 207 | 3-Benzo[b]thiophen-2-yl-6-(1-methyl-piperidin-3-yloxy)-imidazo[1,2-b]pyridazine | 5.6 | 364.0 | 365.0 |
| 208 | 3-(4-Fluoro-phenyl)-6-(1-methyl-piperidin-3-yloxy)-imidazo[1,2-b]pyridazine | 4.75 | 326.0 | 327.0 |

-continued

| EXAMPLE No. | STRUCTURE | Retention time [min] | MW calc. | MW found |
|---|---|---|---|---|
| 209 | 6-(1-Methyl-piperidin-3-yloxy)-3-(2-methylsulfanyl-phenyl)-imidazo[1,2-b]pyridazine | 4.78 | 354.0 | 355.0 |
| 210 | 6-(1-Methyl-piperidin-3-yloxy)-3-(3-trifluoromethoxy-phenyl)-imidazo[1,2-b]pyridazine | 5.47 | 392.0 | 393.0 |
| 211 | 6-(1-Methyl-piperidin-3-yloxy)-3-(3-trifluoromethyl-phenyl)-imidazo[1,2-b]pyridazine | 5.42 | 376.0 | 377.0 |
| 212 | 3-Biphenyl-3-yl-6-(1-methyl-piperidin-3-yloxy)-imidazo[1,2-b]pyridazine | 5.78 | 384.0 | 385.0 |

-continued

| EXAMPLE No. | STRUCTURE | Retention time [min] | MW calc. | MW found |
|---|---|---|---|---|
| 213 | 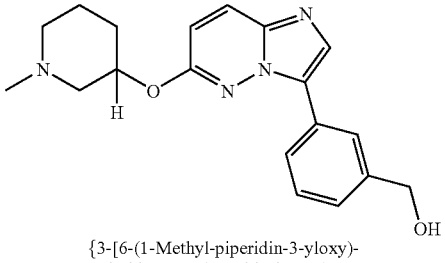<br>{3-[6-(1-Methyl-piperidin-3-yloxy)-imidazo[1,2-b]pyridazin-3-yl]-phenyl}-methanol | 4.05 | 338.0 | 339.0 |
| 214 | 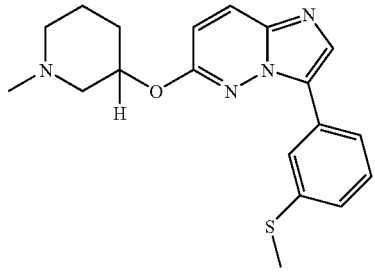 [SMILES: CSc1cccc(-c2cnc3ccc(OC4CCCN(C)C4)nn23)c1]<br>6-(1-Methyl-piperidin-3-yloxy)-3-(3-methylsulfanyl-phenyl)-imidazo[1,2-b]pyridazine | 5.05 | 354.0 | 355.0 |
| 215 | 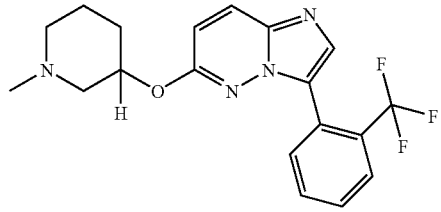 [SMILES: CN1CCCC(Oc2ccc3ncc(-c4ccccc4C(F)(F)F)n3n2)C1]<br>6-(1-Methyl-piperidin-3-yloxy)-3-(2-trifluoromethyl-phenyl)-imidazo[1,2-b]pyridazine | 5.03 | 376.0 | 377.0 |
| 216 | 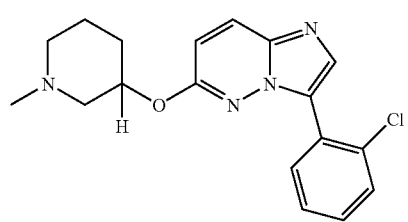 [SMILES: CN1CCCC(Oc2ccc3ncc(-c4ccccc4Cl)n3n2)C1]<br>3-(2-Chloro-phenyl)-6-(1-methyl-piperidin-3-yloxy)-imidazo[1,2-b]pyridazine | 4.75 | 342.0 | 343.0 |
| 217 | 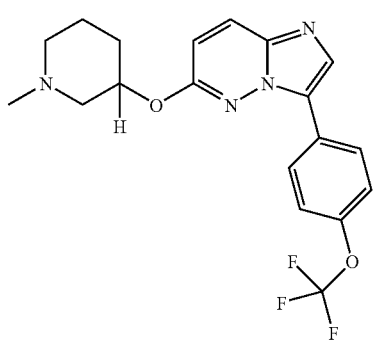 [SMILES: CN1CCCC(Oc2ccc3ncc(-c4ccc(OC(F)(F)F)cc4)n3n2)C1]<br>6-(1-Methyl-piperidin-3-yloxy)-3-(4-trifluoromethoxy-phenyl)-imidazo[1,2-b]pyridazine | 5.62 | 392.0 | 393.0 |

| EXAMPLE No. | STRUCTURE | Retention time [min] | MW calc. | MW found |
|---|---|---|---|---|
| 218 | 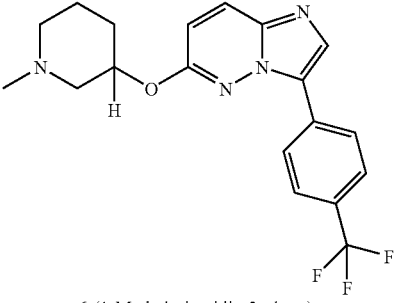<br>6-(1-Methyl-piperidin-3-yloxy)-<br>3-(4-trifluoromethyl-phenyl)-<br>imidazo[1,2-b]pyridazine | 5.5 | 376.0 | 377.0 |
| 219 | 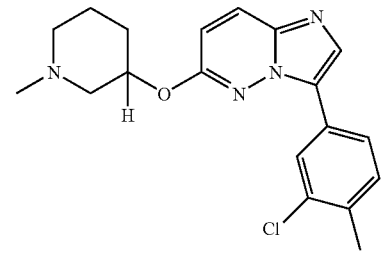 [SMILES: Cc1ccc(-c2cnc3ccc(OC4CCCN(C)C4)nn23)cc1Cl]<br>3-(3-Chloro-4-methyl-phenyl)-6-<br>(1-methyl-piperidin-3-yloxy)-<br>imidazo[1,2-b]pyridazine | 5.4 | 356.0 | 357.0 |
| 220 | 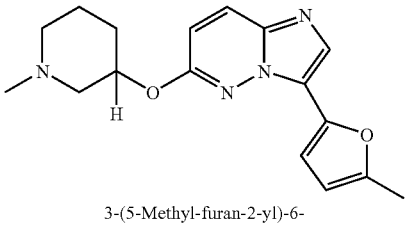<br>3-(5-Methyl-furan-2-yl)-6-<br>(1-methyl-piperidin-3-yloxy)-<br>imidazo[1,2-b]pyridazine | 3.97 | 312.0 | 313.0 |
| 221 | 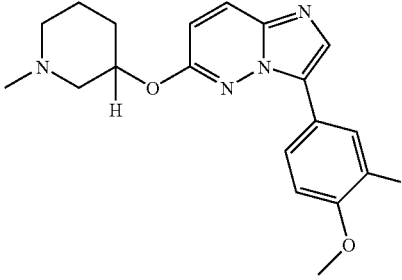<br>3-(3-Fluoro-4-methoxy-phenyl)-6-<br>(1-methyl-piperidin-3-yloxy)-<br>imidazo[1,2-b]pyridazine | 4.82 | 356.0 | 357.0 |
| 222 | 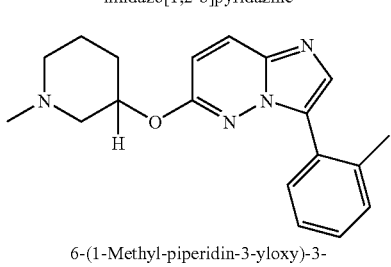<br>6-(1-Methyl-piperidin-3-yloxy)-3-<br>o-tolyl-imidazo[1,2-b]pyridazine | 4.62 | 322.0 | 323.0 |

-continued

| EXAMPLE No. | STRUCTURE | Retention time [min] | MW calc. | MW found |
|---|---|---|---|---|
| 223 | 3-(3-Chloro-4-fluoro-phenyl)-6-(1-methyl-piperidin-3-yloxy)-imidazo[1,2-b]pyridazine | 5.25 | 360.0 | 361.0 |
| 224 | 3-(3-Methoxy-phenyl)-6-(1-methyl-piperidin-3-yloxy)-imidazo[1,2-b]pyridazine | 4.75 | 338.0 | 339.0 |
| 225 | 3-(5-Chloro-thiophen-2-yl)-6-(1-methyl-piperidin-3-yloxy)-imidazo[1,2-b]pyridazine | 5.15 | 348.0 | 349.0 |
| 226 | 3-[6-(1-Methyl-piperidin-3-yloxy)-imidazo[1,2-b]pyridazin-3-yl]-benzonitrile | 4.57 | 333.0 | 334.0 |
| 227 | 6-(1-Methyl-piperidin-3-yloxy)-3-(4-methyl-thiophen-2-yl)-imidazo[1,2-b]pyridazine | 4.89 | 328.0 | 329.0 |

| EXAMPLE No. | STRUCTURE | Retention time [min] | MW calc. | MW found |
|---|---|---|---|---|
| 228 | 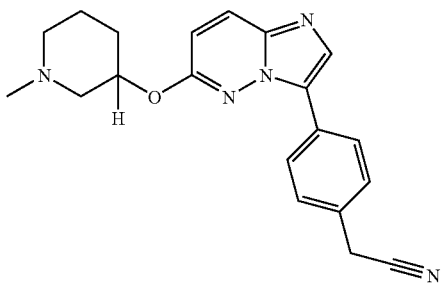 [SMILES: CN1CCCC(Oc2ccc3ncc(-c4ccc(CC#N)cc4)n3n2)C1]<br>{4-[6-(1-Methyl-piperidin-3-yloxy)-imidazo[1,2-b]pyridazin-3-yl]-phenyl}-acetonitrile | 4.52 | 347.0 | 348.0 |
| 229 | 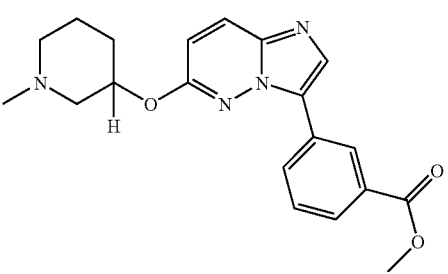 [SMILES: COC(=O)c1cccc(-c2cnc3ccc(OC4CCCN(C)C4)nn23)c1]<br>3-[6-(1-Methyl-piperidin-3-yloxy)-imidazo[1,2-b]pyridazin-3-yl]-benzoic acid methyl ester | 4.82 | 366.0 | 367.0 |
| 230 | 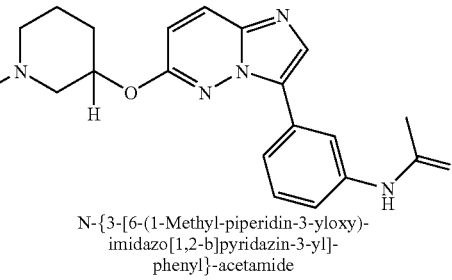<br>N-{3-[6-(1-Methyl-piperidin-3-yloxy)-imidazo[1,2-b]pyridazin-3-yl]-phenyl}-acetamide | 4.1 | 365.0 | 366.0 |
| 231 | 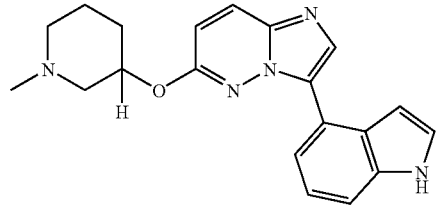 [SMILES: CN1CCCC(Oc2ccc3ncc(-c4cccc5[nH]ccc45)n3n2)C1]<br>3-(1H-Indol-4-yl)-6-(1-methyl-piperidin-3-yloxy)-imidazo[1,2-b]pyridazine | 4.47 | 347.0 | 348.0 |
| 232 | 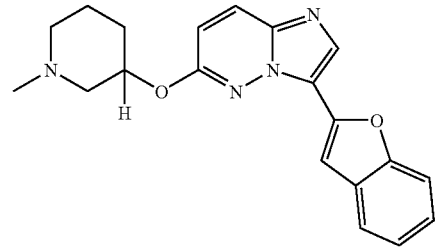 [SMILES: CN1CCCC(Oc2ccc3ncc(-c4cc5ccccc5o4)n3n2)C1]<br>3-Benzofuran-2-yl-6-(1-methyl-piperidin-3-yloxy)-imidazo[1,2-b]pyridazine | 5.62 | 348.0 | 349.0 |

-continued

| EXAMPLE No. | STRUCTURE | Retention time [min] | MW calc. | MW found |
|---|---|---|---|---|
| 233 | 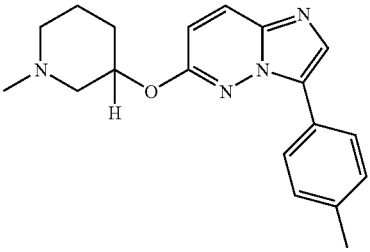 [SMILES: Cc1ccc(-c2cnc3ccc(OC4CCCN(C)C4)nn23)cc1]<br>6-(1-Methyl-piperidin-3-yloxy)-3-p-tolyl-imidazo[1,2-b]pyridazine | 4.92 | 322.0 | 323.0 |
| 234 | 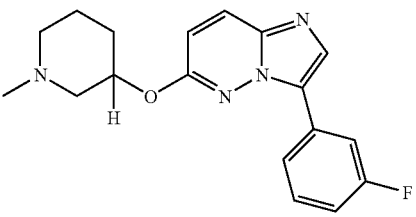 [SMILES: CN1CCCC(Oc2ccc3ncc(-c4cccc(F)c4)n3n2)C1]<br>3-(3-Fluoro-phenyl)-6-(1-methyl-piperidin-3-yloxy)-imidazo[1,2-b]pyridazine | 4.67 | 326.0 | 327.0 |
| 235 | 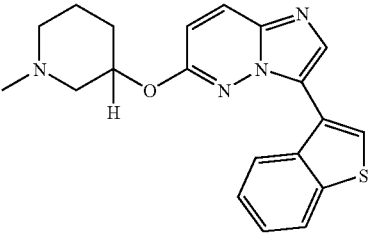 [SMILES: CN1CCCC(Oc2ccc3ncc(-c4csc5ccccc45)n3n2)C1]<br>3-Benzo[b]thiophen-3-yl-6-(1-methyl-piperidin-3-yloxy)-imidazo[1,2-b]pyridazine | 5.24 | 364.0 | 365.0 |
| 236 | 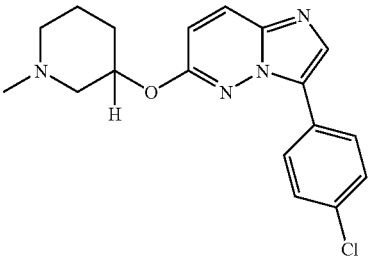<br>3-(4-Chloro-phenyl)-6-(1-methyl-piperidin-3-yloxy)-imidazo[1,2-b]pyridazine | 5.15 | 342.0 | 343.0 |
| 237 | 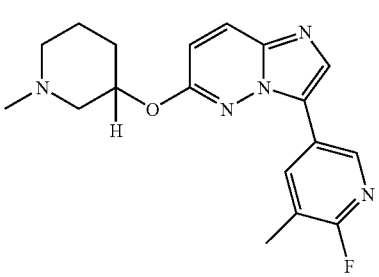 [SMILES: Cc1cc(-c2cnc3ccc(OC4CCCN(C)C4)nn23)cnc1F]<br>3-(6-Fluoro-5-methyl-pyridin-3-yl)-6-(1-methyl-piperidin-3-yloxy)-imidazo[1,2-b]pyridazine | 4.49 | 341.0 | 342.0 |

| EXAMPLE No. | STRUCTURE | Retention time [min] | MW calc. | MW found |
|---|---|---|---|---|
| 238 | 6-(1-Methyl-piperidin-3-yloxy)-3-(2-trifluoromethoxy-phenyl)-imidazo[1,2-b]pyridazine | 5.24 | 392.0 | 393.0 |
| 239 | 3-(4-Ethanesulfonyl-phenyl)-6-(1-methyl-piperidin-3-yloxy)-imidazo[1,2-b]pyridazine | 4.57 | 400.0 | 401.0 |
| 240 | 6-(1-Methyl-piperidin-3-yloxy)-3-(3-pyrrolidin-1-yl-phenyl)-imidazo[1,2-b]pyridazine | 5.1 | 377.0 | 378.0 |
| 241 | 3-(4-Cyclopropylmethoxy-phenyl)-6-(1-methyl-piperidin-3-yloxy)-imidazo[1,2-b]pyridazine | 5.52 | 378.0 | 379.0 |

-continued

| EXAMPLE No. | STRUCTURE | Retention time [min] | MW calc. | MW found |
|---|---|---|---|---|
| 242 | 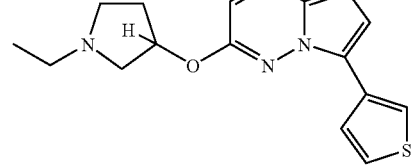<br>6-(1-Ethyl-pyrrolidin-3-yloxy)-3-thiophen-3-yl-imidazo[1,2-b]pyridazine | 4.3 | 314.0 | 315.0 |
| 243 | 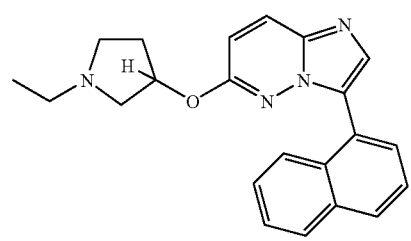<br>6-(1-Ethyl-pyrrolidin-3-yloxy)-3-naphthalen-1-yl-imidazo[1,2-b]pyridazine | 4.97 | 358.0 | 359.0 |
| 244 | 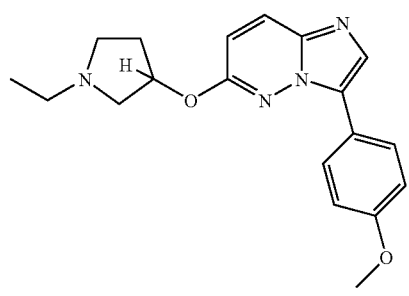<br>6-(1-Ethyl-pyrrolidin-3-yloxy)-3-(4-methoxy-phenyl)-imidazo[1,2-b]pyridazine | 4.62 | 338.0 | 339.0 |
| 245 | 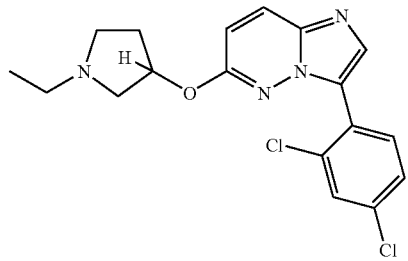<br>3-(2,4-Dichloro-phenyl)-6-(1-ethyl-pyrrolidin-3-yloxy)-imidazo[1,2-b]pyridazine | 5.25 | 376.0 | 377.0 |
| 246 | 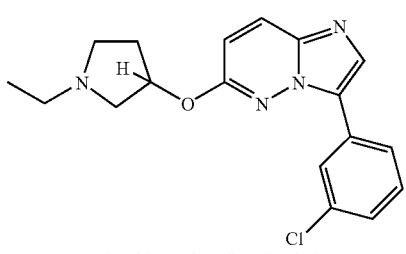<br>3-(3-Chloro-phenyl)-6-(1-ethyl-pyrrolidin-3-yloxy)-imidazo[1,2-b]pyridazine | 4.9 | 342.0 | 343.0 |

-continued

| EXAMPLE No. | STRUCTURE | Retention time [min] | MW calc. | MW found |
|---|---|---|---|---|
| 247 | 3-Benzo[b]thiophen-2-yl-6-(1-ethyl-pyrrolidin-3-yloxy)-imidazo[1,2-b]pyridazine | 5.57 | 364.0 | 365.0 |
| 248 | 6-(1-Ethyl-pyrrolidin-3-yloxy)-3-(4-fluoro-phenyl)-imidazo[1,2-b]pyridazine | 4.65 | 326.0 | 327.0 |
| 249 | 6-(1-Ethyl-pyrrolidin-3-yloxy)-3-phenyl-imidazo[1,2-b]pyridazine | 4.44 | 308.0 | 309.0 |
| 250 | 6-(1-Ethyl-pyrrolidin-3-yloxy)-3-(4-methylsulfanyl-phenyl)-imidazo[1,2-b]pyridazine | 5.02 | 354.0 | 355.0 |
| 251 | 3-(4-Chloro-phenyl)-6-(1-ethyl-pyrrolidin-3-yloxy)-imidazo[1,2-b]pyridazine | 5.07 | 342.0 | 343.0 |

-continued
| EXAMPLE No. | STRUCTURE | Retention time [min] | MW calc. | MW found |
|---|---|---|---|---|
| 252 | 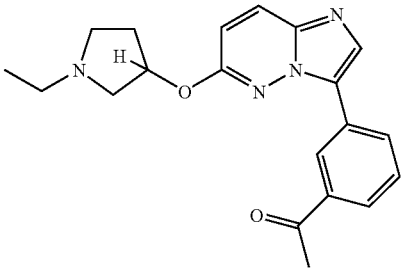<br>1-{3-[6-(1-Ethyl-pyrrolidin-3-yloxy)-imidazo[1,2-b]pyridazin-3-yl]-phenyl}-ethanone | 4.47 | 350.0 | 351.0 |
| 253 | 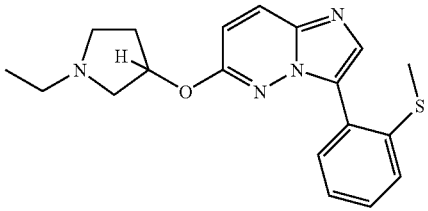<br>6-(1-Ethyl-pyrrolidin-3-yloxy)-3-(2-methylsulfanyl-phenyl)-imidazo[1,2-b]pyridazine | 4.72 | 354.0 | 355.0 |
| 254 | 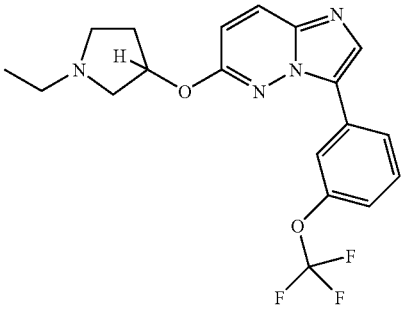<br>6-(1-Ethyl-pyrrolidin-3-yloxy)-3-(3-trifluoromethoxy-phenyl)-imidazo[1,2-b]pyridazine | 5.42 | 392.0 | 393.0 |
| 255 | 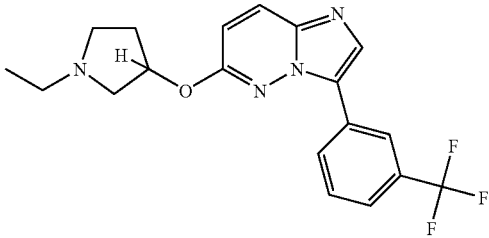<br>6-(1-Ethyl-pyrrolidin-3-yloxy)-3-(3-trifluoromethyl-phenyl)-imidazo[1,2-b]pyridazine | 5.34 | 376.0 | 377.0 |

-continued

| EXAMPLE No. | STRUCTURE | Retention time [min] | MW calc. | MW found |
|---|---|---|---|---|
| 256 | 3-Biphenyl-3-yl-6-(1-ethyl-pyrrolidin-3-yloxy)-imidazo[1,2-b]pyridazine | 5.75 | 384.0 | 385.0 |
| 257 | {3-[6-(1-Ethyl-pyrrolidin-3-yloxy)-imidazo[1,2-b]pyridazin-3-yl]-phenyl}-methanol | 3.98 | 338.0 | 339.0 |
| 258 | 6-(1-Ethyl-pyrrolidin-3-yloxy)-3-(3-methylsulfanyl-phenyl)-imidazo[1,2-b]pyridazine | 4.97 | 354.0 | 355.0 |
| 259 | 6-(1-Ethyl-pyrrolidin-3-yloxy)-3-(2-trifluoromethyl-phenyl)-imidazo[1,2-b]pyridazine | 4.97 | 376.0 | 377.0 |
| 260 | 3-(2-Chloro-phenyl)-6-(1-ethyl-pyrrolidin-3-yloxy)-imidazo[1,2-b]pyridazine | 4.67 | 342.0 | 343.0 |

-continued

| EXAMPLE No. | STRUCTURE | Retention time [min] | MW calc. | MW found |
|---|---|---|---|---|
| 261 | 6-(1-Ethyl-pyrrolidin-3-yloxy)-3-(4-trifluoromethoxy-phenyl)-imidazo[1,2-b]pyridazine | 5.57 | 392.0 | 393.0 |
| 262 | 6-(1-Ethyl-pyrrolidin-3-yloxy)-3-(4-trifluoromethyl-phenyl)-imidazo[1,2-b]pyridazine | 5.44 | 376.0 | 377.0 |
| 263 | 3-(3-Chloro-4-methyl-phenyl)-6-(1-ethyl-pyrrolidin-3-yloxy)-imidazo[1,2-b]pyridazine | 5.34 | 356.0 | 357.0 |
| 264 | 3-(3-Chloro-4-fluoro-phenyl)-6-(1-ethyl-pyrrolidin-3-yloxy)-imidazo[1,2-b]pyridazine | 5.17 | 360.0 | 361.0 |

-continued

| EXAMPLE No. | STRUCTURE | Retention time [min] | MW calc. | MW found |
|---|---|---|---|---|
| 265 | 6-(1-Ethyl-pyrrolidin-3-yloxy)-3-(3-methoxy-phenyl)-imidazo[1,2-b]pyridazine | 4.65 | 338.0 | 339.0 |
| 266 | 3-(5-Chloro-thiophen-2-yl)-6-(1-ethyl-pyrrolidin-3-yloxy)-imidazo[1,2-b]pyridazine | 5.09 | 348.0 | 349.0 |
| 267 | 3-[6-(1-Ethyl-pyrrolidin-3-yloxy)-imidazo[1,2-b]pyridazin-3-yl]-benzonitrile | 4.45 | 333.0 | 334.0 |
| 268 | 6-(1-Ethyl-pyrrolidin-3-yloxy)-3-(4-methyl-thiophen-2-yl)-imidazo[1,2-b]pyridazine | 4.82 | 328.0 | 329.0 |
| 269 | 3-[6-(1-Ethyl-pyrrolidin-3-yloxy)-imidazo[1,2-b]pyridazin-3-yl]-benzoic acid methyl ester | 4.78 | 366.0 | 367.0 |

| EXAMPLE No. | STRUCTURE | Retention time [min] | MW calc. | MW found |
|---|---|---|---|---|
| 270 | N-{3-[6-(1-Ethyl-pyrrolidin-3-y-imidazo[1,2-b]pyridazin-3-yl]-acetamide | 4.12 | 365.0 | 366.0 |
| 271 | 6-(1-Ethyl-pyrrolidin-3-yloxy)-3-(1H-indol-4-yl)-imidazo[1,2-b]pyridazine | 4.32 | 347.0 | 348.0 |
| 272 | 3-Benzofuran-2-yl-6-(1-ethyl-pyrrolidin-3-yloxy)-imidazo[1,2-b]pyridazine | 5.59 | 348.0 | 349.0 |
| 273 | 6-(1-Ethyl-pyrrolidin-3-yloxy)-3-p-tolyl-imidazo[1,2-b]pyridazine | 4.85 | 322.0 | 323.0 |
| 274 | 6-(1-Ethyl-pyrrolidin-3-yloxy)-3-(3-fluoro-phenyl)-imidazo[1,2-b]pyridazine | 4.65 | 326.0 | 327.0 |

| EXAMPLE No. | STRUCTURE | Retention time [min] | MW calc. | MW found |
|---|---|---|---|---|
| 275 | 3-(4-Chloro-phenyl)-6-(1-ethyl-pyrrolidin-3-yloxy)-imidazo[1,2-b]pyridazine | 5.09 | 342.0 | 343.0 |
| 276 | 6-(1-Ethyl-pyrrolidin-3-yloxy)-3-(6-fluoro-5-methyl-pyridin-3-yl)-imidazo[1,2-b]pyridazine | 4.44 | 341.0 | 342.0 |
| 277 | 6-(1-Ethyl-pyrrolidin-3-yloxy)-3-(2-trifluoromethoxy-phenyl)-imidazo[1,2-b]pyridazine | 5.09 | 392.0 | 393.0 |
| 278 | 3-(4-Ethanesulfonyl-phenyl)-6-(1-ethyl-pyrrolidin-3-yloxy)-imidazo[1,2-b]pyridazine | 4.52 | 400.0 | 401.0 |

-continued

| EXAMPLE No. | STRUCTURE | Retention time [min] | MW calc. | MW found |
|---|---|---|---|---|
| 279 | 6-(1-Ethyl-pyrrolidin-3-yloxy)-3-(3-pyrrolidin-1-yl-phenyl)-imidazo[1,2-b]pyridazine | 5.02 | 377.0 | 378.0 |
| 280 | 3-(4-Cyclopropylmethoxy-phenyl)-6-(1-ethyl-pyrrolidin-3-yloxy)-imidazo[1,2-b]pyridazine | 5.39 | 378.0 | 379.0 |
| 281 | 6-(3-Piperidin-1-yl-propoxy)-3-thiophen-3-yl-imidazo[1,2-b]pyridazine | 4.74 | 342.0 | 343.0 |
| 282 | 3-Naphthalen-1-yl-6-(3-piperidin-1-yl-propoxy)-imidazo[1,2-b]pyridazine | 5.4 | 386.0 | 387.0 |

| EXAMPLE No. | STRUCTURE | Retention time [min] | MW calc. | MW found |
|---|---|---|---|---|
| 283 | 3-(4-Methoxy-phenyl)-6-(3-piperidin-1-yl-propoxy)-imidazo[1,2-b]pyridazine | 4.97 | 366.0 | 367.0 |
| 284 | 6-(3-Piperidin-1-yl-propoxy)-3-m-tolyl-imidazo[1,2-b]pyridazine | 5.19 | 350.0 | 351.0 |
| 285 | 3-(3-Chloro-phenyl)-6-(3-piperidin-1-yl-propoxy)-imidazo[1,2-b]pyridazine | 5.35 | 370.0 | 371.0 |
| 286 | 3-Benzo[b]thiophen-2-yl-6-(3-piperidin-1-yl-propoxy)-imidazo[1,2-b]pyridazine | 5.8 | 392.0 | 393.0 |
| 287 | 3-(4-Fluoro-phenyl)-6-(3-piperidin-1-yl-propoxy)-imidazo[1,2-b]pyridazine | 4.94 | 354.0 | 355.0 |

-continued

| EXAMPLE No. | STRUCTURE | Retention time [min] | MW calc. | MW found |
|---|---|---|---|---|
| 288 | 3-Phenyl-6-(3-piperidin-1-yl-propoxy)-imidazo[1,2-b]pyridazine | 4.84 | 336.0 | 337.0 |
| 289 | 3-(4-Methylsulfanyl-phenyl)-6-(3-piperidin-1-yl-propoxy)-imidazo[1,2-b]pyridazine | 5.4 | 382.0 | 383.0 |
| 290 | 3-(4-Chloro-phenyl)-6-(3-piperidin-1-yl-propoxy)-imidazo[1,2-b]pyridazine | 5.35 | 370.0 | 371.0 |
| 291 | 1-{3-[6-(3-Piperidin-1-yl-propoxy)-imidazo[1,2-b]pyridazin-3-yl]-phenyl}-ethanone | 4.72 | 378.0 | 379.0 |
| 292 | 3-(2-Methylsulfanyl-phenyl)-6-(3-piperidin-1-yl-propoxy)-imidazo[1,2-b]pyridazine | 5.07 | 382.0 | 383.0 |

| EXAMPLE No. | STRUCTURE | Retention time [min] | MW calc. | MW found |
|---|---|---|---|---|
| 293 | 6-(3-Piperidin-1-yl-propoxy)-3-(3-trifluoromethoxy-phenyl)-imidazo[1,2-b]pyridazine | 5.77 | 420.0 | 421.0 |
| 294 | 6-(3-Piperidin-1-yl-propoxy)-3-(3-trifluoromethyl-phenyl)-imidazo[1,2-b]pyridazine | 5.7 | 404.0 | 405.0 |
| 295 | 3-Biphenyl-3-yl-6-(3-piperidin-1-yl-propoxy)-imidazo[1,2-b]pyridazine | 5.92 | 412.0 | 413.0 |
| 296 | {3-[6-(3-Piperidin-1-yl-propoxy)-imidazo[1,2-b]pyridazin-3-yl]-phenyl}-methanol | 4.34 | 366.0 | 367.0 |

-continued

| EXAMPLE No. | STRUCTURE | Retention time [min] | MW calc. | MW found |
|---|---|---|---|---|
| 297 | 3-(3-Methylsulfanyl-phenyl)-6-(3-piperidin-1-yl-propoxy)-imidazo[1,2-b]pyridazine | 5.37 | 382.0 | 383.0 |
| 298 | 6-(3-Piperidin-1-yl-propoxy)-3-(2-trifluoromethyl-phenyl)-imidazo[1,2-b]pyridazine | 5.27 | 404.0 | 405.0 |
| 299 | 3-(2-Chloro-phenyl)-6-(3-piperidin-1-yl-propoxy)-imidazo[1,2-b]pyridazine | 4.94 | 370.0 | 371.0 |
| 300 | 6-(3-Piperidin-1-yl-propoxy)-3-(4-trifluoromethoxy-phenyl)-imidazo[1,2-b]pyridazine | 5.85 | 420.0 | 421.0 |

| EXAMPLE No. | STRUCTURE | Retention time [min] | MW calc. | MW found |
|---|---|---|---|---|
| 301 | 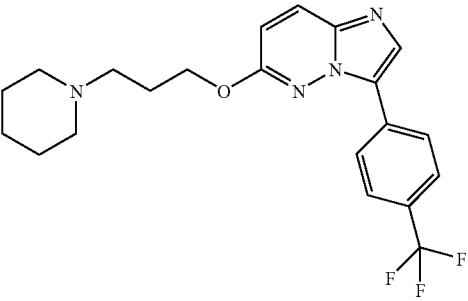 [SMILES: FC(F)(F)c1ccc(-c2cnc3ccc(OCCCN4CCCCC4)nn23)cc1]<br>6-(3-Piperidin-1-yl-propoxy)-3-(4-trifluoromethyl-phenyl)-imidazo[1,2-b]pyridazine | 5.78 | 404.0 | 405.0 |
| 302 | 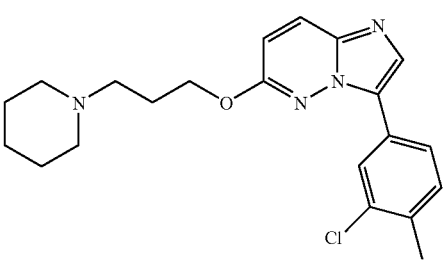 [SMILES: Cc1ccc(-c2cnc3ccc(OCCCN4CCCCC4)nn23)cc1Cl]<br>3-(3-Chloro-4-methyl-phenyl)-6-(3-piperidin-1-yl-propoxy)-imidazo[1,2-b]pyridazine | 5.62 | 384.0 | 385.0 |
| 303 | 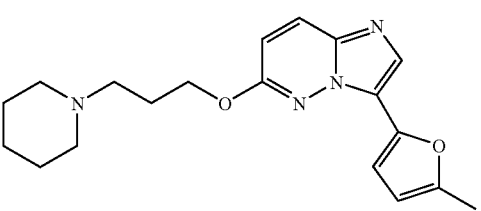 [SMILES: Cc1ccc(-c2cnc3ccc(OCCCN4CCCCC4)nn23)o1]<br>3-(5-Methyl-furan-2-yl)-6-(3-piperidin-1-yl-propoxy)-imidazo[1,2-b]pyridazine | 4.17 | 340.0 | 341.0 |
| 304 | 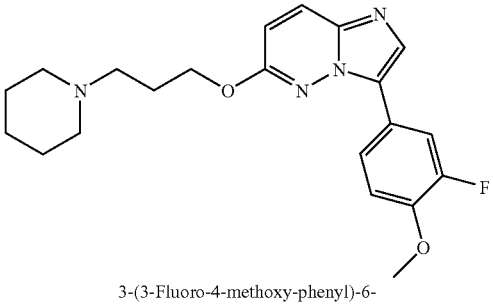<br>3-(3-Fluoro-4-methoxy-phenyl)-6-(3-piperidin-1-yl-propoxy)-imidazo[1,2-b]pyridazine | 5.09 | 384.0 | 385.0 |
| 305 | 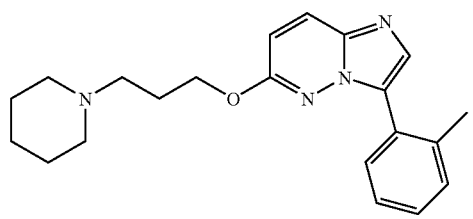 [SMILES: Cc1ccccc1-c1cnc2ccc(OCCCN3CCCCC3)nn12]<br>6-(3-Piperidin-1-yl-propoxy)-3-o-tolyl-imidazo[1,2-b]pyridazine | 4.99 | 350.0 | 351.0 |

| EXAMPLE No. | STRUCTURE | Retention time [min] | MW calc. | MW found |
|---|---|---|---|---|
| 306 | 3-(3-Chloro-4-fluoro-phenyl)-6-(3-piperidin-1-yl-propoxy)-imidazo[1,2-b]pyridazine | 5.47 | 388.0 | 389.0 |
| 307 | 3-(3-Methoxy-phenyl)-6-(3-piperidin-1-yl-propoxy)-imidazo[1,2-b]pyridazine | 4.92 | 366.0 | 367.0 |
| 308 | 3-(5-Chloro-thiophen-2-yl)-6-(3-piperidin-1-yl-propoxy)-imidazo[1,2-b]pyridazine | 5.39 | 376.0 | 377.0 |
| 309 | 3-[6-(3-Piperidin-1-yl-propoxy)-imidazo[1,2-b]pyridazin-3-yl]-benzonitrile | 4.89 | 361.0 | 362.0 |
| 310 | 3-(4-Methyl-thiophen-2-yl)-6-(3-piperidin-1-yl-propoxy)-imidazo[1,2-b]pyridazine | 5.19 | 356.0 | 357.0 |

| EXAMPLE No. | STRUCTURE | Retention time [min] | MW calc. | MW found |
|---|---|---|---|---|
| 311 | 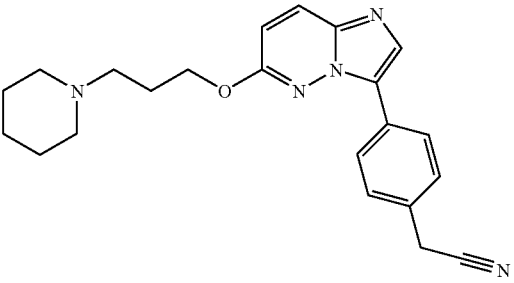 [SMILES: N#CCc1ccc(-c2cnc3ccc(OCCCN4CCCCC4)nn23)cc1]<br>{4-[6-(3-Piperidin-1-yl-propoxy)-imidazo[1,2-b]pyridazin-3-yl]-phenyl}-acetonitrile | 4.7 | 375.0 | 376.0 |
| 312 | 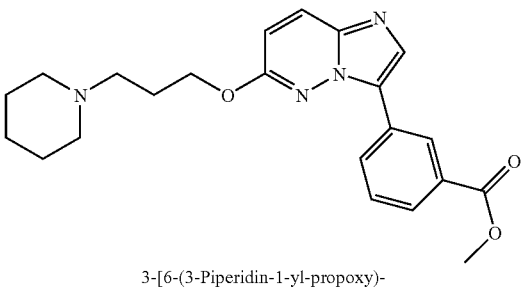<br>3-[6-(3-Piperidin-1-yl-propoxy)-imidazo[1,2-b]pyridazin-3-yl]-benzoic acid methyl ester | 5.07 | 394.0 | 395.0 |
| 313 | 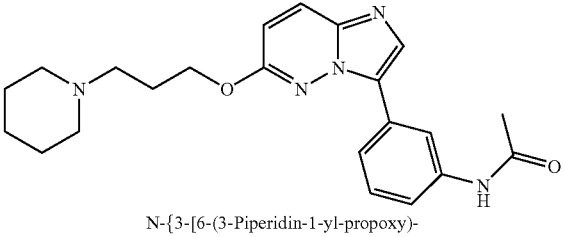<br>N-{3-[6-(3-Piperidin-1-yl-propoxy)-imidazo[1,2-b]pyridazin-3-yl]-phenyl}-acetamide | 4.4 | 393.0 | 394.0 |
| 314 | 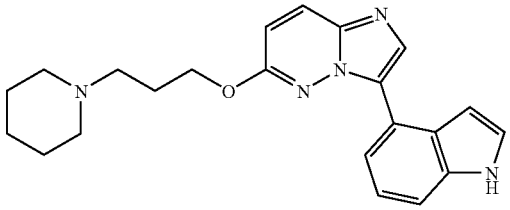 [SMILES: c1cc(-c2cnc3ccc(OCCCN4CCCCC4)nn23)c2cc[nH]c2c1]<br>3-(1H-Indol-4-yl)-6-(3-piperidin-1-yl-propoxy)-imidazo[1,2-b]pyridazine | 4.74 | 375.0 | 376.0 |
| 315 | 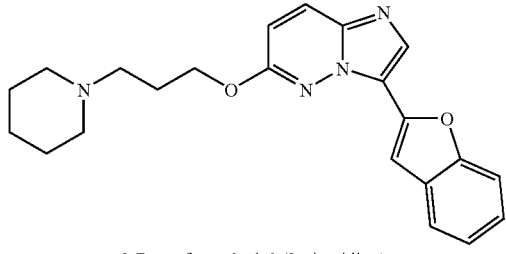<br>3-Benzofuran-2-yl-6-(3-piperidin-1-yl-propoxy)-imidazo[1,2-b]pyridazine | 5.78 | 376.0 | 377.0 |

-continued

| EXAMPLE No. | STRUCTURE | Retention time [min] | MW calc. | MW found |
|---|---|---|---|---|
| 316 | 6-(3-Piperidin-1-yl-propoxy)-3-p-tolyl-imidazo[1,2-b]pyridazine | 5.2 | 350.0 | 351.0 |
| 317 | 3-(3-Fluoro-phenyl)-6-(3-piperidin-1-yl-propoxy)-imidazo[1,2-b]pyridazine | 5.02 | 354.0 | 355.0 |
| 318 | 3-Benzo[b]thiophen-3-yl-6-(3-piperidin-1-yl-propoxy)-imidazo[1,2-b]pyridazine | 5.37 | 392.0 | 393.0 |
| 319 | 3-(4-Chloro-phenyl)-6-(3-piperidin-1-yl-propoxy)-imidazo[1,2-b]pyridazine | 5.39 | 370.0 | 371.0 |
| 320 | 3-(6-Fluoro-5-methyl-pyridin-3-yl)-6-(3-piperidin-1-yl-propoxy)-imidazo[1,2-b]pyridazine | 4.8 | 369.0 | 370.0 |

-continued

| EXAMPLE No. | STRUCTURE | Retention time [min] | MW calc. | MW found |
|---|---|---|---|---|
| 321 | 6-(3-Piperidin-1-yl-propoxy)-3-(2-trifluoromethoxy-phenyl)-imidazo[1,2-b]pyridazine | 5.39 | 420.0 | 421.0 |
| 322 | 3-(4-Ethanesulfonyl-phenyl)-6-(3-piperidin-1-yl-propoxy)-imidazo[1,2-b]pyridazine | 4.8 | 428.0 | 429.0 |
| 323 | 6-(3-Piperidin-1-yl-propoxy)-3-(3-pyrrolidin-1-yl-phenyl)-imidazo[1,2-b]pyridazine | 5.37 | 405.0 | 406.0 |
| 324 | 3-(4-Cyclopropylmethoxy-phenyl)-6-(3-piperidin-1-yl-propoxy)-imidazo[1,2-b]pyridazine | 5.64 | 406.0 | 407.0 |

-continued

| EXAMPLE No. | STRUCTURE | Retention time [min] | MW calc. | MW found |
|---|---|---|---|---|
| 325 | Dimethyl-[4-(3-thiophen-3-yl-imidazo [1,2-b]pyridazin-6-yloxy)-butyl]-amine | 4.59 | 316.0 | 317.0 |
| 326 | Dimethyl-[4-(3-naphthalen-1-yl-imidazo [1,2-b]pyridazin-6-yloxy)-butyl]-amine | 5.17 | 360.0 | 361.0 |
| 327 | {4-[3-(4-Methoxy-phenyl)-imidazo [1,2-b]pyridazin-6-yloxy]-butyl}- dimethyl-amine | 4.87 | 340.0 | 341.0 |
| 328 | Dimethyl-[4-(3-m-tolyl-imidazo[1,2- b]pyridazin-6-yloxy)-butyl]-amine | 5.09 | 324.0 | 325.0 |
| 329 | {4-[3-(4-Fluoro-phenyl)-imidazo [1,2-b]pyridazin-6-yloxy]-butyl}- dimethyl-amine | 4.9 | 328.0 | 329.0 |

| EXAMPLE No. | STRUCTURE | Retention time [min] | MW calc. | MW found |
|---|---|---|---|---|
| 330 | 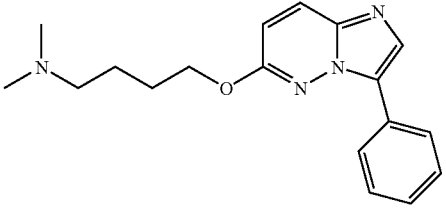 [SMILES: CN(C)CCCCOc1ccc2ncc(-c3ccccc3)n2n1]<br>Dimethyl-[4-(3-phenyl-imidazo[1,2-b]pyridazin-6-yloxy)-butyl]-amine | 4.74 | 310.0 | 311.0 |
| 331 | 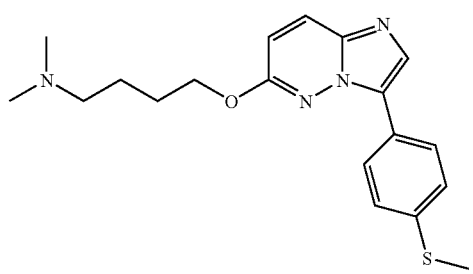<br>Dimethyl-{4-[3-(4-methylsulfanyl-phenyl)-imidazo[1,2-b]pyridazin-6-yloxy]-butyl}-amine | 5.27 | 356.0 | 357.0 |
| 332 | 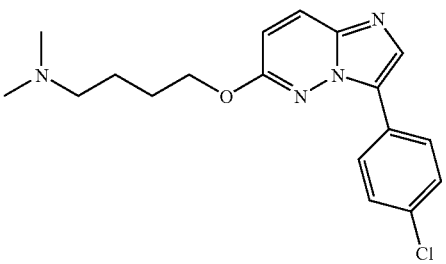 [SMILES: CN(C)CCCCOc1ccc2ncc(-c3ccc(Cl)cc3)n2n1]<br>{4-[3-(4-Chloro-phenyl)-imidazo[1,2-b]pyridazin-6-yloxy]-butyl}-dimethyl-amine | 5.17 | 344.0 | 345.0 |
| 333 | 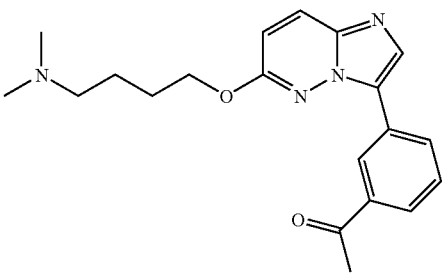 [SMILES: CC(=O)c1cccc(-c2cnc3ccc(OCCCCN(C)C)nn23)c1]<br>1-{3-[6-(4-Dimethylamino-butoxy)-imidazo[1,2-b]pyridazin-3-yl]-phenyl}-ethanone | 4.67 | 352.0 | 353.0 |
| 334 | 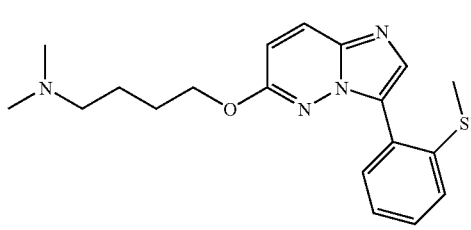 [SMILES: CSc1ccccc1-c1cnc2ccc(OCCCCN(C)C)nn12]<br>Dimethyl-{4-[3-(2-methylsulfanyl-phenyl)-imidazo[1,2-b]pyridazin-6-yloxy]-butyl}-amine | 4.97 | 356.0 | 357.0 |

| EXAMPLE No. | STRUCTURE | Retention time [min] | MW calc. | MW found |
|---|---|---|---|---|
| 335 | Dimethyl-{4-[3-(3-trifluoromethoxy-phenyl)-imidazo[1,2-b]pyridazin-6-yloxy]-butyl}-amine | 5.6 | 394.0 | 395.0 |
| 336 | Dimethyl-{4-[3-(3-trifluoromethyl-phenyl)-imidazo[1,2-b]pyridazin-6-yloxy]-butyl}-amine | 5.4 | 378.0 | 379.0 |
| 337 | [4-(3-Biphenyl-3-yl-imidazo[1,2-b]pyridazin-6-yloxy)-butyl]-dimethyl-amine | 5.89 | 386.0 | 387.0 |
| 338 | {3-[6-(4-Dimethylamino-butoxy)-imidazo[1,2-b]pyridazin-3-yl]-phenyl}-methanol | 4.22 | 340.0 | 341.0 |

| EXAMPLE No. | STRUCTURE | Retention time [min] | MW calc. | MW found |
|---|---|---|---|---|
| 339 | Dimethyl-{4-[3-(3-methylsulfanyl-phenyl)-imidazo[1,2-b]pyridazin-6-yloxy]-butyl}-amine | 5.24 | 356.0 | 357.0 |
| 340 | Dimethyl-{4-[3-(2-trifluoromethyl-phenyl)-imidazo[1,2-b]pyridazin-6-yloxy]-butyl}-amine | 5.07 | 378.0 | 379.0 |
| 341 | Dimethyl-{4-[3-(4-trifluoromethoxy-phenyl)-imidazo[1,2-b]pyridazin-6-yloxy]-butyl}-amine | 5.7 | 394.0 | 395.0 |
| 342 | Dimethyl-{4-[3-(4-trifluoromethyl-phenyl)-imidazo[1,2-b]pyridazin-6-yloxy]-butyl}-amine | 5.6 | 378.0 | 379.0 |

| EXAMPLE No. | STRUCTURE | Retention time [min] | MW calc. | MW found |
|---|---|---|---|---|
| 343 | 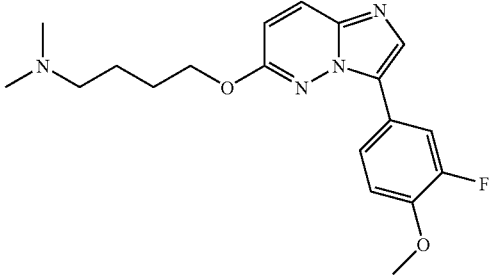 [SMILES: COc1ccc(-c2cnc3ccc(OCCCCN(C)C)nn23)cc1F]<br>{4-[3-(3-Fluoro-4-methoxy-phenyl)-imidazo[1,2-b]pyridazin-6-yloxy]-butyl}-dimethyl-amine | 4.99 | 358.0 | 359.0 |
| 344 | 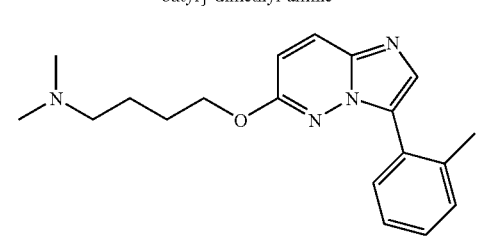<br>Dimethyl-[4-(3-o-tolyl-imidazo[1,2-b]pyridazin-6-yloxy)-butyl]-amine | 4.89 | 324.0 | 325.0 |
| 345 | 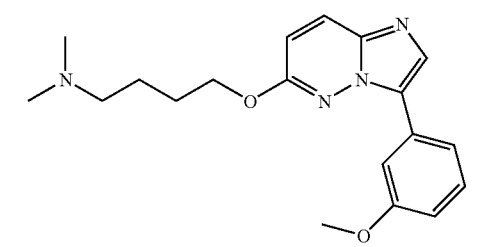 [SMILES: COc1cccc(-c2cnc3ccc(OCCCCN(C)C)nn23)c1]<br>{4-[3-(3-Methoxy-phenyl)-imidazo[1,2-b]pyridazin-6-ylIoxy]-butyl}-dimethyl-amine | 4.9 | 340.0 | 341.0 |
| 346 | 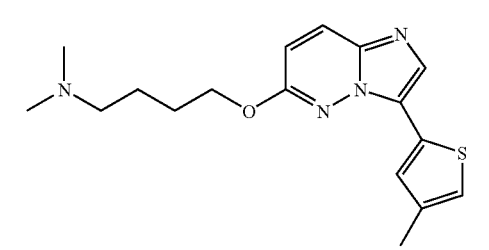 [SMILES: Cc1csc(-c2cnc3ccc(OCCCCN(C)C)nn23)c1]<br>Dimethyl-{4-[3-(4-methyl-thiophen-2-yl)-imidazo[1,2-b]pyridazin-6-yloxy]-butyl}-amine | 5.09 | 330.0 | 331.0 |
| 347 | 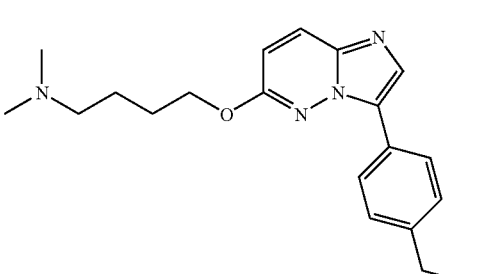 [SMILES: Cc1ccc(-c2cnc3ccc(OCCCCN(C)C)nn23)cc1]<br>{4-[6-(4-Dimethylamino-butoxy)-imidazo[1,2-b]pyridazin-3-yl]-phenyl}-acetonitrile | 4.59 | 349.0 | 350.0 |

-continued

| EXAMPLE No. | STRUCTURE | Retention time [min] | MW calc. | MW found |
|---|---|---|---|---|
| 348 | 3-[6-(4-Dimethylamino-butoxy)-imidazo [1,2-b]pyridazin-3-yl]-benzoic acid methyl ester | 4.95 | 368.0 | 369.0 |
| 349 | N-{3-[6-(4-Dimethylamino-butoxy)-imidazo [1,2-b]pyridazin-3-yl]-phenyl}-acetamide | 4.2 | 367.0 | 368.0 |
| 350 | {4-[3-(1H-Indol-4-yl)-imidazo[1,2-b] pyridazin-6-yloxy]-butyl}-dimethyl-amine | 4.65 | 349.0 | 350.0 |
| 351 | Dimethyl-[4-(3-p-tolyl-imidazo[1,2-b] pyridazin-6-yloxy)-butyl]-amine | 5.09 | 324.0 | 325.0 |
| 352 | Dimethyl-{4-[3-(2-trifluoromethoxy-phenyl)-imidazo[1,2-b]pyridazin-6-yloxy]-butyl}-amine | 5.35 | 394.0 | 395.0 |

-continued
| EXAMPLE No. | STRUCTURE | Retention time [min] | MW calc. | MW found |
|---|---|---|---|---|
| 353 | 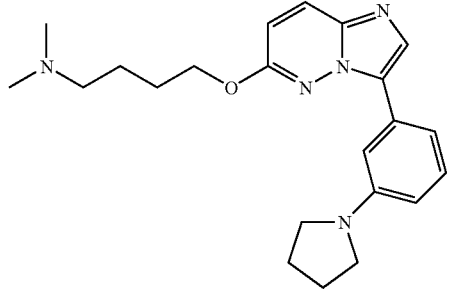 [SMILES: CN(C)CCCCOc1ccc2ncc(-c3cccc(N4CCCC4)c3)n2n1]<br>Dimethyl-{4-[3-(3-pyrrolidin-1-yl-phenyl)-imidazo[1,2-b]pyridazin-6-yloxy]-butyl}-amine | 5.17 | 379.0 | 380.0 |
| 354 | 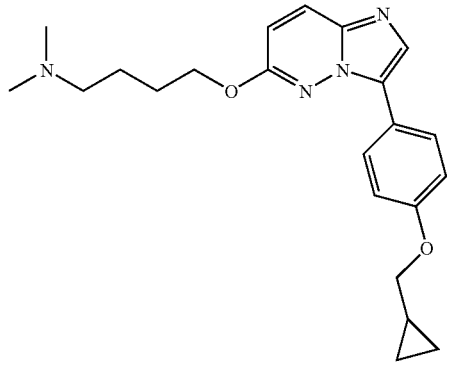 [SMILES: CN(C)CCCCOc1ccc2ncc(-c3ccc(OCC4CC4)cc3)n2n1]<br>{4-[3-(4-Cyclopropylmethoxy-phenyl)-imidazo[1,2-b]pyridazin-6-yloxy]-butyl}-dimethyl-amine | 5.62 | 380.0 | 381.0 |
The following are prepared in the manner described:
| EXAMPLE No. | Structure | Retention time [min] | MW calc. | MW found |
|---|---|---|---|---|
| 355 | 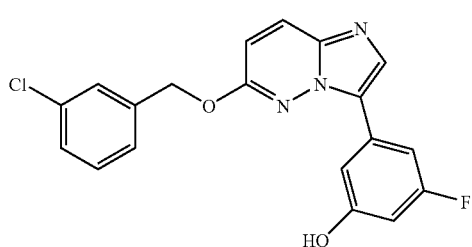 [SMILES: Oc1cc(F)cc(-c2cnc3ccc(OCc4cccc(Cl)c4)nn23)c1] | 7.51 | 369 | 370 |

| EXAMPLE No. | Structure | Retention time [min] | MW calc. | MW found |
|---|---|---|---|---|
| 356 | 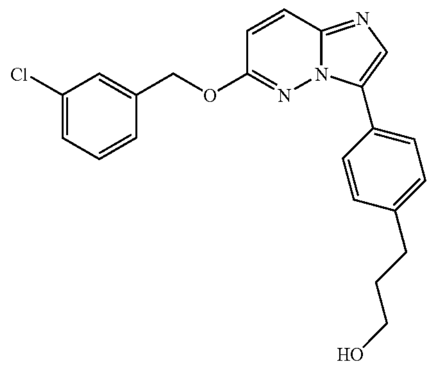 [SMILES: OCCCc1ccc(-c2cnc3ccc(OCc4cccc(Cl)c4)nn23)cc1] | 7.03 | 393 | 394 |
| 357 | 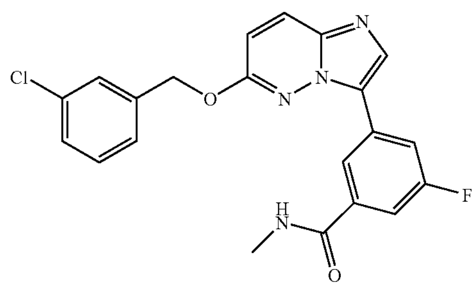 [SMILES: CNC(=O)c1cc(F)cc(-c2cnc3ccc(OCc4cccc(Cl)c4)nn23)c1] | 7.56 | 410 | 411 |
| 358 | 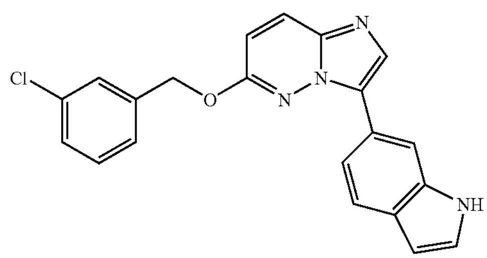 [SMILES: Clc1cccc(COc2ccc3ncc(-c4ccc5cc[nH]c5c4)n3n2)c1] | 7.5 | 374 | 375 |
| 359 | 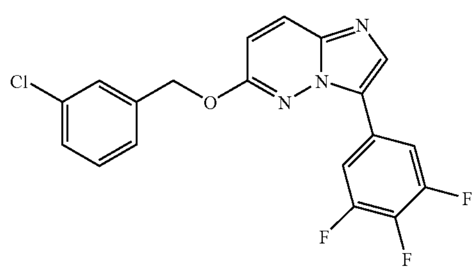 [SMILES: Fc1cc(-c2cnc3ccc(OCc4cccc(Cl)c4)nn23)cc(F)c1F] | 10.16 | 389 | 390 |
| 340 | 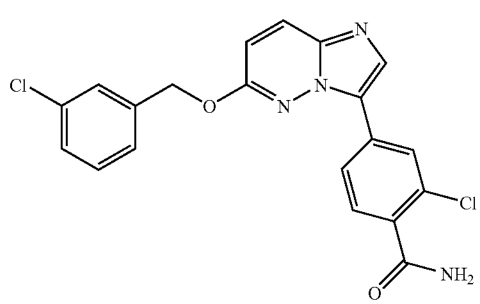 [SMILES: NC(=O)c1ccc(-c2cnc3ccc(OCc4cccc(Cl)c4)nn23)cc1Cl] | 6.92 | 413 | 413 |

-continued

| EXAMPLE No. | Structure | Retention time [min] | MW calc. | MW found |
|---|---|---|---|---|
| 341 | 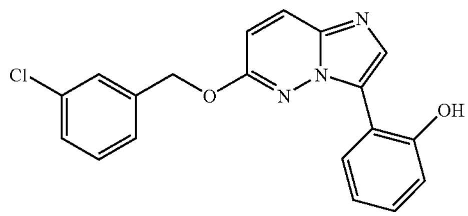 [SMILES: Oc1ccccc1-c1cnc2ccc(OCc3cccc(Cl)c3)nn12] | 7.01 | 351 | 352 |
| 342 | 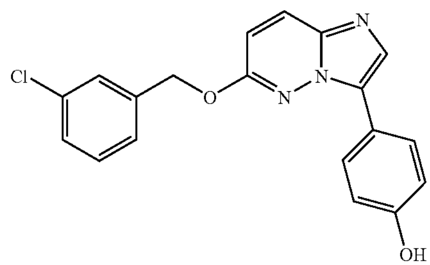 [SMILES: Oc1ccc(-c2cnc3ccc(OCc4cccc(Cl)c4)nn23)cc1] | 6.85 | 351 | 352 |
| 343 | 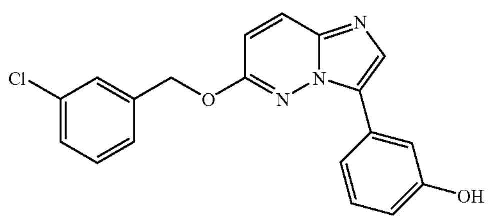 [SMILES: Oc1cccc(-c2cnc3ccc(OCc4cccc(Cl)c4)nn23)c1] | 7.04 | 351 | 352 |
| 344 | 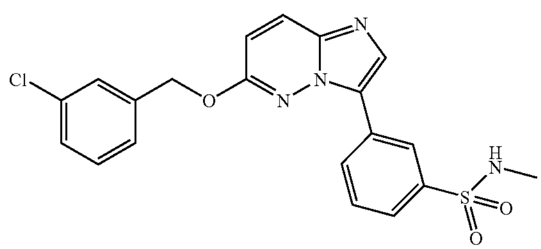 [SMILES: CNS(=O)(=O)c1cccc(-c2cnc3ccc(OCc4cccc(Cl)c4)nn23)c1] | 7.56 | 428 | 429 |
| 345 | 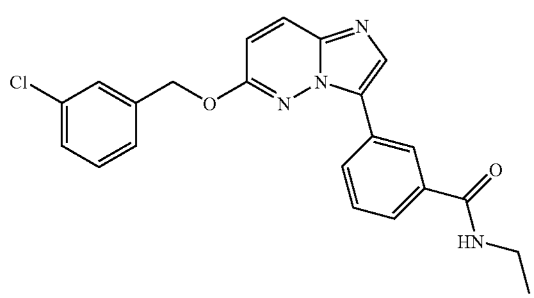 [SMILES: CCNC(=O)c1cccc(-c2cnc3ccc(OCc4cccc(Cl)c4)nn23)c1] | 7.07 | 406 | 407 |
| 346 | 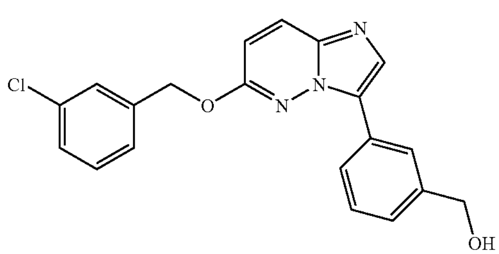 [SMILES: OCc1cccc(-c2cnc3ccc(OCc4cccc(Cl)c4)nn23)c1] | 6.83 | 365 | 366 |

-continued

| EXAMPLE No. | Structure | Retention time [min] | MW calc. | MW found |
|---|---|---|---|---|
| 347 | 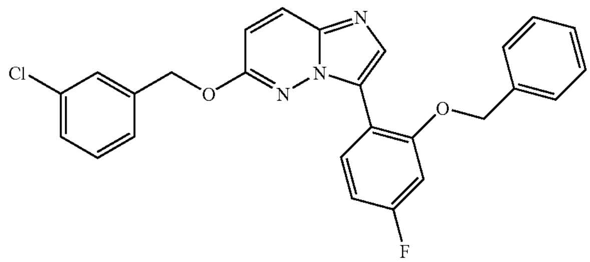 [SMILES: Fc1ccc(-c2cnc3ccc(OCc4cccc(Cl)c4)nn23)c(OCc2ccccc2)c1] | 8.87 | 459 | 460 |
| 348 | 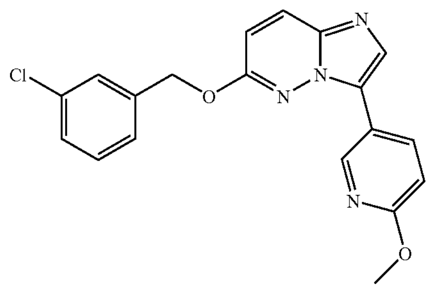 [SMILES: COc1ccc(-c2cnc3ccc(OCc4cccc(Cl)c4)nn23)cn1] | 7.68 | 366 | 367 |
| 349 | 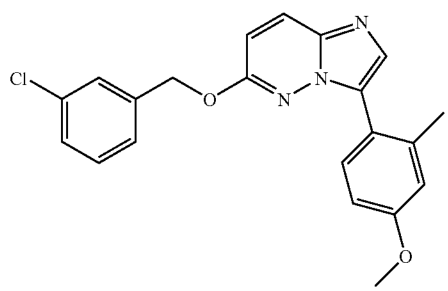 [SMILES: COc1ccc(-c2cnc3ccc(OCc4cccc(Cl)c4)nn23)c(C)c1] | 7.67 | 379 | 380 |
| 350 | 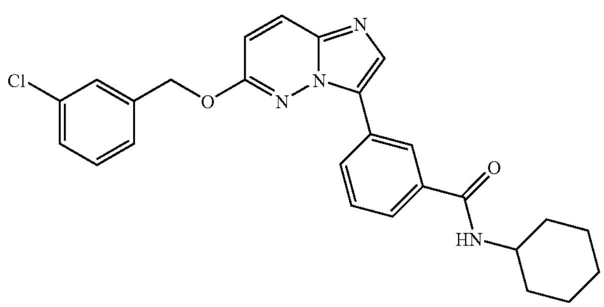 [SMILES: O=C(NC1CCCCC1)c1cccc(-c2cnc3ccc(OCc4cccc(Cl)c4)nn23)c1] | 8.48 | 460 | 461 |
| 351 | 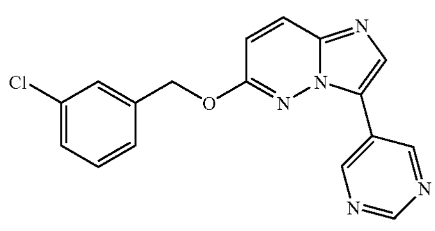 [SMILES: Clc1cccc(COc2ccc3ncc(-c4cncnc4)n3n2)c1] | 9.68 | 337 | 338 |

-continued

| EXAMPLE No. | Structure | Retention time [min] | MW calc. | MW found |
|---|---|---|---|---|
| 352 | 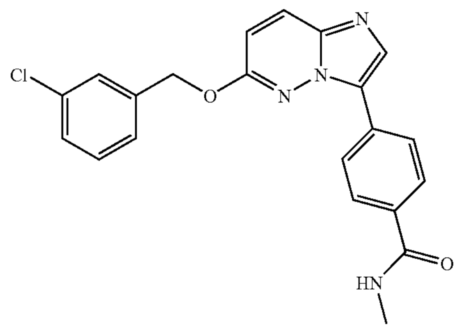 [SMILES: CNC(=O)c1ccc(-c2cnc3ccc(OCc4cccc(Cl)c4)nn23)cc1] | 6.72 | 392 | 393 |
| 353 | 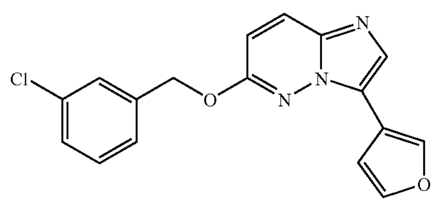 [SMILES: Clc1cccc(COc2ccc3ncc(-c4ccoc4)n3n2)c1] | 7.73 | 325 | 326 |
| 354 | 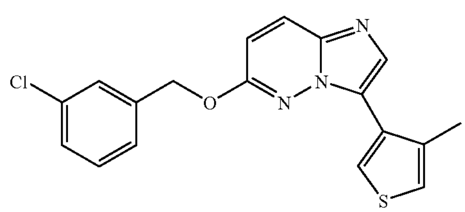 [SMILES: Cc1cscc1-c1cnc2ccc(OCc3cccc(Cl)c3)nn12] | 7.95 | 355 | 356 |
| 355 | 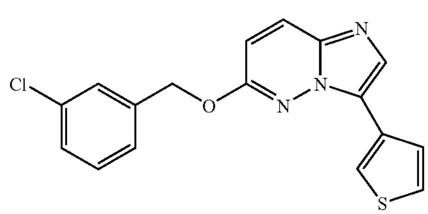 [SMILES: Clc1cccc(COc2ccc3ncc(-c4ccsc4)n3n2)c1] | 8.01 | 341 | 342 |
| 356 | 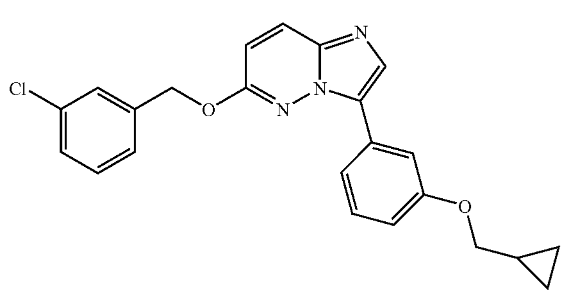 [SMILES: Clc1cccc(COc2ccc3ncc(-c4cccc(OCC5CC5)c4)n3n2)c1] | 8.98 | 405 | 406 |

| EXAMPLE No. | Structure | Retention time [min] | MW calc. | MW found |
|---|---|---|---|---|
| 357 | 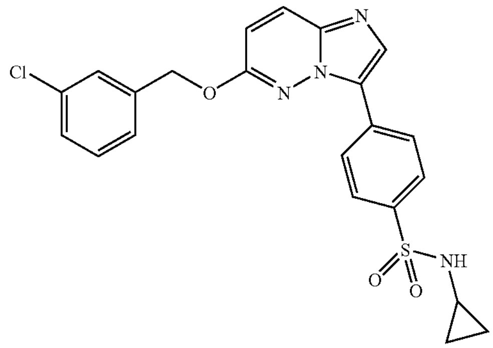 [SMILES: O=S(=O)(NC1CC1)c1ccc(-c2cnc3ccc(OCc4cccc(Cl)c4)nn23)cc1] | 8.02 | 454 | 455 |
| 358 | 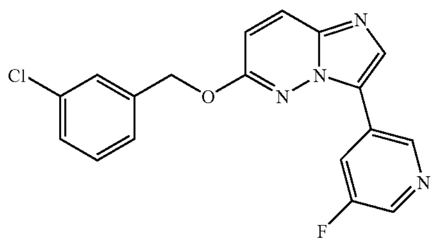 [SMILES: Fc1cncc(-c2cnc3ccc(OCc4cccc(Cl)c4)nn23)c1] | 8.38 | 354 | 355 |
| 359 | 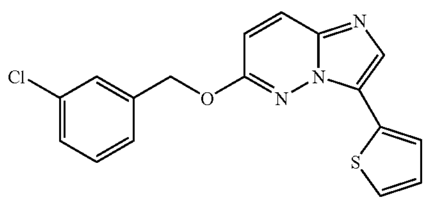 [SMILES: Clc1cccc(COc2ccc3ncc(-c4cccs4)n3n2)c1] | 9.7 | 341 | 342 |
| 360 | 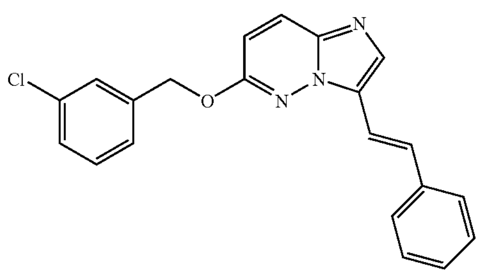 [SMILES: Clc1cccc(COc2ccc3ncc(/C=C/c4ccccc4)n3n2)c1] | 8.99 | 361 | 362 |
| 361 | 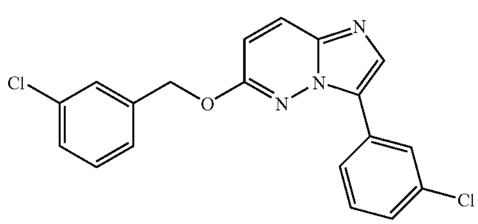 [SMILES: Clc1cccc(COc2ccc3ncc(-c4cccc(Cl)c4)n3n2)c1] | 9.5 | 370 | 370 |
| 362 | 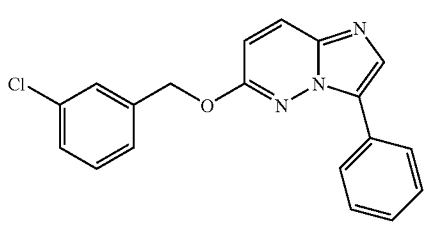 [SMILES: Clc1cccc(COc2ccc3ncc(-c4ccccc4)n3n2)c1] | 8.02 | 335 | 336 |

| EXAMPLE No. | Structure | Retention time [min] | MW calc. | MW found |
|---|---|---|---|---|
| 363 | 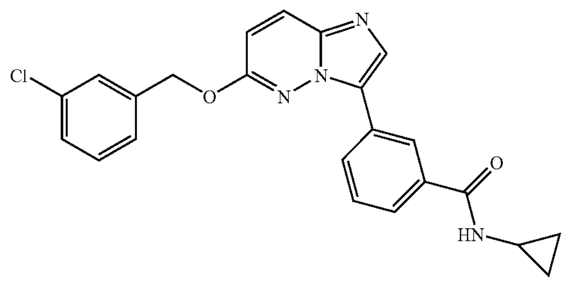 [SMILES: O=C(NC1CC1)c1cccc(-c2cnc3ccc(OCc4cccc(Cl)c4)nn23)c1] | 7.25 | 418 | 419 |
| 364 | 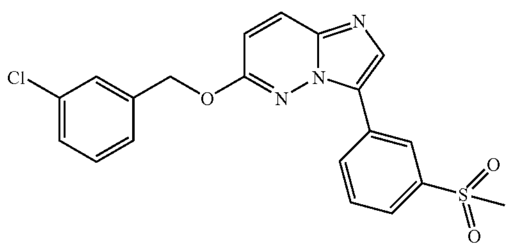 [SMILES: CS(=O)(=O)c1cccc(-c2cnc3ccc(OCc4cccc(Cl)c4)nn23)c1] | 7.71 | 413 | 414 |
| 365 | 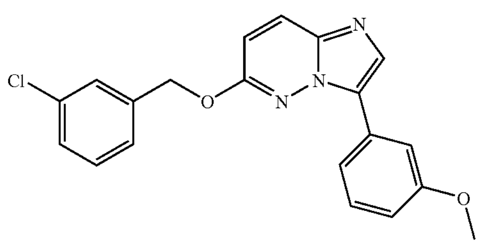 [SMILES: COc1cccc(-c2cnc3ccc(OCc4cccc(Cl)c4)nn23)c1] | 8.13 | 365 | 366 |
| 366 | 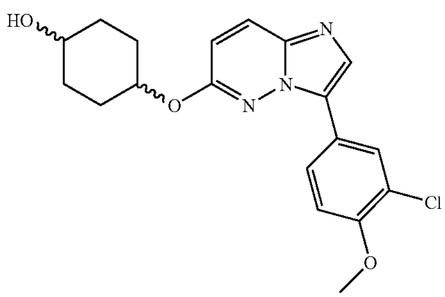 [SMILES: COc1ccc(-c2cnc3ccc(OC4CCC(O)CC4)nn23)cc1Cl] | 5.98 | 373 | 374 |
| 367 | 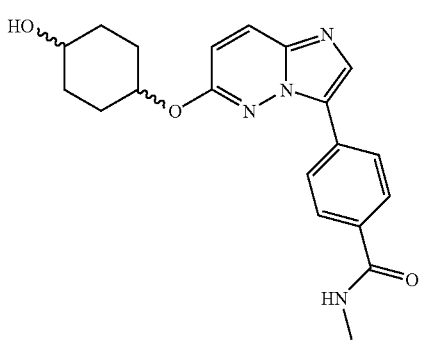 [SMILES: CNC(=O)c1ccc(-c2cnc3ccc(OC4CCC(O)CC4)nn23)cc1] | 4.66 | 366 | 367 |

-continued

| EXAMPLE No. | Structure | Retention time [min] | MW calc. | MW found |
|---|---|---|---|---|
| 368 | 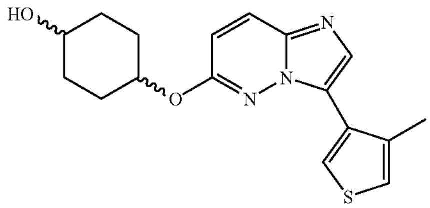 [SMILES: Cc1cscc1-c1cnc2ccc(OC3CCC(O)CC3)nn12] | 5.56 | 329 | 330 |
| 369 | 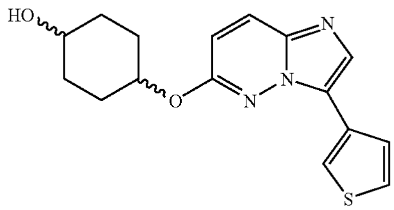 [SMILES: OC1CCC(Oc2ccc3ncc(-c4ccsc4)n3n2)CC1] | 5.43 | 315 | 316 |
| 370 | 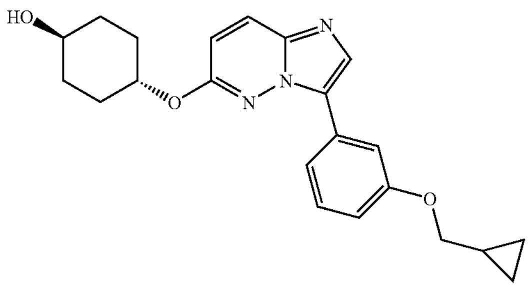 | 6.29 | 379 | 380 |
| 371 | 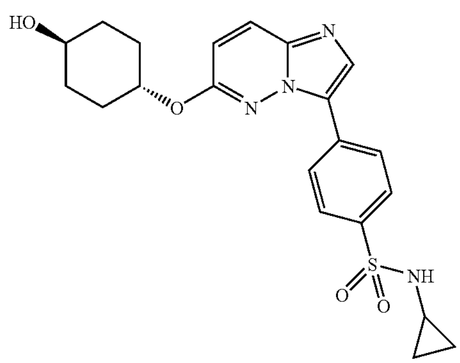 [SMILES: O=S(=O)(NC1CC1)c1ccc(-c2cnc3ccc(O[C@H]4CC[C@H](O)CC4)nn23)cc1] | 5.51 | 428 | 429 |
| 372 | 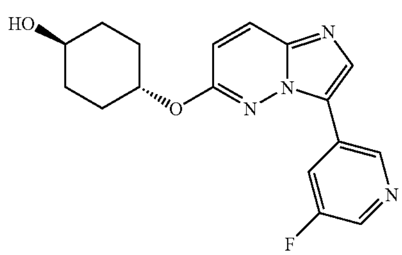 [SMILES: O[C@H]1CC[C@H](Oc2ccc3ncc(-c4cncc(F)c4)n3n2)CC1] | 4.91 | 328 | 329 |

-continued

| EXAMPLE No. | Structure | Retention time [min] | MW calc. | MW found |
|---|---|---|---|---|
| 373 | 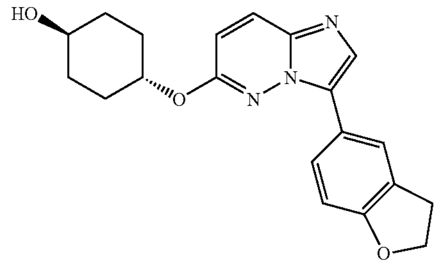 [SMILES: O[C@H]1CC[C@H](Oc2ccc3ncc(-c4ccc5c(c4)CCO5)n3n2)CC1] | 5.37 | 351 | 352 |
| 374 | 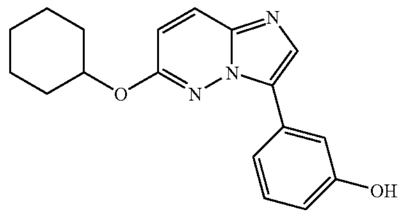 [SMILES: Oc1cccc(-c2cnc3ccc(OC4CCCCC4)nn23)c1] | 6.61 | 309 | 310 |
| 375 | 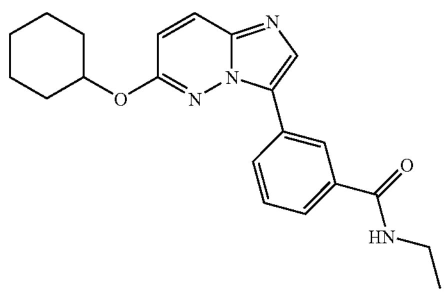 [SMILES: CCNC(=O)c1cccc(-c2cnc3ccc(OC4CCCCC4)nn23)c1] | 6.64 | 364 | 365 |
| 376 | 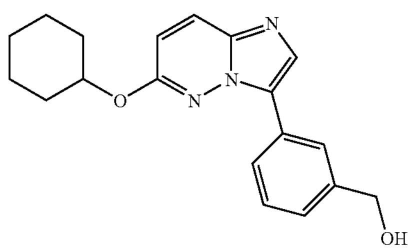 [SMILES: OCc1cccc(-c2cnc3ccc(OC4CCCCC4)nn23)c1] | 6.4 | 323 | 324 |
| 377 | 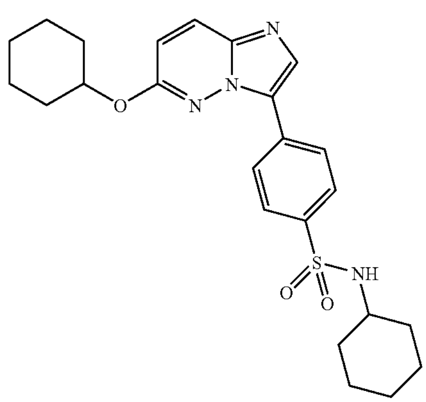 [SMILES: O=S(=O)(NC1CCCCC1)c1ccc(-c2cnc3ccc(OC4CCCCC4)nn23)cc1] | 8.71 | 454 | 455 |

-continued
| EXAMPLE No. | Structure | Retention time [min] | MW calc. | MW found |
|---|---|---|---|---|
| 378 | 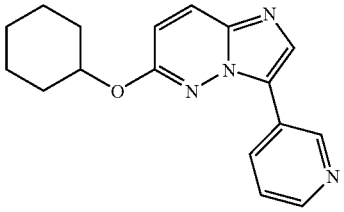 [SMILES: c1cncc(-c2cnc3ccc(OC4CCCCC4)nn23)c1] | 5.83 | 294 | 295 |
| 379 | 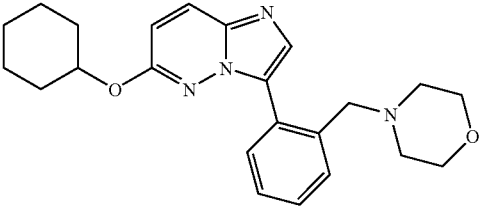 [SMILES: c1ccc(-c2cnc3ccc(OC4CCCCC4)nn23)c(CN2CCOCC2)c1] | 5.29 | 392 | 393 |
| 380 | 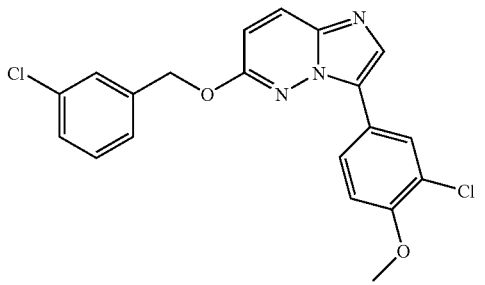 [SMILES: COc1ccc(-c2cnc3ccc(OCc4cccc(Cl)c4)nn23)cc1Cl] | 8.59 | 400 | 400 |
| 381 | 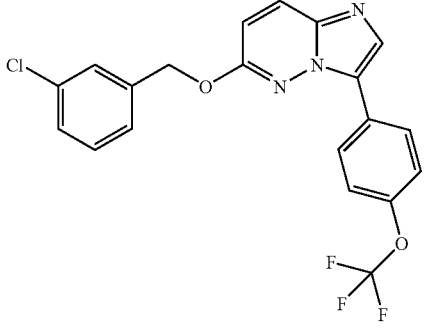 [SMILES: FC(F)(F)Oc1ccc(-c2cnc3ccc(OCc4cccc(Cl)c4)nn23)cc1] | 9.63 | 419 | 420 |
| 382 | 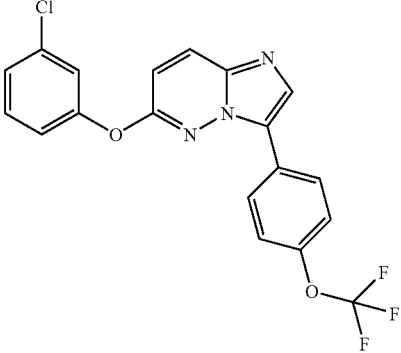 [SMILES: FC(F)(F)Oc1ccc(-c2cnc3ccc(Oc4cccc(Cl)c4)nn23)cc1] | 11.19 | 405 | 406 |

-continued

| EXAMPLE No. | Structure | Retention time [min] | MW calc. | MW found |
|---|---|---|---|---|
| 383 | 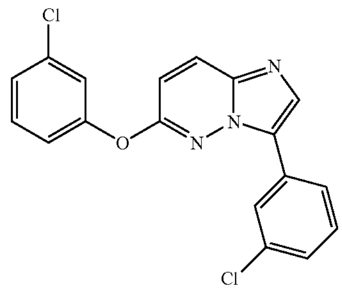 [SMILES: Clc1cccc(Oc2ccc3ncc(-c4cccc(Cl)c4)n3n2)c1] | 11.01 | 356 | 356 |
| 384 | 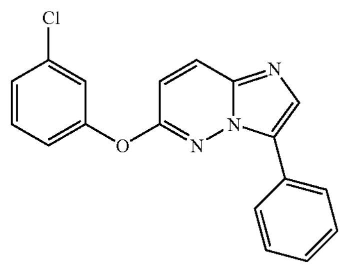 [SMILES: Clc1cccc(Oc2ccc3ncc(-c4ccccc4)n3n2)c1] | 9.48 | 321 | 322 |
| 385 | 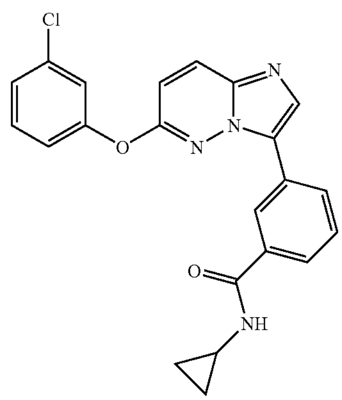 [SMILES: O=C(NC1CC1)c1cccc(-c2cnc3ccc(Oc4cccc(Cl)c4)nn23)c1] | 7.86 | 404 | 405 |
| 386 | 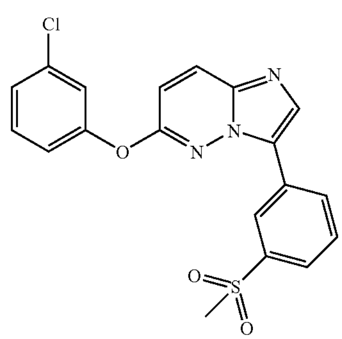 [SMILES: CS(=O)(=O)c1cccc(-c2cnc3ccc(Oc4cccc(Cl)c4)nn23)c1] | 8.2 | 399 | 400 |
| 387 | 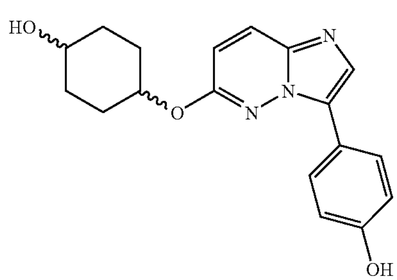 [SMILES: Oc1ccc(-c2cnc3ccc(OC4CCC(O)CC4)nn23)cc1] | 4.7 | 325 | 326 |

| EXAMPLE No. | Structure | Retention time [min] | MW calc. | MW found |
|---|---|---|---|---|
| 388 | 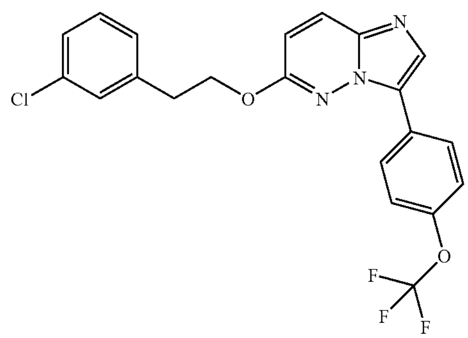 [SMILES: FC(F)(F)Oc1ccc(-c2cnc3ccc(OCCc4cccc(Cl)c4)nn23)cc1] | 10.32 | 433 | 434 |
| 389 | 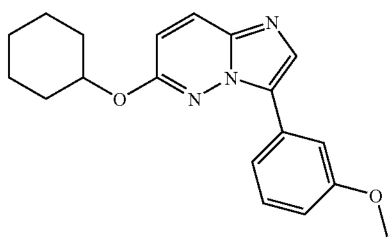 [SMILES: COc1cccc(-c2cnc3ccc(OC4CCCCC4)nn23)c1] | 7.88 | 323 | 324 |
| 390 | 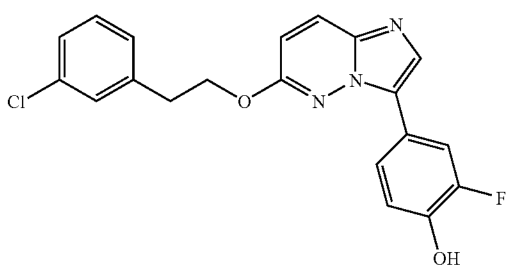 [SMILES: Oc1ccc(-c2cnc3ccc(OCCc4cccc(Cl)c4)nn23)cc1F] | 7.27 | 383 | 384 |
| 391 | 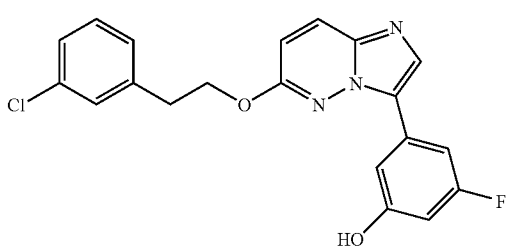 [SMILES: Oc1cc(F)cc(-c2cnc3ccc(OCCc4cccc(Cl)c4)nn23)c1] | 8.02 | 383 | 384 |
| 392 | 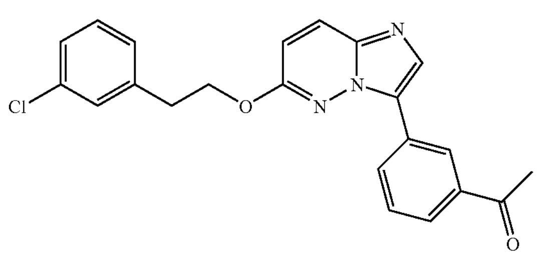 [SMILES: CC(=O)c1cccc(-c2cnc3ccc(OCCc4cccc(Cl)c4)nn23)c1] | 8.66 | 391 | 392 |

-continued

| EXAMPLE No. | Structure | Retention time [min] | MW calc. | MW found |
|---|---|---|---|---|
| 393 | 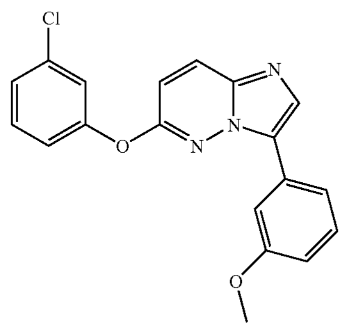 [SMILES: COc1cccc(-c2cnc3ccc(Oc4cccc(Cl)c4)nn23)c1] | 9.52 | 351 | 352 |
| 394 | 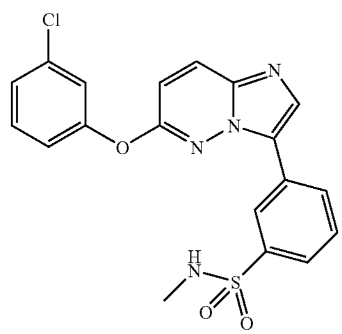 [SMILES: CNS(=O)(=O)c1cccc(-c2cnc3ccc(Oc4cccc(Cl)c4)nn23)c1] | 8.25 | 414 | 415 |
| 395 | 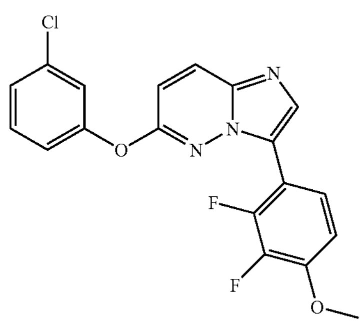 [SMILES: COc1ccc(-c2cnc3ccc(Oc4cccc(Cl)c4)nn23)c(F)c1F] | 10.18 | 387 | 388 |
| 396 | 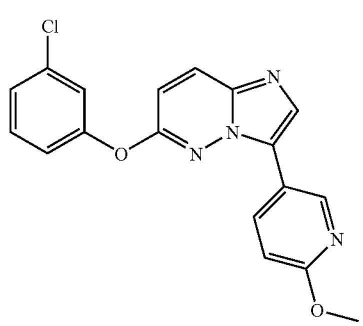 [SMILES: COc1ccc(-c2cnc3ccc(Oc4cccc(Cl)c4)nn23)cn1] | 9.16 | 352 | 353 |

-continued

| EXAMPLE No. | Structure | Retention time [min] | MW calc. | MW found |
|---|---|---|---|---|
| 397 | 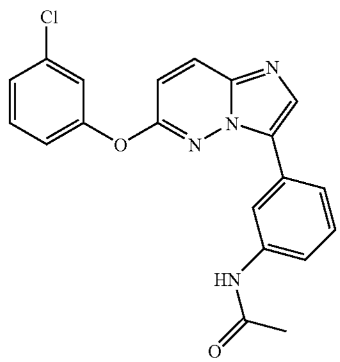 [SMILES: CC(=O)Nc1cccc(-c2cnc3ccc(Oc4cccc(Cl)c4)nn23)c1] | 7.03 | 378 | 379 |
| 398 | 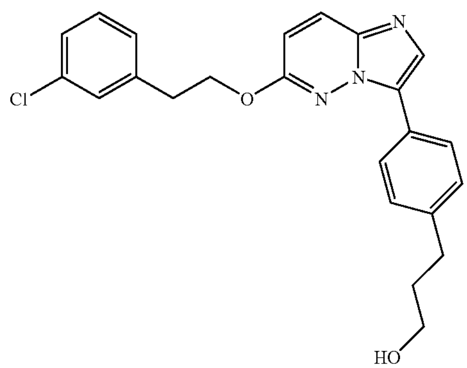 [SMILES: OCCCc1ccc(-c2cnc3ccc(OCCc4cccc(Cl)c4)nn23)cc1] | 7.22 | 407 | 408 |
| 399 | 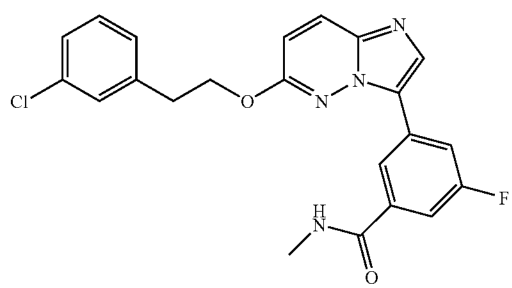 [SMILES: CNC(=O)c1cc(F)cc(-c2cnc3ccc(OCCc4cccc(Cl)c4)nn23)c1] | 8.14 | 424 | 425 |
| 400 | 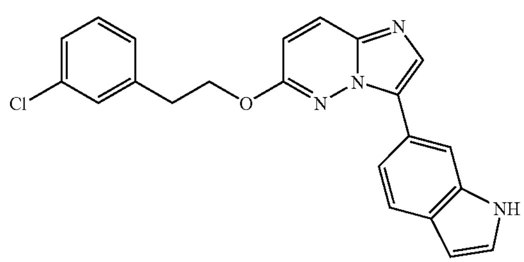 [SMILES: Clc1cccc(CCOc2ccc3ncc(-c4ccc5cc[nH]c5c4)n3n2)c1] | 7.58 | 388 | 389 |
| 401 | 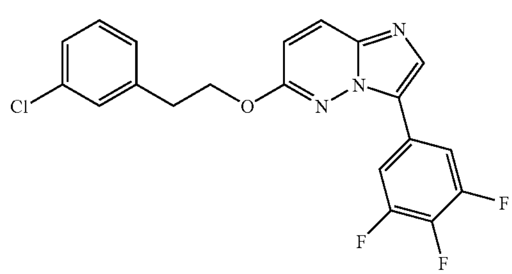 [SMILES: Fc1cc(-c2cnc3ccc(OCCc4cccc(Cl)c4)nn23)cc(F)c1F] | 10.97 | 403 | 404 |

-continued

| EXAMPLE No. | Structure | Retention time [min] | MW calc. | MW found |
|---|---|---|---|---|
| 402 | 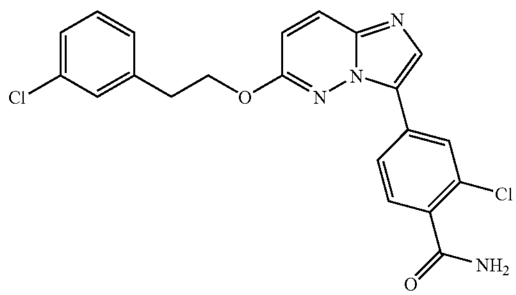 [SMILES: NC(=O)c1ccc(-c2cnc3ccc(OCCc4cccc(Cl)c4)nn23)cc1Cl] | 7.47 | 427 | 427 |
| 403 | 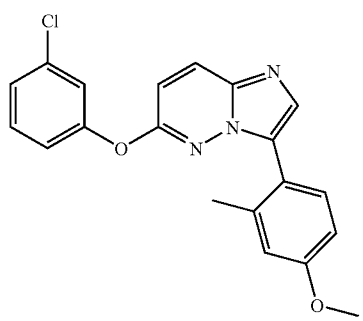 [SMILES: COc1ccc(-c2cnc3ccc(Oc4cccc(Cl)c4)nn23)c(C)c1] | 8.18 | 365 | 366 |
| 404 | 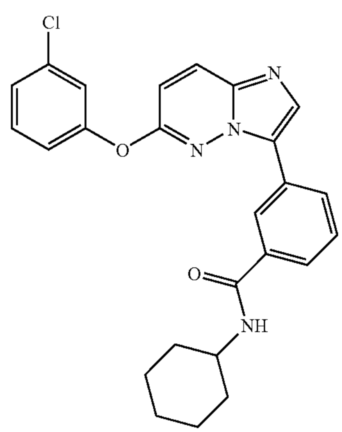 [SMILES: O=C(NC1CCCCC1)c1cccc(-c2cnc3ccc(Oc4cccc(Cl)c4)nn23)c1] | 9.63 | 446 | 447 |
| 405 | 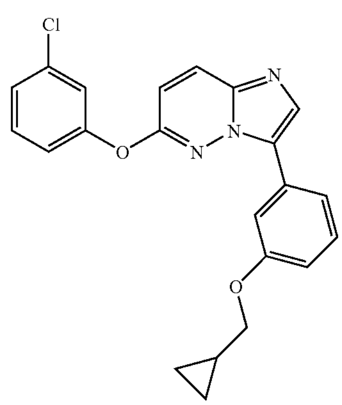 [SMILES: Clc1cccc(Oc2ccc3ncc(-c4cccc(OCC5CC5)c4)n3n2)c1] | 10.55 | 391 | 392 |

-continued

| EXAMPLE No. | Structure | Retention time [min] | MW calc. | MW found |
|---|---|---|---|---|
| 406 | 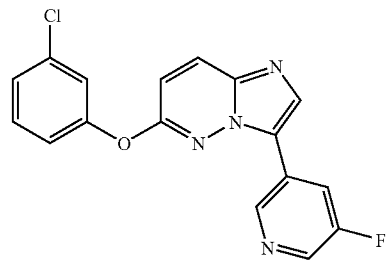 [SMILES: Fc1cncc(-c2cnc3ccc(Oc4cccc(Cl)c4)nn23)c1] | 9.17 | 340 | 341 |
| 407 | 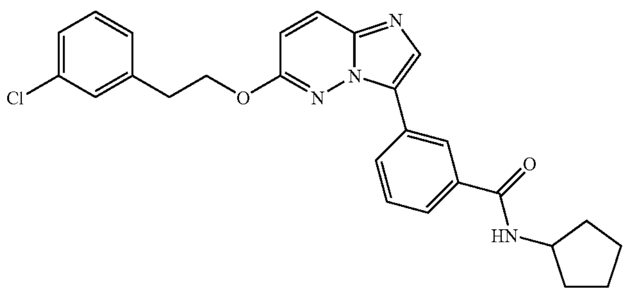 [SMILES: O=C(NC1CCCC1)c1cccc(-c2cnc3ccc(OCCc4cccc(Cl)c4)nn23)c1] | 8.68 | 460 | 461 |
| 408 | 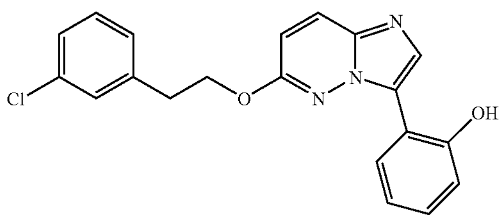 [SMILES: Oc1ccccc1-c1cnc2ccc(OCCc3cccc(Cl)c3)nn12] | 6.86 | 365 | 366 |
| 409 | 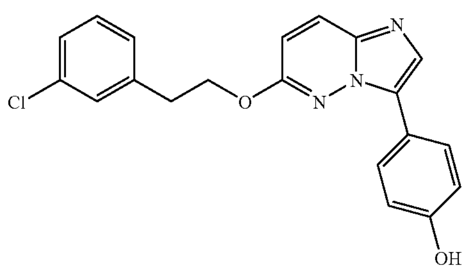 [SMILES: Oc1ccc(-c2cnc3ccc(OCCc4cccc(Cl)c4)nn23)cc1] | 6.73 | 365 | 366 |
| 410 | 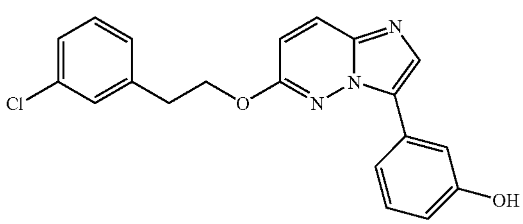 [SMILES: Oc1cccc(-c2cnc3ccc(OCCc4cccc(Cl)c4)nn23)c1] | 7.16 | 365 | 366 |
| 411 | 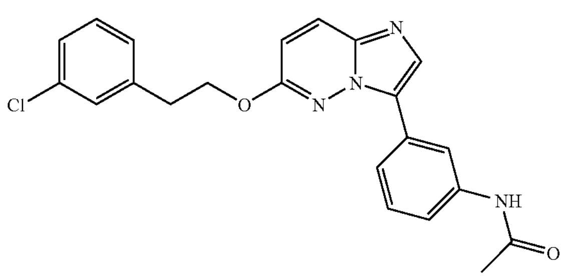 [SMILES: CC(=O)Nc1cccc(-c2cnc3ccc(OCCc4cccc(Cl)c4)nn23)c1] | 6.98 | 406 | 407 |

-continued

| EXAMPLE No. | Structure | Retention time [min] | MW calc. | MW found |
|---|---|---|---|---|
| 412 | 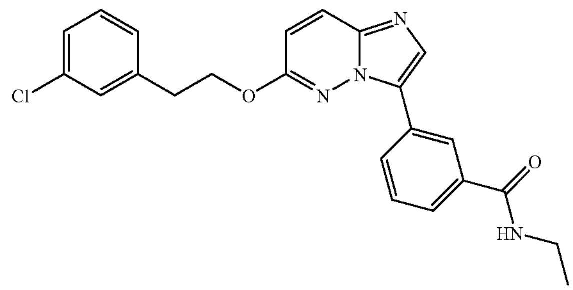 [SMILES: CCNC(=O)c1cccc(-c2cnc3ccc(OCCc4cccc(Cl)c4)nn23)c1] | 7.47 | 420 | 421 |
| 413 | 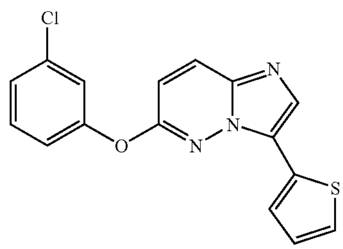 [SMILES: Clc1cccc(Oc2ccc3ncc(-c4cccs4)n3n2)c1] | 9.77 | 327 | 328 |
| 414 | 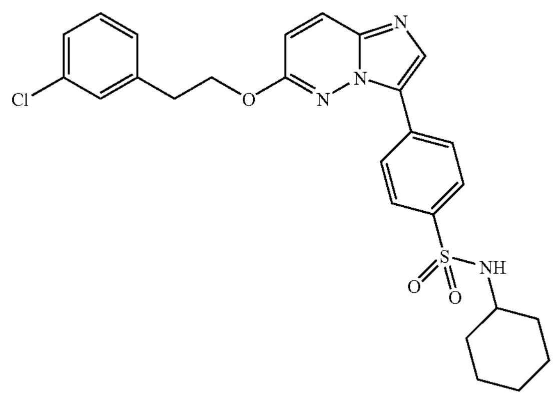 [SMILES: O=S(=O)(NC1CCCCC1)c1ccc(-c2cnc3ccc(OCCc4cccc(Cl)c4)nn23)cc1] | 9.83 | 511 | 511 |
| 415 | 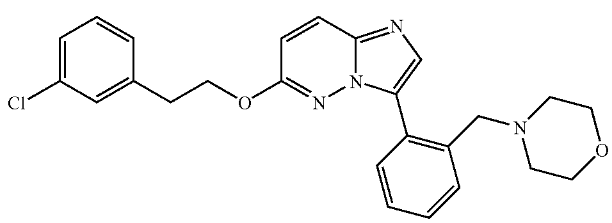 [SMILES: Clc1cccc(CCOc2ccc3ncc(-c4ccccc4CN4CCOCC4)n3n2)c1] | 5.7 | 448 | 449 |
| 416 | 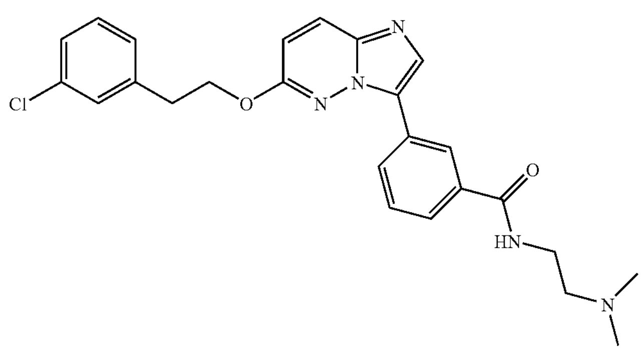 [SMILES: CN(C)CCNC(=O)c1cccc(-c2cnc3ccc(OCCc4cccc(Cl)c4)nn23)c1] | 5.58 | 463 | 464 |

-continued

| EXAMPLE No. | Structure | Retention time [min] | MW calc. | MW found |
|---|---|---|---|---|
| 417 | 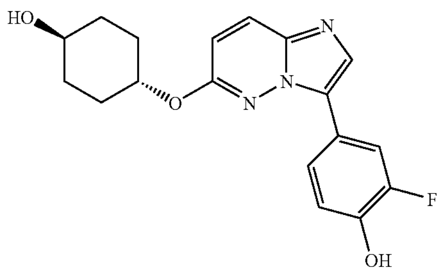 [SMILES: Oc1ccc(-c2cnc3ccc(O[C@H]4CC[C@H](O)CC4)nn23)cc1F] | 4.93 | 343 | 344 |
| 418 | 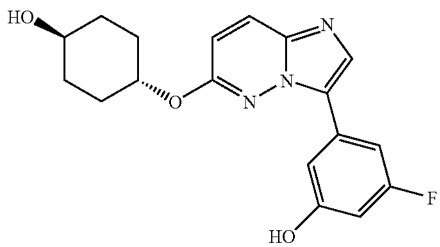 [SMILES: Oc1cc(F)cc(-c2cnc3ccc(O[C@H]4CC[C@H](O)CC4)nn23)c1] | 5.13 | 343 | 344 |
| 419 | 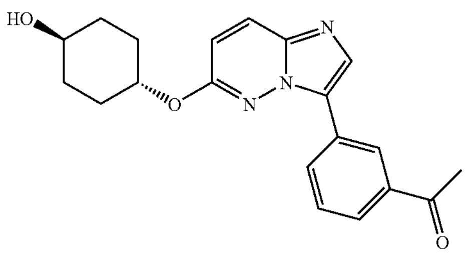 [SMILES: CC(=O)c1cccc(-c2cnc3ccc(O[C@H]4CC[C@H](O)CC4)nn23)c1] | 5.14 | 351 | 352 |
| 420 | 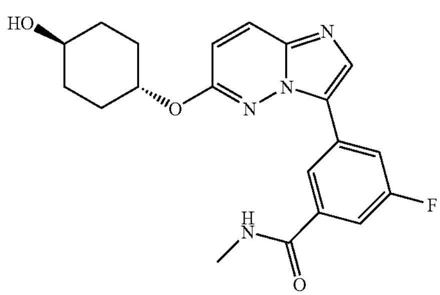 [SMILES: CNC(=O)c1cc(F)cc(-c2cnc3ccc(O[C@H]4CC[C@H](O)CC4)nn23)c1] | 4.96 | 384 | 385 |
| 421 | 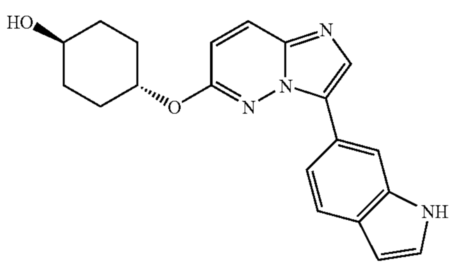 [SMILES: O[C@H]1CC[C@H](Oc2ccc3ncc(-c4ccc5cc[nH]c5c4)n3n2)CC1] | 5.38 | 348 | 349 |

-continued

| EXAMPLE No. | Structure | Retention time [min] | MW calc. | MW found |
|---|---|---|---|---|
| 422 | 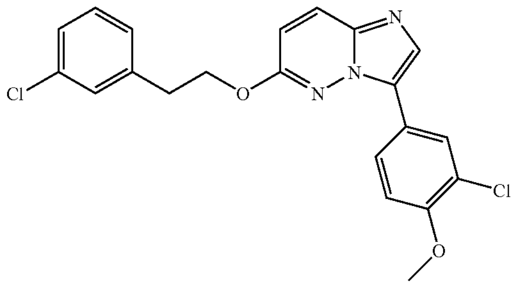 [SMILES: COc1ccc(-c2cnc3ccc(OCCc4cccc(Cl)c4)nn23)cc1Cl] | 9.36 | 414 | 414 |
| 423 | 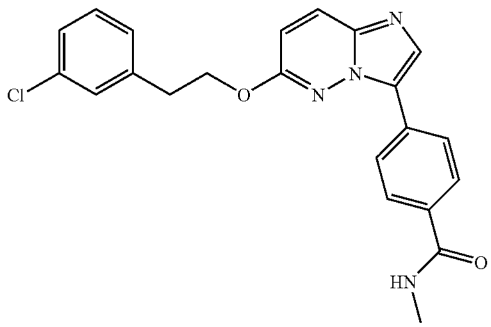 [SMILES: CNC(=O)c1ccc(-c2cnc3ccc(OCCc4cccc(Cl)c4)nn23)cc1] | 7.09 | 406 | 407 |
| 424 | 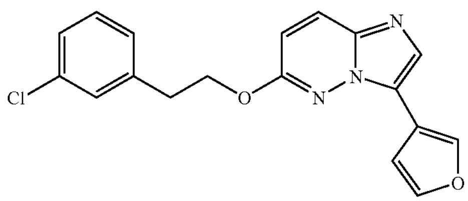 [SMILES: Clc1cccc(CCOc2ccc3ncc(-c4ccoc4)n3n2)c1] | 8.1 | 339 | 340 |
| 425 | 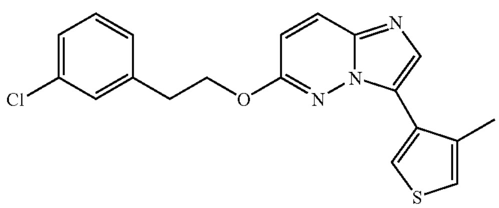 [SMILES: Cc1cscc1-c1cnc2ccc(OCCc3cccc(Cl)c3)nn12] | 8.53 | 369 | 370 |
| 426 | 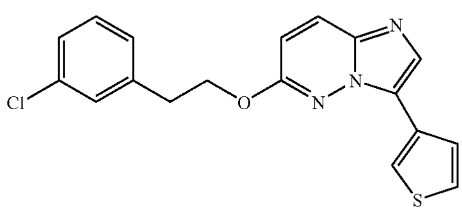 [SMILES: Clc1cccc(CCOc2ccc3ncc(-c4ccsc4)n3n2)c1] | 8.65 | 355 | 356 |
| 427 | 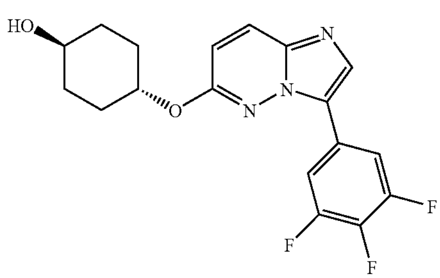 [SMILES: O[C@H]1CC[C@H](Oc2ccc3ncc(-c4cc(F)c(F)c(F)c4)n3n2)CC1] | 6.62 | 363 | 364 |

-continued

| EXAMPLE No. | Structure | Retention time [min] | MW calc. | MW found |
|---|---|---|---|---|
| 428 | 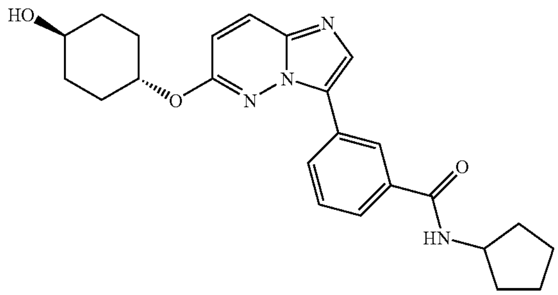 [SMILES: O=C(NC1CCCC1)c1cccc(-c2cnc3ccc(O[C@H]4CC[C@H](O)CC4)nn23)c1] | 5.53 | 420 | 421 |
| 429 | 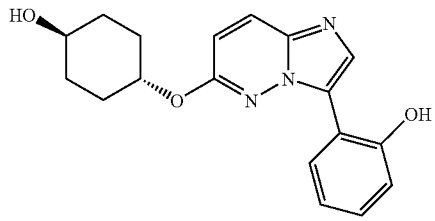 [SMILES: Oc1ccccc1-c1cnc2ccc(O[C@H]3CC[C@H](O)CC3)nn12] | 4.81 | 325 | 326 |
| 430 | 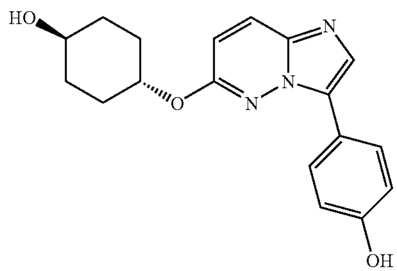 [SMILES: Oc1ccc(-c2cnc3ccc(O[C@H]4CC[C@H](O)CC4)nn23)cc1] | 4.76 | 325 | 326 |
| 431 | 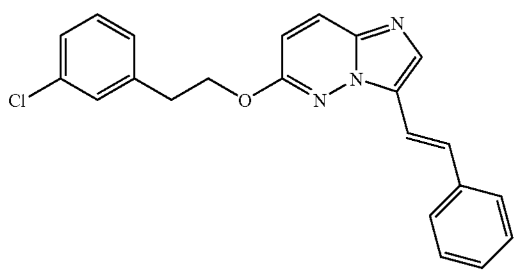 [SMILES: Clc1cccc(CCOc2ccc3ncc(/C=C/c4ccccc4)n3n2)c1] | 9.73 | 375 | 376 |
| 432 | 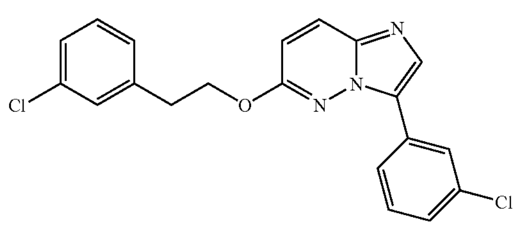 [SMILES: Clc1cccc(CCOc2ccc3ncc(-c4cccc(Cl)c4)n3n2)c1] | 10.61 | 384 | 384 |
| 433 | 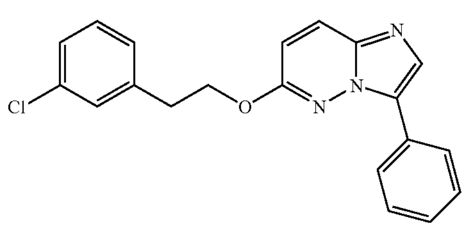 [SMILES: Clc1cccc(CCOc2ccc3ncc(-c4ccccc4)n3n2)c1] | 8.77 | 349 | 350 |

| EXAMPLE No. | Structure | Retention time [min] | MW calc. | MW found |
|---|---|---|---|---|
| 434 | 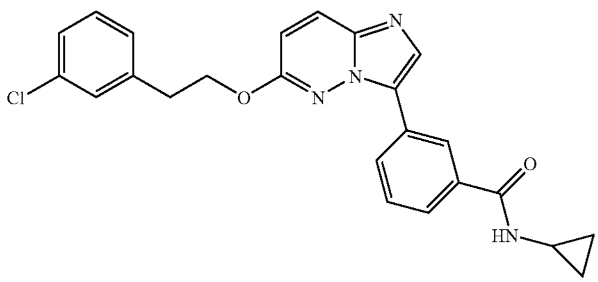 [SMILES: O=C(NC1CC1)c1cccc(-c2cnc3ccc(OCCc4cccc(Cl)c4)nn23)c1] | 7.52 | 432 | 433 |
| 435 | 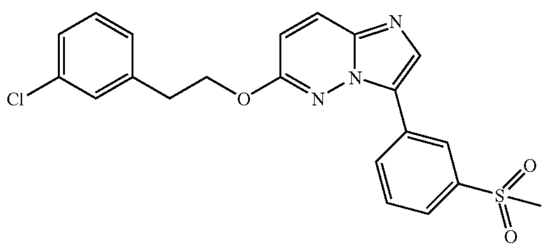 [SMILES: CS(=O)(=O)c1cccc(-c2cnc3ccc(OCCc4cccc(Cl)c4)nn23)c1] | 8.17 | 427 | 428 |
| 436 | 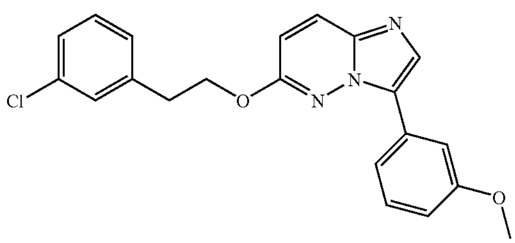 [SMILES: COc1cccc(-c2cnc3ccc(OCCc4cccc(Cl)c4)nn23)c1] | 8.93 | 379 | 380 |
| 437 | 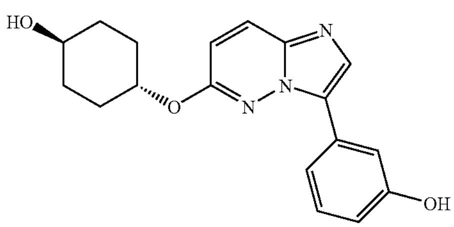 [SMILES: Oc1cccc(-c2cnc3ccc(O[C@H]4CC[C@H](O)CC4)nn23)c1] | 4.83 | 325 | 326 |
| 438 | 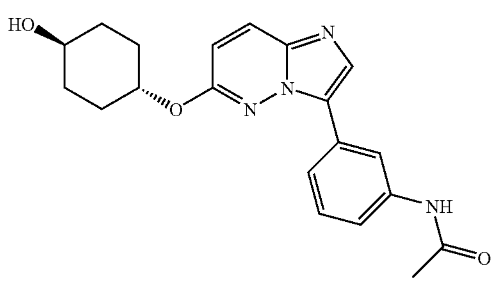 [SMILES: CC(=O)Nc1cccc(-c2cnc3ccc(O[C@H]4CC[C@H](O)CC4)nn23)c1] | 4.58 | 366 | 367 |

-continued

| EXAMPLE No. | Structure | Retention time [min] | MW calc. | MW found |
|---|---|---|---|---|
| 439 | 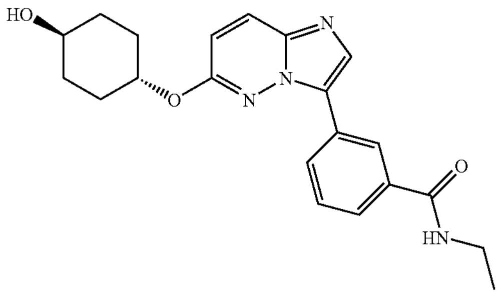 [SMILES: CCNC(=O)c1cccc(-c2cnc3ccc(O[C@H]4CC[C@H](O)CC4)nn23)c1] | 4.76 | 380 | 381 |
| 440 | 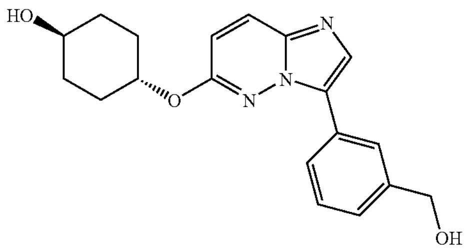 [SMILES: OCc1cccc(-c2cnc3ccc(O[C@H]4CC[C@H](O)CC4)nn23)c1] | 4.7 | 339 | 340 |
| 441 | 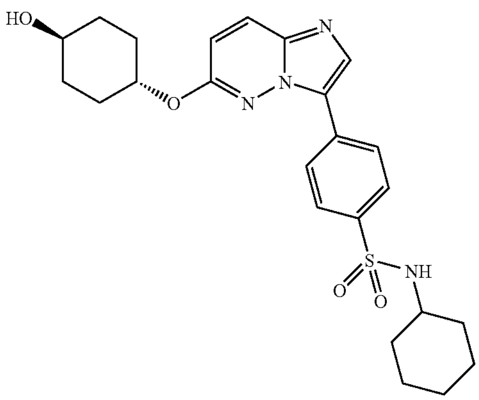 [SMILES: O=S(=O)(NC1CCCCC1)c1ccc(-c2cnc3ccc(O[C@H]4CC[C@H](O)CC4)nn23)cc1] | 6.58 | 470 | 471 |
| 442 | 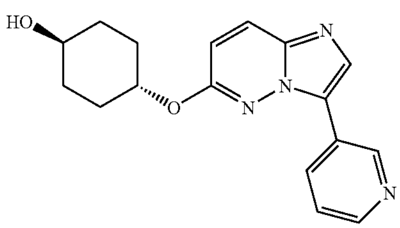 [SMILES: O[C@H]1CC[C@H](Oc2ccc3ncc(-c4cccnc4)n3n2)CC1] | 4.0 | 310 | 311 |
| 443 | 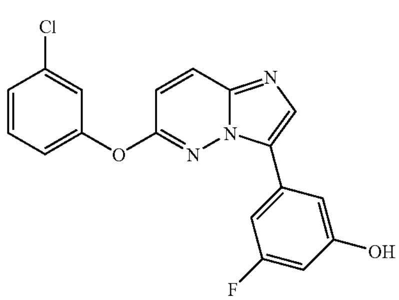 [SMILES: Oc1cc(F)cc(-c2cnc3ccc(Oc4cccc(Cl)c4)nn23)c1] | 8.27 | 355 | 356 |

-continued

| EXAMPLE No. | Structure | Retention time [min] | MW calc. | MW found |
|---|---|---|---|---|
| 444 | 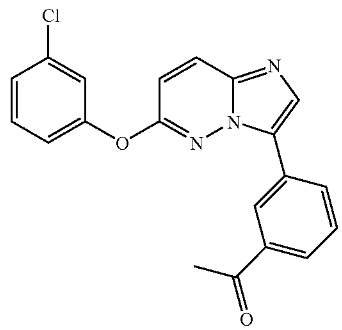 [SMILES: CC(=O)c1cccc(-c2cnc3ccc(Oc4cccc(Cl)c4)nn23)c1] | 8.96 | 363 | 364 |
| 445 | 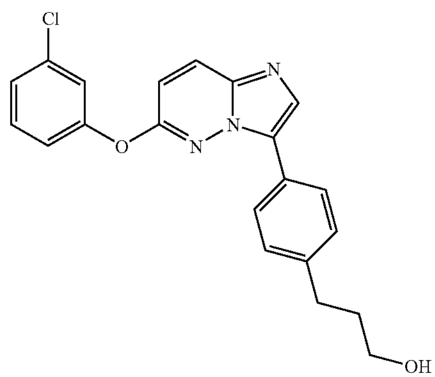 [SMILES: OCCCc1ccc(-c2cnc3ccc(Oc4cccc(Cl)c4)nn23)cc1] | 7.55 | 379 | 380 |
| 446 | 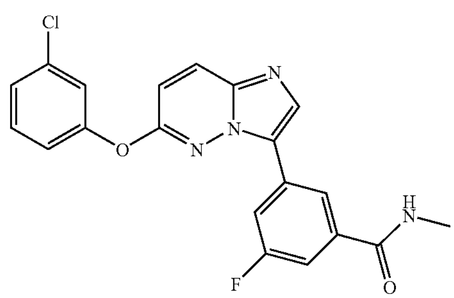 [SMILES: CNC(=O)c1cc(F)cc(-c2cnc3ccc(Oc4cccc(Cl)c4)nn23)c1] | 8.18 | 396 | 397 |
| 447 | 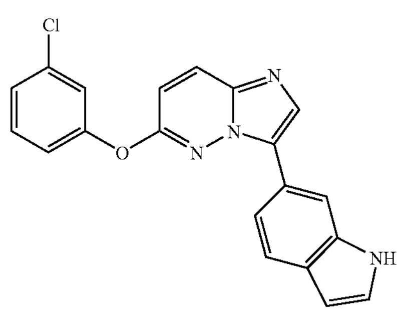 [SMILES: Clc1cccc(Oc2ccc3ncc(-c4ccc5cc[nH]c5c4)n3n2)c1] | 8.08 | 360 | 361 |

-continued

| EXAMPLE No. | Structure | Retention time [min] | MW calc. | MW found |
|---|---|---|---|---|
| 448 | 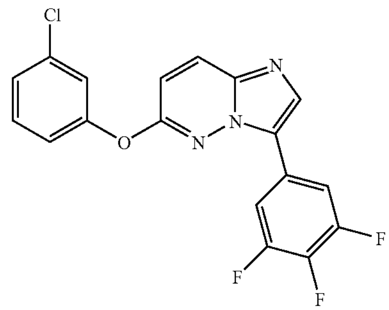 [SMILES: Fc1cc(-c2cnc3ccc(Oc4cccc(Cl)c4)nn23)cc(F)c1F] | 11.26 | 375 | 376 |
| 449 | 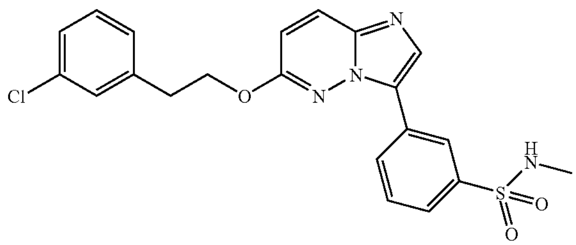 [SMILES: CNS(=O)(=O)c1cccc(-c2cnc3ccc(OCCc4cccc(Cl)c4)nn23)c1] | 7.92 | 442 | 443 |
| 450 | 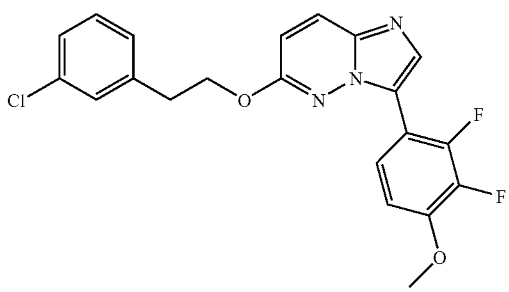 [SMILES: COc1ccc(-c2cnc3ccc(OCCc4cccc(Cl)c4)nn23)c(F)c1F] | 9.41 | 415 | 416 |
| 451 | 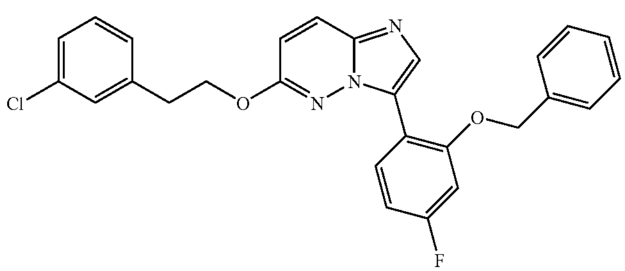 [SMILES: Fc1ccc(-c2cnc3ccc(OCCc4cccc(Cl)c4)nn23)c(OCc2ccccc2)c1] | 9.13 | 473 | 474 |
| 452 | 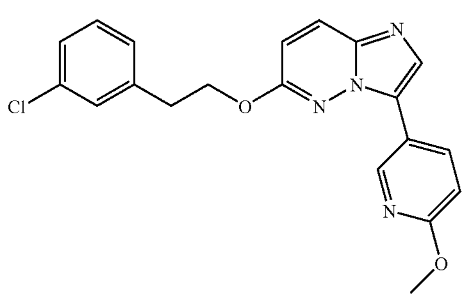 [SMILES: COc1ccc(-c2cnc3ccc(OCCc4cccc(Cl)c4)nn23)cn1] | 8.54 | 380 | 381 |

-continued
| EXAMPLE No. | Structure | Retention time [min] | MW calc. | MW found |
|---|---|---|---|---|
| 453 | 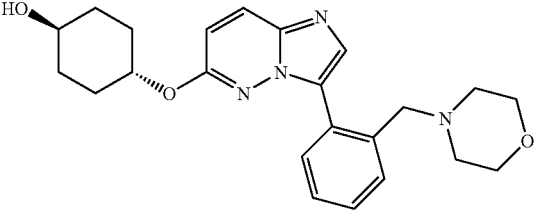 [SMILES: O[C@H]1CC[C@H](Oc2ccc3ncc(-c4ccccc4CN4CCOCC4)n3n2)CC1] | 4.02 | 408 | 409 |
| 454 | 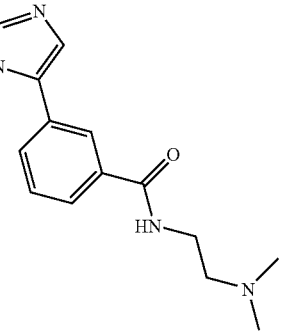 | 4.13 | 423 | 424 |
| 455 | 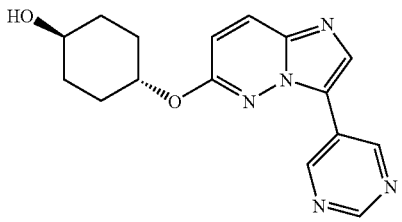 | 4.31 | 311 | 312 |
| 456 | 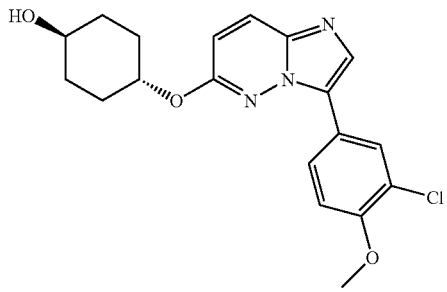 [SMILES: COc1ccc(-c2cnc3ccc(O[C@H]4CC[C@H](O)CC4)nn23)cc1Cl] | 5.78 | 373 | 374 |
| 457 | 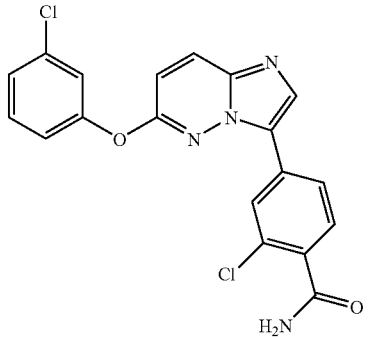 [SMILES: NC(=O)c1ccc(-c2cnc3ccc(Oc4cccc(Cl)c4)nn23)cc1Cl] | 7.4 | 399 | 399 |

-continued

| EXAMPLE No. | Structure | Retention time [min] | MW calc. | MW found |
|---|---|---|---|---|
| 458 | 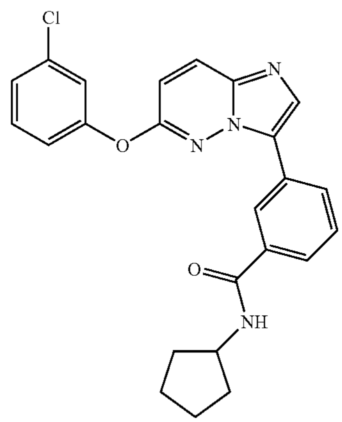 [SMILES: O=C(NC1CCCC1)c1cccc(-c2cnc3ccc(Oc4cccc(Cl)c4)nn23)c1] | 9.35 | 432 | 433 |
| 459 | 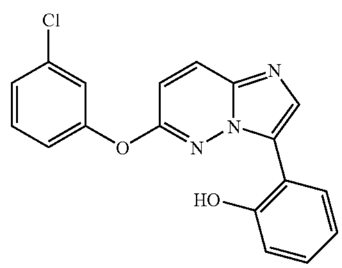 [SMILES: Oc1ccccc1-c1cnc2ccc(Oc3cccc(Cl)c3)nn12] | 6.82 | 337 | 338 |
| 460 | 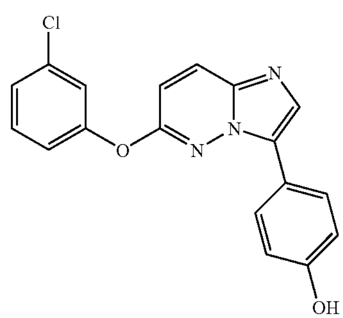 [SMILES: Oc1ccc(-c2cnc3ccc(Oc4cccc(Cl)c4)nn23)cc1] | 6.92 | 337 | 338 |
| 461 | 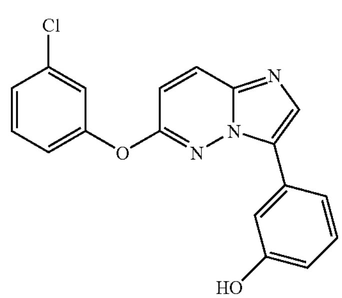 [SMILES: Oc1cccc(-c2cnc3ccc(Oc4cccc(Cl)c4)nn23)c1] | 7.51 | 337 | 338 |
| 462 | 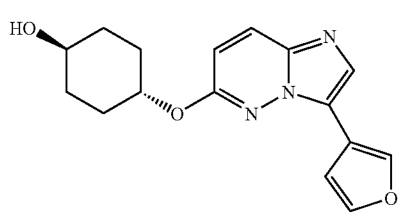 [SMILES: O[C@H]1CC[C@H](Oc2ccc3ncc(-c4ccoc4)n3n2)CC1] | 4.9 | 299 | 300 |

-continued

| EXAMPLE No. | Structure | Retention time [min] | MW calc. | MW found |
|---|---|---|---|---|
| 463 | 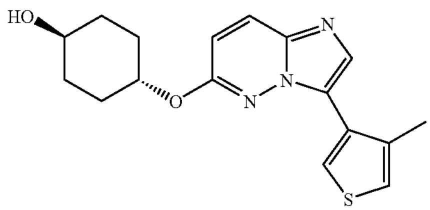 [SMILES: Cc1cscc1-c1cnc2ccc(O[C@H]3CC[C@H](O)CC3)nn12] | 5.38 | 329 | 330 |
| 464 | 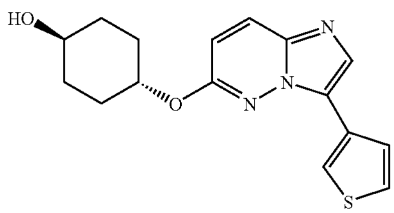 [SMILES: O[C@H]1CC[C@H](Oc2ccc3ncc(-c4ccsc4)n3n2)CC1] | 5.12 | 315 | 316 |
| 465 | 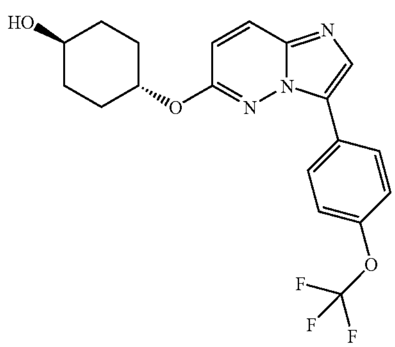 [SMILES: O[C@H]1CC[C@H](Oc2ccc3ncc(-c4ccc(OC(F)(F)F)cc4)n3n2)CC1] | 6.42 | 393 | 394 |
| 466 | 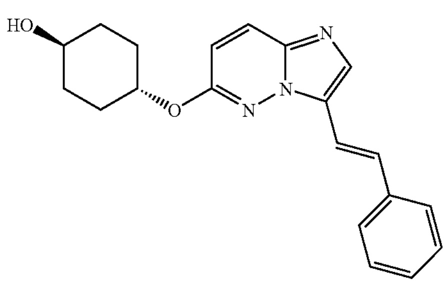 [SMILES: O[C@H]1CC[C@H](Oc2ccc3ncc(/C=C/c4ccccc4)n3n2)CC1] | 6.05 | 335 | 336 |
| 467 | 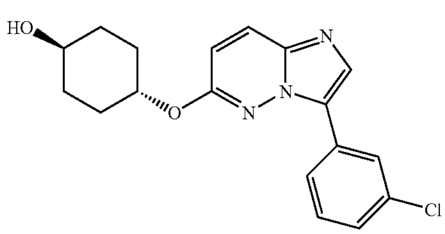 [SMILES: O[C@H]1CC[C@H](Oc2ccc3ncc(-c4cccc(Cl)c4)n3n2)CC1] | 6.08 | 343 | 344 |

-continued

| EXAMPLE No. | Structure | Retention time [min] | MW calc. | MW found |
|---|---|---|---|---|
| 468 | 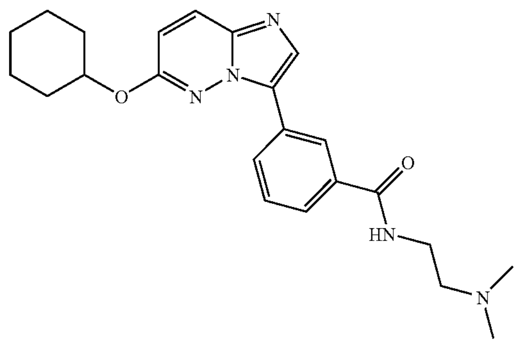 [SMILES: CN(C)CCNC(=O)c1cccc(-c2cnc3ccc(OC4CCCCC4)nn23)c1] | 5.28 | 407 | 408 |
| 469 | 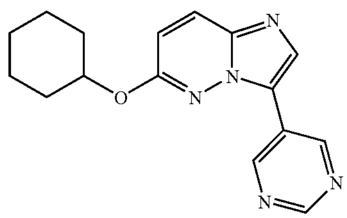 | 6.66 | 295 | 296 |
| 470 | 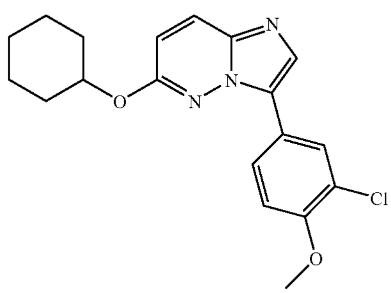 [SMILES: COc1ccc(-c2cnc3ccc(OC4CCCCC4)nn23)cc1Cl] | 8.45 | 357 | 358 |
| 471 | 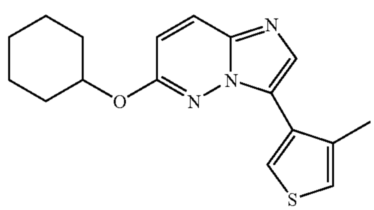 [SMILES: Cc1cscc1-c1cnc2ccc(OC3CCCCC3)nn12] | 7.79 | 313 | 314 |
| 472 | 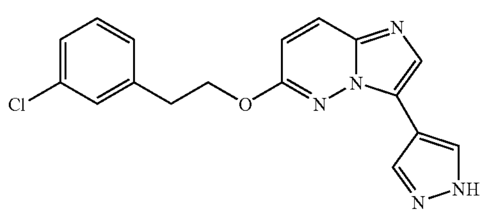 [SMILES: Clc1cccc(CCOc2ccc3ncc(-c4cn[nH]c4)n3n2)c1] | 6.26 | 339 | 340 |
| 473 | 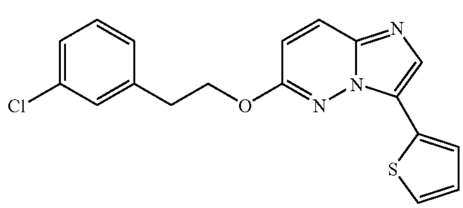 [SMILES: Clc1cccc(CCOc2ccc3ncc(-c4cccs4)n3n2)c1] | 9.86 | 355 | 356 |

-continued
| EXAMPLE No. | Structure | Retention time [min] | MW calc. | MW found |
|---|---|---|---|---|
| 474 | 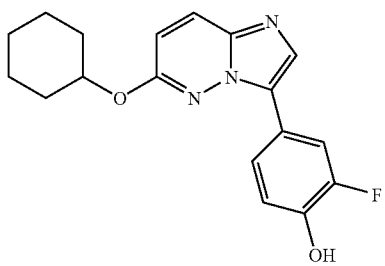 [SMILES: Oc1ccc(-c2cnc3ccc(OC4CCCCC4)nn23)cc1F] | 6.66 | 327 | 328 |
| 475 | 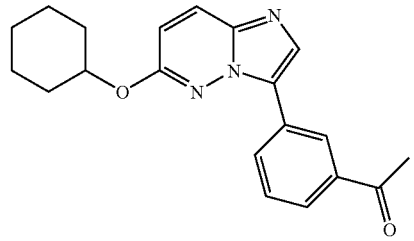 [SMILES: CC(=O)c1cccc(-c2cnc3ccc(OC4CCCCC4)nn23)c1] | 7.47 | 335 | 336 |
| 476 | 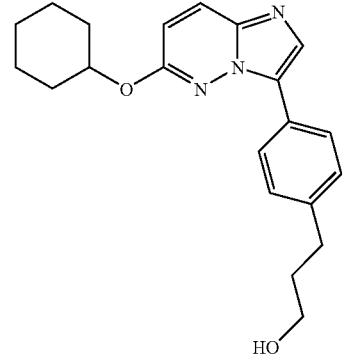 [SMILES: OCCCc1ccc(-c2cnc3ccc(OC4CCCCC4)nn23)cc1] | 6.6 | 351 | 352 |
| 477 | 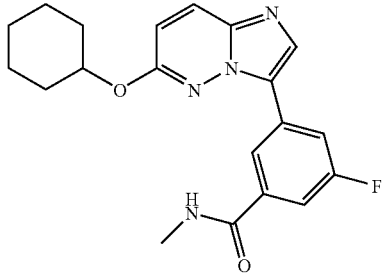 [SMILES: CNC(=O)c1cc(F)cc(-c2cnc3ccc(OC4CCCCC4)nn23)c1] | 7.04 | 368 | 369 |
| 478 | 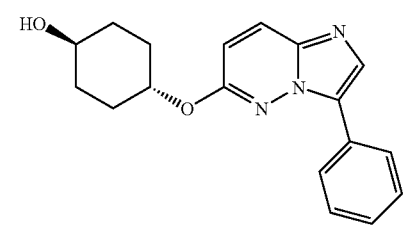 | 5.23 | 309 | 310 |

-continued

| EXAMPLE No. | Structure | Retention time [min] | MW calc. | MW found |
|---|---|---|---|---|
| 479 | 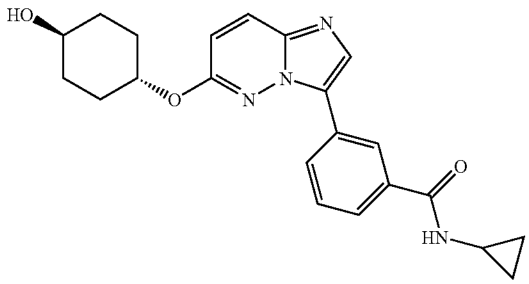 [SMILES: O=C(NC1CC1)c1cccc(-c2cnc3ccc(O[C@H]4CC[C@H](O)CC4)nn23)c1] | 4.82 | 392 | 393 |
| 480 | 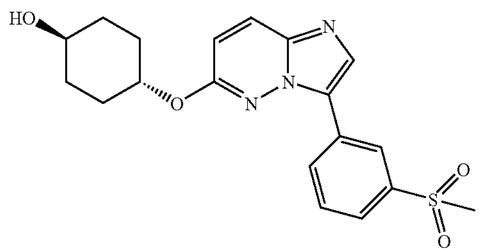 [SMILES: CS(=O)(=O)c1cccc(-c2cnc3ccc(O[C@H]4CC[C@H](O)CC4)nn23)c1] | 5.0 | 387 | 388 |
| 481 | 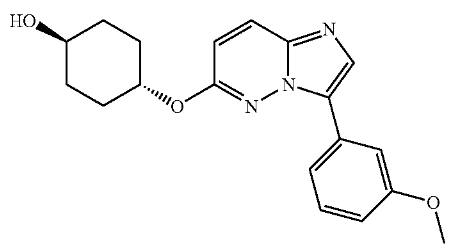 [SMILES: COc1cccc(-c2cnc3ccc(O[C@H]4CC[C@H](O)CC4)nn23)c1] | 5.48 | 339 | 340 |
| 482 | 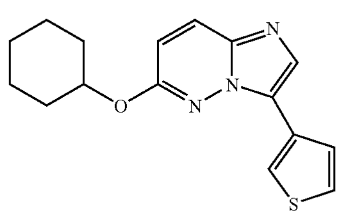 [SMILES: c1cc(-c2cnc3ccc(OC4CCCCC4)nn23)cs1] | 7.77 | 299 | 300 |
| 483 | 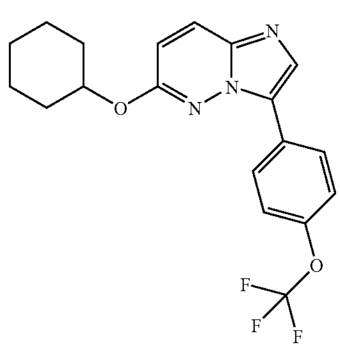 [SMILES: FC(F)(F)Oc1ccc(-c2cnc3ccc(OC4CCCCC4)nn23)cc1] | 9.24 | 377 | 378 |

-continued

| EXAMPLE No. | Structure | Retention time [min] | MW calc. | MW found |
|---|---|---|---|---|
| 484 | 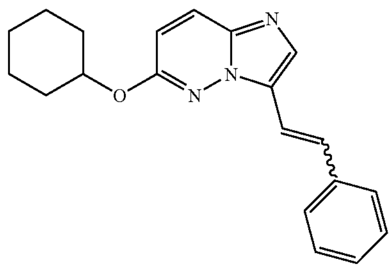 [SMILES: C(=Cc1cnc2ccc(OC3CCCCC3)nn12)c1ccccc1] | 8.75 | 319 | 320 |
| 485 | 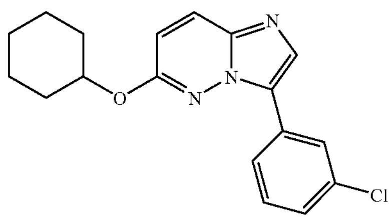 [SMILES: Clc1cccc(-c2cnc3ccc(OC4CCCCC4)nn23)c1] | 9.61 | 327 | 328 |
| 486 | 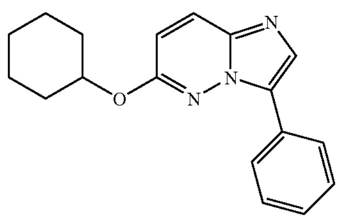 [SMILES: c1ccc(-c2cnc3ccc(OC4CCCCC4)nn23)cc1] | 7.82 | 293 | 294 |
| 487 | 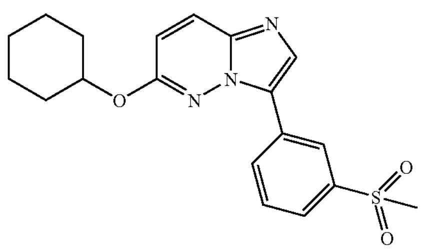 [SMILES: CS(=O)(=O)c1cccc(-c2cnc3ccc(OC4CCCCC4)nn23)c1] | 7.05 | 371 | 372 |
| 488 | 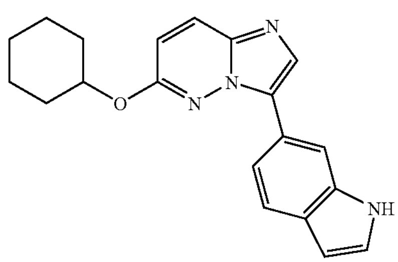 [SMILES: c1cc2ccc(-c3cnc4ccc(OC5CCCCC5)nn34)cc2[nH]1] | 7.23 | 332 | 333 |
| 489 | 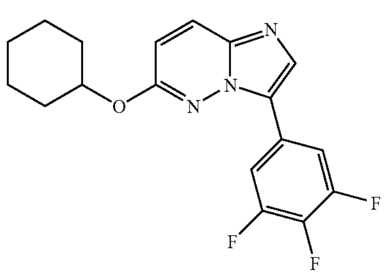 [SMILES: Fc1cc(-c2cnc3ccc(OC4CCCCC4)nn23)cc(F)c1F] | 10.36 | 347 | 348 |

-continued
| EXAMPLE No. | Structure | Retention time [min] | MW calc. | MW found |
|---|---|---|---|---|
| 490 | 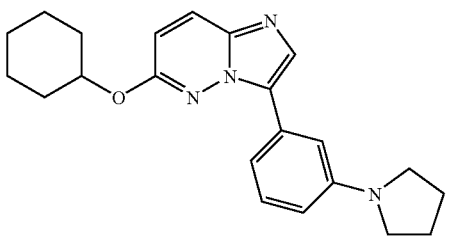 [SMILES: c1cc(-c2cnc3ccc(OC4CCCCC4)nn23)cc(N2CCCC2)c1] | 8.69 | 362 | 363 |
| 491 | 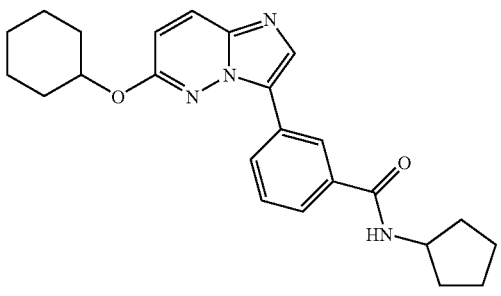 [SMILES: O=C(NC1CCCC1)c1cccc(-c2cnc3ccc(OC4CCCCC4)nn23)c1] | 7.5 | 404 | 405 |
| 492 | 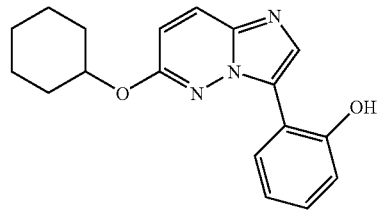 [SMILES: Oc1ccccc1-c1cnc2ccc(OC3CCCCC3)nn12] | 6.67 | 309 | 310 |
| 493 | 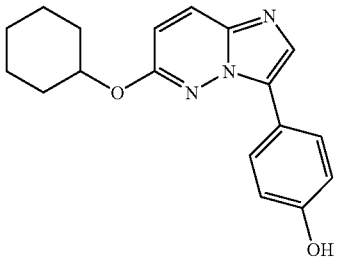 [SMILES: Oc1ccc(-c2cnc3ccc(OC4CCCCC4)nn23)cc1] | 6.51 | 309 | 310 |
| 494 | 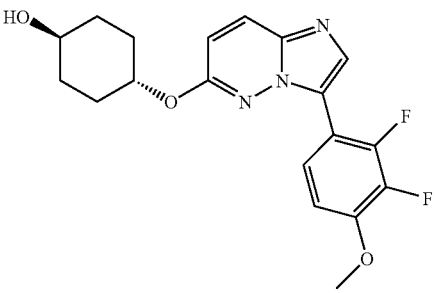 [SMILES: COc1ccc(-c2cnc3ccc(O[C@H]4CC[C@H](O)CC4)nn23)c(F)c1F] | 5.84 | 375 | 376 |

-continued

| EXAMPLE No. | Structure | Retention time [min] | MW calc. | MW found |
|---|---|---|---|---|
| 495 | 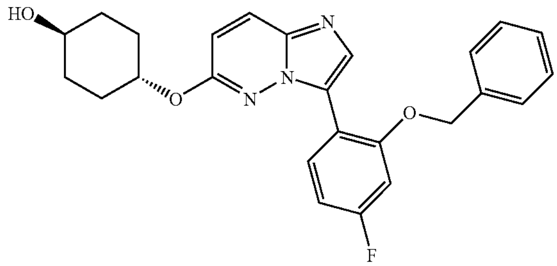 | 6.57 | 433 | 434 |
| 496 | 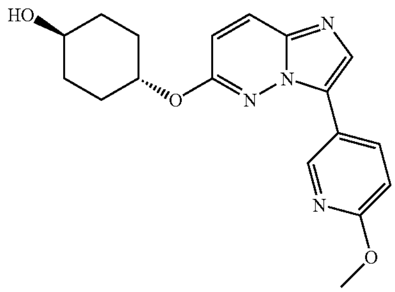 [SMILES: COc1ccc(-c2cnc3ccc(O[C@H]4CC[C@H](O)CC4)nn23)cn1] | 4.96 | 340 | 341 |
| 497 | 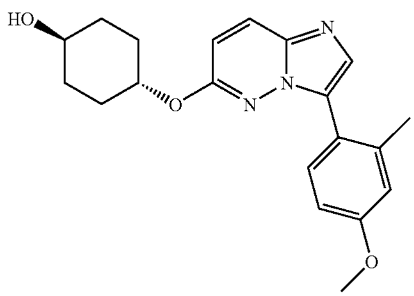 | 5.35 | 353 | 354 |
| 498 | 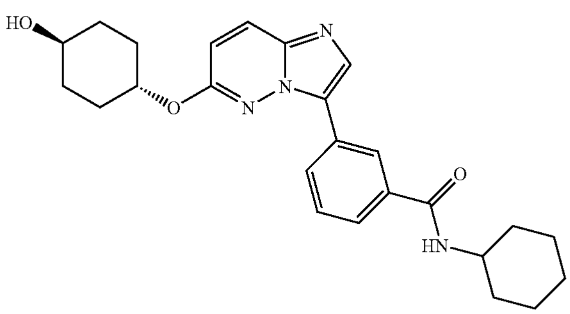 [SMILES: O=C(NC1CCCCC1)c1cccc(-c2cnc3ccc(O[C@H]4CC[C@H](O)CC4)nn23)c1] | 5.88 | 434 | 435 |
| 499 | 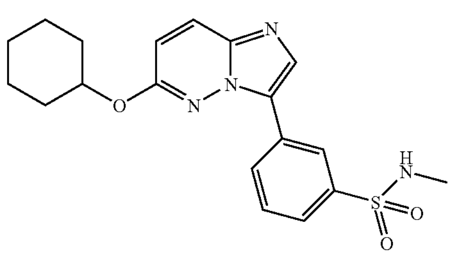 [SMILES: CNS(=O)(=O)c1cccc(-c2cnc3ccc(OC4CCCCC4)nn23)c1] | 6.95 | 386 | 387 |

-continued
| EXAMPLE No. | Structure | Retention time [min] | MW calc. | MW found |
|---|---|---|---|---|
| 500 | 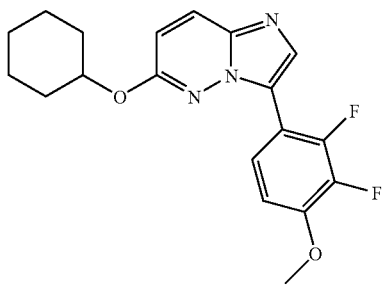 [SMILES: COc1ccc(-c2cnc3ccc(OC4CCCCC4)nn23)c(F)c1F] | 0.0 | 359 | 360 |
| 501 | 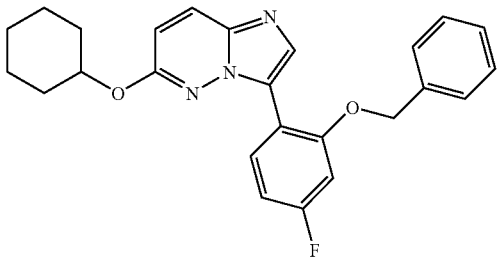 [SMILES: Fc1ccc(-c2cnc3ccc(OC4CCCCC4)nn23)c(OCc2ccccc2)c1] | 8.58 | 417 | 418 |
| 502 | 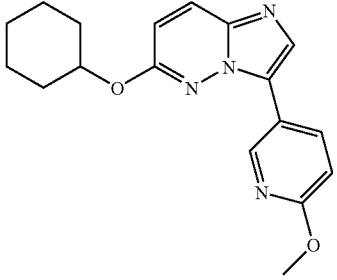 [SMILES: COc1ccc(-c2cnc3ccc(OC4CCCCC4)nn23)cn1] | 7.43 | 324 | 325 |
| 503 | 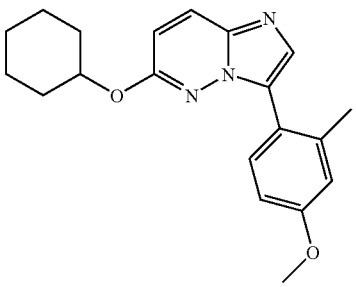 [SMILES: COc1ccc(-c2cnc3ccc(OC4CCCCC4)nn23)c(C)c1] | 7.37 | 337 | 338 |
| 504 | 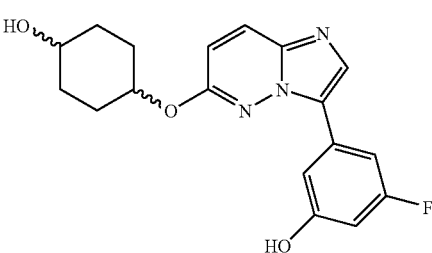 [SMILES: Oc1cc(F)cc(-c2cnc3ccc(OC4CCC(O)CC4)nn23)c1] | 5.22 | 343 | 344 |

-continued
| EXAMPLE No. | Structure | Retention time [min] | MW calc. | MW found |
|---|---|---|---|---|
| 505 | 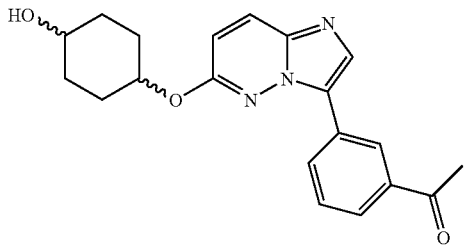 [SMILES: CC(=O)c1cccc(-c2cnc3ccc(OC4CCC(O)CC4)nn23)c1] | 5.26 | 351 | 352 |
| 506 | 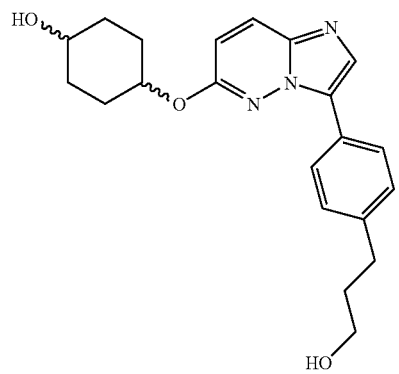 [SMILES: OCCCc1ccc(-c2cnc3ccc(OC4CCC(O)CC4)nn23)cc1] | 4.98 | 367 | 368 |
| 507 | 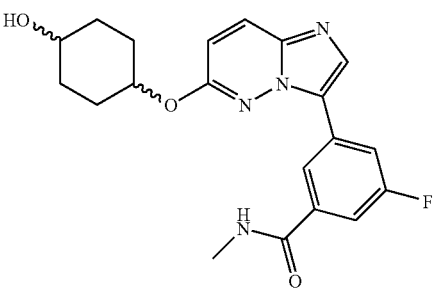 [SMILES: CNC(=O)c1cc(F)cc(-c2cnc3ccc(OC4CCC(O)CC4)nn23)c1] | 4.99 | 384 | 385 |
| 508 | 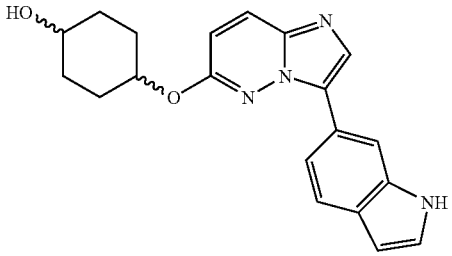 [SMILES: OC1CCC(Oc2ccc3ncc(-c4ccc5cc[nH]c5c4)n3n2)CC1] | 5.6 | 348 | 349 |
| 509 | 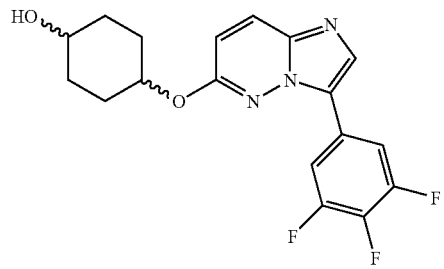 [SMILES: OC1CCC(Oc2ccc3ncc(-c4cc(F)c(F)c(F)c4)n3n2)CC1] | 6.62 | 363 | 364 |

-continued
| EXAMPLE No. | Structure | Retention time [min] | MW calc. | MW found |
|---|---|---|---|---|
| 510 | 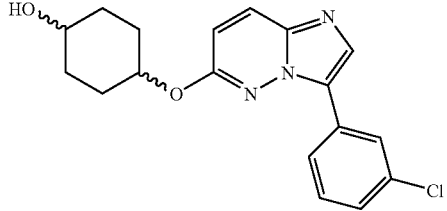 [SMILES: OC1CCC(Oc2ccc3ncc(-c4cccc(Cl)c4)n3n2)CC1] | 6.16 | 343 | 344 |
| 511 | 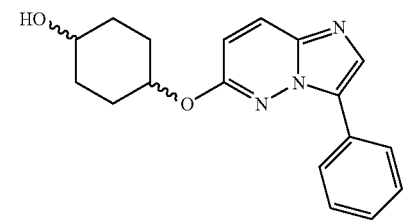 [SMILES: OC1CCC(Oc2ccc3ncc(-c4ccccc4)n3n2)CC1] | 5.51 | 309 | 310 |
| 512 | 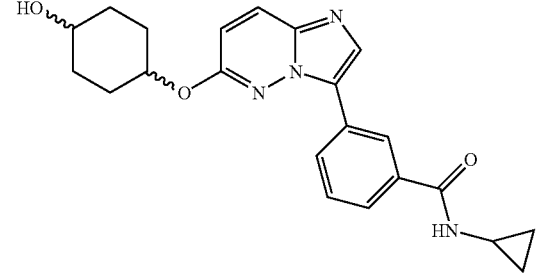 [SMILES: O=C(NC1CC1)c1cccc(-c2cnc3ccc(OC4CCC(O)CC4)nn23)c1] | 4.94 | 392 | 393 |
| 513 | 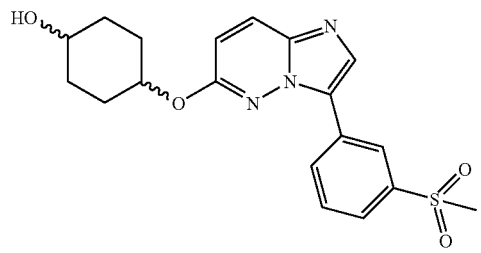 [SMILES: CS(=O)(=O)c1cccc(-c2cnc3ccc(OC4CCC(O)CC4)nn23)c1] | 4.93 | 387 | 388 |
| 514 | 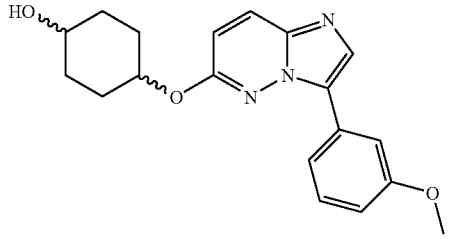 [SMILES: COc1cccc(-c2cnc3ccc(OC4CCC(O)CC4)nn23)c1] | 5.59 | 339 | 340 |
| 515 | 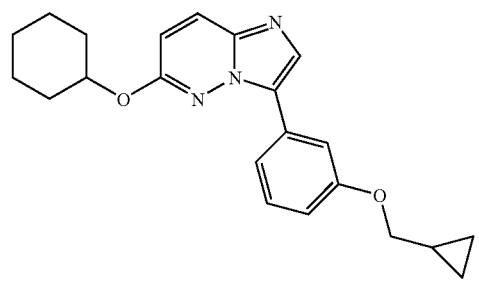 [SMILES: c1cc(OCC2CC2)cc(-c2cnc3ccc(OC4CCCCC4)nn23)c1] | 8.86 | 363 | 364 |

-continued

| EXAMPLE No. | Structure | Retention time [min] | MW calc. | MW found |
|---|---|---|---|---|
| 516 | 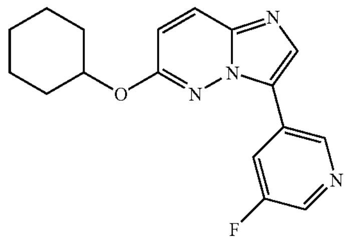 [SMILES: Fc1cncc(-c2cnc3ccc(OC4CCCCC4)nn23)c1] | 8.11 | 312 | 313 |
| 517 | 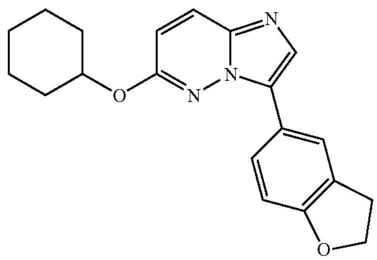 [SMILES: c1cc2c(cc1-c1cnc3ccc(OC4CCCCC4)nn13)CCO2] | 7.47 | 335 | 336 |
| 518 | 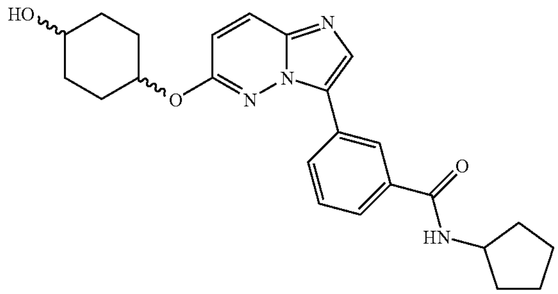 [SMILES: O=C(NC1CCCC1)c1cccc(-c2cnc3ccc(OC4CCC(O)CC4)nn23)c1] | 5.68 | 420 | 421 |
| 519 | 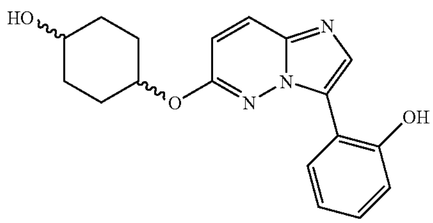 [SMILES: Oc1ccccc1-c1cnc2ccc(OC3CCC(O)CC3)nn12] | 4.78 | 325 | 326 |
| 520 | 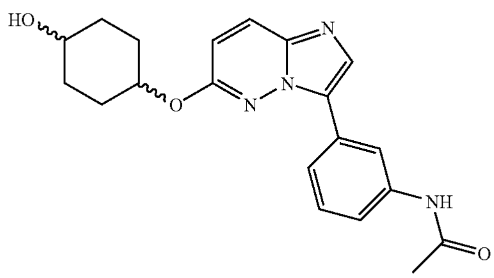 [SMILES: CC(=O)Nc1cccc(-c2cnc3ccc(OC4CCC(O)CC4)nn23)c1] | 4.77 | 366 | 367 |
| 521 | 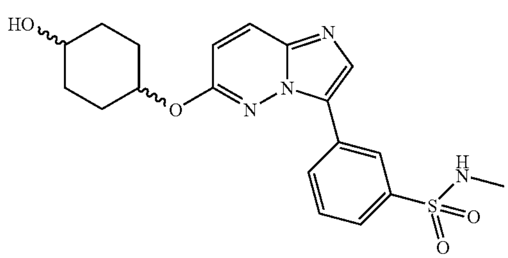 [SMILES: CNS(=O)(=O)c1cccc(-c2cnc3ccc(OC4CCC(O)CC4)nn23)c1] | 5.08 | 402 | 403 |

| EXAMPLE No. | Structure | Retention time [min] | MW calc. | MW found |
|---|---|---|---|---|
| 522 | 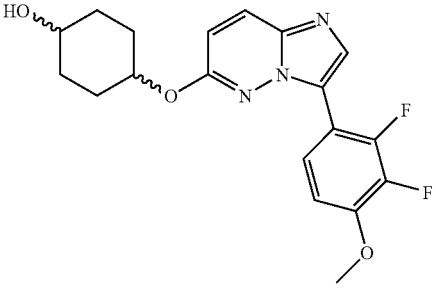 [SMILES: COc1ccc(-c2cnc3ccc(OC4CCC(O)CC4)nn23)c(F)c1F] | 5.94 | 375 | 376 |
| 523 | 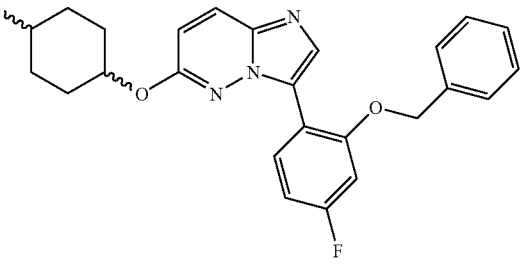 | 6.55 | 433 | 434 |
| 524 | 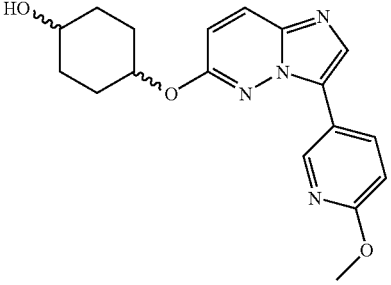 [SMILES: COc1ccc(-c2cnc3ccc(OC4CCC(O)CC4)nn23)cn1] | 5.09 | 340 | 341 |
| 525 | 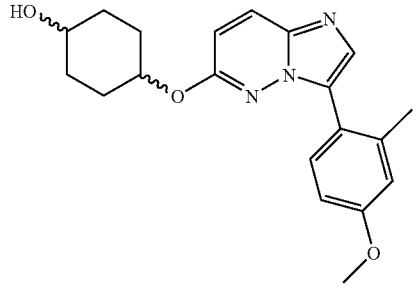 [SMILES: COc1ccc(-c2cnc3ccc(OC4CCC(O)CC4)nn23)c(C)c1] | 5.67 | 353 | 354 |
| 526 | 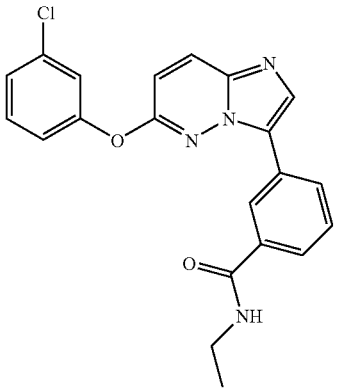 [SMILES: CCNC(=O)c1cccc(-c2cnc3ccc(Oc4cccc(Cl)c4)nn23)c1] | 7.71 | 392 | 393 |

-continued
| EXAMPLE No. | Structure | Retention time [min] | MW calc. | MW found |
|---|---|---|---|---|
| 527 | 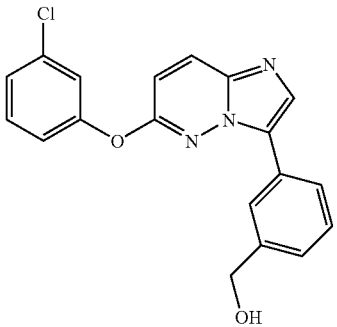 [SMILES: OCc1cccc(-c2cnc3ccc(Oc4cccc(Cl)c4)nn23)c1] | 7.18 | 351 | 352 |
| 528 | 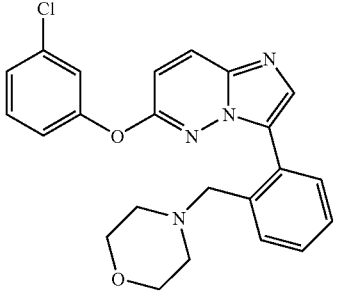 [SMILES: Clc1cccc(Oc2ccc3ncc(-c4ccccc4CN4CCOCC4)n3n2)c1] | 5.25 | 420 | 421 |
| 529 | 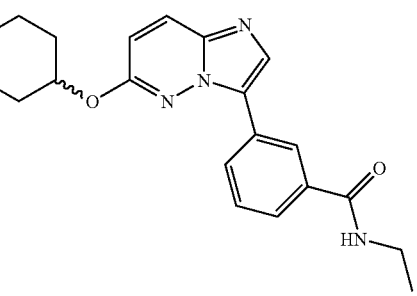 | 4.82 | 380 | 381 |
| 530 | 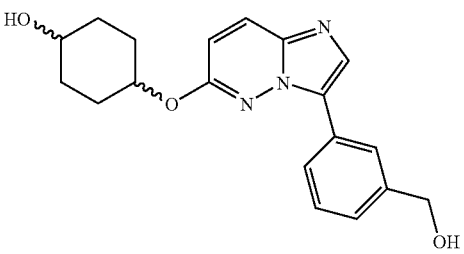 [SMILES: OCc1cccc(-c2cnc3ccc(OC4CCC(O)CC4)nn23)c1] | 4.62 | 339 | 340 |

-continued
| EXAMPLE No. | Structure | Retention time [min] | MW calc. | MW found |
|---|---|---|---|---|
| 531 | 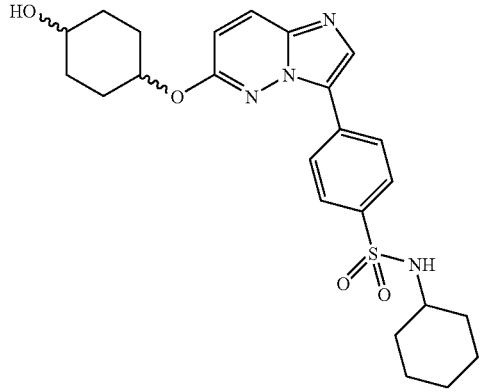 [SMILES: O=S(=O)(NC1CCCCC1)c1ccc(-c2cnc3ccc(OC4CCC(O)CC4)nn23)cc1] | 6.45 | 470 | 471 |
| 532 | 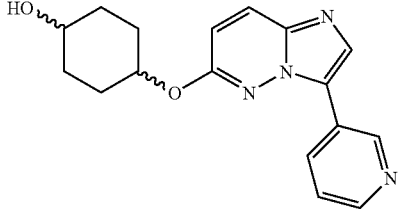 [SMILES: OC1CCC(Oc2ccc3ncc(-c4cccnc4)n3n2)CC1] | 4.06 | 310 | 311 |
| 533 | 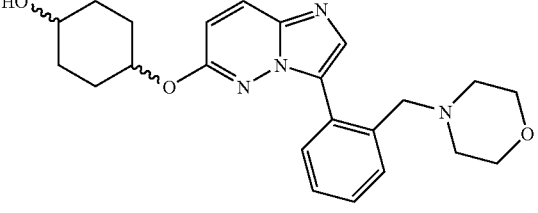 | 3.96 | 408 | 409 |
| 534 | 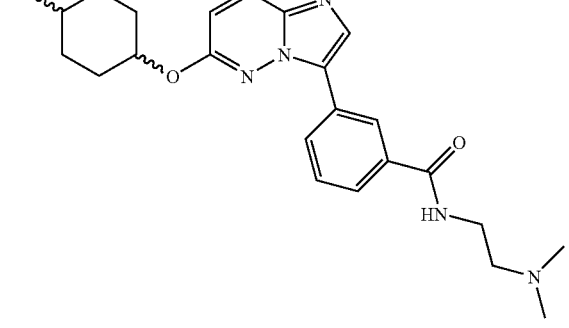 | 4.02 | 423 | 424 |
| 535 | 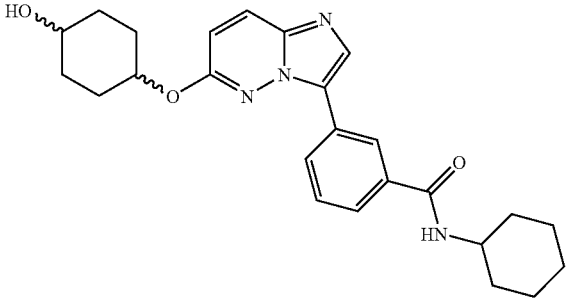 [SMILES: O=C(NC1CCCCC1)c1cccc(-c2cnc3ccc(OC4CCC(O)CC4)nn23)c1] | 5.98 | 434 | 435 |

| EXAMPLE No. | Structure | Retention time [min] | MW calc. | MW found |
|---|---|---|---|---|
| 536 | 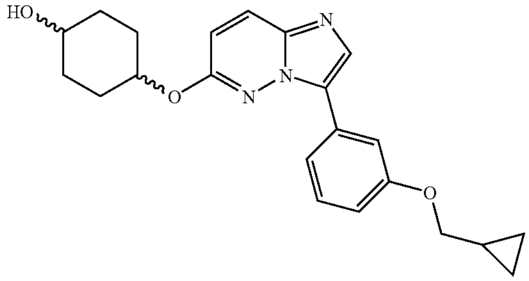 [SMILES: OC1CCC(Oc2ccc3ncc(-c4cccc(OCC5CC5)c4)n3n2)CC1] | 6.33 | 379 | 380 |
| 537 | 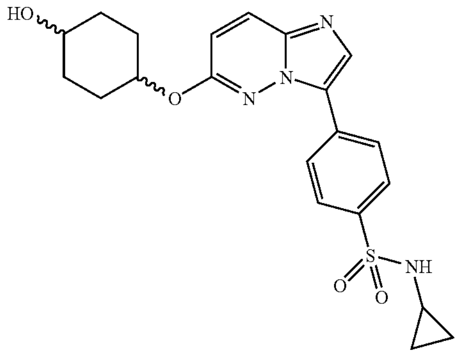 [SMILES: O=S(=O)(NC1CC1)c1ccc(-c2cnc3ccc(OC4CCC(O)CC4)nn23)cc1] | 5.47 | 428 | 429 |
| 538 | 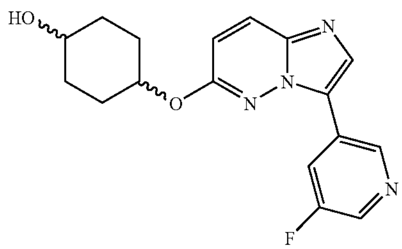 [SMILES: OC1CCC(Oc2ccc3ncc(-c4cncc(F)c4)n3n2)CC1] | 4.97 | 328 | 329 |
| 539 | 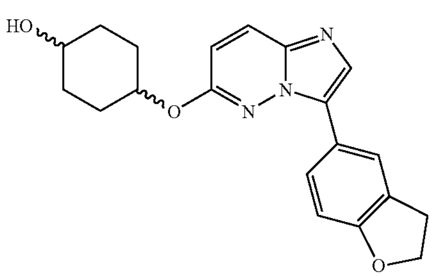 [SMILES: OC1CCC(Oc2ccc3ncc(-c4ccc5c(c4)CCO5)n3n2)CC1] | 5.38 | 351 | 352 |

-continued

| EXAMPLE No. | Structure | Retention time [min] | MW calc. | MW found |
|---|---|---|---|---|
| 540 | 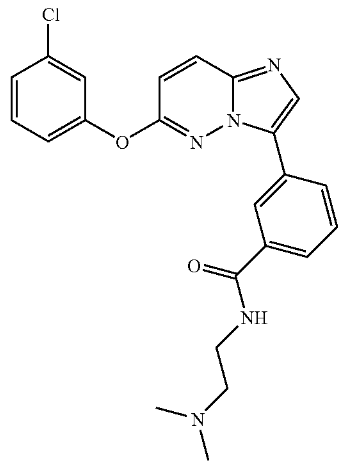 [SMILES: CN(C)CCNC(=O)c1cccc(-c2cnc3ccc(Oc4cccc(Cl)c4)nn23)c1] | 5.29 | 435 | 436 |
| 541 | 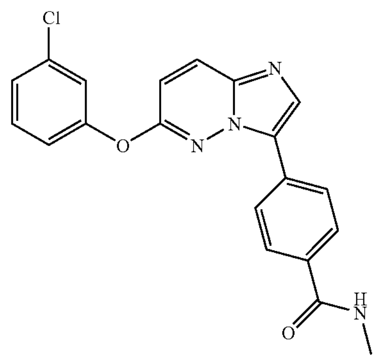 [SMILES: CNC(=O)c1ccc(-c2cnc3ccc(Oc4cccc(Cl)c4)nn23)cc1] | 7.39 | 378 | 379 |
| 542 | 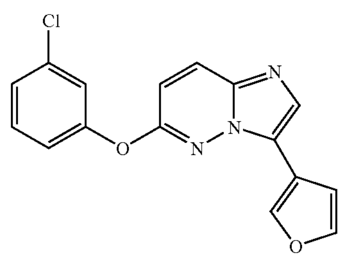 [SMILES: Clc1cccc(Oc2ccc3ncc(-c4ccoc4)n3n2)c1] | 9.08 | 311 | 312 |
| 543 | 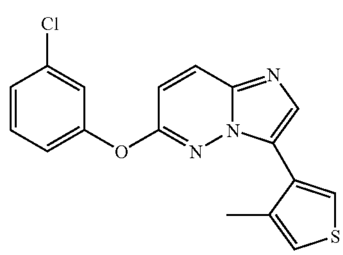 [SMILES: Cc1cscc1-c1cnc2ccc(Oc3cccc(Cl)c3)nn12] | 9.46 | 341 | 342 |
| 544 | 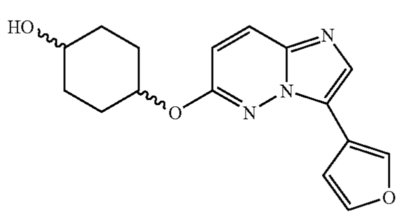 [SMILES: OC1CCC(Oc2ccc3ncc(-c4ccoc4)n3n2)CC1] | 5.18 | 299 | 300 |

-continued
| EXAMPLE No. | Structure | Retention time [min] | MW calc. | MW found |
|---|---|---|---|---|
| 545 | 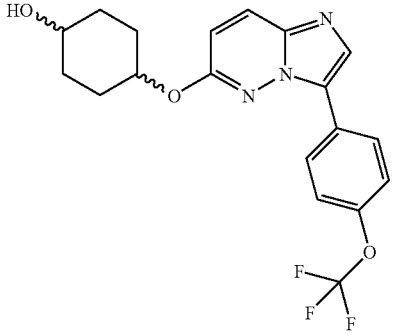 [SMILES: OC1CCC(Oc2ccc3ncc(-c4ccc(OC(F)(F)F)cc4)n3n2)CC1] | 6.61 | 393 | 394 |
| 546 | 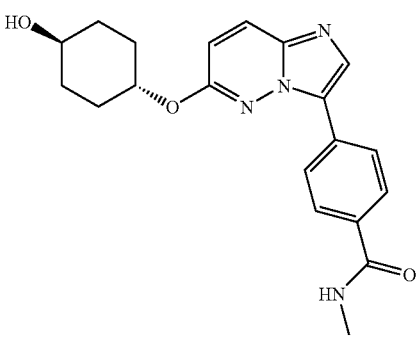 [SMILES: CNC(=O)c1ccc(-c2cnc3ccc(O[C@H]4CC[C@H](O)CC4)nn23)cc1] | 4.61 | 366 | 367 |
| 547 | 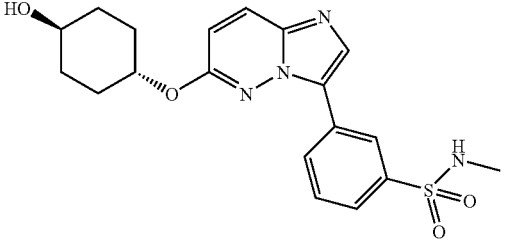 [SMILES: CNS(=O)(=O)c1cccc(-c2cnc3ccc(O[C@H]4CC[C@H](O)CC4)nn23)c1] | 5.0 | 402 | 403 |
| 548 | 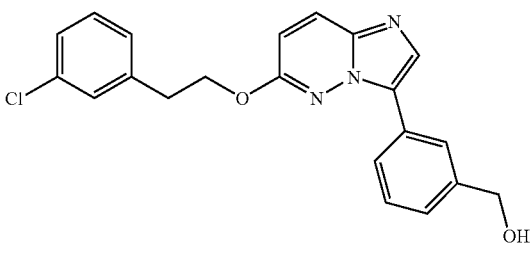 [SMILES: OCc1cccc(-c2cnc3ccc(OCCc4cccc(Cl)c4)nn23)c1] | 6.98 | 379 | 380 |
| 549 | 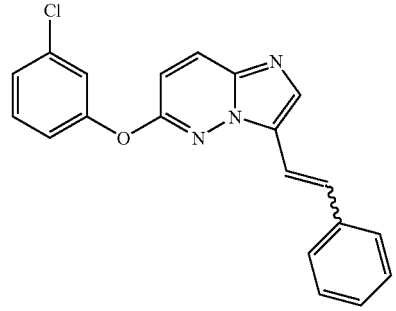 [SMILES: Clc1cccc(Oc2ccc3ncc(C=Cc4ccccc4)n3n2)c1] | 11.07 | 347 | 348 |

-continued

| EXAMPLE No. | Structure | Retention time [min] | MW calc. | MW found |
|---|---|---|---|---|
| 550 | 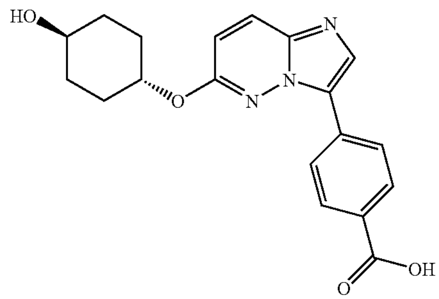 [SMILES: O=C(O)c1ccc(-c2cnc3ccc(O[C@H]4CC[C@H](O)CC4)nn23)cc1] | 4.92 | 353 | 354 |
| 551 | 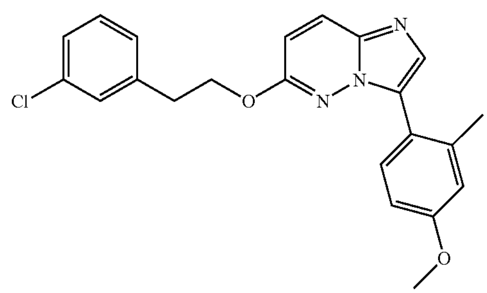 [SMILES: COc1ccc(-c2cnc3ccc(OCCc4cccc(Cl)c4)nn23)c(C)c1] | 7.77 | 393 | 394 |
| 552 | 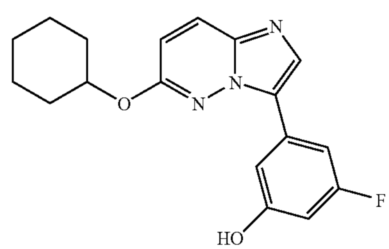 [SMILES: Oc1cc(F)cc(-c2cnc3ccc(OC4CCCCC4)nn23)c1] | 7.18 | 327 | 328 |
| 553 | 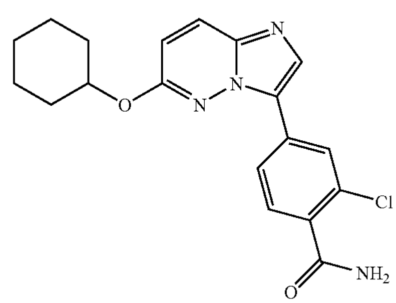 [SMILES: NC(=O)c1ccc(-c2cnc3ccc(OC4CCCCC4)nn23)cc1Cl] | 6.42 | 370 | 371 |
| 554 | 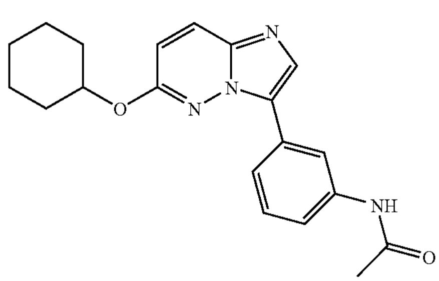 [SMILES: CC(=O)Nc1cccc(-c2cnc3ccc(OC4CCCCC4)nn23)c1] | 6.32 | 350 | 351 |

-continued

| EXAMPLE No. | Structure | Retention time [min] | MW calc. | MW found |
|---|---|---|---|---|
| 555 | 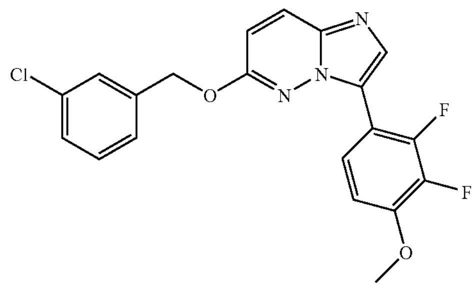 [SMILES: COc1ccc(-c2cnc3ccc(OCc4cccc(Cl)c4)nn23)c(F)c1F] | 8.8 | 401 | 402 |
| 556 | 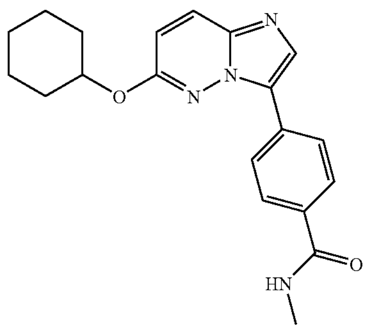 [SMILES: CNC(=O)c1ccc(-c2cnc3ccc(OC4CCCCC4)nn23)cc1] | 6.17 | 350 | 351 |
| 557 | 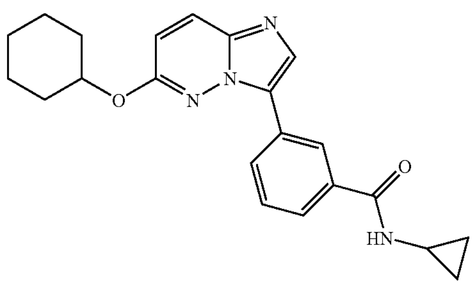 [SMILES: O=C(NC1CC1)c1cccc(-c2cnc3ccc(OC4CCCCC4)nn23)c1] | 6.56 | 376 | 377 |
| 558 | 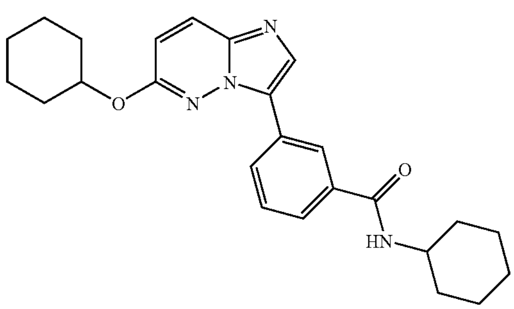 [SMILES: O=C(NC1CCCCC1)c1cccc(-c2cnc3ccc(OC4CCCCC4)nn23)c1] | 7.93 | 418 | 419 |

Variant B

This variant for preparing the final compounds can likewise be carried out with parallel syntheses, for example in an automatic synthesizer.

Example 559

6-Benzyloxy-3-(3-chlorophenyl)imidazo[1,2-b]pyridazine

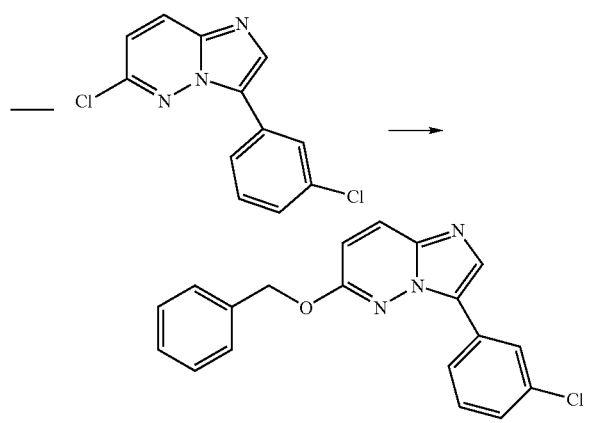

12 mg (0.26 mmol) of sodium hydride (60% in liquid paraffin) are suspended in 2 ml of THF under a protective gas atmosphere. Then 0.031 ml of benzyl alcohol (0.3 mmol) in 0.5 ml THF are added. After 15 min, 47 mg (0.15 mmol) of 6-chloro-3-(3-chlorophenyl)imidazo[1,2-b]pyridazine are added. The reaction mixture is shaken for 12 h.

Addition of a half-saturated aqueous sodium chloride solution is followed by extraction of the resulting mixture with ethyl acetate. The organic phase is separated off and the solvent is evaporated off. The crude product obtained in this way is purified by preparative HPLC. 20 mg (40%) of the desired product are obtained.

HPLC-MS (analytical) of the purified product:
(Detection: UV=254 nM; column: Purospher STAR RP18e, 125×4 mm, 5μ (Merck KgGa, Darmstadt); eluent: A: $H_2O$/0.1% TFA, B: $CH_3CN$/0.1% TFA, gradient: 5 to 95% B in 10 min; flow rate: 1 ml/min):

Retention time of the product=8.66 min; MS of the product: m/z=355 ([M+H$^+$])

The following were prepared analogously:

| Example No. | Structure | Retention time [min] | MW calc. | MW found |
|---|---|---|---|---|
| 560 | 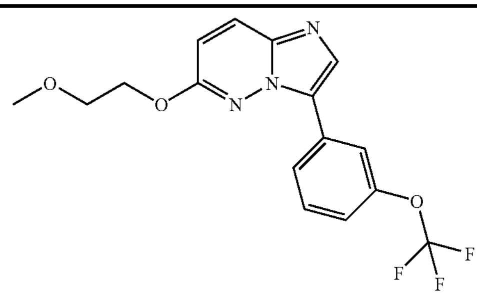 | 7.22 | 353 | 354 |
| 561 | 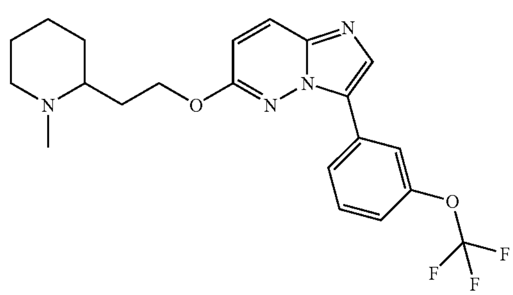 [SMILES: CN1CCCCC1CCOc1ccc2ncc(-c3cccc(OC(F)(F)F)c3)n2n1] | 5.75 | 420 | 421 |
| 562 | 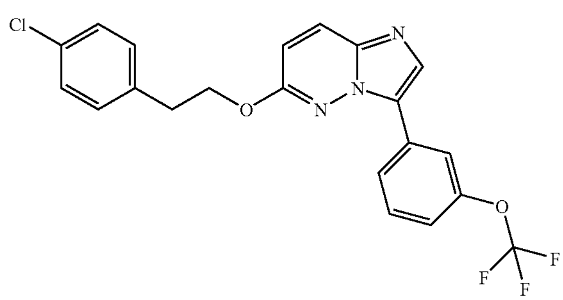 [SMILES: FC(F)(F)Oc1cccc(-c2cnc3ccc(OCCc4ccc(Cl)cc4)nn23)c1] | 9.77 | 433 | 434 |

-continued

| Example No. | Structure | Retention time [min] | MW calc. | MW found |
|---|---|---|---|---|
| 563 | 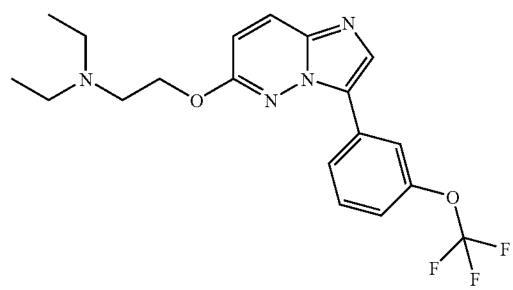 [SMILES: CCN(CC)CCOc1ccc2ncc(-c3cccc(OC(F)(F)F)c3)n2n1] | 5.64 | 394 | 395 |
| 564 | 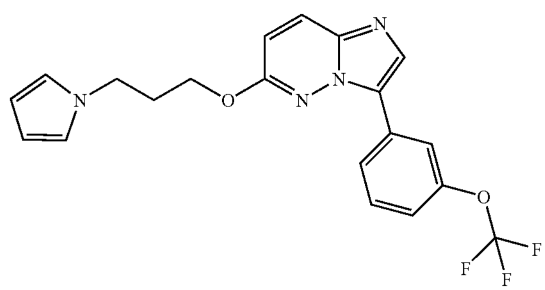 [SMILES: FC(F)(F)Oc1cccc(-c2cnc3ccc(OCCCn4cccc4)nn23)c1] | 8.45 | 402 | 403 |
| 565 | 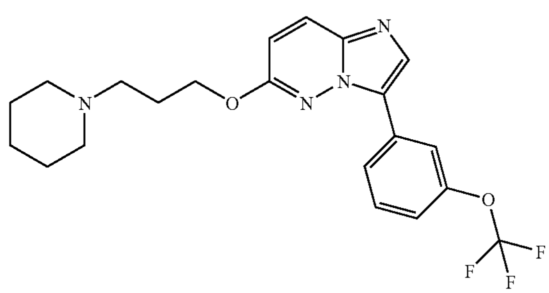 [SMILES: FC(F)(F)Oc1cccc(-c2cnc3ccc(OCCCN4CCCCC4)nn23)c1] | 5.8 | 420 | 421 |
| 566 | 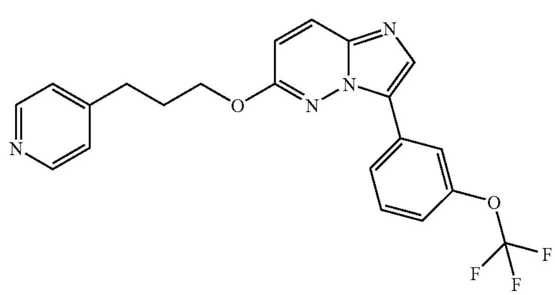 [SMILES: FC(F)(F)Oc1cccc(-c2cnc3ccc(OCCCc4ccncc4)nn23)c1] | 5.81 | 414 | 415 |
| 567 | 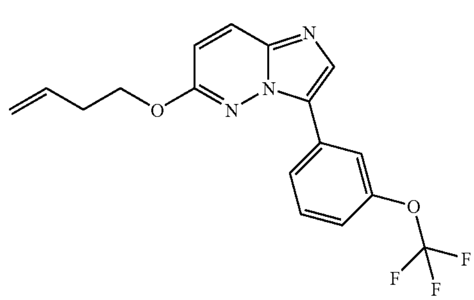 [SMILES: C=CCCOc1ccc2ncc(-c3cccc(OC(F)(F)F)c3)n2n1] | 8.61 | 349 | 350 |

| Example No. | Structure | Retention time [min] | MW calc. | MW found |
|---|---|---|---|---|
| 568 | 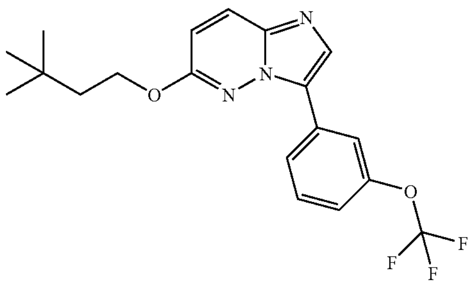 [SMILES: CC(C)(C)CCOc1ccc2ncc(-c3cccc(OC(F)(F)F)c3)n2n1] | 10.24 | 379 | 380 |
| 569 | 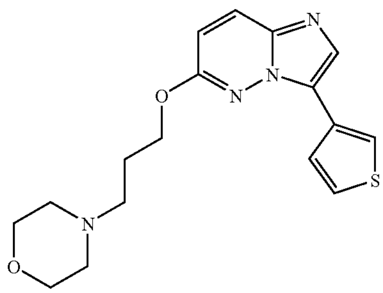 [SMILES: c1cc(-c2cnc3ccc(OCCCN4CCOCC4)nn23)cs1] | 4.26 | 344 | 345 |
| 570 | 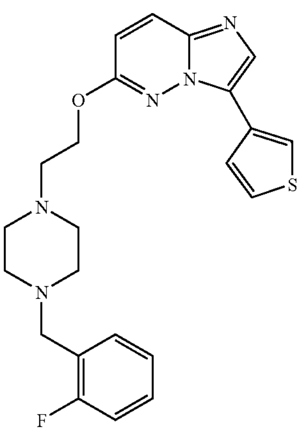 [SMILES: Fc1ccccc1CN1CCN(CCOc2ccc3ncc(-c4ccsc4)n3n2)CC1] | 4.97 | 437 | 438 |
| 571 | 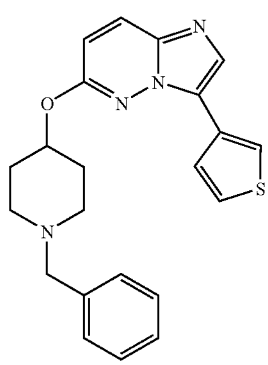 [SMILES: c1ccc(CN2CCC(Oc3ccc4ncc(-c5ccsc5)n4n3)CC2)cc1] | 5.17 | 390 | 391 |

-continued

| Example No. | Structure | Retention time [min] | MW calc. | MW found |
|---|---|---|---|---|
| 572 | 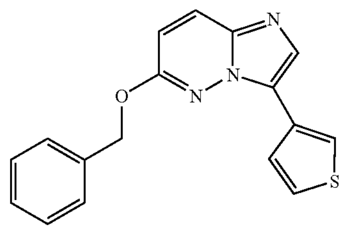 [SMILES: c1ccc(COc2ccc3ncc(-c4ccsc4)n3n2)cc1] | 7.46 | 307 | 308 |
| 573 | 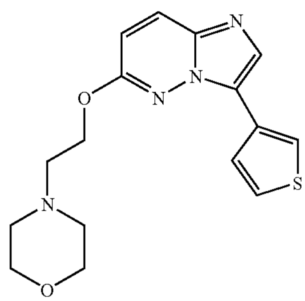 [SMILES: c1cc(-c2cnc3ccc(OCCN4CCOCC4)nn23)cs1] | 4.17 | 330 | 331 |
| 574 | 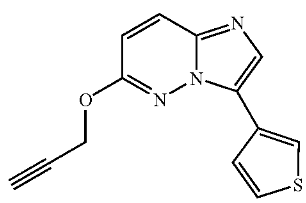 [SMILES: C#CCOc1ccc2ncc(-c3ccsc3)n2n1] | 6.22 | 255 | 256 |
| 575 | 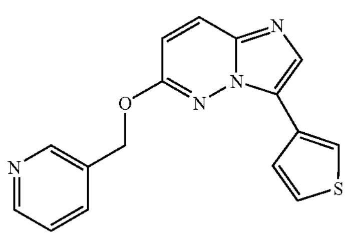 [SMILES: c1cncc(COc2ccc3ncc(-c4ccsc4)n3n2)c1] | 4.4 | 308 | 309 |
| 576 | 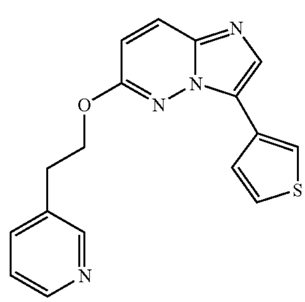 [SMILES: c1cncc(CCOc2ccc3ncc(-c4ccsc4)n3n2)c1] | 4.64 | 322 | 323 |
| 577 | 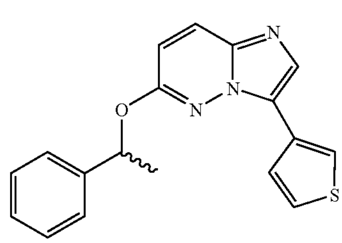 [SMILES: CC(Oc1ccc2ncc(-c3ccsc3)n2n1)c1ccccc1] | 7.51 | 321 | 322 |

| Example No. | Structure | Retention time [min] | MW calc. | MW found |
|---|---|---|---|---|
| 578 | 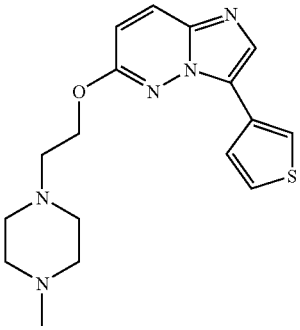 [SMILES: CN1CCN(CCOc2ccc3ncc(-c4ccsc4)n3n2)CC1] | 4.11 | 343 | 344 |
| 579 | 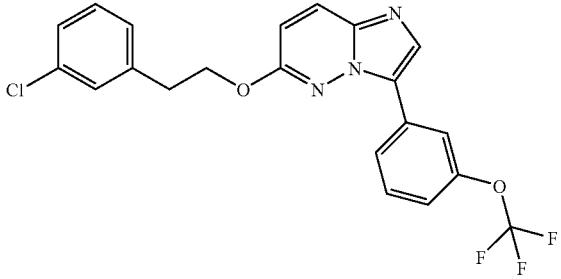 [SMILES: FC(F)(F)Oc1cccc(-c2cnc3ccc(OCCc4cccc(Cl)c4)nn23)c1] | 9.85 | 433 | 434 |
| 580 | 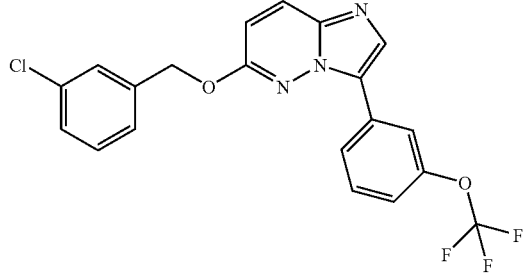 [SMILES: FC(F)(F)Oc1cccc(-c2cnc3ccc(OCc4cccc(Cl)c4)nn23)c1] | 9.74 | 419 | 420 |
| 581 | 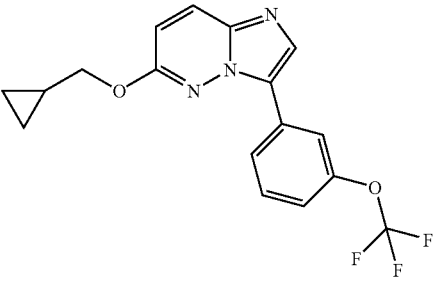 [SMILES: FC(F)(F)Oc1cccc(-c2cnc3ccc(OCC4CC4)nn23)c1] | 8.45 | 349 | 350 |
| 582 | 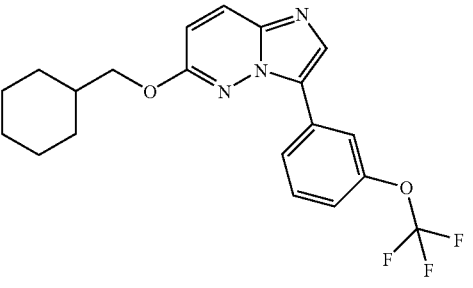 [SMILES: FC(F)(F)Oc1cccc(-c2cnc3ccc(OCC4CCCCC4)nn23)c1] | 10.8 | 391 | 392 |

| Example No. | Structure | Retention time [min] | MW calc. | MW found |
|---|---|---|---|---|
| 583 | 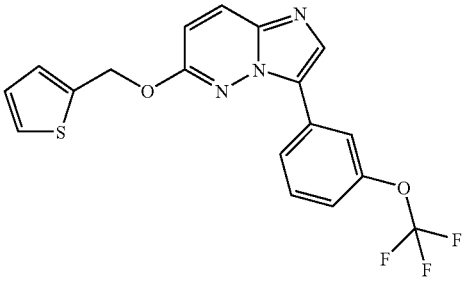 [SMILES: FC(F)(F)Oc1cccc(-c2cnc3ccc(OCc4cccs4)nn23)c1] | 8.82 | 391 | 392 |
| 584 | 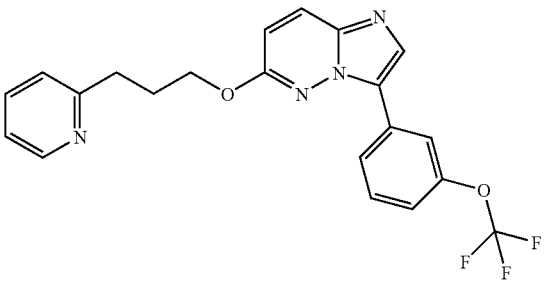 [SMILES: FC(F)(F)Oc1cccc(-c2cnc3ccc(OCCCc4ccccn4)nn23)c1] | 0 | 414 | 415 |
| 585 | 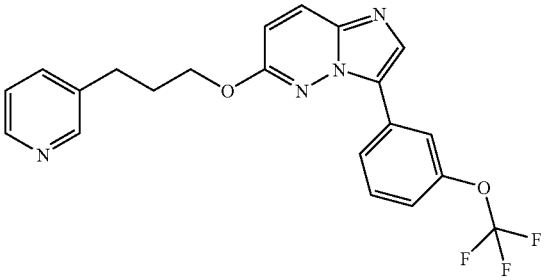 [SMILES: FC(F)(F)Oc1cccc(-c2cnc3ccc(OCCCc4cccnc4)nn23)c1] | 5.73 | 414 | 415 |
| 586 | 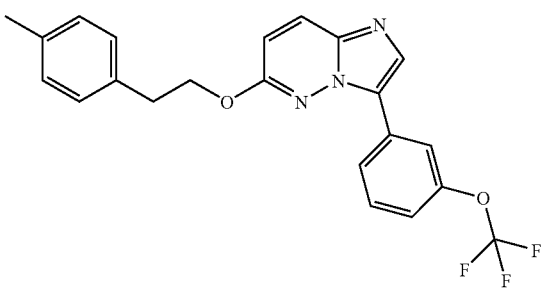 [SMILES: Cc1ccc(CCOc2ccc3ncc(-c4cccc(OC(F)(F)F)c4)n3n2)cc1] | 9.8 | 413 | 414 |
| 587 | 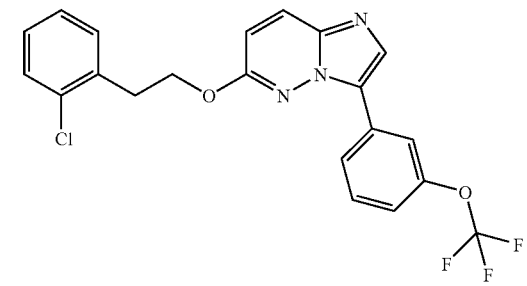 [SMILES: FC(F)(F)Oc1cccc(-c2cnc3ccc(OCCc4ccccc4Cl)nn23)c1] | 9.96 | 433 | 434 |

| Example No. | Structure | Retention time [min] | MW calc. | MW found |
|---|---|---|---|---|
| 588 | 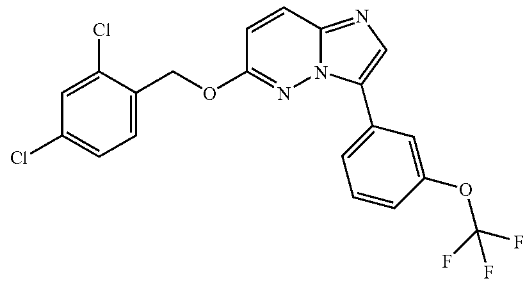 [SMILES: FC(F)(F)Oc1cccc(-c2cnc3ccc(OCc4ccc(Cl)cc4Cl)nn23)c1] | 10.72 | 454 | 454 |
| 589 | 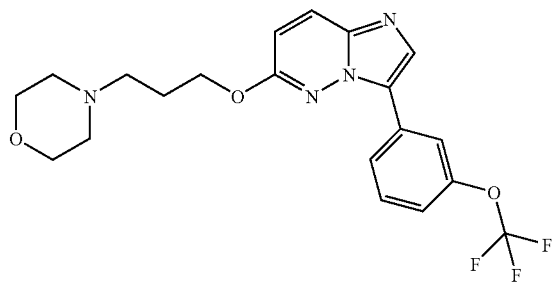 [SMILES: FC(F)(F)Oc1cccc(-c2cnc3ccc(OCCCN4CCOCC4)nn23)c1] | 5.47 | 422 | 423 |
| 590 | 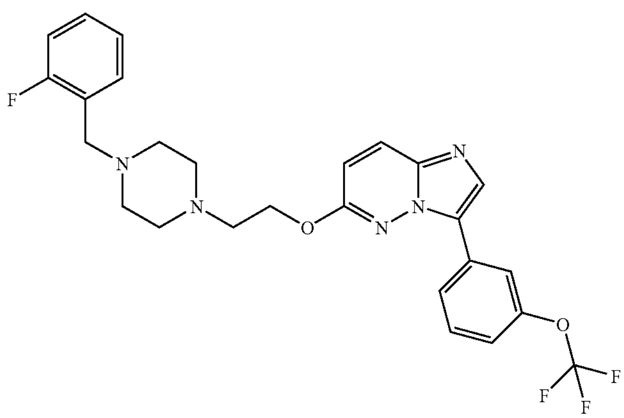 [SMILES: Fc1ccccc1CN1CCN(CCOc2ccc3ncc(-c4cccc(OC(F)(F)F)c4)n3n2)CC1] | 5.92 | 515 | 516 |
| 591 | 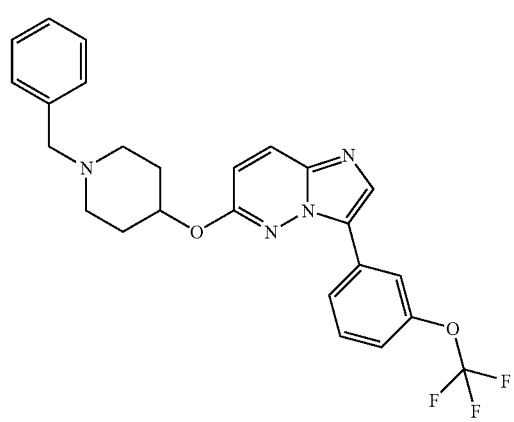 [SMILES: FC(F)(F)Oc1cccc(-c2cnc3ccc(OC4CCN(Cc5ccccc5)CC4)nn23)c1] | 6.22 | 468 | 469 |

-continued
| Example No. | Structure | Retention time [min] | MW calc. | MW found |
|---|---|---|---|---|
| 592 | 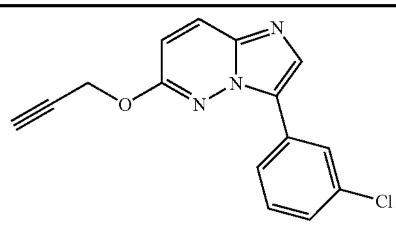 | 7.27 | 283 | 284 |
| 593 | 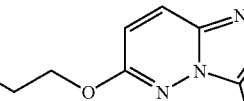 | 5.34 | 350 | 351 |
| 594 | 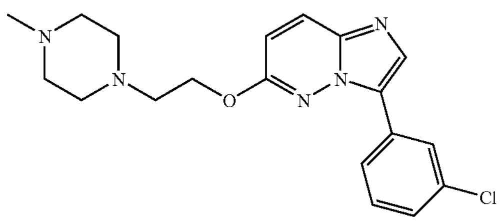 [SMILES: CN1CCN(CCOc2ccc3ncc(-c4cccc(Cl)c4)n3n2)CC1] | 4.65 | 371 | 372 |
| 595 | 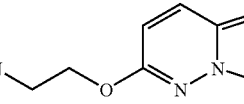 | 10.58 | 327 | 328 |
| 596 | 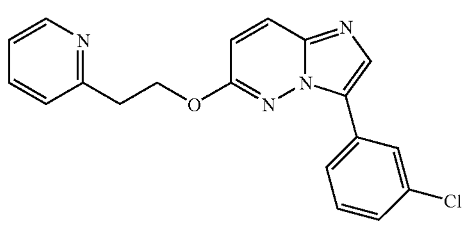 [SMILES: Clc1cccc(-c2cnc3ccc(OCCc4ccccn4)nn23)c1] | 5.1 | 350 | 351 |
| 597 | 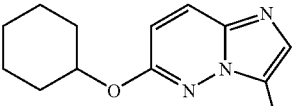 | 5.31 | 370 | 371 |
| 598 | 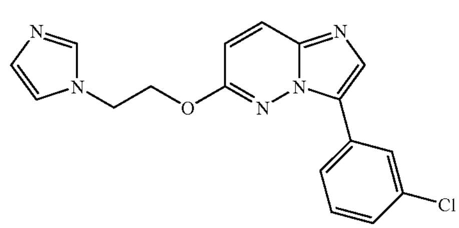 [SMILES: Clc1cccc(-c2cnc3ccc(OCCn4ccnc4)nn23)c1] | 55 | 339 | 340 |

-continued

| Example No. | Structure | Retention time [min] | MW calc. | MW found |
|---|---|---|---|---|
| 599 | 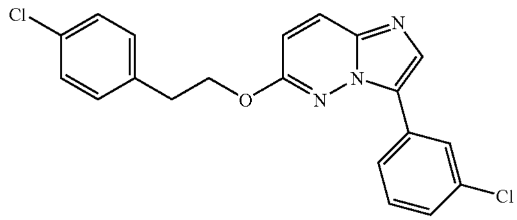 [SMILES: Clc1ccc(CCOc2ccc3ncc(-c4cccc(Cl)c4)n3n2)cc1] | 9.58 | 384 | 384 |
| 600 | 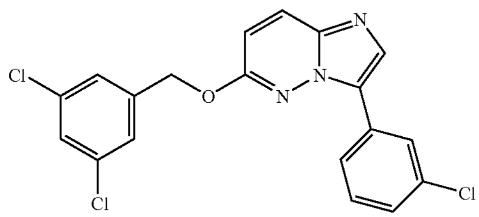 [SMILES: Clc1cc(Cl)cc(COc2ccc3ncc(-c4cccc(Cl)c4)n3n2)c1] | 10.17 | 404 | 404 |
| 601 | 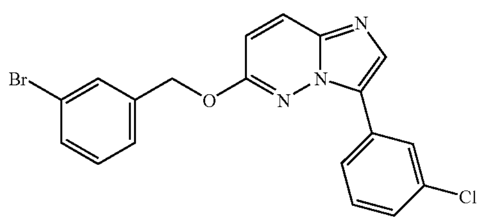 [SMILES: Clc1cccc(-c2cnc3ccc(OCc4cccc(Br)c4)nn23)c1] | 9.41 | 414 | 414 |
| 602 | 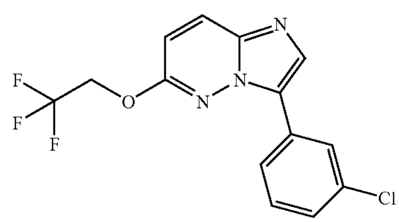 [SMILES: FC(F)(F)COc1ccc2ncc(-c3cccc(Cl)c3)n2n1] | 8.43 | 327 | 328 |
| 603 | 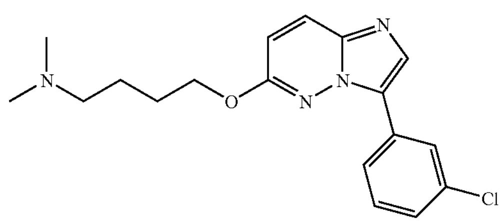 [SMILES: CN(C)CCCCOc1ccc2ncc(-c3cccc(Cl)c3)n2n1] | 5.12 | 344 | 345 |
| 604 | 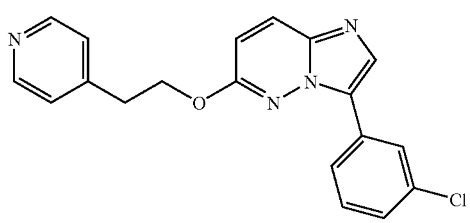 [SMILES: Clc1cccc(-c2cnc3ccc(OCCc4ccncc4)nn23)c1] | 5.2 | 350 | 351 |
| 605 | 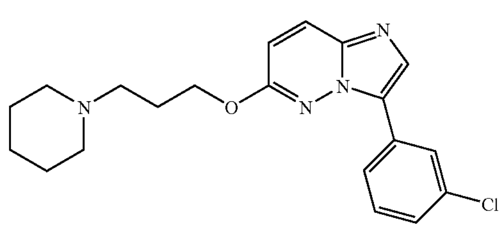 [SMILES: Clc1cccc(-c2cnc3ccc(OCCCN4CCCCC4)nn23)c1] | 5.39 | 370 | 371 |

| Example No. | Structure | Retention time [min] | MW calc. | MW found |
|---|---|---|---|---|
| 606 | 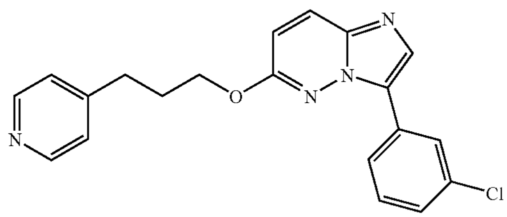 [SMILES: Clc1cccc(-c2cnc3ccc(OCCCc4ccncc4)nn23)c1] | 5.3 | 364 | 365 |
| 607 | 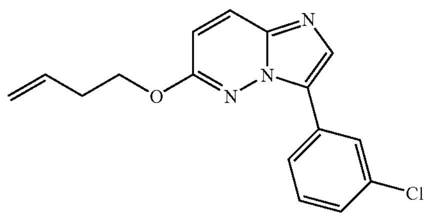 [SMILES: C=CCCOc1ccc2ncc(-c3cccc(Cl)c3)n2n1] | 8.21 | 299 | 300 |
| 608 | 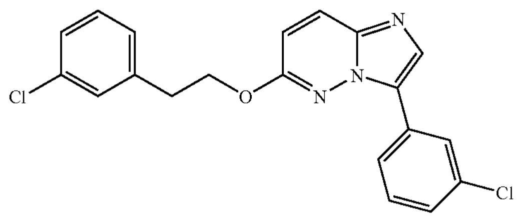 [SMILES: Clc1cccc(CCOc2ccc3ncc(-c4cccc(Cl)c4)n3n2)c1] | 9.56 | 384 | 384 |
| 609 | 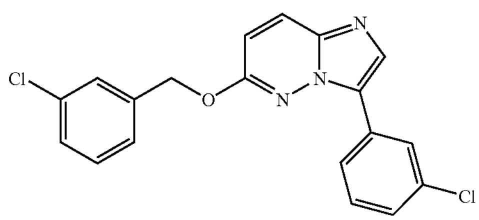 [SMILES: Clc1cccc(COc2ccc3ncc(-c4cccc(Cl)c4)n3n2)c1] | 9.27 | 370 | 370 |
| 610 | 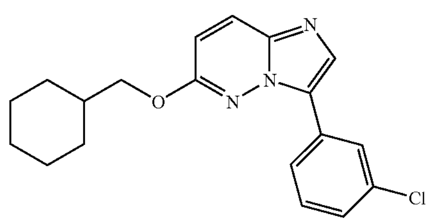 [SMILES: Clc1cccc(-c2cnc3ccc(OCC4CCCCC4)nn23)c1] | 10.6 | 341 | 342 |
| 611 | 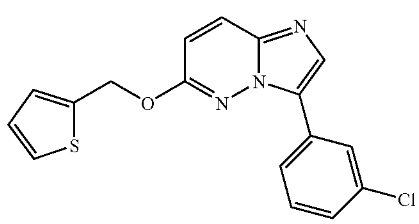 [SMILES: Clc1cccc(-c2cnc3ccc(OCc4cccs4)nn23)c1] | 8.39 | 341 | 342 |
| 612 | 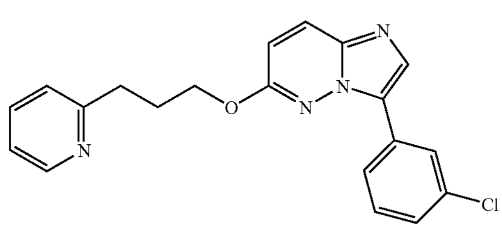 [SMILES: Clc1cccc(-c2cnc3ccc(OCCCc4ccccn4)nn23)c1] | 5.26 | 364 | 365 |

-continued

| Example No. | Structure | Retention time [min] | MW calc. | MW found |
|---|---|---|---|---|
| 613 | 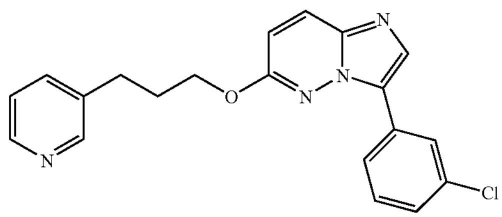 [SMILES: Clc1cccc(-c2cnc3ccc(OCCCc4cccnc4)nn23)c1] | 5.36 | 364 | 365 |
| 614 | 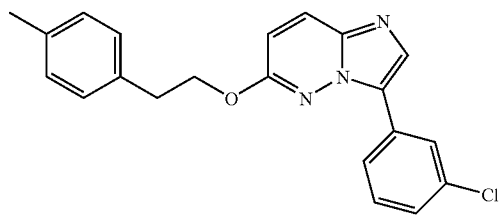 [SMILES: Cc1ccc(CCOc2ccc3ncc(-c4cccc(Cl)c4)n3n2)cc1] | 9.55 | 363 | 364 |
| 615 | 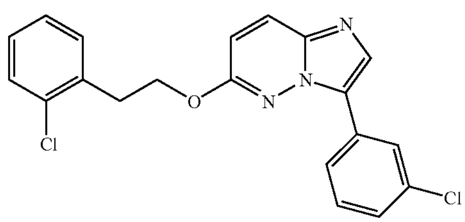 [SMILES: Clc1cccc(-c2cnc3ccc(OCCc4ccccc4Cl)nn23)c1] | 9.45 | 384 | 384 |
| 616 | 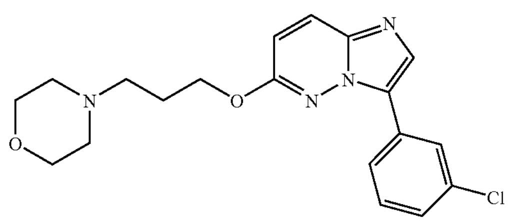 [SMILES: Clc1cccc(-c2cnc3ccc(OCCCN4CCOCC4)nn23)c1] | 5.1 | 372 | 373 |
| 617 | 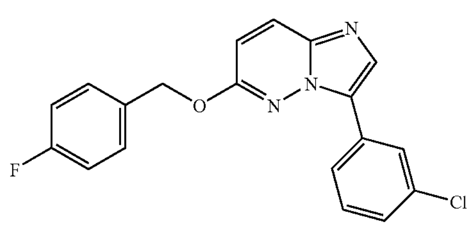 [SMILES: Fc1ccc(COc2ccc3ncc(-c4cccc(Cl)c4)n3n2)cc1] | 8.71 | 353 | 354 |
| 618 | 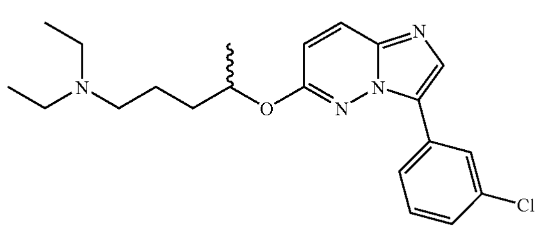 [SMILES: CCN(CC)CCCC(C)Oc1ccc2ncc(-c3cccc(Cl)c3)n2n1] | 5.61 | 386 | 387 |

-continued

| Example No. | Structure | Retention time [min] | MW calc. | MW found |
|---|---|---|---|---|
| 619 | 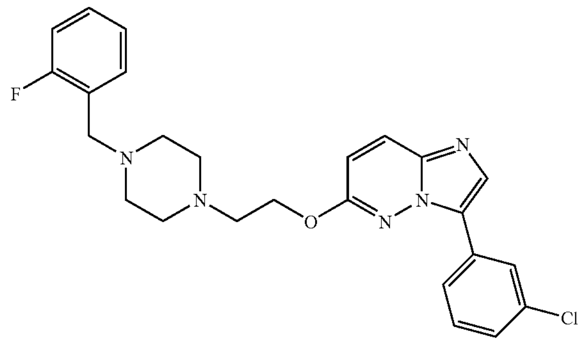 [SMILES: Fc1ccccc1CN1CCN(CCOc2ccc3ncc(-c4cccc(Cl)c4)n3n2)CC1] | 5.57 | 465 | 466 |
| 620 | 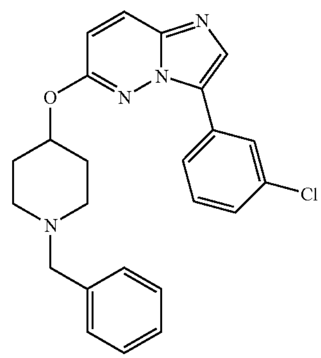 [SMILES: Clc1cccc(-c2cnc3ccc(OC4CCN(Cc5ccccc5)CC4)nn23)c1] | 5.91 | 418 | 419 |
| 621 | 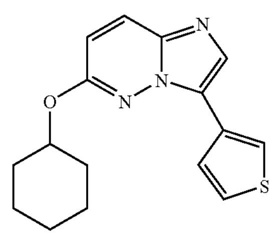 [SMILES: c1cc(-c2cnc3ccc(OC4CCCCC4)nn23)cs1] | 8 | 299 | 300 |
| 622 | 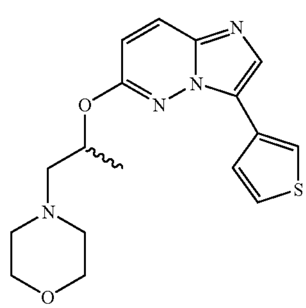 [SMILES: CC(CN1CCOCC1)Oc1ccc2ncc(-c3ccsc3)n2n1] | 4.54 | 344 | 345 |
| 623 | 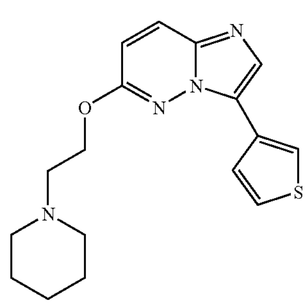 [SMILES: c1cc(-c2cnc3ccc(OCCN4CCCCC4)nn23)cs1] | 4.47 | 328 | 329 |

-continued

| Example No. | Structure | Retention time [min] | MW calc. | MW found |
|---|---|---|---|---|
| 624 | 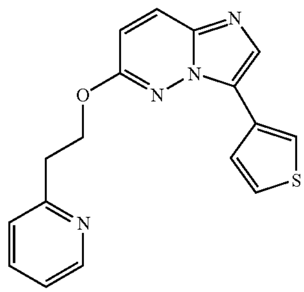 [SMILES: c1ccc(CCOc2ccc3ncc(-c4ccsc4)n3n2)nc1] | 4.44 | 322 | 323 |
| 625 | 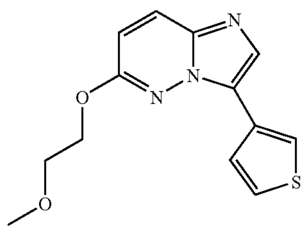 [SMILES: COCCOc1ccc2ncc(-c3ccsc3)n2n1] | 5.8 | 275 | 276 |
| 626 | 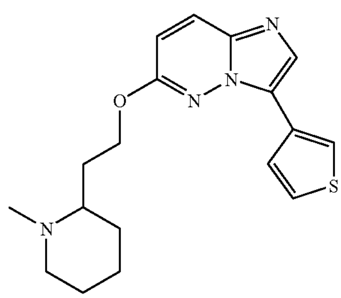 [SMILES: CN1CCCCC1CCOc1ccc2ncc(-c3ccsc3)n2n1] | 4.81 | 342 | 343 |
| 627 | 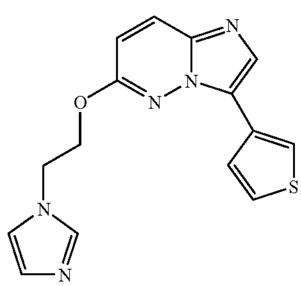 [SMILES: c1cn(CCOc2ccc3ncc(-c4ccsc4)n3n2)cn1] | 4.32 | 311 | 312 |
| 628 | 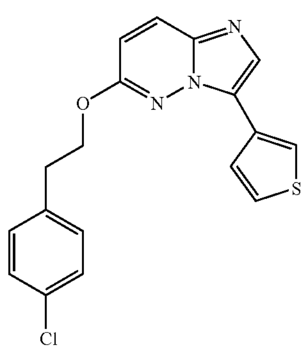 [SMILES: Clc1ccc(CCOc2ccc3ncc(-c4ccsc4)n3n2)cc1] | 8.17 | 355 | 356 |

-continued

| Example No. | Structure | Retention time [min] | MW calc. | MW found |
|---|---|---|---|---|
| 629 | 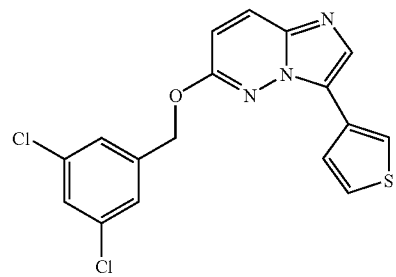 [SMILES: Clc1cc(Cl)cc(COc2ccc3ncc(-c4ccsc4)n3n2)c1] | 8.76 | 376 | 376 |
| 630 | 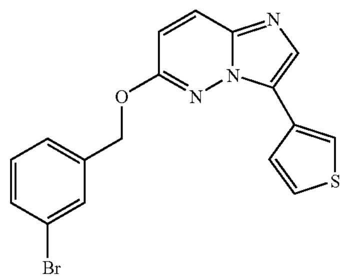 [SMILES: Brc1cccc(COc2ccc3ncc(-c4ccsc4)n3n2)c1] | 8 | 386 | 386 |
| 631 | 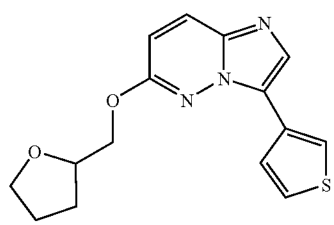 [SMILES: c1cc(-c2cnc3ccc(OCC4CCCO4)nn23)cs1] | 67 | 301 | 302 |
| 632 | 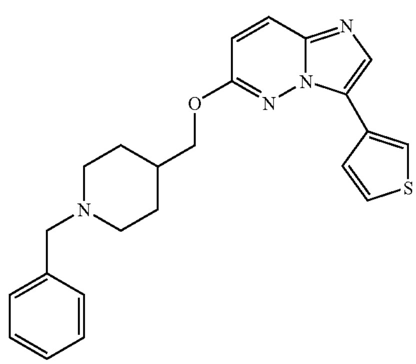 [SMILES: c1ccc(CN2CCC(COc3ccc4ncc(-c5ccsc5)n4n3)CC2)cc1] | 5.57 | 404 | 405 |
| 633 | 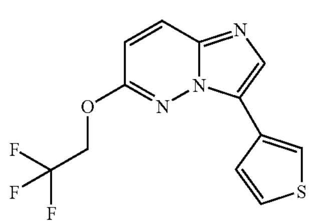 [SMILES: FC(F)(F)COc1ccc2ncc(-c3ccsc3)n2n1] | 7.11 | 299 | 300 |

| Example No. | Structure | Retention time [min] | MW calc. | MW found |
|---|---|---|---|---|
| 634 | 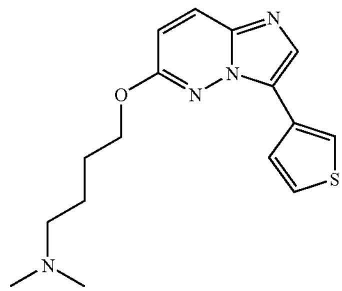 [SMILES: CN(C)CCCCOc1ccc2ncc(-c3ccsc3)n2n1] | 4.6 | 316 | 317 |
| 635 | 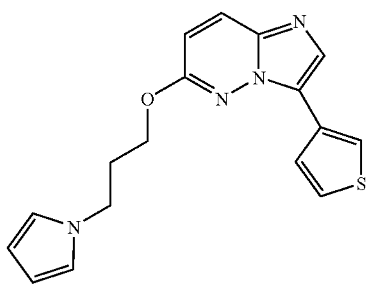 [SMILES: c1ccn(CCCOc2ccc3ncc(-c4ccsc4)n3n2)c1] | 7.16 | 324 | 325 |
| 636 | 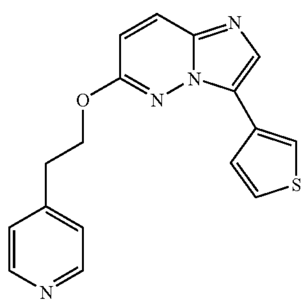 [SMILES: c1cc(CCOc2ccc3ncc(-c4ccsc4)n3n2)ccn1] | 4.65 | 322 | 323 |
| 637 | 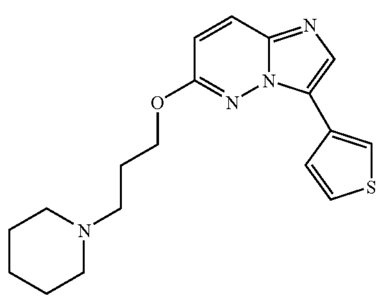 [SMILES: c1cc(-c2cnc3ccc(OCCCN4CCCCC4)nn23)cs1] | 4.77 | 342 | 343 |
| 638 | 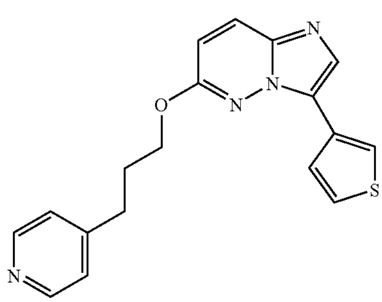 [SMILES: c1cc(CCCOc2ccc3ncc(-c4ccsc4)n3n2)ccn1] | 4.76 | 336 | 337 |

-continued

| Example No. | Structure | Retention time [min] | MW calc. | MW found |
|---|---|---|---|---|
| 639 | 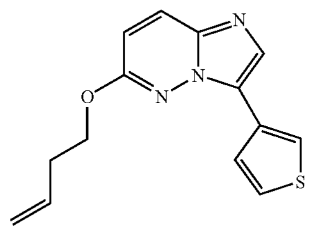 [SMILES: C=CCCOc1ccc2ncc(-c3ccsc3)n2n1] | 72 | 271 | 272 |
| 640 | 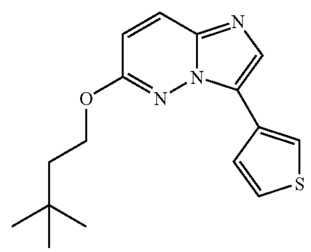 [SMILES: CC(C)(C)CCOc1ccc2ncc(-c3ccsc3)n2n1] | 8.38 | 301 | 302 |
| 641 | 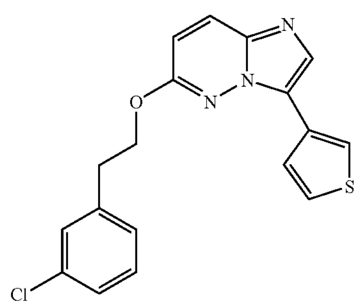 [SMILES: Clc1cccc(CCOc2ccc3ncc(-c4ccsc4)n3n2)c1] | 8.24 | 355 | 356 |
| 642 | 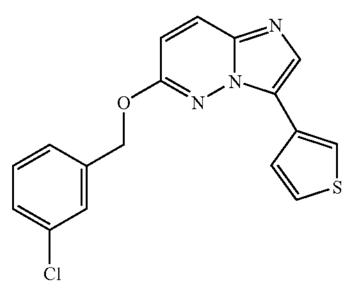 [SMILES: Clc1cccc(COc2ccc3ncc(-c4ccsc4)n3n2)c1] | 7.88 | 341 | 342 |
| 643 | 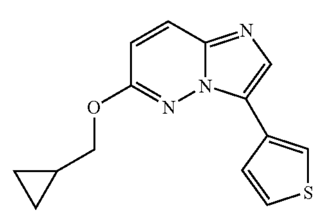 [SMILES: c1cc(-c2cnc3ccc(OCC4CC4)nn23)cs1] | 6.87 | 271 | 272 |
| 644 | 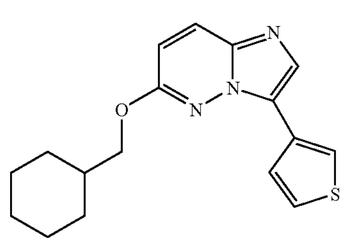 [SMILES: c1cc(-c2cnc3ccc(OCC4CCCCC4)nn23)cs1] | 8.78 | 313 | 314 |

-continued

| Example No. | Structure | Retention time [min] | MW calc. | MW found |
|---|---|---|---|---|
| 645 | 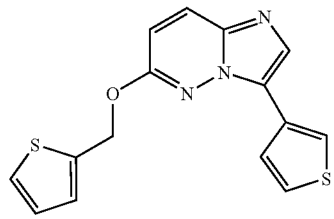 [SMILES: c1csc(COc2ccc3ncc(-c4ccsc4)n3n2)c1] | 7.49 | 313 | 314 |
| 646 | 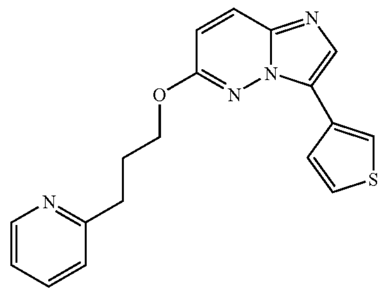 [SMILES: c1ccc(CCCOc2ccc3ncc(-c4ccsc4)n3n2)nc1] | 4.57 | 336 | 337 |
| 647 | 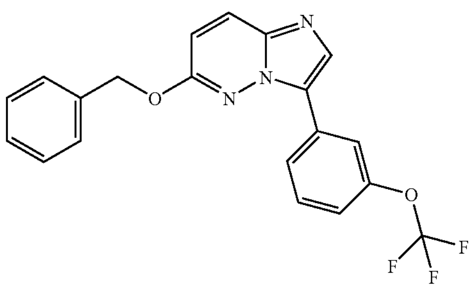 [SMILES: FC(F)(F)Oc1cccc(-c2cnc3ccc(OCc4ccccc4)nn23)c1] | 9.11 | 385 | 386 |
| 648 | 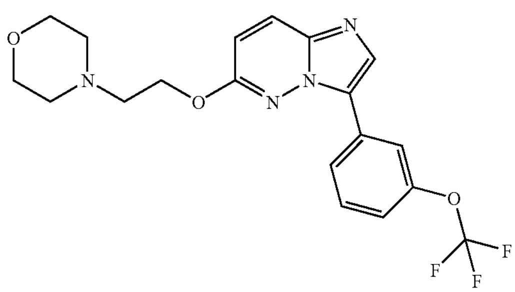 [SMILES: FC(F)(F)Oc1cccc(-c2cnc3ccc(OCCN4CCOCC4)nn23)c1] | 5.37 | 408 | 409 |
| 649 | 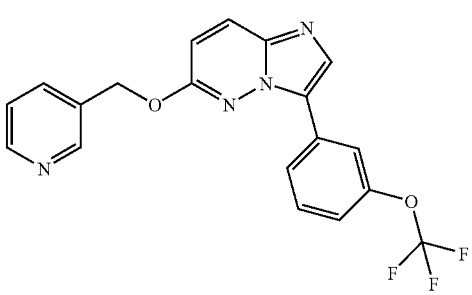 [SMILES: FC(F)(F)Oc1cccc(-c2cnc3ccc(OCc4cccnc4)nn23)c1] | 5.64 | 386 | 387 |

| Example No. | Structure | Retention time [min] | MW calc. | MW found |
|---|---|---|---|---|
| 650 | 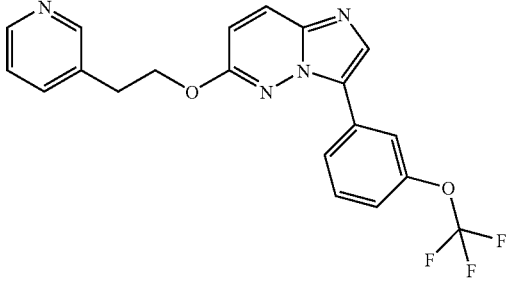 [SMILES: FC(F)(F)Oc1cccc(-c2cnc3ccc(OCCc4cccnc4)nn23)c1] | 5.68 | 400 | 401 |
| 651 | 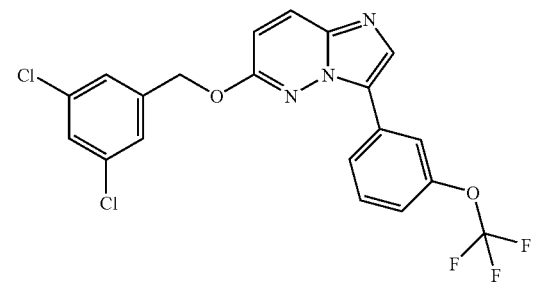 [SMILES: FC(F)(F)Oc1cccc(-c2cnc3ccc(OCc4cc(Cl)cc(Cl)c4)nn23)c1] | 10.67 | 454 | 454 |
| 652 | 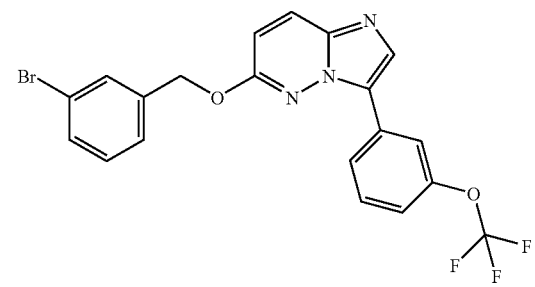 [SMILES: FC(F)(F)Oc1cccc(-c2cnc3ccc(OCc4cccc(Br)c4)nn23)c1] | 9.91 | 464 | 464 |
| 653 | 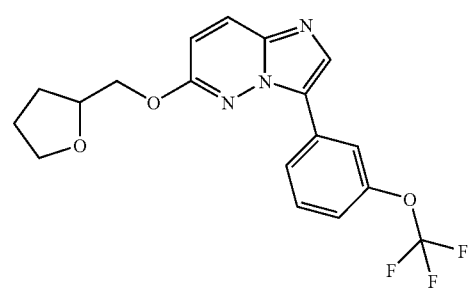 [SMILES: FC(F)(F)Oc1cccc(-c2cnc3ccc(OCC4CCCO4)nn23)c1] | 7.5 | 379 | 380 |
| 654 | 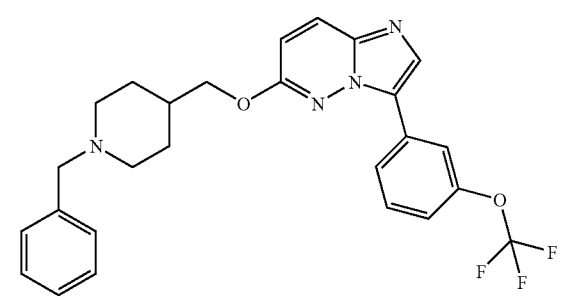 [SMILES: FC(F)(F)Oc1cccc(-c2cnc3ccc(OCC4CCN(Cc5ccccc5)CC4)nn23)c1] | 6.39 | 482 | 483 |

-continued

| Example No. | Structure | Retention time [min] | MW calc. | MW found |
|---|---|---|---|---|
| 655 | 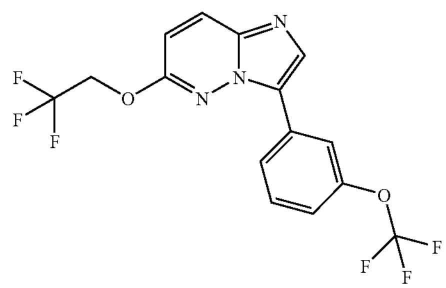 [SMILES: FC(F)(F)COc1ccc2ncc(-c3cccc(OC(F)(F)F)c3)n2n1] | 8.97 | 377 | 378 |
| 656 | 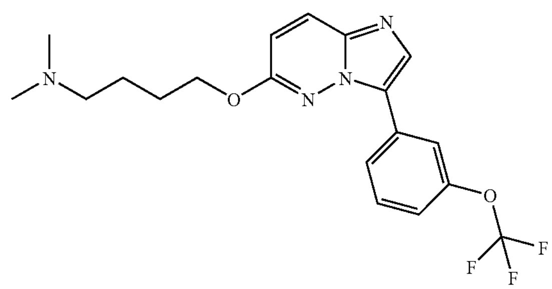 [SMILES: CN(C)CCCCOc1ccc2ncc(-c3cccc(OC(F)(F)F)c3)n2n1] | 5.68 | 394 | 395 |
| 657 | 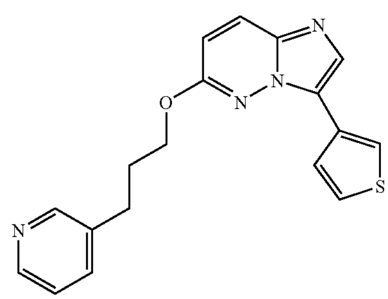 [SMILES: c1cncc(CCCOc2ccc3ncc(-c4ccsc4)n3n2)c1] | 4.66 | 336 | 337 |
| 658 | 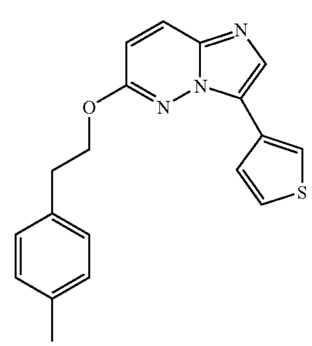 [SMILES: Cc1ccc(CCOc2ccc3ncc(-c4ccsc4)n3n2)cc1] | 8.42 | 335 | 336 |
| 659 | 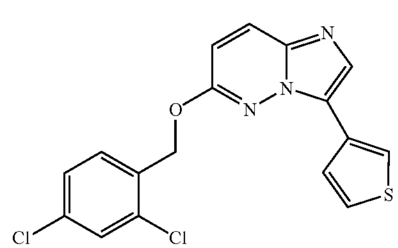 [SMILES: Clc1ccc(COc2ccc3ncc(-c4ccsc4)n3n2)c(Cl)c1] | 9.55 | 376 | 376 |

-continued

| Example No. | Structure | Retention time [min] | MW calc. | MW found |
|---|---|---|---|---|
| 660 | 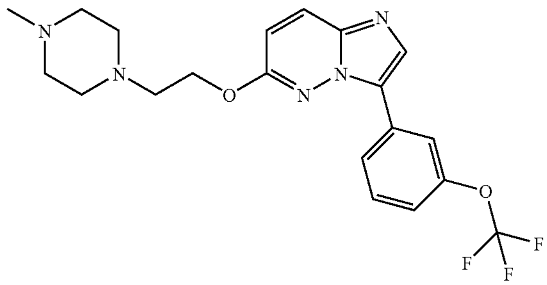 [SMILES: CN1CCN(CCOc2ccc3ncc(-c4cccc(OC(F)(F)F)c4)n3n2)CC1] | 5.15 | 421 | 422 |
| 661 | 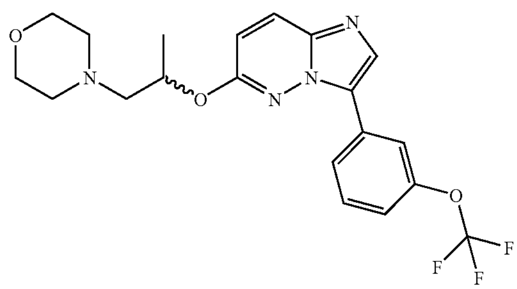 [SMILES: CC(CN1CCOCC1)Oc1ccc2ncc(-c3cccc(OC(F)(F)F)c3)n2n1] | 5.72 | 422 | 423 |
| 662 | 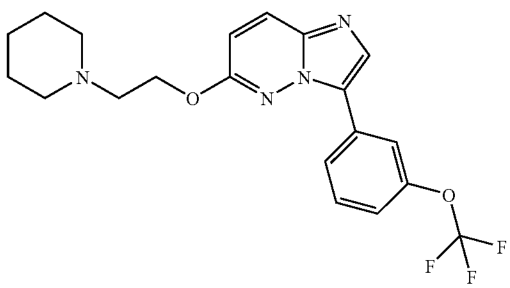 [SMILES: FC(F)(F)Oc1cccc(-c2cnc3ccc(OCCN4CCCCC4)nn23)c1] | 5.76 | 406 | 407 |
| 663 | 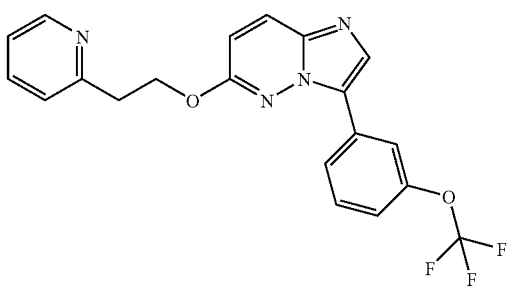 [SMILES: FC(F)(F)Oc1cccc(-c2cnc3ccc(OCCc4ccccn4)nn23)c1] | 5.55 | 400 | 401 |
| 664 | 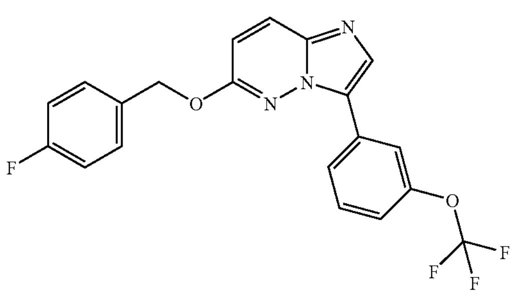 [SMILES: Fc1ccc(COc2ccc3ncc(-c4cccc(OC(F)(F)F)c4)n3n2)cc1] | 9.1 | 403 | 404 |

-continued

| Example No. | Structure | Retention time [min] | MW calc. | MW found |
|---|---|---|---|---|
| 665 | 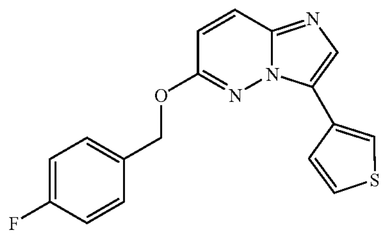 [SMILES: Fc1ccc(COc2ccc3ncc(-c4ccsc4)n3n2)cc1] | 7.94 | 325 | 326 |
| 666 | 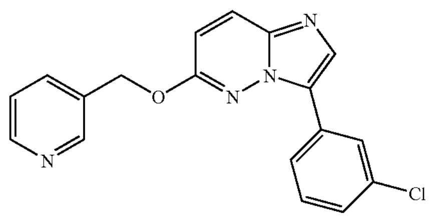 [SMILES: Clc1cccc(-c2cnc3ccc(OCc4cccnc4)nn23)c1] | 5.12 | 336 | 337 |
| 667 | 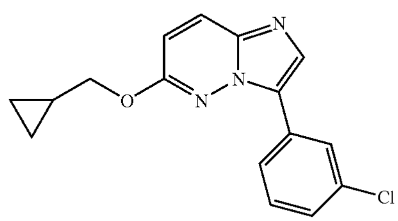 [SMILES: Clc1cccc(-c2cnc3ccc(OCC4CC4)nn23)c1] | 82 | 299 | 300 |
| 668 | 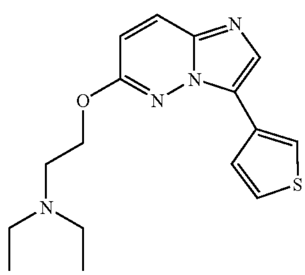 [SMILES: CCN(CC)CCOc1ccc2ncc(-c3ccsc3)n2n1] | 4.51 | 316 | 317 |
| 669 | 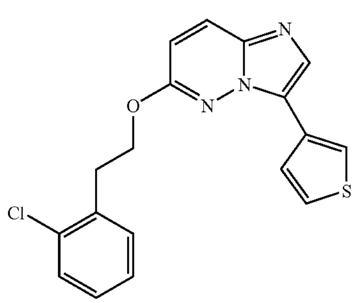 [SMILES: Clc1ccccc1CCOc1ccc2ncc(-c3ccsc3)n2n1] | 8.61 | 355 | 356 |
| 670 | 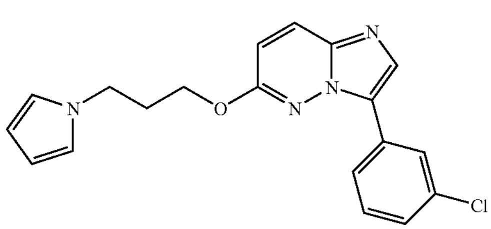 [SMILES: Clc1cccc(-c2cnc3ccc(OCCCn4cccc4)nn23)c1] | 87 | 352 | 353 |

-continued

| Example No. | Structure | Retention time [min] | MW calc. | MW found |
|---|---|---|---|---|
| 671 | 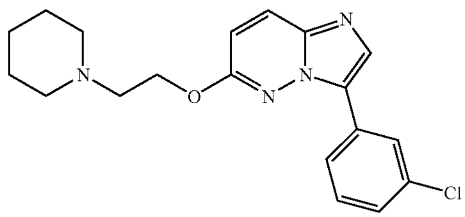 [SMILES: Clc1cccc(-c2cnc3ccc(OCCN4CCCCC4)nn23)c1] | 5.27 | 356 | 357 |

The following examples describe the biological effect of the compounds of the invention:

Significance of IL-2 in the T Cell Immune Response

The extent to which test substance influence antibody-induced interleukin 2 (IL-2) secretion was investigated in the following test system. IL-2 represents a central cytokine which is produced and released by activated T cells. IL-2 synthesis in the T cells is regulated by a plurality of kinases. An inhibitory effect of substances on kinases leads inter alia to inhibition of IL-2 synthesis and inhibition of the T cell immune response. The cytokine determinations were carried out using an ELISA kit.

Description of the Test System

Peripheral blood mononuclear cells (PBMC) were isolated from heparinized human whole blood by gradient centrifugation using Histopaque 1077 (Sigma) at room temperature, and the erythrocytes were lyzed hypotonically and, after washing twice in PBS, taken up in cell culture medium (10% fetal inactivated calf serum in RPMI-1640+Glutamax-I [Gibco]).

The 96 well culture plates (Costar) were previously incubated with 100 µl of antibody solution in PBS 0.1 µg/ml in PBS [Gibco]) per well at 4° C. for 18 hours. The antibodies used were anti-CD3 and anti-CD28 monoclonal antibodies (PharMingen). After washing with PBS three times, the plates were charged with 200 µl of the cell suspension (40 000 cells/well). In addition, the test substances were added in concentrations such that they were present in concentrations of $1 \times 10^{-6}$-$1 \times 10^{-12}$ M.

The cultures were incubated in an incubator at 37° C. for 20 hours. After this incubation, the plates were briefly shaken and centrifuged, and 250 µl of supernatant were removed, and the supernatants were then frozen at −20° C.

Interleukin-2 was determined using an ELISA kit (Bioscience), and the absorption of the color change was analyzed in a SpectraMax 340 PC (wavelength 450 nm). Active substances brought about a reduction in the absorption.

TABLE 1

Assay data

| Example No. | Structure | Inhibition of PKC theta IC50 [mol/l] | IC50 [mol/l] (concentration for 50% inhibition of IL-2) inhibition at 10 µM |
|---|---|---|---|
| 1 | 3-(3-Chloro-phenyl)-6-(3-morpholin-4-yl-propoxy)-imidazo[1,2-b]pyridazine | $4.1 \times 10^{-6}$ | $1.3 \times 10^{-6}$, >95% inhibition at 10 µM |

PKC-Theta Kinase Assay

Inhibition of the enzymic activity of the protein kinase C theta was determined with the aid of the PKC-theta HTRF assay.

Recombinant PKC-theta protein was purchased from ProQinase (Freiburg). The kinase substrate used was the biotinylated peptide having the amino acid sequence biotin-RFARKGSLRQKNVHEVK, which was purchased from Biosynthan (Berlin).

PKC-theta [0.7 nM in the assay mixture, assay volume 5 µl] was incubated at 22° C. for 15 min in the presence of various concentrations of test substances (0 µM, and 10 measurement points within the range 0.001-20 µM in duplicates) in assay buffer [50 mM Hepes/NaOH pH 7.4, 1.0 mM MnCl$_2$, 10.0 mM MgCl$_2$, 1.0 mM dithiothreitol, 0.1 mM sodium orthovanadate, 10 µM adenosine triphosphate (ATP), 0.5 µM substrate peptide, 0.1 mg/ml phosphatidyl serine, 0.01 mg/ml diacylglycerol, 1% (v/v) dimethyl sulfoxide]. The reaction was stopped by adding 5 µl of an EDTA/detection solution [50 mM Hepes/NaOH pH 7.4, 400 mM KF, 40 mM EDTA, 0.1% bovine serum albumin, 100 nM streptavidin-XLent (from Cisbio, #611SAXLB), 1.8 nM anti-phospho PKC substrate crypate conjugate antibody (CisBio: #61P03KAZ)]. After incubation at 22° C. for 60 minutes, during which formation of the trimeric complex of biotinylated and phosphorylated substrate peptide, streptavidin-XLent and anti-

The invention claimed is:
1. A compound of the formula (I),

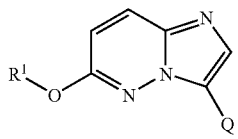

in which
Q is an aryl or heteroaryl radical linked through a carbon atom thereof to the imidazo[1,2b]pyridazine residue and which may optionally be substituted independently of one another by 1-3
hydroxy groups, halogen atoms, nitro groups or cyano groups,
$C_1$-$C_6$-alkyl or $C_3$-$C_8$-cycloalkyl groups which may optionally be substituted by 1-3 hydroxy, halogen, cyano, ($C_1$-$C_5$)-alkoxy, COOR$^6$, NHR$^6$, NHCOR$^6$, N(R$^2$)$_2$ groups,
$C_1$-$C_6$-fluoroalkyl groups which may optionally be substituted by 1-3 hydroxy, optionally fluorinated ($C_1$-$C_5$)-alkoxy, or COOR$^2$ groups,
pyrrolidinyl groups,
(CH$_2$)$_u$—SO$_2$—R$^2$ groups in which u is 1, 2 or 3,
R$^2$ groups or O—CO—R$^6$ groups,
CO—O—R groups,
CO—N(R$^6$)$_2$ groups,
NH—CO—R$^6$ groups,
CONR$^7$R$^8$ groups,
(CH$_2$)$_n$—NR$^7$R$^8$ groups,
NH—CONHR$^6$ groups,
OR$^6$ groups,
SO$_2$—R$^2$ groups,
SO$_2$—OR$^2$ groups,
SO$_2$—N(R$^2$)$_2$ groups,
NHSO$_2$R$^2$ groups,
or
SR$^2$ groups,
in which R$^2$ is in each case independently of one another
a hydrogen atom, a phenyl radical, an optionally partly or completely fluorinated $C_1$-$C_5$-alkyl radical or
a $C_1$-$C_5$-alkyl radical which is in turn optionally substituted 1-5 times by hydroxy radicals, cyano groups, phenyl groups, $C_3$-$C_7$-cycloalkyl radicals, SO$_2$($C_1$-$C_3$-alkyl) radicals, NH($C_1$-$C_3$-alkyl) radicals, N[($C_1$-$C_3$-alkyl)]$_2$ radicals, and/or $C_1$-$C_5$-alkoxy radicals, or a $C_3$-$C_7$-cycloalkyl radical,
in which R$^6$ is in each case independently of one another
either
a radical R$^2$,
an aryl or heteroaryl radical which may in turn optionally be substituted independently of one another 1-3 times by hydroxy radicals, halogen atoms, cyano groups or $C_1$-$C_5$-alkoxy radicals,
a radical —(CH$_2$)$_u$-Q$^8$ in which u is 1, 2 or 3, and in which Q$^s$ is an aryl or heteroaryl radical which may in turn optionally be substituted independently of one another 1-3 times by hydroxy radicals, halogen atoms, cyano groups or $C_1$-$C_5$-alkoxy radicals,
and in which R$^1$ is a
3-dimethylaminopropyl,
3-diethylaminopropyl,
3-piperidin-1-ylpropyl,
2-dimethylaminoethyl,
2-diethylaminoethyl,
1-methylpiperidin-3-ylmethyl,
1-methylpyrrolidin-2-ylethyl,
4-diethylamino-1-methylbutyl, or
3-(4-methyl)piperazin-1-ylpropyl radical,
or a stereoisomer, or a salt or salt of the stereoisomer thereof with physiologically tolerated counterions.

2. A compound of Formula I

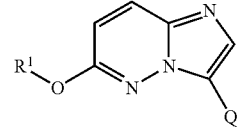

in which Q is phenyl, biphenyl, naphthyl, tetralinyl, anthranyl, indanyl, indenyl, pyrazinyl, pyrimidinyl, pyridazinyl, triazinyl, azaindolizinyl, furanyl, oxazolyl, thiazolyl, furazanyl, isoxazolyl, isothiazolyl, oxadiazolyl, triazolyl, tetrazolyl, thiadiazolyl, phthalidyl, thiophthalidyl, benzothiophenyl, indolyl, isoindolyl, indazolyl, benzothiazolyl, indolonyl, isoindolonyl, benzofuranyl, benzimidazolyl, benzoxazinonyl, phthalazinonyl, quinolinyl, isoquinolinyl, quinolonyl, isoquinolonyl, quinazolinyl, quinoxalinyl, cinnolinyl, phthalazinyl, 1,7- or 1,8-naphthyridinyl, coumarinyl, isocoumarinyl, indolizinyl, isobenzofuranyl, azaindolyl, azaisoindolyl, furanopyridyl, furanopyrimidinyl, furanopyrazinyl, furanopyidazinyl, chromenyl, isochromenyl, chromenonyl, isochromenonyl group, 4-aminopyridyl, chromanyl, isochromanyl, thiochromanyl, in which Q may optionally be substituted independently of one another by 1-3
hydroxy groups, halogen atoms, nitro groups or cyano groups,
$C_1$-$C_6$-alkyl or $C_3$-$C_8$-cycloalkyl groups which may optionally be substituted by 1-3 hydroxy, halogen, cyano, ($C_1$-$C_5$)-alkoxy, COOR$^6$, NHR$^6$, NHCOR$^6$, or N(R$^2$)$_2$ groups
$C_1$-$C_6$-fluoroalkyl groups which may optionally be substituted by 1-3 hydroxy, optionally fluorinated ($C_1$-$C_5$)-alkoxy, or COOR$^2$ groups,
pyrrolidinyl groups,
(CH$_2$)$_u$—SO$_2$—R$^2$ groups in which u is 1, 2 or 3,
R$^2$ groups or O—CO—R$^6$ groups,
CO—O—R$^6$ groups,
CO—N(R$^6$)$_2$ groups,
NH—CO—R$^6$ groups, CONR$^7$R$^8$ groups,
(CH$_2$)$_n$—NR$^7$R$^8$ groups,
NH—CONHR$^6$ groups,
OR$^6$ groups,
SO$_2$—R$^2$ groups,
SO$_2$—OR$^2$ groups,
SO$_2$—N(R$^2$)$_2$ groups,
NHSO$_2$R$^2$ groups,
or
SR$^2$ groups,
in which R$^2$ is in each case independently of one another
  a hydrogen atom, a phenyl radical, an optionally partly or completely fluorinated C$_1$-C$_5$-alkyl radical or
  a C$_1$-C$_5$-alkyl radical which is in turn optionally substituted 1-5 times by hydroxy radicals, cyano groups, phenyl groups, C$_3$-C$_7$-cycloalkyl radicals, SO$_2$(C$_1$-C$_3$-alkyl) radicals, NH(C$_1$-C$_3$-alkyl) radicals, N[(C$_1$-C$_3$-alkyl)]$_2$ radicals, and/or C$_1$-C$_5$-alkoxy radicals,
  or a C$_3$-C$_7$-cycloalkyl radical,
in which R$^6$ is in each case independently of one another
  either
    a radical R$^2$,
    an aryl or heteroaryl radical which may in turn optionally be substituted independently of one another 1-3 times by hydroxy radicals, halogen atoms, cyano groups or C$_1$-C$_5$-alkoxy radicals,
  a radical —(CH$_2$)$_u$-Q$^s$ in which u is 1, 2 or 3 and in which Q$^s$ is aryl or heteroaryl radical which may in turn optionally be substituted independently of one another 1-3 times by hydroxy radicals, halogen atoms, cyano groups or C$_1$-C$_5$-alkoxy radicals,
and in which R$^1$ is
  a C$_1$-C$_6$-alkyl radical which may be substituted 1-3 times by —R$^2$, —NR$^3$R$^4$, —NR$^7$R$^8$ or —OR$^2$,
  a C$_2$-C$_6$-alkenyl radical which may be substituted 1-3 times by —R$^2$, —NR$^3$R$^4$, —NR$^7$R$^8$ or —OR$^2$,
  a C$_2$-C$_6$-alkynyl radical which may be substituted 1-3 times by —R, —NR$^3$R$^4$, —NR$^7$R$^8$ or —OR$^2$,
  a —(CH$_2$)$_n$—NR$^3$R$^4$ radical where n is a number 2-6 and in which R$^3$ and R$^4$ are independently of one another a hydrogen atom, a —COR$^6$ radical, a —SO$_2$R$^2$ radical, or a C$_1$-C$_8$-alkyl radical which is in turn optionally substituted 1-3 times by a halogen atom, a hydroxy group, a cyano group, a nitro group, a group —R$^2$, a group —NHR$^2$, a group —N(R$^2$)$_2$, a group —CO$_2$R$^6$, a group —OCOR$^6$, a group —SO$_2$R$^2$ or a group —OR$^2$,
  a —(CH$_2$)$_t$—Z—(CH$_2$)$_m$—NR$^3$R$^4$ radical,
    where Z is a group —O—, —S—, —NR$^2$—, —CHR$^5$— or —C(R$^5$)$_2$—,
    m is a number 0, 1 or 2, t is a number 0, 1, 2 or 3,
    and in which R$^5$ is a C$_1$-C$_3$-alkyl, C$_2$-C$_3$-alkenyl, C$_2$-C$_3$-alkynyl, a phenyl or a C$_3$-C$_6$-cycloalkyl radical,
  a —(CH$_2$)$_{n'}$—NR$^7$R$^8$ radical where n' is a number 1-6 and in which R$^7$ and R$^8$ together form a 3-7-membered ring, where the 3-7-membered ring may comprise a further heteroatom, and where the 3-7-membered ring is optionally substituted 1-3 times by a halogen atom, a hydroxy group, a cyano group, a nitro group, a group —R$^6$, a group —NHR$^2$, a group —N(R$^2$)$_2$, a group —CO$_2$R$^6$, a group —OCOR$^6$, a group —SO$_2$R$^2$ or a group —OR$^2$,
  a —(CH$_2$)$_n$—(CH)R$^7$R$^8$ radical,
  a —(CH$_2$)$_t$—Z—(CH$_2$)$_m$—NR$^7$R$^8$ radical,
  a —(CH$_2$)$_t$—Z—(CH$_2$)$_m$—(CH)R$^7$R$^8$ radical,
  a —(CH$_2$)$_r$—Y$^1$ radical where r is a number 0-3, and Y$^1$ is a piperidinyl or pyrrolidinyl ring, where the piperidinyl or pyrrolidinyl ring is optionally substituted 1-3 times independently of one another by a halogen atom, a hydroxy group, a cyano group, a nitro group, a group —R$^6$, a group —NHR$^2$, a group —N(R$^2$)$_2$, a group —CO$_2$R$^6$, a group —OCOR$^6$, a group —SO$_2$R$^2$ or a group —OR$^2$,
  a —(CH$_2$)$_t$—Z—(CH$_2$)$_m$—Y$^1$ radical,
  a —(CH$_2$)$_r$—Y$^2$ radical where r is a number 0-3, and Y$^2$ is a morpholinyl ring, where the morpholinyl ring is optionally substituted 1-3 times by a halogen atom, a hydroxy group, a cyano group, a nitro group, a group —R$^6$, a group —NHR$^2$, a group —N(R$^2$)$_2$, a group —CO$_2$R$^6$, a group —OCOR$^6$, a group —SO$_2$R$^2$ or a group —OR$^2$,
  a —(CH$_2$)$_t$—Z—(CH$_2$)$_m$—Y$^2$ radical,
  a —(CH$_2$)$_r$—Y$^3$ radical where r is a number 0-3, and Y$^3$ is a piperazinyl ring which optionally has a C$_1$-C$_3$-alkyl or a C$_1$-C$_3$-acyl group on the nitrogen atom, where the piperazinyl ring is optionally substituted 1-3 times by a halogen atom, a hydroxy group, a cyano group, a nitro group, a group —R$^6$, a group —NHR$^2$, a group —N(R$^2$)$_2$, a group —CO$_2$R$^6$, a group —OCOR$^6$, a group —SO$_2$R$^2$ or a group —OR$^2$,
  a —(CH$_2$)$_t$—Z—(CH$_2$)$_m$—Y$^3$ radical,
  a —(CH$_2$)$_r$—Y$^4$ radical where r is a number 0-3, and Y$^3$ is a C$_3$-C$_8$-cycloalkyl ring which is optionally substituted 1-3 times by a halogen atom, a hydroxy group, a cyano group, a nitro group, a group —R$^6$, a group —NHR$^2$, a group —N(R$^2$)$_2$, a group —CO$_2$R$^6$, a group —OCOR$^6$, a group —SO$_2$R$^2$ or a group —OR$^2$,
  a —(CH$_2$)$_t$—Z—(CH$_2$)$_m$—Y$^4$ radical,
  a —(CH$_2$)$_r$—Y$^5$ radical where r is a number 0-3, and Y$^5$ is an aryl or heteroaryl ring which is optionally substituted 1-3 times by a halogen atom, a hydroxy group, a cyano group, a nitro group, a group R$^6$, a group —NHR$^2$, a group —N(R$^2$)$_2$, a group —CO$_2$R$^6$, a group —OCOR$^6$, a group —SO$_2$R$^2$, a group —SO$_2$N(R$^2$)$_2$, a group —NHSO$_2$R$^2$, a group —NHCOR$^6$, a group —NHCONHR$^6$ or a group —OR$^2$,
  a —(CH$_2$)$_t$—Z—(CH$_2$)$_m$—Y$^5$ radical,
  R$^2$ is in each case independently of one another
    a hydrogen atom, a phenyl radical, an optionally partly or completely fluorinated C$_1$-C$_5$-alkyl radical or
    a C$_1$-C$_5$-alkyl radical which is in turn optionally substituted 1-5 times by hydroxy radicals, cyano groups, phenyl groups, C$_3$-C$_7$-cycloalkyl radicals, SO$_2$(C$_1$-C$_3$-alkyl) radicals, NH(C$_1$-C$_3$-alkyl) radicals, N[(C$_1$-C$_3$-alkyl)]$_2$ radicals, and/or C$_1$-C$_5$-alkoxy radicals,
    or a C$_3$-C$_7$-cycloalkyl radical,
  in which R$^6$ is in each case independently of one another
    either
    a radical R$^2$,
    an aryl or heteroaryl radical which may in turn optionally be substituted independently of one another 1-3 times by hydroxy radicals, halogen atoms, cyano groups and/or C$_1$-C$_5$-alkoxy radicals,
    a radical —(CH$_2$)$_u$-Q$^s$ in which u is the numbers 1, 2 or 3, and in which Q$^s$ is an aryl or heteroaryl radical which may in turn optionally be substituted independently of one another 1-3 times by hydroxy radicals, halogen atoms, cyano groups and/or C$_1$-C$_5$-alkoxy radicals, or a stereoisomer, or a salt or salt of the stereoisomer thereof with physiologically tolerated counterions.

3. The compound as claimed in claim 1, in which $R^1$ is a $—(CH_2)_n—NR^3R^4$ radical where n is 3 or 4, and in which $R^3$ and $R^4$ are independently of one another a $C_1$-$C_3$ alkyl radical.

4. The compound as claimed in claim 2, in which $R^1$ is a $—(CH_2)_n—NR^7R^8$ radical where n is 3 or 4, and in which $R^7$ and $R^8$ together form a 5-7-membered ring.

5. The compound as claimed in claim 2, in which Q is an optionally substituted phenyl, biphenyl, furanyl, benzofuranyl, indolyl, benzothiophenyl or naphthyl radical.

6. The compound as claimed in claim 5, in which the aryl or heteroaryl radical present in Q is substituted by at least one of the following radicals: cyclopropylmethoxy-fluoro, chloro, hydroxy-, cyano-, trifluoromethyl-, trifluoromethoxy-, methyl-, methoxy-, pyrrolidinyl-, —CO—OCH$_3$, —CO$_2$H, —CO—NH$_2$, CH$_2$—CN, CH$_2$—OH, —S—CH$_3$, —SO$_2$—CH$_2$CH$_3$, or —NHCOCH$_3$.

7. A compound of the formula
6-[3-(4-methylpiperazin-1-yl)propoxy]-3-thiophen-3-ylimidazo[1,2-b]pyridazine; 3-(2,4-dichlorophenyl)-6-[3-(4-methylpiperazin-1-yl)propoxy]imidazo[1,2b]pyridazine; 6-[3-(4-methylpiperazin-1-yl)propoxy]-3-m-tolylimidazo[1,2b]pyridazine; 3-(3-chlorophenyl)-6-[3-(4-methylpiperazin-1-yl)propoxy]imidazo[1,2-b]pyridazine; 3-benzo[b]thiophen-2-yl-6-[3-(4-methylpiperazin-1yl)propoxy]imidazo[1,2-b]pyridazine; 3-(4-fluorophenyl)-6-[3-(4-methylpiperazin-1-yl)propoxy]imidazo[1,2-b]pyridazine; 6-[3-(4-methylpiperazin-1-yl)propoxy]-3-phenylimidazo[1,2-b]pyridazine; 6-[3-(4-methylpiperazin-1-yl)propoxy]-3-(4-methylsulfanylphenyl)imidazo[1,2b]pyridazine; 3-(4-chlorophenyl)-6-[3-(4-methylpiperazin-1-yl)propoxy]imidazo[1,2-b]pyridazine; 1-(3-{6-[3-(4-methylpiperazin-1yl)propoxy]imidazo[1,2-b]pyridazin-3-yl}phenyl)ethanone; 6-[3-(4-methylpiperazin-1-yl)propoxy]-3-(2-methylsulfanylphenyl)imidazo[1,2b]pyridazine; 6-[3-(4-methylpiperazin-1-yl)propoxy]-3-(3-trifluoromethoxyphenyl)imidazo[1,2-b]pyridazine; 3-biphenyl-3-yl-6-[3-(4-methylpiperazin-1-yl)propoxy]imidazo[1,2-b]pyridazine; (3-{6-[3-(4-methylpiperazin-1-yl)propoxy]imidazo[1,2-b]pyridazin-3-yl}phenyl)methanol; 6-[3-(4-methylpiperazin-1yl)propoxy]-3-(3-methylsulfanylphenyl)imidazo[1,2-b]pyridazine; 3-(2-chlorophenyl)-6-[3-(4-methylpiperazin-1-yl)propoxy]imidazo[1,2-b]pyridazine; 6-[3-(4-methylpiperazin-1-yl)propoxy]-3-(4-trifluoromethoxyphenyl)imidazo[1,2b]pyridazine; 3-(3-chloro-4-methylphenyl)-6-[3-(4-methylpiperazin-1yl)propoxy]imidazo[1,2-b]pyridazine; 3-(5-methylfuran-2-yl)-6-[3-(4-methylpiperazin-1-yl)propoxy]imidazo[1,2-b]pyridazine; 3-(3-fluoro-4-methoxyphenyl)-6-[3-(4-methylpiperazin-1-yl)propoxy]imidazo[1,2b]pyridazine; 6-[3-(4-methylpiperazin-1-yl)propoxy]-3-o-tolylimidazo[1,2b]pyridazine; 3-(3-chloro-4-fluorophenyl)-6-[3-(4-methylpiperazin-1-yl)propoxy]imidazo[1,2-b]pyridazine; 3-(5-chlorothiophen-2-yl)-6-[3-(4-methylpiperazin-1-yl)propoxy]imidazo[1,2-b]pyridazine; 3-{6-[3-(4-methylpiperazin-1-yl)propoxy]imidazo[1,2-b]pyridazin-3-yl}benzonitrile; 6-[3-(4-methylpiperazin-1-yl)propoxy]-3-(4-methylthiophen-2-yl)imidazo[1,2b]pyridazine; (4-{6-[3-(4-methylpiperazin-1-yl)propoxy]imidazo[1,2-b]pyridazin3-yl}phenyl)acetonitrile; 3-{6-[3-(4-methylpiperazin-1-yl)propoxy]imidazo[1,2b]pyridazin-3-yl}benzoic acid methyl ester; 3-(1H-indol-4-yl)-6-[3-(4-methylpiperazin-1-yl)propoxy]imidazo[1,2-b]pyridazine; 3-benzofuran-2-yl-6-[3-(4-methylpiperazin-1-yl)propoxy]imidazo[1,2-b]pyridazine; 6-[3-(4-methylpiperazin-1-yl)propoxy]-3-p-tolylimidazo[1,2-b]pyridazine; 3-(3-fluorophenyl)-6-[3-(4-methylpiperazin-1-yl)propoxy]imidazo[1,2-b]pyridazine; 3-benzo[b]thiophen-3-yl-6-[3-(4-methylpiperazin-1-yl)propoxy]imidazo[1,2b]pyridazine; 3-(4-chlorophenyl)-6-[3-(4-methylpiperazin-1yl)propoxy]imidazo[1,2-b]pyridazine; 3-(6-fluoro-5-methylpyridin-3-yl)-6-[3-(4-methylpiperazin-1-yl)propoxy]imidazo[1,2-b]pyridazine; 3-(2-chloro-6-methylpyridin-3-yl)-6-[3-(4-methylpiperazin-1-yl)propoxy]imidazo[1,2b]pyridazine; 6-[3-(4-methylpiperazin-1-yl)propoxy]-3-(2-trifluoromethoxyphenyl)imidazo[1,2-b]pyridazine; 3-(4-ethanesulfonylphenyl)-6-[3-(4-methylpiperazin-1-yl)propoxy]imidazo[1,2-b]pyridazine; 6-[3-(4-methylpiperazin-1-yl)propoxy]-3-(3-pyrrolidin-1-ylphenyl)imidazo[1,2-b]pyridazine; 3-(4-cyclopropylmethoxyphenyl)-6-[3-(4-methylpiperazin-1yl)propoxy]imidazo[1,2-b]pyridazine; diethyl-{4-[3-thiophen-3-ylimidazo[1,2-b]pyridazin-6-yloxy)pentyl]amine; {4-[3-(2,4-dichlorophenyl)imidazo[1,2b]pyridazin-6-yloxy]pentyl}diethylamine; diethyl-[4-(3-m-tolylimidazo[1,2b]pyridazin-6-yloxy)pentyl]amine; {4-[3-(3-chlorophenyl)imidazo[1,2b]pyridazin-6-yloxy]pentyl}diethylamine; [4-(3-benzo[b]thiophen-2-ylimidazo[1,2-b]pyridazin-6-yloxy)pentyl]diethylamine; diethyl-{4-[3-(4-fluorophenyl)imidazo[1,2b]pyridazin-6-yloxy]pentyl}amine; diethyl-{4-[3-(4-fluorophenyl)imidazo[1,2-b]pyridazin-6-yloxy)pentyl}amine; {4-[3-(4-chlorophenyl)imidazo[1,2b]pyridazin-6-yloxy]pentyl}diethylamine; 1-{3-[6-(4-diethylamino-1-methylbutoxy)imidazo[1,2-b]pyridazin-3-yl]phenyl}ethanone; diethyl-{4-[3-(2-methylsulfanylphenyl)imidazo[1,2-b]pyridazin-6-yloxy]pentyl}amine; diethyl-{4-[3-(3-trifluoromethoxyphenyl)imidazo[1,2b]pyridazin-6-yloxy]pentyl}amine; [4-(3-biphenyl-3-ylimidazo[1,2-b]pyridazin-6-yloxy)pentyl]diethylamine; {3-[6-(4-diethylamino-1-methylbutoxy)imidazo[1,2b]pyridazin-3-yl]phenyl}methanol; diethyl-{4-[3-(3-methylsulfanylphenyl)imidazo[1,2-b]pyridazin-6-yloxy]pentyl}amine; diethyl-{4-[3-(2-trifluoromethylphenyl)imidazo[1,2-b]pyridazin-6-yloxy]pentyl}amine; diethyl-{4-[3-(4-trifluoromethoxyphenyl)imidazo[1,2-b]pyridazin-6-yloxy]pentyl}amine; {4-[3-(3 chloro-4-methylphenyl)imidazo[1,2-b]pyridazin-6-yloxy]pentyl}diethylamine; diethyl-{4-[3-(5-methylfuran-2-yl)imidazo[1,2-b]pyridazin-6-yloxy]pentyl}amine; diethyl-{4-[3-(3-fluoro-4-methoxyphenyl)imidazo[1,2-b]pyridazin-6-yloxy]pentyl}amine; diethyl-[4-(3-o-tolylimidazo[1,2-b]pyridazin-6-yloxy)pentyl]amine; {4-[3-(3-chloro-4-fluorophenyl)imidazo[1,2-b]pyridazin-6-yloxy]pentyl}diethylamine; {4-[3-(5-chlorothiophen-2-yl)imidazo[1,2-b]pyridazin-6-yloxy]pentyl}diethylamine; 3-[6-(4-diethylamino-1-methylbutoxy)imidazo[1,2b]pyridazin-3-yl]benzonitrile; diethyl-{4-[3-(4-methylthiophen-2-yl)imidazo[1,2b]pyridazin-6-yloxy]pentyl}amine; {4-[6-(4-diethylamino-1methylbutoxy)imidazo[1,2-b]pyridazin-3-yl]phenyl}acetonitrile; 3-[6-(4-diethylamino-1-methylbutoxy)imidazo[1,2-b]pyridazin-3-yl]benzoic acid methyl ester; diethyl-{4-[3-

(1H-indol-4-yl)imidazo[1,2-b]pyridazin-6-yloxy]pentyl}amine; [4-(3-benzofuran-2-ylimidazo[1,2-b]pyridazin-6-yloxy)pentyl]diethylamine; diethyl-[4-(3-p-tolylimidazo[1,2-b]pyridazin-6-yloxy)pentyl]amine; diethyl-{4-[3-(3-fluorophenyl)imidazo[1,2-b]pyridazin-6-yloxy]pentyl}amine; [4-(3-benzo[b]thiophen-3-ylimidazo[1,2-b]pyridazin-6-yloxy)pentyl]diethylamine; {4-[3-(4-chlorophenyl)imidazo[1,2-b]pyridazin-6-yloxy]pentyl}diethylamine; diethyl-{4-[3-(6-fluoro-5-methylpyridin-3-yl)imidazo[1,2-b]pyridazin-6-yloxy]pentyl}amine; diethyl-{4-[3-(2-trifluoromethoxyphenyl)imidazo[1,2-b]pyridazin-6-yloxy]pentyl}amine; diethyl-{4-[3-(3pyrrolidin-1-ylphenyl)imidazo[1,2-b]pyridazin-6-yloxy]pentyl}amine; {5-[6-(4diethylamino-1-methylbutoxy)imidazo[1,2-b]pyridazin-3-yl]thiophen-2yl}methanol; {4-[3-(4-cyclopropylmethoxyphenyl)imidazo[1,2-b]pyridazin-6-yloxy]pentyl}diethylamine; 6-[2-(1-methylpyrrolidin-2-yl)ethoxy]-3-thiophen-3-ylimidazo[1,2-b]pyridazine; 3-(2,4-dichlorophenyl)-6-[2-(1-methylpyrrolidin-2-yl)ethoxy]imidazo[1,2-b]pyridazine; 6-[2-(1-methylpyrrolidin-2-yl)ethoxy]-3-mtolylimidazo[1,2-b]pyridazine; 3-(3-chlorophenyl)-6-[2-(1-methylpyrrolidin-2-yl)ethoxy]imidazo[1,2-b]pyridazine; 3-benzo[b]thiophen-2-yl-6-[2-(1-methylpyrrolidin-2-yl)ethoxy]imidazo[1,2-b]pyridazine; 3-(4-fluorophenyl)-6-[2-(1 methylpyrrolidin-2-yl)ethoxy]imidazo[1,2-b]pyridazine; 6-[2-(1-methylpyrrolidin2-yl)ethoxy]-3-phenylimidazo[1,2-b]pyridazine; 6-[2-(1-methylpyrrolidin-2-yl)ethoxy]-3-(4-methylsulfanylphenyl)imidazo[1,2-b]pyridazine; 3-(4chlorophenyl)-6-[2-(1-methylpyrrolidin-2-yl)ethoxy]imidazo[1,2-b]pyridazine; 1-(3-{6-[2-(1-methylpyrrolidin-2-yl)ethoxy]imidazo[1,2-b]pyridazin-3yl}phenyl)ethanone; 6-[2-(1-methylpyrrolidin-2-yl)ethoxy]-3-(2-methylsulfanylphenyl)imidazo[1,2-b]pyridazine; 6-[2-(1-methylpyrrolidin-2-yl)ethoxy]-3-(3-trifluoromethoxyphenyl)imidazo[1,2-b]pyridazine; 3-biphenyl-3-yl-6-[2-(1-methylpyrrolidin-2-yl)ethoxy]imidazo[1,2-b]pyridazine; (3-{6-[2-(1-methylpyrrolidin-2-yl)ethoxy]imidazo[1,2-b]pyridazin-3-yl}phenyl)methanol; 6-[2-(1-methylpyrrolidin-2-yl)ethoxy]-3-(3-methylsulfanylphenyl)imidazo[1,2b]pyridazine; 6-[2-(1-methylpyrrolidin-2-yl)ethoxy]-3-(2-trifluoromethylphenyl)imidazo[1,2-b]pyridazine; 3-(2-chlorophenyl)-6-[2-(1-methylpyrrolidin-2-yl)ethoxy]imidazo[1,2-b]pyridazine; 6-[2-(1-methylpyrrolidin-2-yl)ethoxy]-3-(4-trifluoromethoxyphenyl)imidazo[1,2-b]pyridazine; 3-(3-chloro-4-methylphenyl)-6-[2-(1-methylpyrrolidin-2-yl)ethoxy]imidazo[1,2-b]pyridazine; 3-(3-fluoro-4-methoxyphenyl)-6-[2-(1-methylpyrrolidin-2-yl)ethoxy]imidazo[1,2-b]pyridazine; 6-[2-(1-methylpyrrolidin-2-yl)ethoxy]-3-o-tolylimidazo[1,2-b]pyridazine; 3-(3 chloro-4-fluorophenyl)-6-[2-(1-methylpyrrolidin-2-yl)ethoxy]imidazo[1,2b]pyridazine; 3-{6-[2-(1-methylpyrrolidin-2-yl)ethoxy]imidazo[1,2-b]pyridazin-3yl}benzonitrile; 6-[2-(1-methylpyrrolidin-2-yl)ethoxy]-3-(4-methylthiophen-2-yl)imidazo[1,2-b]pyridazine; (4-{6-[2-(1-methylpyrrolidin-2yl)ethoxy]imidazo[1,2-b]pyridazin-3-yl}phenyl)acetonitrile; 3-{6-[2-(1-methylpyrrolidin-2-yl)ethoxy]imidazo[1,2-b]pyridazin-3-yl}benzoic acid methyl ester; 3-(1H-indol-4-yl)-6-[2-(1-methylpyrrolidin-2-yl)ethoxy]imidazo[1,2-b]pyridazine; 3-(2-fluoro-pyridin-3-yl)-6-[2-(1-methylpyrrolidin-2yl)ethoxy]imidazo[1,2-b]pyridazine; 3-benzofuran-2-yl-6-[2-(1-methylpyrrolidin2-yl)ethoxy]imidazo[1,2-b]pyridazine; 6-[2-(1-methylpyrrolidin-2-yl)ethoxy]-3-ptolylimidazo[1,2-b]pyridazine; 3-(3-fluorophenyl)-6-[2-(1-methylpyrrolidin-2-yl)ethoxy]imidazo[1,2-b]pyridazine; 3-benzo[b]thiophen-3-yl-6-[2-(1-methylpyrrolidin-2-yl)ethoxy]imidazo[1,2-b]pyridazine; 3-(4-chlorophenyl)-6-[2(1-methylpyrrolidin-2-yl)ethoxy]imidazo[1,2-b]pyridazine; 3-(6-fluoro-5-methylpyridin-3-yl)-6-[2-(1-methylpyrrolidin-2-yl)ethoxy]imidazo[1,2b]pyridazine; 3-(2-chloro-6-methylpyridin-3-yl)-6-[2-(1-methylpyrrolidin-2-yl)ethoxy]imidazo[1,2-b]pyridazine; 6-[2-(1-methylpyrrolidin-2-yl)ethoxy]-3-(2-trifluoromethoxyphenyl)imidazo[1,2-b]pyridazine; 3-(4-ethanesulfonylphenyl)-6-[2-(1-methylpyrrolidin-2-yl)ethoxy]imidazo[1,2-b]pyridazine; 6-[2-(1-methylpyrrolidin-2-yl)ethoxy]-3-(3-pyrrolidin-1-ylphenyl)imidazo[1,2-b]pyridazine; 3(4-cyclopropylmethoxyphenyl)-6-[2-(1-methylpyrrolidin-2-yl)ethoxy]imidazo[1,2-b]pyridazine; 6-(1-methylpiperidin-3-ylmethoxy)-3-thiophen-3-ylimidazo[1,2-b]pyridazine; 3-(2,4-dichlorophenyl)-6-(1 methylpiperidin-3-ylmethoxy)imidazo[1,2-b]pyridazine; 3-(3-chlorophenyl)-6-(1 methylpiperidin-3-ylmethoxy)imidazo[1,2-b]pyridazine; 3-benzo[b]thiophen-2-yl-6-(1-methylpiperidin-3-ylmethoxy)imidazo[1,2-b]pyridazine; 3-(4-fluorophenyl)-6-(1-methylpiperidin-3-ylmethoxy)imidazo[1,2-b]pyridazine; 6-(1 methylpiperidin-3-ylmethoxy)-3-phenylimidazo[1,2-b]pyridazine; 6-(1-methylpiperidin-3-ylmethoxy)-3-(4-methylsulfanylphenyl)imidazo[1,2-b]pyridazine; 3 (4-chlorophenyl)-6-(1-methylpiperidin-3-ylmethoxy)imidazo[1,2-b]pyridazine; 1{3-[6-(1-methylpiperidin-3-ylmethoxy)imidazo[1,2-b]pyridazin-3yl]phenyl}ethanone; 6-(1-methylpiperidin-3-ylmethoxy)-3-(2-methylsulfanylphenyl)imidazo[1,2-b]pyridazine; 6-(1-methylpiperidin-3-ylmethoxy)-3-(3-trifluoromethoxyphenyl)imidazo[1,2-b]pyridazine; 3-biphenyl3-yl-6-(1-methylpiperidin-3-ylmethoxy)imidazo[1,2-b]pyridazine; {3-[6-(1methylpiperidin-3-ylmethoxy)imidazo[1,2-b]pyridazin-3-yl]phenyl}methanol; 6(1-methylpiperidin-3-ylmethoxy)-3-(3-methylsulfanylphenyl)imidazo[1,2-b]pyridazine; 6-(1-methylpiperidin-3-ylmethoxy)-3-(2-trifluoromethylphenyl)imidazo[1,2-b]pyridazine; 3-(2-chlorophenyl)-6-(1-methylpiperidin-3-ylmethoxy)imidazo[1,2-b]pyridazine; 6-(1-methylpiperidin-3-ylmethoxy)-3-(4-trifluoromethoxyphenyl)imidazo[1,2-b]pyridazine; 3-(3-chloro-4-methylphenyl)6-(1-methylpiperidin-3-ylmethoxy)imidazo[1,2-b]pyridazine; 3-(5-methylfuran2-yl)-6-(1-methylpiperidin-3-ylmethoxy)imidazo[1,2-b]pyridazine; 3-(3-fluoro-4-methoxyphenyl)-6-(1-methylpiperidin-3-ylmethoxy)imidazo[1,2-b]pyridazine; 6(1-methylpiperidin-3-ylmethoxy)-3-o-tolylimidazo[1,2-b]pyridazine; 3-(3-chloro-4-fluorophenyl)-6-(1-methylpiperidin-3-ylmethoxy)imidazo[1,2-b]pyridazine; 3 (5-chlorothiophen-2-yl)-6-(1-methylpiperidin-3-ylmethoxy)imidazo[1,2-b]pyridazine; 3-[6-(1-methylpiperidin-3-ylmethoxy)imidazo[1,2-b]pyridazin-3yl]benzonitrile; 6-(1-methylpiperidin-3-ylmethoxy)-3-(4-methylthiophen-2-yl)imidazo[1,2-b]pyridazine; {4-[6-(1-methylpiperidin-3-ylmethoxy)imidazo[1,2b]pyridazin-3-yl]phenyl}acetonitrile; 3-[6-(1-methylpiperidin-3-ylmethoxy)imidazo[1,2-b]pyridazin-3-yl]benzoic acid methyl ester; 3-(1H-indol4-yl)-6-(1-methylpiperidin-3- ylmethoxy)imidazo[1,2-b]pyridazine; 3-(2-fluoropyridin-3-yl)-6-(1-methylpiperidin-3-ylmethoxy)imidazo[1,2-b]pyridazine; 3-benzofuran-2-yl-6-(1-methylpiperidin-3-ylmethoxy)imidazo[1,2-b]pyridazine; 6(1-methylpiperidin-3-ylmethoxy)-3-p-tolylimidazo[1,2-b]pyridazine; 3-(3-fluorophenyl)-6-(1-methylpiperidin-3-ylmethoxy)imidazo[1,2-b]pyridazine; 3-benzo[b]thiophen-3-yl-6-(1-methylpiperidin-3-ylmethoxy)imidazo[1,2b]pyridazine; 3-(4-chlorophenyl)-6-(1-methylpiperidin-3-ylmethoxy)imidazo[1,2b]pyridazine; 3-(6-fluoro-5-methylpyridin-3-yl)-6-(1-methylpiperidin-3-ylmethoxy)imidazo[1,2-b]pyridazine; 6-(1-methylpiperidin-3-ylmethoxy)-3-(2-trifluoromethoxyphenyl)imidazo[1,2-b]pyridazine; 3-(4-ethanesulfonylphenyl)6-(1-methylpiperidin-3-ylmethoxy)imidazo[1,2-b]pyridazine; 6-(1 methylpiperidin-3-ylmethoxy)-3-(3-pyrrolidin-1-ylphenyl)imidazo[1,2b]pyridazine; 3-(4-cyclopropylmethoxyphenyl)-6-(1-methylpiperidin-3-ylmethoxy)imidazo[1,2-b]pyridazine; diethyl-[3-(3-thiophen-3-ylimidazo[1,2b]pyridazin-6-yloxy)propyl]amine; diethyl-[3-(3-naphthalen-1-ylimidazo[1,2b]pyridazin-6-yloxy)propyl]amine; diethyl-{3-[3-(4-methoxyphenyl)imidazo[1,2b]pyridazin-6-yloxy]propyl}amine; diethyl-[3-(3-m-tolylimidazo[1,2-b]pyridazin6-yloxy)propyl]amine; {3-[3-(3-chlorophenyl)imidazo[1,2-b]pyridazin-6-yloxy]propyl}diethylamine; [3-(3-benzo[b]thiophen-2-ylimidazo[1,2-b]pyridazin6-yloxy)propyl]diethylamine; diethyl-{3-[3-(4-fluorophenyl)imidazo[1,2b]pyridazin-6-yloxy)propyl}amine; diethyl-[3-(3-phenylimidazo[1,2-b]pyridazin6-yloxy)propyl]amine; diethyl-{3-[3-(4-methylsulfanylphenyl)imidazo[1,2b]pyridazin-6-yloxy]propyl}amine; {3-[3-(4-chlorophenyl)imidazo[1,2b]pyridazin-6-yloxy]propyl}diethylamine; 1-{3-[6-(3-diethylaminopropoxy)imidazo[1,2-b]pyridazin-3-yl]phenyl}ethanone; diethyl-{3-[3-(2-methylsulfanylphenyl)imidazo[1,2-b]pyridazin-6-yloxy]propyl}amine; diethyl-{3-[3-(3-trifluoromethoxyphenyl)imidazo[1,2-b]pyridazin-6-yloxy]propyl}amine; diethyl {3-[3-(3-trifluoromethylphenyl)imidazo[1,2-b]pyridazin-6-yloxy]propyl}amine; [3(3-biphenyl-3-ylimidazo[1,2-b]pyridazin-6-yloxy)propyl]diethylamine; {3-[6-(3diethylaminopropoxy)imidazo[1,2-b]pyridazin-3-yl]phenyl}methanol; diethyl-{3[3-(3-methylsulfanylphenyl)imidazo[1,2-b]pyridazin-6-yloxy]propyl}amine; diethyl-{3-[3-(2-trifluoromethylphenyl)imidazo[1,2-b]pyridazin-6-yloxy]propyl}amine; {3-[3-(2-chlorophenyl)imidazo[1,2-b]pyridazin-6-yloxy]propyl}diethylamine; diethyl-{3-[3-(4-trifluoromethoxyphenyl)imidazo[1,2b]pyridazin-6-yloxy)propyl}amine; diethyl-{3-[3-(4-trifluoromethylphenyl)imidazo[1,2-b]pyridazin-6-yloxy]propyl}amine; {3-[3-(3-chloro-4-methylphenyl)imidazo[1,2-b]pyridazin-6-yloxy]propyl}diethylamine; diethyl-{3-[3-(5-methylfuran-2-yl)imidazo[1,2-b]pyridazin-6-yloxy]propyl}amine; diethyl-{3-[3-(3 fluoro-4-methoxyphenyl)imidazo[1,2-b]pyridazin-6-yloxy]propyl}amine; diethyl[3-(3-o-tolylimidazo[1,2-b]pyridazin-6-yloxy)propyl]amine; {3-[3-(3-chloro-4-fluorophenyl)imidazo[1,2-b]pyridazin-6-yloxy]propyl}diethylamine; diethyl-{3-[3(3-methoxyphenyl)imidazo[1,2-b]pyridazin-6-yloxy]propyl}amine; {3-[3-(5chlorothiophen-2-yl)imidazo[1,2-b]pyridazin-6-yloxy]propyl}diethylamine; 3-[6-(3-diethylaminopropoxy)imidazo[1,2-b]pyridazin-3-yl]benzonitrile; diethyl-{3-[3 (4-methylthiophen-2-yl)imidazo[1,2-b]pyridazin-6-yloxy]propyl}amine; {4-[6-(3-diethylaminopropoxy)imidazo[1,2-b]pyridazin-3-yl]phenyl}acetonitrile; 3-[6-(3-diethylaminopropoxy)imidazo[1,2-b]pyridazin-3-yl]benzoic acid methyl ester; N-{3-[6-(3-diethylaminopropoxy)imidazo[1,2-b]pyridazin-3yl]phenyl}acetamide; diethyl-{3-[3-(1H-indol-4-yl)imidazo[1,2-b]pyridazin-6-yloxy]propyl}amine; [3-(3-benzofuran-2-ylimidazo[1,2-b]pyridazin-6-yloxy)propyl]diethylamine; diethyl-[3-(3-p-tolylimidazo[1,2-b]pyridazin-6-yloxy)propyl]amine; diethyl-{3-[3-(3-fluorophenyl)imidazo[1,2-b]pyridazin-6-yloxy]propyl}amine; [3-(3-benzo[b]thiophen-3-ylimidazo[1,2-b]pyridazin-6-yloxy)propyl]diethylamine; {3-[3-(4-chlorophenyl)imidazo[1,2-b]pyridazin-6-yloxy]propyl}diethylamine; diethyl-{3-[3-(6-fluoro-5-methylpyridin-3yl)imidazo[1,2-b]pyridazin-6-yloxy]propyl}amine; diethyl-{3-[3-(2-trifluoromethoxyphenyl)imidazo[1,2-b]pyridazin-6-yloxy]propyl}amine; {3-[3-(4-ethanesulfonylphenyl)imidazo[1,2-b]pyridazin-6-yloxy]propyl}diethylamine; diethyl-{3-[3-(3-pyrrolidin-1-ylphenyl)imidazo[1,2-b]pyridazin-6-yloxy]propyl}amine; {3-[3-(4-cyclopropylmethoxyphenyl)imidazo[1,2b]pyridazin-6-yloxy]propyl}diethylamine; 6-(1-methylpiperidin-3-yloxy)-3thiophen-3-ylimidazo[1,2-b]pyridazine; 6-(1-methylpiperidin-3-yloxy)-3-naphthalen-1-ylimidazo[1,2-b]pyridazine; 3-(4-methoxyphenyl)-6-(1 methylpiperidin-3-yloxy)imidazo[1,2-b]pyridazine; 3-(2,4-dichlorophenyl)-6-(1 methylpiperidin-3-yloxy)imidazo[1,2-b]pyridazine; 6-(1-methylpiperidin-3-yloxy)-3-m-tolylimidazo[1,2-b]pyridazine; 3-(3-chlorophenyl)-6-(1 methylpiperidin-3-yloxy)imidazo[1,2-b]pyridazine; 3-benzo[b]thiophen-2-yl-6(1-methylpiperidin-3-yloxy)imidazo[1,2-b]pyridazine; 3-(4-fluorophenyl)-6-(1 methylpiperidin-3-yloxy)imidazo[1,2-b]pyridazine; 6-(1-methylpiperidin-3-yloxy)-3-(2-methylsulfanylphenyl)imidazo[1,2-b]pyridazine; 6-(1 methylpiperidin-3-yloxy)-3-(3-trifluoromethoxyphenyl)imidazo[1,2-b]pyridazine; 6-(1-methylpiperidin-3-yloxy)-3-(3-trifluoromethylphenyl)imidazo[1,2b]pyridazine; 3-biphenyl-3-yl-6-(1-methylpiperidin-3-yloxy)imidazo[1,2b]pyridazine; {3-[6-(1-methylpiperidin-3-yloxy)imidazo[1,2-b]pyridazin-3-yl]phenyl}methanol; 6-(1-methylpiperidin-3-yloxy)-3-(3methylsulfanylphenyl)imidazo[1,2-b]pyridazine; 6-(1-methylpiperidin-3-yloxy)-3-(2-trifluoromethylphenyl)imidazo[1,2-b]pyridazine; 3-(2-chlorophenyl)-6-(1 methylpiperidin-3-yloxy)imidazo[1,2-b]pyridazine; 6-(1-methylpiperidin-3-yloxy)-3-(4-trifluoromethoxyphenyl)imidazo[1,2-b]pyridazine; 6-(1 methylpiperidin-3-yloxy)-3-(4-trifluoromethylphenyl)imidazo[1,2-b]pyridazine; 3-(3-chloro-4-methylphenyl)-6-(1-methylpiperidin-3-yloxy)imidazo[1,2b]pyridazine; 3-(5-methylfuran-2-yl)-6-(1-methylpiperidin-3-yloxy)imidazo[1,2b]pyridazine; 3-(3-fluoro-4-methoxyphenyl)-6-(1-methylpiperidin-3-yloxy)imidazo[1,2-b]pyridazine; 6-(1-methylpiperidin-3-yloxy)-3-otolylimidazo[1,2-b]pyridazine; 3-(3-chloro-4-fluorophenyl)-6-(1-methylpiperidin3-yloxy)imidazo[1,2-b]pyridazine; 3-(3-methoxyphenyl)-6-(1-methylpiperidin-3-yloxy)imidazo[1,2-b]pyridazine; 3-(5-chlorothiophen-2-yl)-6-(1-methylpiperidin3-yloxy)imidazo[1,2-b]pyridazine; 3-[6-(1-methylpiperidin-3-yloxy)imidazo[1,2b]pyridazin-3-yl]benzonitrile; 6-(1-methylpiperidin-3-yloxy)-3-(4-methylthiophen-2- yl)imidazo[1,2-b]pyridazine; {4-[6-(1-methylpiperidin-3-yloxy)imidazo[1,2-b]pyridazin-3-yl]phenyl}acetonitrile; 3-[6-(1-methylpiperidin3-yloxy)imidazo[1,2-b]pyridazin-3-yl]benzoic acid methyl ester; N-{3-[6-(1methylpiperidin-3-yloxy)imidazo[1,2-b]pyridazin-3-yl]phenyl}acetamide; 3-(1Hindol-4-yl)-6-(1-methylpiperidin-3-yloxy)imidazo[1,2-b]pyridazine; 3-benzofuran-2-yl-6-(1-methylpiperidin-3-yloxy)imidazo[1,2-b]pyridazine; 6-(1 methylpiperidin-3-yloxy)-3-p-tolylimidazo[1,2-b]pyridazine; 3-(3-fluorophenyl)6-(1-methylpiperidin-3-yloxy)imidazo[1,2-b]pyridazine; 3-benzo[b]thiophen-3-yl-6-(1-methylpiperidin-3-yloxy)imidazo[1,2-b]pyridazine; 3-(4-chlorophenyl)-6-(1-methylpiperidin-3-yloxy)imidazo[1,2-b]pyridazine; 3-(6-fluoro-5-methylpyridin-3-yl)-6-(1-methylpiperidin-3-yloxy)imidazo[1,2-b]pyridazine; 6-(1 methylpiperidin-3-yloxy)-3-(2-trifluoromethoxyphenyl)imidazo; [1,2b]pyridazine; 3-(4-ethanesulfonylphenyl)-6-(1-methylpiperidin-3-yloxy)imidazo[1,2-b]pyridazine; 6-(1-methylpiperidin-3-yloxy)-3-(3-pyrrolidin-1-ylphenyl)imidazo[1,2-b]pyridazine; 3-(4-cyclopropylmethoxyphenyl)-6-(1 methylpiperidin-3-yloxy)imidazo[1,2-b]pyridazine; 6-(1-ethylpyrrolidin-3-yloxy)-3-thiophen-3-ylimidazo[1,2-b]pyridazine; 6-(1-ethylpyrrolidin-3-yloxy)-3 naphthalen-1-ylimidazo[1,2-b]pyridazine; 6-(1-ethylpyrrolidin-3-yloxy)-3-(4-methoxyphenyl)imidazo[1,2-b]pyridazine; 3-(2,4-dichlorophenyl)-6-(1-ethylpyrrolidin-3-yloxy)imidazo[1,2-b]pyridazine; 3-(3-chlorophenyl)-6-(1 ethylpyrrolidin-3-yloxy)imidazo[1,2-b]pyridazine; 3-benzo[b]thiophen-2-yl-6-(1 ethylpyrrolidin-3-yloxy)imidazo[1,2-b]pyridazine; 6-(1-ethylpyrrolidin-3-yloxy)-3 (4-fluorophenyl)imidazo[1,2-b]pyridazine; 6-(1-ethylpyrrolidin-3-yloxy)-3-phenylimidazo[1,2-b]pyridazine; 6-(1-ethylpyrrolidin-3-yloxy)-3-(4-methylsulfanylphenyl)imidazo[1,2-b]pyridazine; 3-(4-chlorophenyl)-6-(1 ethylpyrrolidin-3-yloxy)imidazo[1,2-b]pyridazine; 1-{3-[6-(1-ethylpyrrolidin-3yloxy)imidazo[1,2-b]pyridazin-3-yl]phenyl}ethanone; 6-(1-ethylpyrrolidin-3-yloxy)-3-(2-methylsulfanylphenyl)imidazo[1,2-b]pyridazine; 6-(1-ethylpyrrolidin3-yloxy)-3-(3-trifluoromethoxyphenyl)imidazo[1,2-b]pyridazine; 6-(1 ethylpyrrolidin-3-yloxy)-3-(3-trifluoromethylphenyl)imidazo[1,2-b]pyridazine; 3biphenyl-3-yl-6-(1-ethylpyrrolidin-3-yloxy)imidazo[1,2-b]pyridazine; {3-[6-(1 ethylpyrrolidin-3-yloxy)imidazo[1,2-b]pyridazin-3-yl]phenyl}methanol; 6-(1 ethylpyrrolidin-3-yloxy)-3-(3-methylsulfanylphenyl)imidazo[1,2-b]pyridazine; 6-(1-ethylpyrrolidin-3-yloxy)-3-(2-trifluoromethylphenyl)imidazo[1,2-b]pyridazine; 3-(2-chlorophenyl)-6-(1-ethylpyrrolidin-3-yloxy)imidazo[1,2-b]pyridazine; 6-(1 ethylpyrrolidin-3-yloxy)-3-(4-trifluoromethoxyphenyl)imidazo[1,2-b]pyridazine; 6-(1-ethylpyrrolidin-3-yloxy)-3-(4-trifluoromethylphenyl)imidazo[1,2b]pyridazine; 3-(3-chloro-4-methylphenyl)-6-(1-ethylpyrrolidin-3yloxy)imidazo[1,2-b]pyridazine; 3-(3-chloro-4-fluorophenyl)-6-(1 ethylpyrrolidin-3-yloxy)imidazo[1,2-b]pyridazine; 6-(1-ethylpyrrolidin-3-yloxy)-3 (3-methoxyphenyl)imidazo[1,2-b]pyridazine; 3-(5-chlorothiophen-2-yl)-6-(1 ethylpyrrolidin-3-yloxy)imidazo[1,2-b]pyridazine; 3-[6-(1-ethylpyrrolidin-3-yloxy)imidazo[1,2-b]pyridazin-3-yl]benzonitrile; 6-(1-ethylpyrrolidin-3-yloxy)-3 (4-methylthiophen-2-yl)imidazo[1,2-b]pyridazine; 3-[6-(1-ethylpyrrolidin-3-yloxy)imidazo[1,2-b]pyridazin-3-yl]benzoic acid methyl ester; N-{3-[6-(1ethylpyrrolidin-3-yloxy)imidazo[1,2-b]pyridazin-3-yl]phenyl}acetamide; 6-(1 ethylpyrrolidin-3-yloxy)-3-(1H-indol-4-yl)imidazo[1,2-b]pyridazine; 3benzofuran-2-yl-6-(1-ethylpyrrolidin-3-yloxy)imidazo[1,2-b]pyridazine; 6-(1-ethylpyrrolidin-3-yloxy)-3-p-tolylimidazo[1,2-b]pyridazine; 6-(1-ethylpyrrolidin3-yloxy)-3-(3-fluorophenyl)imidazo[1,2-b]pyridazine; 3-(4-chlorophenyl)-6-(1 ethylpyrrolidin-3-yloxy)imidazo[1,2-b]pyridazine; 6-(1-ethylpyrrolidin-3-yloxy)-3 (6-fluoro-5-methylpyridin-3-yl)imidazo[1,2-b]pyridazine; 6-(1-ethylpyrrolidin-3-yloxy)-3-(2-trifluoromethoxyphenyl)imidazo[1,2-b]pyridazine; 3-(4ethanesulfonylphenyl)-6-(1-ethylpyrrolidin-3-yloxy)imidazo[1,2-b]pyridazine; 6-(1-ethylpyrrolidin-3-yloxy)-3-(3-pyrrolidin-1-ylphenyl)imidazo[1,2-b]pyridazine; 3-(4-cyclopropylmethoxyphenyl)-6-(1-ethylpyrrolidin-3-yloxy)imidazo[1,2b]pyridazine; 6-(3-piperidin-1-ylpropoxy)-3-thiophen-3-ylimidazo[1,2-b]pyridazine; 3-naphthalen-1-yl-6-(3-piperidin-1-ylpropoxy)imidazo[1,2-b]pyridazine; 3-(4-methoxyphenyl)-6-(3-piperidin-1-ylpropoxy)imidazo[1,2-b]pyridazine; 6-(3-piperidin-1-ylpropoxy)-3-m-tolylimidazo[1,2-b]pyridazine; 3(3-chlorophenyl)-6-(3-piperidin-1-ylpropoxy)imidazo[1,2-b]pyridazine; 3benzo[b]thiophen-2-yl-6-(3-piperidin-1-ylpropoxy)imidazo[1,2-b]pyridazine; 3(4-fluorophenyl)-6-(3-piperidin-1-ylpropoxy)imidazo[1,2-b]pyridazine; 3-phenyl6-(3-piperidin-1-ylpropoxy)imidazo[1,2-b]pyridazine; 3-(4-methylsulfanylphenyl)-6-(3-piperidin-1-ylpropoxy)imidazo[1,2-b]pyridazine; 3 (4-chlorophenyl)-6-(3-piperidin-1-ylpropoxy)imidazo[1,2-b]pyridazine; 1-{3-[6(3-piperidin-1-ylpropoxy)imidazo[1,2-b]pyridazin-3-yl]phenyl}ethanone; 3-(2-methylsulfanylphenyl)-6-(3-piperidin-1-ylpropoxy)imidazo[1,2-b]pyridazine; 6(3-piperidin-1-ylpropoxy)-3-(3-trifluoromethoxyphenyl)imidazo[1,2b]pyridazine; 6-(3-piperidin-1-ylpropoxy)-3-(3-trifluoromethylphenyl)imidazo[1,2-b]pyridazine; 3-biphenyl-3-yl-6-(3-piperidin-1-ylpropoxy)imidazo[1,2-b]pyridazine; {3-[6-(3-piperidin-1-ylpropoxy)imidazo[1,2b]pyridazin-3-yl]phenyl}methanol; 3-(3-methylsulfanylphenyl)-6-(3-piperidin-1ylpropoxy)imidazo[1,2-b]pyridazine; 6-(3-piperidin-1-ylpropoxy)-3-(2-trifluoromethylphenyl)imidazo[1,2-b]pyridazine; 3-(2-chlorophenyl)-6-(3piperidin-1-ylpropoxy)imidazo[1,2-b]pyridazine; 6-(3-piperidin-1-ylpropoxy)-3(4-trifluoromethoxyphenyl)imidazo[1,2-b]pyridazine; 6-(3-piperidin-1ylpropoxy)-3-(4-trifluoromethylphenyl)imidazo[1,2-b]pyridazine; 3-(3-chloro-4-methylphenyl)-6-(3-piperidin-1-ylpropoxy)imidazo[1,2-b]pyridazine; 3-(5-methylfuran-2-yl)-6-(3-piperidin-1-ylpropoxy)imidazo[1,2-b]pyridazine; 3-(3 fluoro-4-methoxyphenyl)-6-(3-piperidin-1-ylpropoxy)imidazo[1,2-b]pyridazine; 6-(3-piperidin-1-ylpropoxy)-3-o-tolylimidazo[1,2-b]pyridazine; 3-(3-chloro-4-fluorophenyl)-6-(3-piperidin-1-ylpropoxy)imidazo[1,2-b]pyridazine; 3-(3methoxyphenyl)-6-(3-piperidin-1-ylpropoxy)imidazo[1,2-b]pyridazine; 3-(5-chlorothiophen-2-yl)-6-(3-piperidin-1-ylpropoxy)imidazo[1,2-b]pyridazine; 3-[6 (3-piperidin-1-ylpropoxy)imidazo[1,2-b]pyridazin-3-yl]benzonitrile; 3-[6-(3piperidin-1-ylpropoxy)imidazo[1,2-b]pyridazin-3-yl]benzonitrile; {4-[6-(3piperidin-1-ylpropoxy)imidazo[1,2-b]pyridazin-3-yl]phenyl}acetonitrile; 3-[6-(3piperidin-1-ylpropoxy)imidazo[1,2-b]pyridazin-3-yl]benzoic acid methyl ester; N-{3-[6-(3-piperidin-1-ylpropoxy)imidazo[1,2-b]pyridazin-3yl]phenyl}acetamide; 3-(1H-indol-4-yl)-

6-(3-piperidin-1-ylpropoxy)imidazo[1,2b]pyridazine; 3-benzofuran-2-yl-6-(3-piperidin-1-ylpropoxy)imidazo[1,2b]pyridazine; 6-(3-piperidin-1-ylpropoxy)-3-p-tolylimidazo[1,2-b]pyridazine; 3(3-fluorophenyl)-6-(3-piperidin-1-ylpropoxy)imidazo[1,2-b]pyridazine; 3-(4-chlorophenyl)-6-(3-piperidin-1-ylpropoxy)imidazo[1,2-b]pyridazine; 3-(6-fluoro5-methylpyridin-3-yl)-6-(3-piperidin-1-ylpropoxy)imidazo[1,2-b]pyridazine; 6-(3piperidin-1-ylpropoxy)-3-(2-trifluoromethoxyphenyl)imidazo[1,2-b]pyridazine; 3 (4-ethanesulfonylphenyl)-6-(3-piperidin-1-ylpropoxy) imidazo[1,2-b]pyridazine; 6-(3-piperidin-1-ylpropoxy)-3-(3-pyrrolidin-1-ylphenyl)imidazo[1,2-b]pyridazine; 3-(4-cyclopropylmethoxyphenyl)-6-(3-piperidin-1-ylpropoxy)imidazo[1,2b]pyridazine; dimethyl-[4-(3-thiophen-3-ylimidazo[1,2-b]pyridazin-6-yloxy)butyl]amine; dimethyl-[4-(3-naphthalen-1-ylimidazo[1,2-b]pyridazin-6-yloxy)butyl]amine; {4-[3-(4-methoxyphenyl)imidazo[1,2-b]pyridazin-6-yloxy]butyl}dimethylamine; dimethyl-[4-(3-m-tolylimidazo[1,2-b]pyridazin-6-yloxy)butyl]amine; {4-[3-(4-fluorophenyl)imidazo[1,2-b]pyridazin-6-yloxy]butyl}dimethylamine; dimethyl-[4-(3-phenylimidazo[1,2-b]pyridazin-6-yloxy)butyl]amine; dimethyl-{4-[3-(4-methylsulfanylphenyl)imidazo[1,2b]pyridazin-6-yloxy]butyl}amine; {4-[3-(4-chlorophenyl)imidazo[1,2-b]pyridazin6-yloxy]butyl}dimethylamine; 1-{3-[6-(4-dimethylaminobutoxy)imidazo[1,2b]pyridazin-3-yl]phenyl}ethanone; dimethyl-{4-[3-(2-methylsulfanylphenyl)imidazo[1,2-b]pyridazin-6-yloxy]butyl}amine; dimethyl-{4-[3-(3-trifluoromethoxyphenyl)imidazo[1,2-b]pyridazin-6-yloxy]butyl}amine; dimethyl-{4-[3-(3-trifluoromethylphenyl)imidazo[1,2-b]pyridazin-6-yloxy]butyl}amine; [4-(3biphenyl-3-ylimidazo[1,2-b]pyridazin-6-yloxy)butyl]dimethylamine; {3-[6-(4-dimethylaminobutoxy)imidazo[1,2-b]pyridazin-3-yl]phenyl}methanol; dimethyl-{4-[3-(3-methylsulfanylphenyl)imidazo[1,2-b]pyridazin-6-yloxy]butyl}amine; dimethyl-{4-[3-(2-trifluoromethylphenyl)imidazo[1,2-b]pyridazin-6-yloxy]butyl}amine; dimethyl-{4-[3-(4-trifluoromethoxyphenyl)imidazo[1,2b]pyridazin-6-yloxy]butyl}amine; dimethyl-{4-[3-(4-trifluoromethylphenyl)imidazo[1,2-b]pyridazin-6-yloxy]butyl}amine; {4-[3-(3-fluoro-4-methoxyphenyl)imidazo[1,2-b]pyridazin-6-yloxy]butyl}dimethylamine; dimethyl-[4-(3-o-tolylimidazo[1,2-b]pyridazin-6-yloxy)butyl]amine; {4-[3-(3methoxyphenyl)imidazo[1,2-b]pyridazin-6-yloxy]butyl}dimethylamine; dimethyl-{4-[3-(4-methylthiophen-2-yl)imidazo[1,2-b]pyridazin-6-yloxy]butyl}amine; {4[6-(4-dimethylaminobutoxy)imidazo[1,2-b]pyridazin-3-yl]phenyl}acetonitrile; 3[6-(4-dimethylaminobutoxy)imidazo[1,2-b]pyridazin-3-yl]benzoic acid methyl ester; N-{3-[6-(4-dimethylaminobutoxy)imidazo[1,2-b]pyridazin-3yl]phenyl}acetamide; {4-[3-(1H-indol-4-yl)imidazo[1,2-b]pyridazin-6-yloxy]butyl}dimethylamine; dimethyl-[4-(3-p-tolylimidazo[1,2-b]pyridazin-6-yloxy)butyl]amine; dimethyl-{4-[3-(2-trifluoromethoxyphenyl)imidazo[1,2b]pyridazin-6-yloxy]butyl}amine; dimethyl-{4-[3-(3-pyrrolidin-1ylphenyl)imidazo[1,2-b]pyridazin-6-yloxy]butyl}amine; {4-[3-(4-cyclopropylmethoxyphenyl)imidazo[1,2-b]pyridazin-6-yloxy]butyl}dimethylamine; or 6-phenoxy-3-m-tolylimidazo[1,2b]pyridazine.

8. A method for preparing compounds of formula I, where a compound of formula IIb

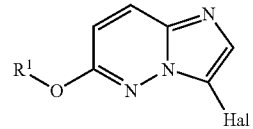

Formula IIb in which R¹ has the meaning defined in claim 1, and in which Hal is a chlorine, bromine or iodine atom, is reacted with a boronic acid in a metal-catalyzed reaction to give a compound of formula I

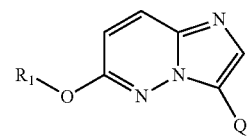

Formula I in which R¹ and Q have the meaning given in claim 1.

9. A method for preparing compounds of formula I, where a compound of formula IIb

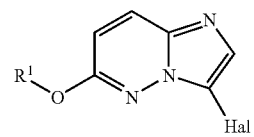

Formula IIb in which R¹ has the meaning defined in claim 1, and in which Hal is a chlorine, bromine or iodine atom, is reacted with a boronic acid with a palladium catalyst to give a compound of formula I

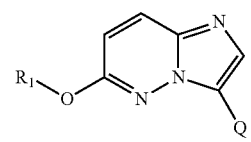

Formula I in which R¹ and Q have the meaning given in claim 1.

10. A pharmaceutical composition comprising at least one compound as claimed in claim 1 and a pharmaceutically acceptable excipient or carrier.

11. The compound as claimed in claim 2, in which Q is an optionally substituted phenyl, biphenyl, naphthyl, tetralinyl, benzothiophenyl, indolyl, indazolyl, benzothiazolyl, benzofuranyl, benzimidazolyl, benzoxazinonyl, isobenzofuranyl, azaindolyl, azaisoindolyl, furanopyridyl, furanopyrimidinyl, furanopyrazinyl, or furanopyidazinyl.

12. The compound as claimed in claim 2, in which Q is an optionally substituted phenyl, biphenyl, naphthyl, benzothiophenyl, indolyl, or benzofuranyl.

13. The compound as claimed in claim 7, which is selected from 3-(3-chlorophenyl)-6-[3-(4-methylpiperazin-1-yl)propoxy]imidazo[1,2-b]pyridazine; 3-benzo[b]thiophen-2-yl-6-[3-(4-methylpiperazin-1yl)propoxy]imidazo[1,2-b]pyridazine; 3-biphenyl-3-yl-6-[3-(4-methylpiperazin-1yl) propoxy]imidazo[1,2-b]pyridazine; 6-[3-(4-methylpiperazin-1-yl)propoxy]-3-(3-methylsulfanylphenyl) imidazo[1,2-b]pyridazine; 3-(3-chloro-4-methylphenyl)-6-[3-(4-methylpiperazin-1yl)propoxy]imidazo[1,2-b] pyridazine; 3-(3-chloro-4-fluorophenyl)-6-[3-(4-methylpiperazin-1yl)propoxy]imidazo[1,2-b]pyridazine; 3-(3-fluorophenyl)-6-[3-(4-methylpiperazin-1-yl)propoxy] imidazo[1,2-b]pyridazine; 3-(4-chlorophenyl)-6-[3-(4-methylpiperazin-1yl)propoxy]imidazo[1,2-b]pyridazine; 6-[3-(4-methylpiperazin-1-yl)propoxy]-3-(2-trifluoromethoxyphenyl)imidazo[1,2-b]pyridazine; 3-(4-ethanesulfonylphenyl)-6-[3-(4-methylpiperazin-1-yl) propoxy]imidazo[1,2-b]pyridazine; 6-[3-(4-methylpiperazin-1-yl)propoxy]-3-(3-pyrrolidin-1-ylphenyl) imidazo[1,2-b]pyridazine; 3-(4-cyclopropylmethoxyphenyl)-6-[3-(4-methylpiperazin-1yl) propoxy]imidazo[1,2-b]pyridazine; diethyl-[4-(3-thiophen-3-ylimidazo[1,2-b]pyridazin-6-yloxy)pentyl]amine; {4-[3-(2,4-dichlorophenyl)imidazo[1,2b]pyridazin-6-yloxy] pentyl}diethylamine; diethyl-[4-(3-m-tolylimidazo[1,2b] pyridazin-6-yloxy)pentyl]amine; {4-[3-(3-chlorophenyl) imidazo[1,2b]pyridazin-6-yloxy]pentyl}diethylamine; [4-(3-benzo[b]thiophen-2-ylimidazo[1,2-b]pyridazin-6-yloxy) pentyl]diethylamine; diethyl-{4-[3-(4-fluorophenyl)imidazo [1,2-b]pyridazin-6-yloxy]pentyl}amine; diethyl-{4-[3-(4-fluorophenyl)imidazo[1,2-b]pyridazin-6-yloxy] pentyl}amine; 1-{3-[6-(4-diethylamino-1-methylbutoxy) imidazo[1,2-b]pyridazin-3-yl]phenyl}ethanone; diethyl-{4-[3-(2-methylsulfanylphenyl)imidazo[1,2-b]pyridazin-6-yloxy]pentyl}amine; diethyl-{4-[3-(3-trifluoromethoxyphenyl)imidazo[1,2b]pyridazin-6-yloxy] pentyl}amine; [4-(3-biphenyl-3-ylimidazo[1,2-b]pyridazin-6-yloxy)pentyl]diethylamine; {3-[6-(4-diethylamino-1-methylbutoxy)imidazo[1,2b]pyridazin-3-yl] phenyl}methanol; diethyl-{4-[3-(3-methylsulfanylphenyl) imidazo[1,2-b]pyridazin-6-yloxy]pentyl}amine; {4-[3-(3 chloro-4-methylphenyl)imidazo[1,2-b]pyridazin-6-yloxy] pentyl}diethylamine; diethyl-{4-[3-(3-fluoro-4-methoxyphenyl)imidazo[1,2-b]pyridazin-6-yloxy]pentyl}amine; {4-[3-(3-chloro-4-fluorophenyl)imidazo[1,2-b]pyridazin-6-yloxy]pentyl}diethylamine; 3-[6-(4-diethylamino-1-methylbutoxy)imidazo[1,2b]pyridazin-3-yl]benzonitrile; diethyl-{4-[3-(1H-indol-4-yl)imidazo[1,2-b]pyridazin-6-yloxy] pentyl}amine; [4-(3-benzofuran-2-ylimidazo[1,2-b] pyridazin-6-yloxy)-pentyl]diethylamine; diethyl-{4-[3-(3-fluorophenyl)imidazo[1,2-b]pyridazin-6-yloxy] pentyl}amine; {4-[3-(4-chlorophenyl)imidazo[1,2-b] pyridazin-6-yloxy]pentyl}diethylamine; 3-(3-chlorophenyl)-6-[2-(1-methylpyrrolidin-2yl)ethoxy] imidazo[1,2-b]pyridazine; 3-benzo[b]thiophen-2-yl-6-[2-(1-methylpyrrolidin-2-yl)ethoxy]imidazo[1,2-b]pyridazine; 1(3-{6-[2-(1-methylpyrrolidin-2-yl)ethoxy]imidazo[1,2-b] pyridazin-3-yl}phenyl)ethanone; 3-biphenyl-3-yl-6-[2-(1-methylpyrrolidin-2-yl)ethoxy]imidazo[1,2-b]pyridazine; 6[2-(1-methylpyrrolidin-2-yl)ethoxy]-3-(3-methylsulfanylphenyl)imidazo[1,2b]pyridazine; 3-(3-chloro-4-methylphenyl)-6-[2-(1-methylpyrrolidin-2-yl)ethoxy]imidazo[1, 2-b]pyridazine; 3-(3-fluoro-4-methoxyphenyl)-6-[2-(1-methylpyrrolidin-2-yl)ethoxy]imidazo[1,2-b]pyridazine; 3-(3chloro-4-fluorophenyl)-6-[2-(1-methylpyrrolidin-2-yl) ethoxy]imidazo[1,2b]pyridazine; 3-{6-[2-(1-methylpyrrolidin-2-yl)ethoxy]imidazo[1,2-b]pyridazin-3-yl}benzonitrile; 3-{6-[2-(1 methylpyrrolidin-2-yl)ethoxy]imidazo[1,2-b]pyridazin-3-yl}benzoic acid methyl ester; 3-(3-fluorophenyl)-6-[2-(1-methylpyrrolidin-2-yl)ethoxy]imidazo[1,2-b]pyridazine; 3-(4-chlorophenyl)-6-[2(1-methylpyrrolidin-2-yl) ethoxy]imidazo[1,2-b]pyridazine; 3-(3-chlorophenyl)-6-(1 methylpiperidin-3-ylmethoxy)imidazo[1,2-b]pyridazine; 3-benzo[b]thiophen-2-yl-6-(1-methylpiperidin-3-ylmethoxy)imidazo[1,2-b]pyridazine; 1{3-[6-(1-methylpiperidin-3-ylmethoxy)imidazo[1,2-b]pyridazin-3yl] phenyl}ethanone; 6-(1-methylpiperidin-3-ylmethoxy)-3-(3-trifluoromethoxyphenyl)imidazo[1,2-b]pyridazine; 3-biphenyl3-yl-6-(1-methylpiperidin-3-ylmethoxy)imidazo [1,2-b]pyridazine; 6(1-methylpiperidin-3-ylmethoxy)-3-(3-methylsulfanylphenyl)imidazo[1,2b]pyridazine; 3-(3-chloro-4-methylphenyl)6-(1-methylpiperidin-3-ylmethoxy) imidazo[1,2-b]pyridazine; 3-(3-chloro-4-fluorophenyl)-6-(1-methylpiperidin-3-ylmethoxy)imidazo[1,2-b]pyridazine; 3-[6-(1-methylpiperidin-3-ylmethoxy)imidazo[1,2-b]pyridazin-3yl]benzonitrile; 3-[6-(1-methylpiperidin-3-yl-methoxy)imidazo[1,2-b]pyridazin-3-yl]benzoic acid methyl ester; 3-(4-chlorophenyl)-6-(1-methylpiperidin-3-ylmethoxy)imidazo[1,2-b]pyridazine; diethyl-{3-[3-(4-methoxyphenyl)imidazo[1,2b]pyridazin-6-yloxy]propyl}amine; diethyl-[3-(3-m-tolylimidazo[1,2-b]pyridazin-6-yloxy)propyl]amine; {3-[3-(3-chlorophenyl)imidazo[1,2-b]pyridazin-6-yloxy]propyl}diethylamine; [3-(3-benzo[b]thiophen-2-ylimidazo[1,2-b]pyridazin6-yloxy)propyl]diethylamine; diethyl-{3-[3-(4-methylsulfanylphenyl)imidazo[1,2b]pyridazin-6-yloxy]propyl}amine; 1-{3-[6-(3-diethylaminopropoxy)imidazo[1,2-b]pyridazin-3-yl]phenyl}ethanone; diethyl-{3-[3-(3-trifluoromethoxyphenyl)imidazo[1,2-b]pyridazin-6-yloxy]propyl}amine; diethyl {3-[3-(3-trifluoromethylphenyl)imidazo[1,2-b]pyridazin-6-yloxy] propyl}amine; [3(3-biphenyl-3-ylimidazo[1,2-b]pyridazin-6-yloxy)propyl]diethylamine; diethyl-{3 [3-(3-methylsulfanylphenyl)imidazo[1,2-b]pyridazin-6-yloxy] propyl}amine; diethyl-{3-[3-(2-trifluoromethylphenyl) imidazo[1,2-b]pyridazin-6-yloxy]propyl}amine; {3-[3-(2-chlorophenyl)imidazo[1,2-b]pyridazin-6-yloxy] propyl}diethylamine; diethyl-{3-[3-(4-trifluoromethoxyphenyl)imidazo[1,2b]pyridazin-6-yloxy] propyl}amine; diethyl-{3-[3-(4-trifluoromethylphenyl) imidazo[1,2-b]pyridazin-6-yloxy]propyl}amine; {3-[3-(3-chloro-4-methylphenyl)imidazo[1,2-b]pyridazin-6-yloxy] propyl}diethylamine; diethyl-{3-[3-(3 fluoro-4-methoxyphenyl)imidazo[1,2-b]pyridazin-6-yloxy] propyl}amine; diethyl[3-(3-o-tolylimidazo[1,2-b]pyridazin-6-yloxy)propyl]amine; {3-[3-(3-chloro-4-fluorophenyl) imidazo[1,2-b]pyridazin-6-yloxy]propyl}diethylamine; diethyl-{3-[3(3-methoxyphenyl)imidazo[1,2-b]pyridazin-6-yloxy]propyl}amine; 3-[6(3-diethylaminopropoxy)imidazo [1,2-b]pyridazin-3-yl]benzonitrile; {4-[6-(3diethylaminopropoxy)imidazo[1,2-b]pyridazin-3-yl]phenyl}acetonitrile; 3-[6-(3-diethylaminopropoxy)imidazo[1,2-b]pyridazin-3-yl]benzoic acid methyl ester; N-{3-[6-(3-diethylaminopropoxy)imidazo[1,2-b]pyridazin-3-yl]phenyl}acetamide; diethyl-{3-[3-(1H-indol-4-yl)imidazo[1,2-b]pyridazin-6-yloxy]propyl}amine; [3-(3-benzofuran-2-ylimidazo[1,2-b] pyridazin-6-yloxy)propyl]diethylamine; diethyl-{3-[3-(3-fluorophenyl)imidazo[1,2-b]pyridazin-6-yloxy] propyl}amine; {3-[3-(4-chlorophenyl)imidazo[1,2-b] pyridazin-6-yloxy]propyl}diethylamine; {3-[3-(4-cyclopropylmethoxyphenyl)imidazo[1,2b]pyridazin-6-yloxy]propyl}diethylamine; 3-[6-(1-methylpiperidin3-yloxy)imidazo[1,2-b]pyridazin-3-yl]benzoic acid methyl ester; 3-(4-chlorophenyl)-6-(1ethylpyrrolidin-3-yloxy)imidazo[1,2-b]pyridazine; 3(3-chlorophenyl)-6-(3-piperidin-1- ylpropoxy)imidazo[1,2-b]pyridazine; 3-benzo[b]thiophen-2-yl-6-(3-piperidin-1-ylpropoxy)imidazo[1,2-b]pyridazine; 6-(3-piperidin-1-ylpropoxy)-3-(3-trifluoromethylphenyl)-imidazo[1,2-b]pyridazine; 3-(3-methylsulfanylphenyl)-6-(3-piperidin-1ylpropoxy)imidazo[1,2-b]pyridazine; 3-(3-chloro-4-methylphenyl)-6-(3-piperidin-1-ylpropoxy)imidazo[1,2-b]pyridazine; 3-(3fluoro-4-methoxyphenyl)-6-(3-piperidin-1-ylpropoxy)imidazo[1,2-b]pyridazine; 3-(3-chloro-4-fluorophenyl)-6-(3-piperidin-1-ylpropoxy)imidazo[1,2-b]pyridazine; 3-[6(3-piperidin-1-ylpropoxy)imidazo[1,2-b]pyridazin-3-yl]benzonitrile; 3-[6-(3piperidin-1-ylpropoxy)imidazo[1,2-b]pyridazin-3-yl]benzonitrile; 3(3-fluorophenyl)-6-(3-piperidin-1-ylpropoxy)imidazo[1,2-b]pyridazine; 3-(4-chlorophenyl)-6-(3-piperidin-1-ylpropoxy)imidazo[1,2-b]pyridazine; dimethyl-{4-[3-(3-trifluoromethylphenyl)imidazo[1,2-b]pyridazin-6-yloxy]butyl}amine; [4-(3biphenyl-3-ylimidazo[1,2-b]pyridazin-6-yloxy)butyl]dimethylamine; dimethyl {4-[3-(3-methylsulfanylphenyl)imidazo[1,2-b]pyridazin-6-yloxy]butyl}amine; {4-[3-(4-cyclopropylmethoxyphenyl)imidazo[1,2-b]pyridazin-6-yloxy]butyl}dimethylamine; or 6-phenoxy-3-m-tolylimidazo[1,2b]pyridazine.

14. The compound as claimed in claim 1, in which Q is an optionally substituted phenyl, biphenyl, furanyl, benzofuranyl, indolyl, benzothiophenyl or naphthyl radical.

15. The compound as claimed in claim 14, in which the aryl or heteroaryl radical present in Q is substituted by at least one of the following radicals: cyclopropylmethoxy-fluoro, chloro, hydroxy-, cyano-, trifluoromethyl-, trifluoromethoxy-, methyl-, methoxy-, pyrrolidinyl-, —CO—OCH$_3$, —CO—CH$_3$, —CO$_2$H, —CO—NH$_2$, —CH$_2$—CN, —CH$_2$—OH, —CH$_2$—S—CH$_3$, —S—CH$_3$, —SO$_2$—CH$_2$CH$_3$, or —NHCOCH$_3$.

16. The compound as claimed in claim 1, in which Q is an optionally substituted phenyl, biphenyl, naphthyl, tetralinyl, benzothiophenyl, indolyl, indazolyl, benzothiazolyl, benzofuranyl, benzimidazolyl, benzoxazinonyl, isobenzofuranyl, azaindolyl, azaisoindolyl, furanopyridyl, furanopyrimidinyl, furanopyrazinyl, or furanopyidazinyl.

17. The compound as claimed in claim 1, in which Q is an optionally substituted phenyl, biphenyl, naphthyl, benzothiophenyl, indolyl, or benzofuranyl.

* * * * *